US007030112B2

(12) United States Patent
Salvati et al.

(10) Patent No.: US 7,030,112 B2
(45) Date of Patent: *Apr. 18, 2006

(54) PYRROLOPYRIDAZINE COMPOUNDS AND METHODS OF USE THEREOF FOR THE TREATMENT OF PROLIFERATIVE DISORDERS

(75) Inventors: Mark E. Salvati, Lawrencevile, NJ (US); Carl R. Illig, Phoenixville, PA (US); Kenneth Jerome Wilson, West Grove, PA (US); Jinsheng Chen, Exton, PA (US); Sanath K. Meegalla, Boothwyn, PA (US); Mark James Wall, Harleysville, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 136 days.

This patent is subject to a terminal disclaimer.

(21) Appl. No.: 10/672,850

(22) Filed: Sep. 26, 2003

(65) Prior Publication Data

US 2004/0209886 A1 Oct. 21, 2004

Related U.S. Application Data

(63) Continuation-in-part of application No. 10/396,197, filed on Mar. 25, 2003.

(51) Int. Cl.

| | |
|---|---|
| ***C07D 487/04*** | (2006.01) |
| ***C07D 487/14*** | (2006.01) |
| ***A61K 31/5025*** | (2006.01) |
| ***A61P 5/28*** | (2006.01) |
| ***A61P 35/00*** | (2006.01) |

(52) U.S. Cl. .................... 514/233.2; 544/235; 544/116; 514/248

(58) Field of Classification Search ................. 544/235; 514/248

See application file for complete search history.

(56) References Cited

U.S. PATENT DOCUMENTS 6,472,389 B1 10/2002 Ohtani et al. ............ 514/233.2

FOREIGN PATENT DOCUMENTS

| | | |
|---|---|---|
| WO | WO 00/12074 | 3/2000 |
| WO | WO 00/12497 | 3/2000 |
| WO | WO 00/56738 | 9/2000 |

OTHER PUBLICATIONS

Letsinger et al. {J. Org. Chem. (1956), 21, 764–6}.*

Flitsch et al. {Tetrahedron Letters (1968), (12), 1479–84}.*

Boyce, B.F. et al., "Requirement of pp60$^{c\text{–}Src}$ Expression for Osteoclasts to Form Ruffled Borders and Resorb Bone in Mice", J. Clin. Invest., vol. 90, pp. 1622–1627 (1992).

Campbell, S.L. et al., "Increasing complexity of Ras signaling", Oncogene, vol. 17, pp. 1395–1413 (1998).

Du, et al., "Abnormal polarization of EGF receptors and autocrine stimulation of cyst epithelial growth in human ADPKD", American Journal of Physiology, vol. 269, No. 2, Part 1, pp. C487–C495 (1995).

Dudley, D.T. et al., "A synthetic inhibitor of the mitogen–activated protein kinase cascade", Proc. Natl. Acad. Sci. USA, vol. 92, pp. 7686–7689 (1995).

Ellis, L.M. et al., "Down–regulation of Vascular Endothelial Growth Factor in a Human Colon Carcinoma Cell Line Transfected with an Antisense Expression Vector Specific for *c–src*", The Journal of Biological Chemistry, vol. 273, No. 2, pp. 1052–1057 (1998).

Gattone II, V.H. et al., "Epidermal Growth Factor Ameliorates Autosomal Recessive Polycystic Kidney Disease in Mice", Developmental Biology, vol. 169, pp. 504–510 (1995).

Henry, J.R. et al., "p38 mitogen–activated protein kinase as a target for drug discovery", Drugs of the Future, vol. 24, No. 12, pp. 1345–1354 (1999).

Missbach, M. et al., "A Novel Inhibitor of the Tyrosine Kinase Src Suppresses Phosphorylation of Its Major Cellular Substrates and Reduces Bone Resorption In Vitro and in Rodent Models in Vivo", Bone, vol. 24, No. 5, pp. 437–449 (1999).

Moreland, L.W. et al., "Etanercept Therapy in Rheumatoid Arthritis", Ann. of Intern. Med., vol. 130, pp. 478–486 (1999).

Nauta, J. et al., "Biliary Epithelial Cells from Mice with Congenital Polycystic Kidney Disease Are Hyperresponsive to Epidermal Growth Factor", Pediatric Research, vol. 37, No. 6, pp. 755–763 (1995).

Nistér, M. et al., "Differential Expression of Platelet–derived Growth Factor Receptors in Human Malignant Glioma Cell Lines", The Journal of Biological Chemistry, vol. 266, No. 25, pp. 16755–16763 (1991).

(Continued)

*Primary Examiner*—Mark L. Berch
*Assistant Examiner*—Kahsay Habte
(74) *Attorney, Agent, or Firm*—Elliott Korsen

(57) ABSTRACT

Disclosed are pyrrolopyridazine compounds of the formula,

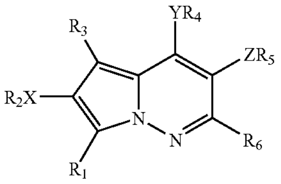

wherein the substituents are defined herein, methods of preparing such compounds, and their use for the treatment of proliferative, inflammatory, and other disorders.

2 Claims, No Drawings

OTHER PUBLICATIONS

O'Reilly, M.S. et al., "Angiostatin: A Novel Angiogenesis Inhibitor That Mediates the Suppression of Metastases by a Lewis Lung Carcinoma", Cell, vol. 79, pp. 315–328 (1994).

O'Reilly, M.S. et al., "Angiostatin induces and sustains dormancy of human primary tumors in mice", Nature Medicine, vol. 2, No. 6, pp. 689–692 (1996).

O'Reilly, M.S. et al., "Endostatin: An Endogenous Inhibitor of Angiogenesis and Tumor Growth", Cell, vol. 88, pp. 277–285 (1997).

Rankin, E.C.C. et al., "The Therapeutic Effects of an Engineered Human Anti–Tumour Necrosis Factor Alpha Antibody (CDP571) in Rheumatoid Arthritis", British Journal of Rheumatology, vol. 34, pp. 334–342 (1995).

Salituro, F.G. et al., "Inhibitors of p38 MAP Kinase: Therapeutic Intervention in Cytokine–Mediated Diseases", Current Medical Chemistry, vol. 6, pp. 807–823 (1999).

Sato, T.N. et al., "Distinct roles of the receptor tyrosine kinases Tie–1 and Tie–2 in blood vessel formation", Nature, vol. 376, pp. 70–74 (1995).

Schwartzberg, P.L., "The many faces of Src: multiple functions of a prototypical tyrosine kinase", Oncogene, vol. 17, pp. 1463–1468 (1998).

Seger, R. et al., "The MAPK signaling cascade", FASEB J., vol. 9, pp. 726–735 (1995).

Sivaraman, V.S. et al., "Hyperexpression of Mitogen–activated Protein Kinase in Human Breast Cancer", J. Clin. Invest., vol. 99, No. 7, pp. 1478–1483 (1997).

Soriano, P. et al., "Targeted Disruption of the *c–src* Proto–Oncogene Leads to Osteopetrosis in Mice", Cell, vol. 64, pp. 693–702 (1991).

Staley, C.A. et al., "Decreased Tumorigenicity of a Human Colon Adenocarcinoma Cell Line by an Antisense Expression Vector Specific for *c–Src*", Cell Growth and Differentiation, vol. 8, pp. 269–274 (1997).

Strawn, L.M. et al., "Inhibition of Glioma Cell Growth by a Truncated Platelet–derived Growth Factor–β Receptor", The Journal of Biological Chemistry, vol. 269, No. 33, pp. 21215–21222 (1994).

Wilson, P.D. et al., "Autocrine, endocrine and paracrine regulation of growth abnormalities in autosomal dominant polycystic kidney disease", European Journal of Cell Biology, vol. 61, pp. 131–138 (1993).

* cited by examiner

PYRROLOPYRIDAZINE COMPOUNDS AND METHODS OF USE THEREOF FOR THE TREATMENT OF PROLIFERATIVE DISORDERS

RELATED APPLICATIONS

This application is continuation-in-part of U.S. Non-Provisional Application No. 10/396,197, filed Mar. 25, 2003, the contents of which are herein incorporated by reference and benefit of which is claimed.

FIELD OF THE INVENTION

The present invention relates to pyrrolopyridazine compounds, methods of preparing such compounds, and their use for the treatment of poliferative and other disorders.

BACKGROUND OF THE INVENTION protein kinases are a class of enzymes that catalyze the transfer of a phosphate group from ATP to a tyrosine, serine, threonine, or histidine residue located on a protein substrate. Protein kinases clearly play a role in normal cell growth. Many of the growth factor receptor proteins have intracellular domains that function as protein kinases and it is through this function that they effect signaling. The interaction of growth factors with their receptors is a necessary event in the normal regulation of cell growth, and the phosphorylation state of substrate proteins often is related to the modulation of cell growth.

The human epidermal growth factor receptor (HER) family consists of four distinct receptor tyrosine kinases referred to as HER1, HER2, HER3, and HER4. These kinases are also referred to as erbB1, erbB2, etc. HER1 is also commonly referred to as the epidermal growth factor receptor (EGFr). With the exception of HER3, these receptors have intrinsic protein kinase activity that is specific for tyrosine residues of phosphoacceptor proteins. The HER kinases are expressed in most epithelial cells as well as tumor cells of epithelial origin. They are also often expressed in tumor cells of mesenchymal origin such as sarcomas or rhabdomyosarcomas. Receptor tyrosine kinases (RTKs) such as HER1 and HER2 are involved in cell proliferation and are associated with diseases such as psoriasis and cancer. Disruption of signal transduction by inhibition of these kinases in target cells is known to have an antiproliferative and therapeutic effect.

The enzymatic activity of receptor tyrosine kinases can be stimulated by either overexpression, or by ligand-mediated dimerization. The formation of homodimers as well as heterodimers has been demonstrated for the HER receptor family. An example of homodimerization is the dimerization of HER1 (EGF receptor) by one of the EGF family of ligands (which includes EGF, transforming growth factor alpha, betacellulin, heparin-binding EGF, and epiregulin). Heterodimerization among the four HER receptor kinases can be promoted by binding to members of the heregulin (also referred to neuregulin) family of ligands. Such heterodimerization, involving HER2 and HER3, or a HER3/HER4 combination, results in a significant stimulation of the tyrosine kinase activity of the receptor dimers even though one of the receptors (HER3) is enzymatically inert. The kinase activity of HER2 has also been shown to be activated by virtue of overexpression of the receptor alone in a variety of cell types. Activation of receptor homodimers and heterodimers results in phosphorylation of tyrosine residues on the receptors and on other intracellular proteins. This is followed by the activation of intracellular signaling pathways such as those involving the microtubule associated protein kinase (MAP kinase) and the phophatidylinositol 3-kinase (P13 kinase). Activation of these pathways has been shown to lead to cellular proliferation and the inhibition of apoptosis. Inhibition of HER kinase signaling has been shown to inhibit cell proliferation and survival.

Deregulation of EGF receptors plays a role in the aberrant growth of epithelial cysts in the disease described as polycystic kidney disease [Du, J., Wilson, P. D., *Amer. J. Physiol.*, 269 (2 Pt 1), 487 (1995); Nauta, J., et al., *Pediatric Research*, 37(6), 755 (1995); Gattone, V. H. et al., *Developmental Biology*, 169(2), 504 (1995); Wilson, P. D. et al., *Eur. J. Cell Biol.*, 61(1), 131, (1993)]. The compounds of this invention, which inhibit the catalytic function of the EGF receptors, are consequently useful for the treatment of this disease.

The mitogen-activated protein kinase (MAPK) pathway is a major pathway in the cellular signal transduction cascade from growth factors to the cell nucleus. The pathway involves kinases at two levels: MAP kinase kinases (MAPKK), and their substances MAP (mitogen activated protein) kinases (MAPK). There are different isoforms in the MAP kinase family. [For review, see Seger, R.; Krebs, E. G. *FASEB*, 9, 726, (1995)]. The compounds of this invention can inhibit the action of one or both of these kinases: MEK, a MAP kinase kinase, and its substrate ERK, a MAP kinase. ERK(extracellular regulated kinases), a p42 MAPK, is found to be essential for cell proliferation and differentiation. Over expression and/or over activation of MEK or ERK has been found to be associated with various human cancers [For example, Sivaraman, V. S. et al., *C.C.J. Clin. Invest.*, 99, 1478 (1997)]. It has been demonstrated that inhibition of MEK prevents activation of ERK and subsequent activation of ERK substrates in cells, resulting in inhibition of cell growth stimulation and reversal of the phenotype of ras-transformed cells [Dudley, D. T. et al., *Proc. Nat. Acad. Sci.*, 92, 7686 (1995)].

Members of the raf family of kinases phosphorylate serine residues on MEK. There are three serine/threonine kinase members of the raf family known as a-raf, b-raf, and c-raf. While mutations in the raf genes are rare in human cancers, c-raf is activated by the ras oncogene which is mutated in a wide number of human tumors. Therefore, inhibition of the kinase activity of c-raf may provide a way to prevent ras mediated tumor growth [Campbell, S. L., *Oncogene*, 17, 1395 (1998)].

The Src family of cytoplasmic protein tyrosine kinases consists of at least eight members (Src, Fyn, Lyn, Yes, Lck, Fgr, Hck and Blk) that participate in a variety of signaling pathways [Schwartzberg, P. L., *Oncogene*, 17, 1463 (1998)]. The prototypical member of this tyrosine kinase family is $p60^{Src}$ (Src). Src is involved in proliferation and migration responses in many cell types. In limited studies, Src activity has been shown to be elevated in breast, colon (~90%), pancreatic (>90%) and liver (>90%) tumors. Greatly increased Src activity is also associated with metastasis (>90%) and poor prognosis. Antisense Src message impedes growth of colon tumor cells in nude mice [Staley et al., *Cell Growth & Differentation*, 8, 269 (1997)], suggesting that Src inhibitors should slow tumor growth. In addition to its role in cell proliferation, Src also acts in stress response pathways, including the hypoxia response. Previous studies have shown that colonic tumor cells genetically engineered to express antisense Src message form tumors demonstrating reduced vascularization in nude mouse models [Ellis, et al., *J. Biol. Chem.*, 273, 1052 (1998)], suggesting that Src inhibitors would be anti-angiogenic as well as anti-proliferative.

Apart from its role in cancer, Src also appears to play a role in osteoporosis. Mice genetically engineered to be deficient in src production were found to exhibit osteopetrosis, the failure to resorb bone [Soriano, P., *Cell,* 64, 693 (1991); Boyce, B. F., *J. Clin. Invest.,* 90, 1622 (1992)]. This defect was characterized by a lack of osteoclast activity. Since osteoclasts normally express high levels of Src, inhibition of Src kinase activity may be useful in the treatment of osteoporosis [Missbach, M., *Bone,* 24, 437 (1999)].

In addition to EGFr, there are several other RTKs including FGFr, the receptor for fibroblast growth factor (FGF); flk-1, also known as KDR, and flt-1, the receptors for vascular endothelial growth factor (VEGF); and PDGFr, the receptor for platelet derived growth factor (PDGF). The formation of new blood vessels, a process known as angiogenesis, is essential for tumor growth. Two natural angiogenesis inhibitors, angiostatin and endostatin, dramatically inhibited the growth of a variety of solid tumors. [O'Reilly, M. S., *Cell,* 79, 315 (1994); O'Reilly, M. S., *Nature Medicine,* 2, 689 (1996); O'Reilly, M. S., *Cell,* 88, 277 (1997)]. Since FGF and VEGF are known to stimulate angiogenesis, inhibition of the kinase activity of their receptors should block the angiogenic effects of these growth factors. In addition, the receptor tyrosine kinases tie-1 and tie-2 also play a key role in angiogenesis [Sato, T. N., *Nature,* 376, 70 (1995)]. Compounds that inhibit the kinase activity of FGFr, flk-1, flt-1, tie-1 or tie-2 may inhibit tumor growth by their effect on angiogenesis.

PDGF is a potent growth factor and chemoattractant for smooth muscle cells (SMCs), and the renarrowing of coronary arteries following angioplasty is due in part to the enhanced proliferation of SMCs in response to increased levels of PDGF. Therefore, compounds that inhibit the kinase activity of PDGFr may be useful in the treatment of restenosis. In addition, since PDGF and PDGFr are overexpressed in several types of human gliomas, small molecules capable of suppressing PDGFr activity have potential utility as anticancer therapeutics [Nister, M., *J. Biol. Chem.,* 266, 16755 (1991); Strawn, L. M., *J. Biol. Chem.* 269, 21215 (1994)].

In addition, a large number of cytokines participate in the inflammatory response, including IL-1, IL-6, IL-8 and TNF-α. Overproduction of cytokines such as IL-1 and TNF-α are implicated in a wide variety of diseases, including inflammatory bowel disease, rheumatoid arthritis, psoriasis, multiple sclerosis, endotoxin shock, osteoporosis, Alzheimer's disease, and congestive heart failure, among others [Henry et al., *Drugs Fut.,* 24:1345–1354 (1999); Salituro et al., *Curr. Med. Chem.,* 6:807–823 (1999)]. Evidence in human patients indicates that protein antagonists of cytokines are effective in treating chronic inflammatory diseases, such as monoclonal antibody to TNF-α (Enbrel) [Rankin et al., *Br. J. Rheumatol.,* 34:334–342 (1995)], and soluble TNF-α receptor-Fc fusion protein (Etanercept) [Moreland et al., *Ann. Intern. Med.,* 130:478–486 (1999)].

The biosynthesis of TNF-α occurs in many cell types in response to an external stimulus, such as a mitogen, an infectious organism, or trauma. Important mediators of TNF-α production are the mitogen-activated protein (MAP) kinases, and in particular, p38 kinase. These kinases are activated in response to various stress stimuli, including but not limited to proinflammatory cytokines, endotoxin, ultraviolet light, and osmotic shock. Activation of p38 requires dual phosphorylation by upstream MAP kinase kinases (MKK3 and MKK6) on threonine and tyrosine within a Thr-Gly-Tyr motif characteristic of p38 isozymes.

There are four known isoforms of p38, i.e., p38-α, p38β, p38γ, and p38δ. The α and β isoforms are expressed in inflammatory cells and are key mediators of TNF-α production. Inhibiting the p38α and β enzymes in cells results in reduced levels of TNF-α expression. Also, administering p38α and β inhibitors in animal models of inflammatory disease has proven that such inhibitors are effective in treating those diseases. Accordingly, the p38 enzymes serve an important role in inflammatory processes mediated by IL-1 and TNF-α. Compounds that reportedly inhibit p38 kinase and cytokines such as IL-1 and TNF-α for use in treating inflammatory diseases are disclosed in the following published international patent applications: WO 00/12497 (quinazoline derivatives as p38 kinase inhibitors); WO 00/56738 (pyridine and pyrimidine derivatives for the same purpose); WO 00/12497 (discusses the relationship between p38 kinase inhibitors); and WO 00/12074 (piperazine and piperidine compounds useful as p38 inhibitors).

In summary, the tight regulation of signal transduction normally exerted by the array of kinase enzymes is often lost in malignant cells. Compounds which modulate these kinases are thus highly desirable for the treatment of disorders associated with aberrant cellular proliferation. Moreover, compounds which modulate the cytokines associated with the inflammatory response are highly desirable for the treatment of inflammatory disorders.

SUMMARY OF THE INVENTION

Advantageously, the present invention provides compositions and methods for the treatment of proliferative disorders, including cancer, and inflammatory diseases. The methods comprise administering a therapeutically effective amount of a kinase inhibitor of formula I, below, or a salt, solvate, prodrug or stereoisomer thereof, and, optionally, at least one additional therapeutic agent. The treatment is preferably administered to a mammalian species, more preferably to a human, in need thereof.

More specifically, the instant invention provides a compound of formula I:

(I)

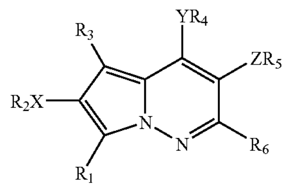

including enantiomers, diastereomers, pharmaceutically acceptable salts, prodrugs, and solvates thereof, wherein:

$R_1$ is selected from the group consisting of H, hydroxyl, alkyl, amino, aralkyl, halogen, —$R_1$', —C(O)$R_1$', —C(O)O$R_1$', —C(O)N$R_1$'$R_1$", —$S(O)_2R_1$'", —$S(O)_2$N$R_1$'$R_1$", O$R_1$', OC(O)$R_1$', OC(O)O$R_1$', OC(O)N$R_1$'$R_1$", $OS(O)_2R_1$'", and $OS(O)_2$N$R_1$'$R_1$";

$R_1$' and $R_1$" are each independently selected from the group consisting of H, hydroxy, alkoxy, alkyl, alkenyl, alkynyl, aryl, aralkyl, amino, heterocyclo, cycloalkyl and alkylamidinyl groups; $R_1$' and $R_1$" may also be taken together to form one of a cycloalkyl, an aryl, and a heterocyclic group;

$R_1$'" is selected from the group consisting of H, alkyl, aryl, aralkyl, heterocyclo, and cycloalkyl;

$R_2$ is selected from the group consisting of H, alkyl, cycloalkyl, aryl, heterocycle, aralkyl, $R_1$'OC(O)—, $R_1$'C(O)N$R_1$", $R_1$'C(O)—, $R_1$'C(S)—, $R_1$"$R_1$'NC(O)—, $R_1$'$R_1$'CN—, $R_1'N{=}C{-}R_1'''O(O)_2S$, $R_1'R_1''N(O)_2S$ and $R_1'''(O)_nS$; wherein n is the integer 1 or 2;

$R_1$ and $R_2$ may be taken together to form a cycloalkyl, aryl, or heterocyclic group;

X is selected from the group consisting of a valence bond, —$CH_2$—, O, —CO, —$C(O)_2$, S, $S(O)_m$ and $NR_2'$; wherein m is 0, 1 or 2; and $R_2'$ is selected from the group consisting of H, alkyl, aralkyl, $C(O)R_1$, $C(O)OR_1$, $SO_2NR_1'R_1''$, $C(O)NR_1'R_1''$ and $SO_2R_1'''$; with the proviso that when X is S, $R_2$ is selected from the group consisting of H, alkyl, cycloalkyl, aryl, heterocycle and aralkyl;

$R_3$ is selected from the group consisting of H, hydroxyl, alkyl, cycloalkyl, heterocycle, aryl, aralkyl, acyl, carbalkoxy, carboxamido, halogen, amine, substituted amine, $OR_3'$, $CH_2OR_3'$, $CH_2NR_3'R_3''$, $CH_2SR_3'$, $OC(O)R_3'$, $OC(O)R_3'$, $OC(O)OR_3''$, $OC(O)NR_3'R_3''$, $OS(O)_2R_3'$, and $OS(O)_2NR_3'R_3''$; wherein $R_3'$ and $R_3''$ are each independently selected from the group consisting of H, alkyl, aralkyl, heterocycle, cycloalkyl, and aryl; $R_3'$ and $R_3''$ may also be taken together to form a cycloalkyl, aryl, or heterocyclic group; when $R_3$ is a carbalkoxy, acyl, or carboxamido group, these groups are optionally substituted with one or two substituent groups, said substituent groups are independently selected from the group consisting of H, alkyl, aralkyl, heterocycle, cycloalkyl, and aryl; said substituent groups may also be taken together to form a cycloalkyl, aryl, or heterocyclic group;

$R_2$ and $R_3$ may also be taken together to form a cycloalkyl, aryl, or heterocyclic group;

$R_4$ is selected from the group consisting of H, alkyl, cycloalkyl, aryl, heterocycle, aralkyl, $R_1'OC(O)$, $R_1'C(O)$, $R_1''R_1'NC(O)$, $R_1'''O(O)_2S$, $R_1'R_1''N(O)_2S$ and $R_1'''(O)_nS$, wherein n is the integer 1 or 2;

Y is selected from the group consisting of a valence bond, O, S, $S(O)_m$ and $NR_4'$; wherein m is 0, 1 or 2; $R_4'$ is selected from the group consisting of H, alkyl, aralkyl, a heterocycle, $C(O)R_1$, $C(O)OR_1$, $S(O_2)NR_1'R_1''$, $C(O)NR_1'R_1''$, and $S(O_2)R_1$; with the proviso that when Y is S, $R_4$ is selected from the group consisting of alkyl, cycloalkyl, aryl, heterocycle and aralkyl; when Y is $NR_4'$, $R_4'$ can be taken together with $R_3$ to form a heterocyclic ring system;

$R_5$ is selected from the group consisting of H, halogen, cyano, alkyl, cycloalkyl, a heterocycle, aryl, aralkyl, acyl, substituted alkylene group, $R_1'OC(O)$, $R_1'C(O)$, $R_1''R_1'NC(O)$, $R_1'''O(O)_2S$, $R_1'R_1''N(O)_2S$ and $R_1'''(O)_nS$; wherein n the integer 1 or 2;

Z is selected from the group consisting of a valence bond, O, —$C(NR^8)$—$NR^9$—$NR^{10}R^{11}$, S, $S(O)_p$ and $NR_5'$; wherein p is 0, 1 or 2; $R_5'$ is selected from the group consisting of H, alkyl, aralkyl and a heterocycle; with the proviso that when Z is a valence bond, $R_5$ is selected from the group consisting of H, halogen, a substituted alkylene group and a cyano group; and, with the further proviso that when Z is S, $R_5$ is selected from the group consisting of H, alkyl, cycloalkyl, aryl, heterocycle and aralkyl;

$R_6$ is selected from the group consisting of H, alkyl, cycloalkyl, aryl, aralkyl, a heterocycle, acyl, carbalkoxy, and carboxamido; said carbalkoxy, acyl, and carboxamido groups are optionally substituted with one or two substituent groups, each of which is independently selected from the group consisting of H, alkyl, aralkyl, and a heterocycle; and $R^8$, $R^9$, $R^{10}$, and $R^{11}$ are independently H, alkyl, or cycloalkyl.

Further provided are pharmaceutical compositions comprising a compound of formula I, above, or a salt, solvate, or stereoisomer thereof, and at least one pharmaceutically acceptable carrier. Optionally, the pharmaceutical composition may also comprise at least one additional therapeutic agent.

Also provided are methods of treating proliferative or inflammatory diseases, in patients in need thereof, by administering a compound of formula I, above, or a salt, solvate, or stereoisomer thereof, and, optionally, at least one additional therapeutic agent.

DETAILED DESCRIPTION OF THE INVENTION

Definitions

The following definitions apply to the terms as used throughout this specification, unless otherwise limited in specific instance.

Unless otherwise indicated, the term "lower alkyl", "alkyl" or "alk" as employed herein alone or in combined form, e.g., aralkyl or haloalkyl, includes both straight and branched chain hydrocarbons, preferably containing 1 to 12 carbons in the case of alkyl or alk, in the normal chain, and preferably 1 to 4 carbons in the case of lower alkyl. Examples of alkyl groups include methyl, ethyl, propyl, isopropyl, butyl, t-butyl, or isobutyl, pentyl, hexyl, isohexyl, heptyl, 4,4-dimethylpentyl, octyl, 2,2,4-trimethylpentyl, nonyl, decyl, undecyl, dodecyl, and the like. Each alkyl group may be optionally substituted with 1 to 4 substituents which may include, but are not limited to, one or more of the following groups; alkyl, alkenyl, alkynyl, aryl, cycloalkyl, heterocyclo, hydroxyl, cyano, nitro, amino, monoalkylamino, dialkylamino, hydroxylamino, sulfonate, sulfamido, oxo, carboalkoxy, carboxamido, acyl, halo (e.g., a single halo substituent or multiple halo substitutents forming, in the latter case, groups such as a perfluoroalkyl group or an alkyl group bearing C13 or CF3), alkoxy, alkylthio, carboxy (i.e., —COOH), alkoxycarbonyl, alkylcarbonyloxy, carbamoyl or substituted carbomoyl, carbamate, urea, amidinyl, thiol (i.e., —SH), —S-aryl, —S-heterocycle, —S(═O)-aryl, —S(═O)-heterocycle, arylalkyl-O—, —S(O)2-aryl, —S(O)2-heterocycle, —NHS(O)2-aryl, —NHS(O)2-heterocycle, —NHS(O)2NH-aryl, —NHS(O)2NH-heterocycle, —P(O)2-aryl, —P(O)2-heterocycle, —NHP(O)2-aryl, —NHP(O)2-heterocycle, —NHP(O)2NH-aryl, —NHP(O)2NH-heterocycle, —O-aryl, —O-heterocycle, —NH-aryl, —NH-heterocycle, —NHC(═O)-aryl, —NHC(═O)-alkyl, —NHC(═O)-heterocycle, —OC(═O)-aryl, —OC(═O)-heterocycle, —NHC(═O)NH-aryl, —NHC(═O)NH-heterocycle, —OC(═O)O-aryl, —OC(═O)O-heterocycle, —OC(═O)NH-aryl, —OC(═O)NH-heterocycle, —NHC(═O)O-aryl, —NHC(═O)O-heterocycle, —NHC(═O)O-alkyl, —C(═O)NH-aryl, —C(═O)NH-heterocycle, —C(═O)O-aryl, —C(═O)O-heterocycle, —N(alkyl)S(O)2-aryl, —N(alkyl)S(O)2-heterocycle, —N(alkyl)S(O)2NH-aryl, —N(alkyl)S(O)2NH-heterocycle, —N(alkyl)P(O)2-aryl, —N(alkyl)P(O)2-heterocycle, —N(alkyl)P(O)2NH-aryl, —N(alkyl)P(O)2NH-heterocycle, —N(alkyl)-aryl, —N(alkyl)-heterocycle, —N(alkyl)C(═O)-aryl, —N(alkyl)C(═O)-heterocycle, —N(alkyl)C(═O)NH-aryl, —N(alkyl)C(═O)NH-heterocycle, —OC(═O)N(alkyl)-aryl, —OC(═O)N(alkyl)-heterocycle, —N(alkyl)C(═O)O-aryl, —N(alkyl)C(═O)O-heterocycle, —C(═O)N(alkyl)-aryl, —C(═O)N(alkyl)-heterocycle, —NHS(O)2N(alkyl)-aryl, —NHS(O)2N(alkyl)-heterocycle, —NHP(O)2N(alkyl)-aryl, NHP(O)2N(alkyl)-heterocycle, —NHC(═O)N(alkyl)-aryl, —NHC(═O)N(alkyl)-heterocycle, —N(alkyl)S(O)2N(alkyl)-aryl, —N(alkyl)S(O)2N(alkyl)-heterocycle, —N(alkyl)P(O)2N(alkyl)-aryl, —N(alkyl)P(O)2N(alkyl)-heterocycle, —N(alkyl)C(═O)N(alkyl)-aryl, and —N(alkyl)C(═O)N(alkyl-heterocycle. In the aforementioned exemplary substitutents, in each instance, groups such as "alkyl", "aryl" and "heterocycle" can themselves be optionally substituted; for example, "alkyl" in the group "NCH(═O)O-alkyl" recited above can be optionally substituted to that both "NHC(═O)O-alkyl" and "NHC(═O)O-substituted alkyl" are exemplary substitutents.

Unless otherwise indicated, the term "cycloalkyl" as employed herein alone or in combined form includes saturated cyclic hydrocarbon groups or partially unsaturated (containing 1 or 2 double bonds) cyclic hydrocarbon groups, containing at least one ring and a total of 3 to 7 carbons, preferably 3 to 6 carbons, forming the ring. Examples of cycloalkyl groups include cyclopropyl, cyclobutyl, cyclopentyl, cyclohexyl, cycloheptyl, cyclopentenyl, cyclohexenyl, and the like. Cycloalkyl groups may optionally be substituted in the same manner as described above for alkyl groups.

The term "aryl" as employed herein alone or in combined form, e.g., aryloxy, refers to monocyclic and bicyclic aromatic groups containing 6 to 10 carbons in the ring portion, such as phenyl, indenyl, indanyl, or naphthyl including 1-naphthyl and 2-naphthyl and the like. Aryl groups may be optionally substituted through available carbon atoms with 1,2, or 3 groups selected from hydrogen, halo, alkyl, cycloalkyl, aralkyl, heterocyclo, haloalkyl, alkoxy, aryloxy, haloalkoxy, alkenyl, trifluoromethyl, trifluoromethoxy, alkynyl, hydroxy, amino, nitro, cyano, carbalkoxy, alkoxycarbonyl, alkylcarbonyloxy, acyl, hydroxylamine, sulfonate, sulfamide, cyano-guanidine, $SO_n$ where n is 0, 1, or 2, carboxamido groups, or monosubstituted amino, or disubstituted amino, wherein the amino substituents are independently alkyl, aralkyl, aryl, acyl, or carbalkoxy groups.

The term "aralkyl" as used herein refers to an aryl group, as defined above, bonded directly through an alkyl moiety, such as benzyl group, for example. An aralkyl group may be optionally substituted with any group described herein as an aryl or alkyl substitutent.

Unless otherwise indicated, the term "lower alkenyl" or "alkenyl" as used herein by itself or in combined form refers to straight or branched chain radicals of 2 to 12 carbons, preferably 2 to 5 carbons, in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, and the like, which may be optionally substituted in the same manner as that described for alkyl groups.

Unless otherwise indicated, the term "lower alkynyl" or "alkynyl" as used herein by itself or in combined form refers to straight or branched chain radicals of 2 to 12 carbons, preferably 2 to 8 carbons, in the normal chain; which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, which may optionally be substituted in the same manner as that described for alkyl groups.

The normal carbon chain of any alkyl, alkenyl, alkynyl, or aralkyl group may optionally be interrupted by one or more heteroatoms.

As used herein, the term "acyl" refers to a group of the formula C(O)R, wherein R represents a hydrogen atom, an alkyl group, an aryl group, a heterocycle, or an aralkyl group.

As used herein, the term "carbalkoxy" refers to a group of the formula C(O)OR, wherein R represents a hydrogen atom, an alkyl group, an aryl group, a heterocycle, or an aralkyl group.

As used herein, the term "carboxamido" refers to a group of the formula $C(O)NR_2$, wherein the R groups, which may be the same or different, represent a hydrogen atom, an alkyl group, an aryl group, a heterocycle, or an aralkyl group. Alternatively, the two R groups, when taken together with the nitrogen atom, may form a heterocyclo group.

As used herein, "alkylamidinyl" refers to a nitrogen radical having the general formula $(NH_2)(alkyl)C{=}N-$. The alkyl portion of an alkylamidinyl group may optionally be substituted in the same manner as described above for alkyl groups.

The terms "heterocyclo", "heterocyclic" and "heterocycle" as used herein refer to an optionally substituted, aromatic or non-aromatic cyclic group, which, for example, is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2, 3, or 4 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Examples of suitable monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydrothiopyranyl, tetrahydropyranyl, morpholinyl, thiamorpholinyl, thiamorpholinyl sulfoxide, tetrahydrothiopyranylsulfone, thiamorpholinyl sulfone, 1,3-dioxolane and tetrahydro-1,1-dioxothienyl, dioxanyl, isothiazolidinyl, thietanyl, thiiranyl, triazinyl, triazolyl, and the like.

Examples of suitable bicyclic hetrocyclic groups include indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, benzoxodiazol, benzothiodiazol, and the like.

In preferred embodiments, at least one of the heteroatoms in the heterocycle is a nitrogen atom.

Examples of suitable substituents for heterocyclic groups include one or more alkyl groups as described above or one or more groups described above as alkyl or aryl substituents. Also suitable are aryl groups and smaller heterocycles, such as epoxides and aziridines.

The term "heteroatom" as used herein includes oxygen, sulfur and nitrogen, where the nitrogen and sulfur heteroatoms may also optionally be oxidized and the nitrogen heteroatoms may also optionally be quaternized.

The term "halogen" or "halo" as used herein alone or as part of another group refers to fluorine, chlorine, bromine, and iodine.

As used herein, the expression "optionally substituted," as in "optionally substituted lower alkyl", "optionally substituted aryl" or the like, refers to alkyl, aryl, and other groups which may be unsubstituted or substituted with the substituents mentioned above. Further, when a moiety is described herein as optionally substituted with more than one substituent, it is intended that each of the multiple substituents be chosen independently from among the substituents mentioned above.

As used herein, the term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such.

Compounds of the Invention

In accordance with the present invention, compounds having formula I, below, are provided.

(I)

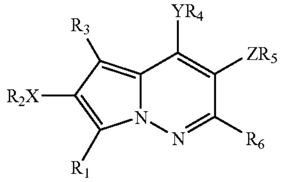

In compounds of formula I, $R_1$ is selected from the group consisting of H, hydroxyl, alkyl, amino, aralkyl, halogen, —$R_1$', —C(O)$R_1$', —C(O)O$R_1$', —C(O)N$R_1$'$R_1$", —S(O)$_2$ $R_1$'", —S(O)$_2$N$R_1$'$R_1$", O$R_1$', OC(O)$R_1$', OC(O)O$R_1$', OC(O)N$R_1$'$R_1$", OS(O)$_2R_1$'", and OS(O)$_2$N$R_1$'$R_1$";

$R_1$' and $R_1$" are each independently selected from the group consisting of H, hydroxy, alkoxy, alkyl, alkenyl, alkynyl, aryl, aralkyl, amino, heterocyclo, cycloalkyl and alkylamidinyl groups; $R_1$' and $R_1$" may also be taken together to form one of a cycloalkyl, an aryl, and a heterocyclic group;

$R_1$'" is selected from the group consisting of H, alkyl, aryl, aralkyl, heterocyclo, and cycloalkyl;

$R_2$ is selected from the group consisting of H, alkyl, cycloalkyl, aryl, heterocycle, aralkyl, $R_1$'OC(O)—, $R_1$'C(O)N$R_1$', $R_1$'C(O)—, $R_1$'C(S)—, $R_1$"$R_1$'NC(O)—, $R_1$'$R_1$"CN—, $R_1$'N=C—$R_1$'"O(O)$_2$S, $R_1$'$R_1$"N(O)$_2$S and $R_1$'"(O)$_n$S; wherein n is the integer 1 or 2;

$R_1$ and $R_2$ may be taken together to form a cycloalkyl, aryl, or heterocyclic group;

X is selected from the group consisting of a valence bond, —$CH_2$—, O, —CO, —C(O)$_2$, S, S(O)$_m$ and N$R_2$'; wherein m is 0, 1 or 2; and $R_2$' is selected from the group consisting of H, alkyl, aralkyl, C(O)$R_1$, C(O)O$R_1$, $SO_2$N$R_1$", C(O)N$R_1$'$R_1$" and $SO_2R_1$'"; with the proviso that when X is S, $R_2$ is selected from the group consisting of H, alkyl, cycloalkyl, aryl, heterocycle and aralkyl;

$R_3$ is selected from the group consisting of H, hydroxyl, alkyl, cycloalkyl, heterocycle, aryl, aralkyl, acyl, carbalkoxy, carboxamido, halogen, amine, substituted amine, O$R_3$', $CH_2$O$R_3$', $CH_2$N$R_3$'$R_3$", $CH_2$S$R_3$', OC(O)$R_3$', OC(O)O$R_3$", OC(O)N$R_3$'$R_3$", OS(O)$_2R_3$', and OS(O)$_2$ N$R_3$'$R_3$"; wherein $R_3$' and $R_3$" are each independently selected from the group consisting of H, alkyl, aralkyl, heterocycle, cycloalkyl, and aryl; $R_3$' and $R_3$" may also be taken together to form a cycloalkyl, aryl, or heterocyclic group; when $R_3$ is a carbalkoxy, acyl, or carboxamido group, these groups are optionally substituted with one or two substituent groups, said substituent groups are independently selected from the group consisting of H, alkyl, aralkyl, heterocycle, cycloalkyl, and aryl; said substituent groups may also be taken together to form a cycloalkyl, aryl, or heterocyclic group;

$R_2$ and $R_3$ may also be taken together to form a cycloalkyl, aryl, or heterocyclic group;

$R_4$ is selected from the group consisting of H, alkyl, cycloalkyl, aryl, heterocycle, aralkyl, $R_1$'OC(O), $R_1$'C(O), $R_1$"$R_1$'NC(O), $R_1$'"O(O)$_2$S, $R_1$'$R_1$"N(O)$_2$S and $R_1$'"(O)$_n$S, wherein n is the integer 1 or 2;

Y is selected from the group consisting of a valence bond, O, S, S(O)$_m$ and N$R_4$'; wherein m is 0, 1 or 2; $R_4$' is selected from the group consisting of H, alkyl, aralkyl, a heterocycle, C(O)$R_1$, C(O)O$R_1$, S($O_2$)N$R_1$'$R_1$", C(O)N$R_1$'$R_1$", and S($O_2$) $R_1$; with proviso that when Y is S, $R_4$ is selected from the group consisting of alkyl, cycloalkyl, aryl, heterocycle and aralkyl; when Y is N$R_4$', $R_4$' can be taken together with $R_3$ to form a heterocyclic ring system;

$R_5$ is selected from the group consisting of H, halogen, cyano, alkyl, cycloalkyl, a heterocycle, aryl, aralkyl, acyl, substituted alkylene group, $R_1$'OC(O), $R_1$'C(O), $R_1$"$R_1$'NC(O), $R_1$'"O(O)$_2$S, $R_1$'$R_1$"N(O)$_2$S and $R_1$'"(O)$_n$S; wherein n the integer 1 or 2;

Z is selected from the group consisting of a valence bond, O, —C(N$R^8$)—N$R^9$—N$R^{10}R^{11}$, S, S(O)$_p$ and N$R_5$'; wherein p is 0, 1 or 2; $R_5$' is selected from the group consisting of H, alkyl, aralkyl and a heterocycle; with the proviso that when Z is a valence bond, $R_5$ is selected from the group consisting of H, halogen, a substituted alkylene group and a cyano group; and, with the further proviso that when Z is S, $R_5$ is selected from the group consisting of H, alkyl, cycloalkyl, aryl, heterocycle and aralkyl;

$R_6$ is selected from the group consisting of H, alkyl, cycloalkyl, aryl, aralkyl, a heterocycle, acyl, carbalkoxy, and carboxamido; said carbalkoxy, acyl, and carboxamido groups are optionally substituted with one or two substituent groups, each of which is independently selected from the group consisting of H, alkyl, aralkyl, and a heterocycle; and $R^8$, $R^9$, $R^{10}$, and $R^{11}$ are independently H, alkyl, or cycloalkyl.

Also included in the invention are the salts, solvates, and stereoisomers enantiomers, and diastereomers of the compounds of formula I.

All stereoisomers of the compounds of formula I are contemplated, either in admixture or in pure or substantially pure form. A compound of formula I may have asymmetric centers at any of its non-aromatic carbon or nitrogen atoms, including those carbon atoms in any of its substituents. Consequently, compounds of formula I can exist in enaniomeric or diastereomeric forms or in mixtures thereof. The processes for preparation can utilize racemates, enantiomers or diastereomers as starting materials. When diastereomeric or enantiomeric products are prepared, they may be separated by conventional methods, for example, chromatographic or fractional crystallization.

Preferred compounds of the invention are compounds of formula I wherein Z is a valence bond and $R_5$ is cyano.

In some preferred embodiments, $R_3$ is an alkyl, aryl or heteroaryl, and is preferably methyl.

In some preferred embodiments, Y is $NR_4'$. In still further embodiments, X is a valence bond, $—CH_2—$, O, or $NR_2'$, $R_2'$ is preferably $R_1'C(O)$ or $—C(O)NR_1'R_2'$ or $—C(O)OR_1'$.

According to some embodiments of the present invention, $R_1'$ and $R_2''$ are independently H, alkyl, cycloalkyl, or heterocycloalkyl.

Other preferred compounds are compounds of formula I wherein $R_4$ is an optionally substituted phenoxyaniline. Also preferred are compounds of formula I wherein Y is $NR_4'$ wherein $R_4'$ is as defined above, or wherein Y is O, and $R_4$ is an aryl or heteroaryl group.

Other preferred compounds of the invention are compounds of formula I wherein Z is a valence bond, $R_5$ is cyano, and $R_3$ is methyl. Preferably, these compounds have one or more of the following substituents: Y is $NR_4'$; $R_1'$ and $R_1''$ are independently H, alkyl, cycloalkyl, or heterocycloalkyl; $R_4$ is alkyl, aryl or heteroaryl; X is a valence bond, O, $NR_2'$ or $S(O)_m$, wherein m is 0, 1 or 2; and $R_2$ is $R_1'C(O)$, $—(C(O)NR_1'R_2'$, or $—C(O)OR_1'$.

Additional preferred compounds of formula I include those in which Z is a valence bond, $R_5$ is cyano, Y is $NR_4'$ wherein $R_4'$ is as defined above, and $R_4$ is a phenyl group or heteroaryl group with one or more substitutions.

Further preferred compounds are illustrated in the examples below.

Methods of Making the Compounds

Generally, compounds of formula I may be made by reacting a pyrrole of formula II:

(II)

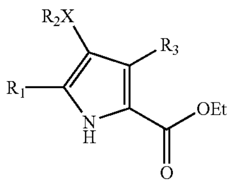

wherein X, $R_1$, $R_2$, and $R_3$ are as previously defined, with an aminating agent in the presence of a base to produce the aminated pyrrole of formula III:

(III)

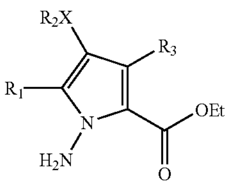

wherein X, $R_1$, $R_2$, and $R_3$ are as previously defined.

The compound of formula III is reacted with a carbonyl of formula $R_6C(O)CH_2ZR_5$ or an acetal of the formula $(RO)_2CR_6CH_2ZR_5$, wherein R is an alkyl group and Z, $R_5$, and $R_6$ are as previously defined, under ring-closure conditions to produce a compound of formula IV.

(IV)

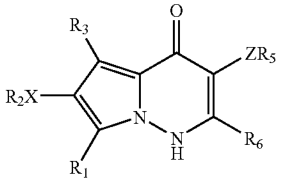

4-Oxo-pyrrolopyridazines of formula IV may be reacted with a reagent providing a leaving group, such as $POCl_3$ or $POCl_5$, to yield a compound of formula V (V)

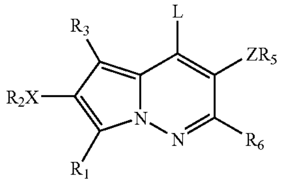

wherein L is a leaving group.

The compound of formula V may be reacted with a compound of the formula $HYR_4$, wherein Y and $R_4$ are as previously defined, to produce a compound of formula I, above.

The compounds of formula I may be prepared by the processes described in the following reaction schemes. Examples of suitable reagents and procedures for conducting these reactions appear hereinafter and in the working examples. Protection and deprotection in the schemes herein may be carried out by procedures generally known in the art. (See, for example, T. W. Greene & P. G. M. Wuts, *Protecting Groups in Organic Synthesis,* 3rd Edition, Wiley, (1999)). In schemes A though D, unless otherwise noted, X, Y, X, $R_1$, $R_2$, $R_3$, $R_4$, $R_5$, and $R_6$ are as defined above. The variables L and L' represent leaving groups. Variables designated with the subscript "a" or "b" have the same scope as, but are chosen independently of, their parent variable. For example, $R_{2a}$, $R_{2a}'$, and $R_{2a}''$ are coextensive with, but not necessarily identical to, $R_2$, $R_2'$, and $R_2''$, respectively.

SCHEME A

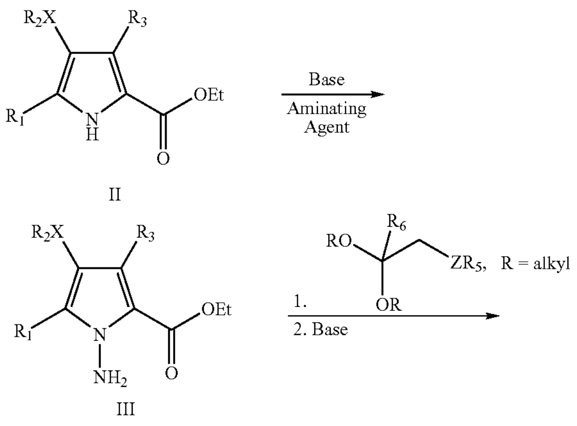

-continued

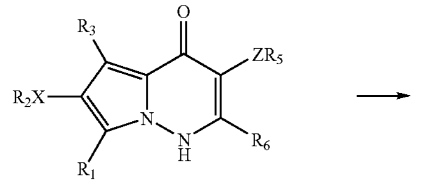

IV

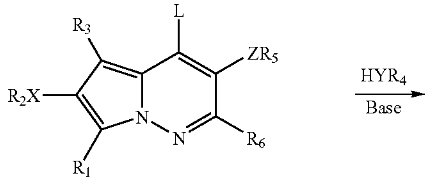

V

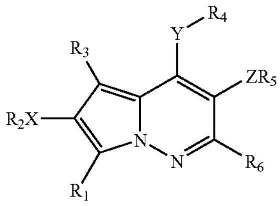

VI

Pyrroles of formula II may be obtained by the processes described in Patent Cooperation Treaty (PCT) publication No. WO 00/71129, pending U.S. patent application Ser. No. 09/573,829, pending PCT Application No. US01/49982 and pending U.S. patent application Ser. No. 10/036,293 (all of which are herein incorporated by reference in their entirety).

Treatment of a pyrrole of formula II with a base in a suitable reaction medium followed by the addition of an aminating reagent generates an aminopyrrole of formula III.

Suitable bases include sodium hydride (NaH), n-BuLi, t-BuLi, NaOH, lithium diisopropylamide (LDA), and lithium hexamethyldisilazide (LiHMDS). Suitable reaction media include tetrahydrofuran (THF), $CH_2Cl_2$, dimethylformamide (DMF), $CH_3CN$ and toluene. Suitable aminating reagents include 2,4-dinitroaminophenol, $NH_2OSO_3H$ and $ClNH_2$. Preferably the aminating reagent is $ClNH_2$ or 2,4-dinitroaminophenol. Preferably, the base is NaH or LDA, the reaction medium is DMF or THF. More preferably, the base is NaH, the reaction medium is DMF, and the aminating reagent is 2,4-dinitroaminophenol.

Condensation of the compound of formula III with an acetal followed by base induced cyclization in a suitable reaction medium provides a pyrrolopyridazine of formula IV. Suitable bases include NaOH, LDA, diisopropylethylamine (DIPEA), 1,8-diazoicyclo[5,4,0]undec-7-ene (DBU), and $K_2CO_3$. Suitable reaction media include THF, $CH_2Cl_2$, DMF and toluene. Preferably, the base is DBU, DIPEA or LDA and the reaction medium is toluene or DMF. More preferably, the base is DBU or DIPEA, and the reaction medium is toluene. Alternatively, compounds of formula IV may be obtained by the reactions of Schemes H, J and K, below.

Conversion of the oxo group at position 4 of the compound of formula IV to a leaving group L, as in compounds of formula V, can then be accomplished using a suitable halogenating reagent, such as $SOCl_2$, $POCl_3$ and $POCl_5$. More preferably, the reagent is $POCl_3$.

Treatment of a compound of formula V with a reagent of formula $HY\text{-}R_4$ in the presence of a base in a reaction medium then provides compounds of formula VI, which are compounds of formula I wherein $R_6$ is H. Suitable bases include NaH, $Et_3N$, DIPEA, $K_2CO_3$ or $Na_2CO_3$ and suitable reaction media include THF, DMF, $CH_2Cl_2$ or $CH_3CN$. Preferably, the base is NaH, $Et_3N$ or $K_2CO_3$ and the solvent is $CH_3CN$ or DMF. More preferably, the base is triethylamine and the reaction medium is acetonitrile.

SCHEME B

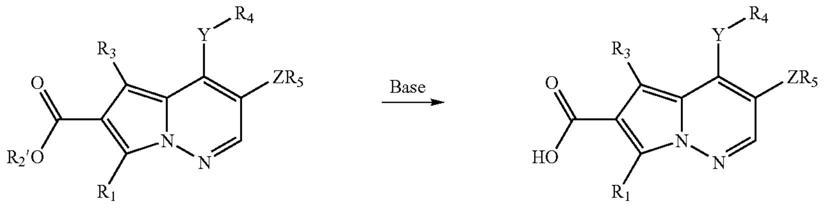

VIa

VII

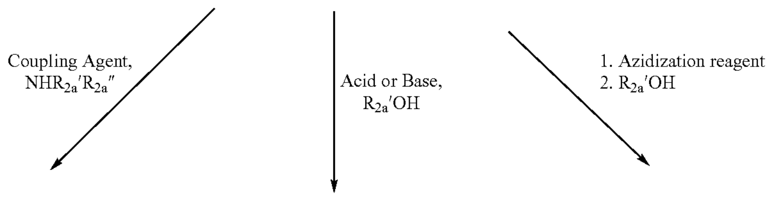

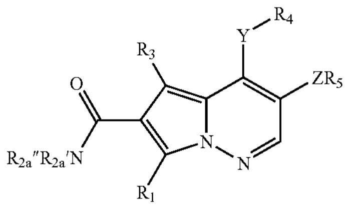

VIII

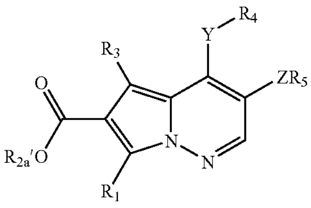

IX

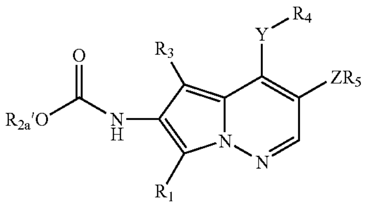

X

Compounds of formula VIa, which are compounds of formula VI wherein X is a valence bond, $R_2$ represents $CO_2R_2'$, $ZR_5$ represents CN, and $R_6$ represents hydrogen, may be saponified with a base to prepare carboxylic acids of formula VII as shown above in Scheme B. Suitable bases NaOH, KOH, LiOH, and $Ba(OH)_2$. Preferably, the base is an alkali metal hydroxide. More preferably, the base is NaOH.

Compounds of formula VIII, which are compounds of formula VI in which $R_2X$ is $R_{2a}'R_{2a}''NC(O)$, $ZR_5$ represents CN, and $R_6$ represents hydrogen, may be prepared via treatment of compounds of formula VII with a coupling reagent and an amine of formula $NH_2R_{2a}'R_{2a}''$ in a reaction medium. Suitable coupling agents include PyBOP [benzotriazol-1-yloxytripyrrolidino-phosphonium hexafluorophosphate], BOP [benzotriazol-1-yloxytris (dimethylamino) phosphonium hexafluorophosphate], CDI (N,N'-carbonyldiimidazole), DCC (N,N'-dicyclohexylcarbodiimide), HBTU [O-benzotriazol-1-yl-N, N,N',N'-tetranethyluronium hexafluorophosphate], HOAt (1-hydroxy-7-azabenzotriazole) and HOBt (1-hydroxybenzotriazole) and EDC [1-ethyl-3-(3-dimethylaminopropyl) carbodimide]. Preferably, the coupling reagent is HOBt, PyBOP or EDC. More preferably, the coupling reagent is HOBt or PyBOP.

Compounds of formula IX, which are compounds of formula VI wherein $XR_2$ is $R_{2a}'OC(O)$, $ZR_5$ represents CN, and $R_6$ represents hydrogen, may be prepared via treatment of a compound of formula VII with an acid or a base and an alcohol of the formula $R_{2a}'OH$. Suitable acids include HCl, $H_2SO_4$, TsOH, 10-camphorsulfonic acid (CSA) and pyridinium p-toluenesulfonates (PPTs). More preferably, the acid is hydrochloric acid.

Compounds of formula X, which are compounds of formula VI where $XR_2$ is $R_{2a}'OC(O)NR_{2a}''$, $ZR_5$ represents CN, and $R_6$ represents hydrogen, may be prepared via treatment of compounds of formula VII with an azidization reagent, that is, a source of $N_3$, followed by the addition of an alcohol of formula $R_{2a}'OH$. Suitable azidization reagents include diphenylphosphorylazide (DPPA) and $NaN_3$. Preferably, the reagent is DPPA.

-continued

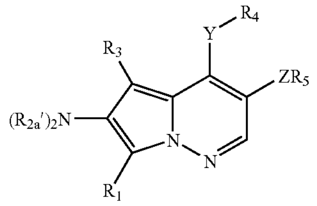

XII

As shown in Scheme C, compounds of formula XII, which are compounds of formula I wherein $XR_2$ is $NH(R_{2a}')_2$, may be prepared via compounds of formula X where the carbalkoxy moiety of the compound of formula X functions as a removable protecting group. The intermediate compound of formula XI may be prepared by removal of the carbalkoxy moiety of the compound of formula X. Preferably, the carbalkoxy group will be a t-butoxycarbonyl (BOC) or benzyloxycarbonyl (Cbz or Z). Suitable conditions for removing these and other suitable protecting groups are disclosed in Green and Wuts, supra. Preferably, the deprotection reaction is an acid cleavage or a hydrogenation reaction.

Compounds of formula XII result from the reductive amination of compounds of formula XI using an aldehyde of formula $R_{2a}'CHO$ and a reducing agent in a suitable reaction medium. Suitable reducing agents include $NaBH_4$, $LiBH_4$, diisobutylaluminum hydride (DIBAL-H), lithium aluminum hydride (LAH) and $NaBH(OAc)_3$. Preferably, the reducing agent is $NaBH(OAc)_3$ or $NaBH_4$. More preferably, the reducing agent is $NaBH(OAc)_3$. Suitable reaction media include 1,2-dichloroethane, $CH_2Cl_2$, THF and $CH_3CN$. Preferred reaction media include 1,2-dichloroethane and $CH_2Cl_2$ and more preferably, the reduction is carried out in 1,2-dichloroethane.

Alternatively, preparation of compounds of formula XII may be accomplished via treatment of compounds of formula XI with a base and a request of formula $R_{2a}'L$. Suitable bases include $K_2CO_3$, $NaHCO_3$, $Et_3N$, DIPEA, $Cs_2CO_3$, DBU and pyridine. Preferably, the base is selected from the group consisting of $K_2CO_3$, $NaHCO_3$ and $Et_3N$. More preferably, the base is sodium bicarbonate.

SCHEME C

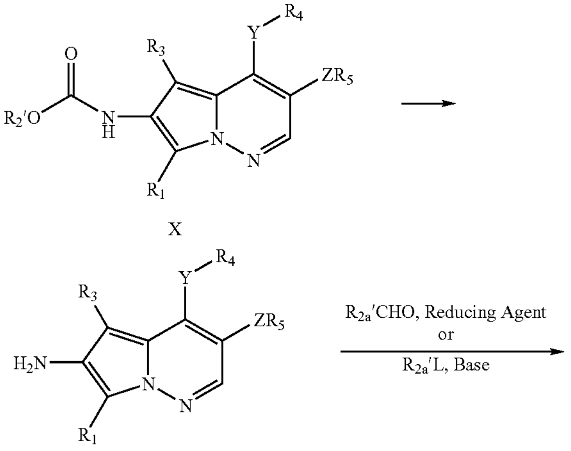

X

XI

SCHEME D

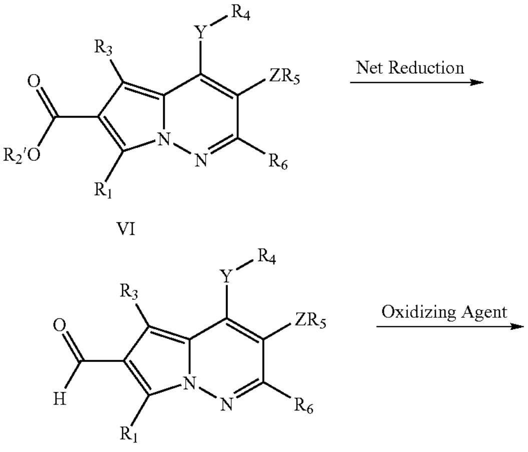

VI

XIII

-continued

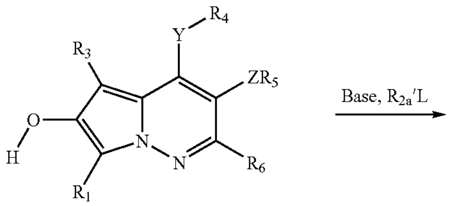

XIV

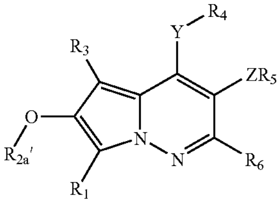

XV

Compounds of formula XV may be prepared via the method shown in Scheme D. Net reduction of compounds of formula VI wherein $XR_2$ is $R_2$'OC(O) provides aldehydes of formula XIII. Suitable means of carrying out a net reduction include reaction with a reducing agent or sequential reaction with a stronger reducing agent and a weaker oxidizing agent. Suitable reducing agents are generally known to those skilled in the art and can be fuond in references such as *Advanced Organic Chemistry III ed., Part B: Reactions and Synthesis,* Francis A. Carey, Richard J. Sundberg, Plenum Publishing Corp., NY (1993) and *March's Advanced Organic Chemistry: Reactions, Mechanisms and Structure,* $5^{th}$ ed., Wiley-InterScience, John Wiley & Sons, Inc., NY (2001) (both herein incorporated by reference).

Suitable combinations of oxidizing agents and reducing agents include diisobutylaluminum hydride (DIBAL-H) with $MnO_2$. Preferably, net reduction is accomplished by sequential reduction and oxidation with a reducing agent such as DIBAL-H, LAH, $NaBH_4$ or $LiBH_4$, and an oxidizing agent such as $MnO_2$, $SO_3$-pyridine, TEMPO (2,2,6,6-tetramethyl-1-piperidinyloxy, free radical), Dess-Martin periodinane, or TPAP (tetrapropylammonium perruthenate) and NMO (N-methylmorpholine-N-oxide) in combination. More preferably, the reduction is carried out first with DIBAL-H to produce an intermediate compound, which is then oxidized with $MnO_2$ to yield the compound of formula XIII.

Subsequent treatment with an oxidizing agent in a suitable reaction medium followed by etherification using a base in a suitable reaction medium and a reagent of formula $R_{2a}$'L yields compounds of formula XV, which are compounds of formula VI wherein $XR_2$ is $OR_{2a}$'. Suitable oxidizing agents include m-chloroperbenzoic acid (m-CPBA) and $H_2O_2$. Suitable bases include NaH, $Et_3N$, DIPEA and $K_2CO_3$. Suitable reaction media include THF, DMF, $CH_2Cl_2$ and $CH_3CN$. More preferably, the oxidizing agent is m-chloro perbenzoic acid (m-CPBA), the base is NaH, and the reaction medium is tetrahydrofuran (THF) or DMF.

SCHEME E

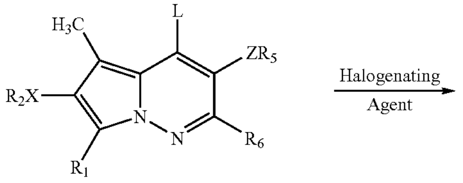

V

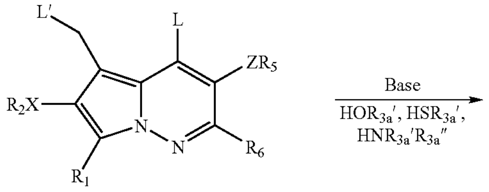

XVI

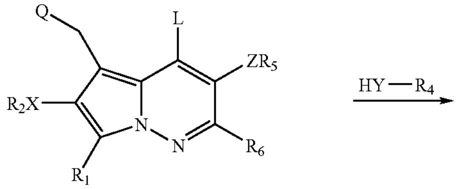

XVII

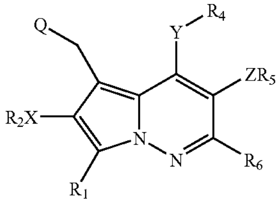

XVIII

L' = Cl, Br, I
Q = $SR_{3a}$', $OR_{3a}$', $NR_{3a}$'$R_{3a}$''

Halogenation of the 5-methyl group of a compound of formula V may be effected by treatment with a halogenating agent. Suitable halogenating agents include, but are not limited to sulfuryl choride, N-Iodosuccinimide, N-Bromosuccinimide, N-chlorosuccinimide, oxalyl choride. Preferably the halogenating agent is N-bromosuccinimide or sulfuryl chloride. The halogenation can be performed under an inert atmosphere, such as $N_2$, in the presence of a catalyst, to produce a halogenated pyrrole intermediate of formula XVI. Preferably, the catalyst is dibenzoyl peroxide or 2,2'-azobisisobutyronitrile, or irradiation.

Treatment of pyrrole of formula XVI with a thiol of formula $HSR_{3a}$', an alcohol intermediate of formula $HOR_{3a}$', or a primary or a secondary amine of formula $HNR_{3a}$'$R_{3a}$'' in the presence of a base affords a pyrrole of formula XVII. Suitable bases include $NaHCO_3$, diisopropyle ethylamine DBU, $KHCO_2$, and trimethylamine. Preferably, the base is $NaHCO_3$ or triethylamine. Acetonitrile is one suitable reaction medium for this reaction.

Treatment of a pyrrole of formula XVII with a reagent of formula $HYR_4$, at room temperature in the presence of a base yields the compound of formula XVIII. Preferably, the base is $NaHCO_3$ or triethylamine. Acetonitrile is one suitable reaction medium for this reaction. Heating the pyrrole of formula XVII with a reagent of formula $HYR_4$ in the absence of base also affords the compound of formula XVIII.

SCHEME F

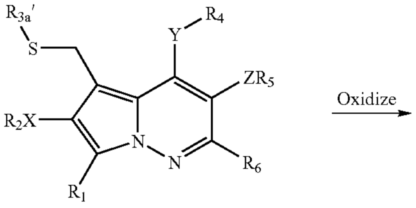

XIX

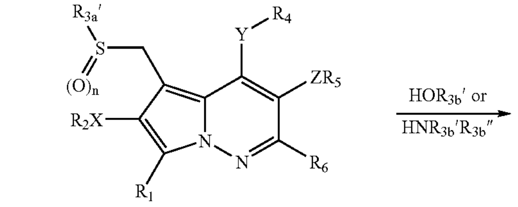

XX

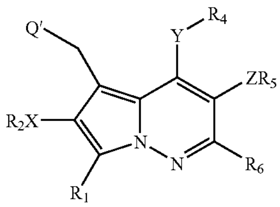

XXI n = 1 or 2
Q' is $OR_{3b}'$ or $NR_{3b}'R_{3b}''$

Compound XIX, which is a compound of formula VI wherein $R_3$ is —$CH_2SR_{3a}'$ (see Scheme A, above), can be oxidized to the sulfoxide of compound XX, wherein n=1, or the sulfone of compound XX, wherein n=2. Suitable oxidizing agents include m-chloroperbenzoic acid (MCPDA), tBu-OOH, $H_2O_2$ $NaIO_4$, and dimethyldioxirane. Preferably, the oxidizing agent is MCPDA. The number of equivalents of oxidizing agent added to the reaction mixture will determine the final oxidation state of the sulfur atom. A compound of formula XX wherein n=1 or 2 can be heated with an excess of an alcohol of formula $HOR_{3b}'$ or a primary or secondary amine of formula $HNR_{3b}'R_{3b}''$ to yield a compound of formula XXI.

SCHEME G

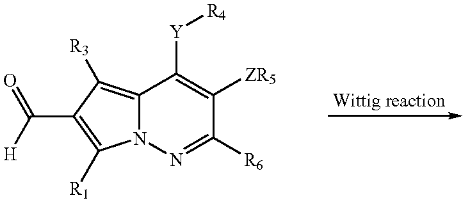

VII

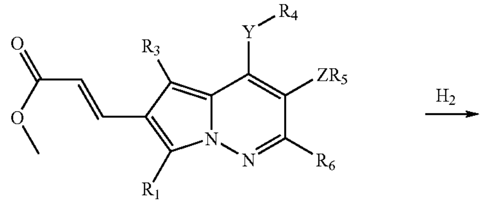

XXII

-continued

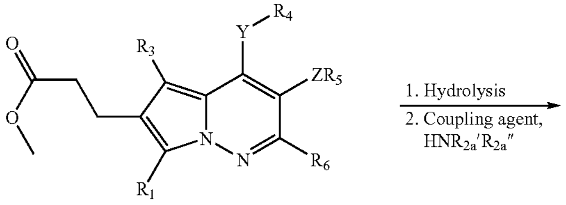

XXIII

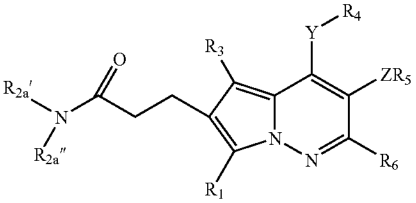

XXIV

Compounds of formula VII, from Scheme B, undergo a Wittig reaction with a phosphonate in the presence of a base to afford a compound of formula XXII. Suitable phosphonates known to those skilled in the art may be used. Preferably, the phosphonate is methyl diethylphosphonoacetate. Dichloroethane and the like are suitable organic reaction media for Wittig reactions. Suitable bases include KH, $K_2CO_3$, N-Butyllithium, sec-Butyllithium, tert-Butyllithium, NaH, preferably NaH.

The double bond in the $R_2$ group of the compound of formula XXII may be hydrogenated in the presence of a catalyst to yield a compound of formula XXIII. Suitable catalysts include $PtO_2$, palladium on carbon (Pd/C), $Pd(OH)_2$, and Raney Ni. Preferably, the catalyst is Pd/C.

Esters of formula XXIII may be hydrolyzed by techniques well known in the art, for example those taught in Green and Wuts, supra, preferably base hydrolysis with NaOH. Subsequent coupling of the resulting acid with an amine in the presence of a coupling agent affords the amide of formula XXIV. Suitable coupling agents are known to those skilled in the art and include those described in *The Practice of Peptide Synthesis, 2nd Ed.*, by Bodanszy, Miklos, Springer-Velag (1993) (herein incorporated by reference). Preferably the coupling agent is N,N'-dicyclohexylcarbodiimide (DCC).

SCHEME H

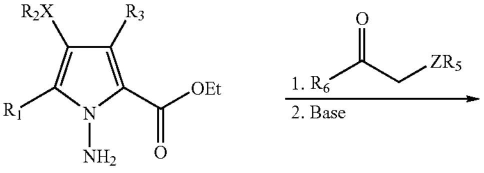

III

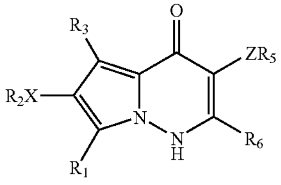

IV

Scheme H depicts an alternative route to the synthesis of compounds of formula IV (see Scheme A, above). Condensation of a pyrrole of formula III with a reagent of formula $R_6C(O)CH_2ZR_5$, followed by base induced cyclization in a suitable reaction medium, yields the intermediate of formula IV. Suitable bases include DBU, NaH, BuLi, $Et_3N$ and DIPEA. Suitable reaction media include toluene, THF, $CH_2Cl_2$, DMF, toulene and $CH_3CN$. Preferably the base is NaH, DBU, or DIPEA and the reaction medium is DMF, toluene or THF. Reagents of formula $R_6C(O)CH_2ZR_5$, particularly those wherein $R_6$ is a substituted oxygen, nitrogen or an alkyl group and $ZR_5$ is a nitrile group, can be purchased from commercial sources or else readily synthesized by those of skill in the art.

SCHEME J

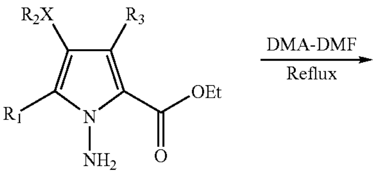

III

SCHEME I

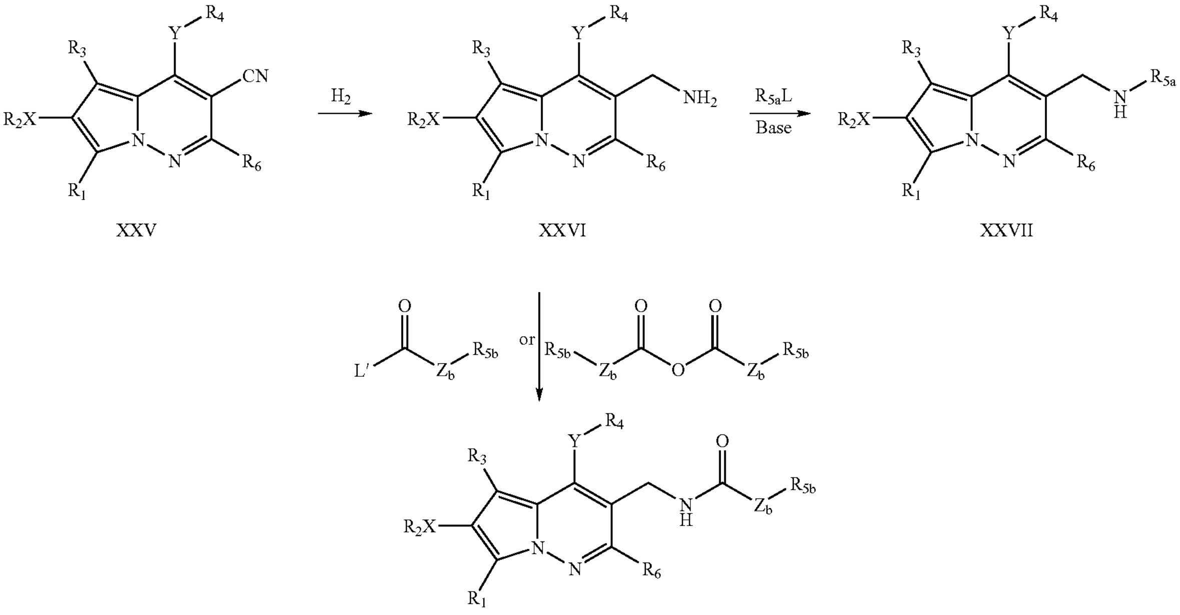

XXV XXVI XXVII

XXVIII

As shown in scheme I, a compound of formula XXV, which is a compound of formula VI wherein $ZR_5$ is a nitrile group (see Scheme A, above), can be reduced in the presence of hydrogen and a catalyst to yield a compound of formula XXVI. Suitable catalysts include $PtO_2$, Pd/C, $Pd(OH)_2$, and Raney Ni. Preferably, the catalyst is palladium on carbon (Pd/C).

Compounds of formula XXVI, when combined with a reagent of formula $R_{5a}L$, wherein L is a leaving group, e.g., a halogen, in the presence of a base, yield compounds of formula XXVII. Suitable bases KH, $K_2CO_3$, N-Butyllithium, sec-Butyllithium, tert-Butyllithium, and NaH. Preferably, the base is NaH. Reagents of formula $R_{5a}L$ are readily available from commercial sources.

Additionally, a compound of formula XXVI can be treated with a reagent of formula $(R_{5b}—Z_b—C(O))_2O$ or $R_{5b}—Z_b—C(O)\text{-}L'$, wherein L' is a leaving group, e.g., a halogen, in the presence of a base to yield a compound of formula XXVII. Suitable bases include $NaHCO_3$, diisopropylethylamine, DBU, $KHCO_3$, trimethylamine. Preferably, the base is triethylamine. Reagents of formula $R_{5b}—Z_b—C(O)—L'$ or $(R_{5b}—Z_b—C(O))_2O$ are readily available from commercial sources, or may be synthesized by those of skill in the art.

-continued

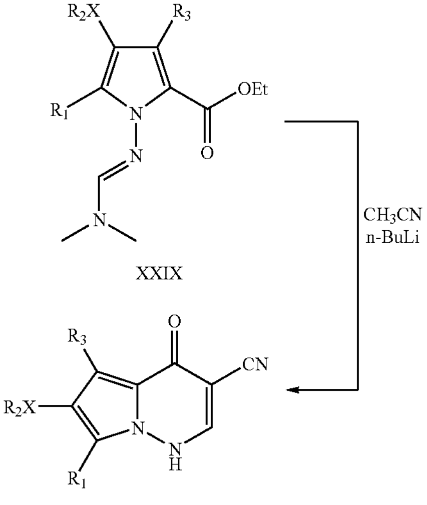

XXIX

XXX

Scheme J depicts the synthesis of a compound of formula XXX, which is a compound of formula IV (see scheme A, above) wherein $R_6$ is hydrogen and $ZR_5$ is a nitrile group. Treatment of a pyrrole of formula III with a reactive intermediate in a high boiling protic solvent yields an intermediate of formula XXIX. Preferably, dimethylformamide (DMF) and dimethylacetamide are used.

Treatment of the intermediate of formula XXIX with acetonitrile in the presence of a base results in cyclization to produce the compound of formula XXX. Suitable bases include, but are not limited to KH, NaH, sec-butyllithium, and preferably N-Butyllithium. As shown in scheme A, above, compounds of formula XXX are intermediates in the synthesis of compounds of formula I wherein $R_6$ is hydrogen and $ZR_5$ is a nitrile group.

SCHEME K

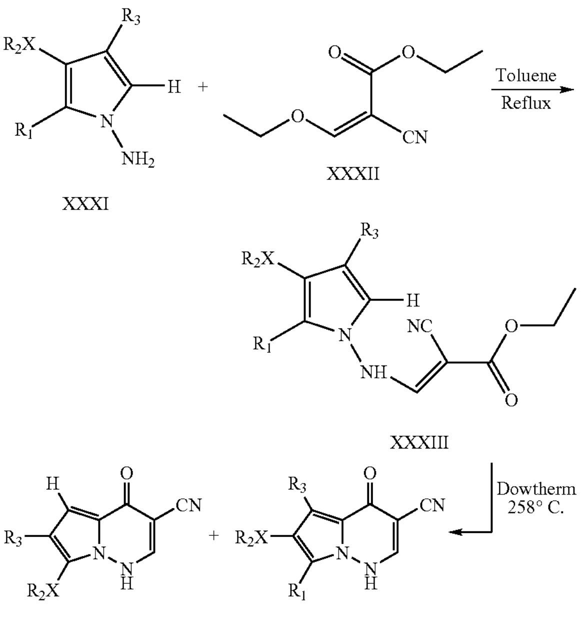

XXXI XXXII XXXIII

XXXV XXXIV

The synthesis of compounds of formula XXXIV and XXXV is shown in Scheme K. Compounds of formula XXXIV and XXXV are intermediates of formula IV (see scheme A, above) wherein $R_6$ is hydrogen and $ZR_5$ is a nitrile group. Treatment of a pyrrole of formula XXXI with a reactive intermediate of formula XXXII in a high boiling solvent yields an intermediate of formula XXXIII. Suitable solvents include but are not limited to xylene, nitrobenzene and toluene, preferably toluene.

Further heating of an intermediate of formula XXXIII in a high boiling solvent results in cyclization to yield intermediates of formula XXXIV and XXXV. Suitable solvents include but are not limited to DMF, DMA, N-methylpyrolidinone, preferably Dowtherm™, or toluene in a high pressure apparatus.

SCHEME L

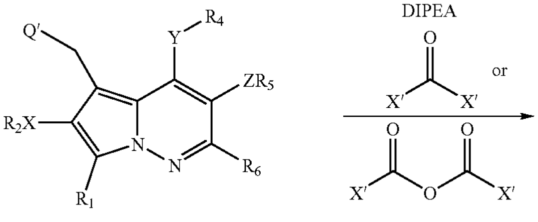

XXI

-continued

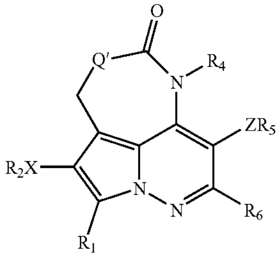

XXXVI

Y = NH
X' = Cl, O-alkyl or O-aryl
Q' is OH or $NHR_{3b}'$

The synthesis of compounds of formula XXXVI is shown in Scheme L. Treatment a compound of formula XXI, from Scheme F, with a reactive intermediate of formula X'C(O)X' or X'C(O)OC(O)X', as decribed in Scheme L, in presence of a base such as diisopropylethyl amine or triethyl amine, with or without heating, yields a compound of formula XXXVI. Suitable solvents include, but are not limited to, methylene chloride, chloroform, tetrahydrofurane or ethyl acetate.

As shown in scheme K, above, compounds of formula XXXIV and XXXV are intermediates in the synthesis of compounds of formula I wherein $R_6$ is hydrogen and $ZR_5$ is a nitrile group. The reactive intermediate of formula XXXII and related reagents of this structure are readily available from commercial sources, or may be synthesized by those of skill in the art.

Schemes 1 through 5, below, summarize several preferred methods of making some of the compounds of the invention. In schemes 1 through 5, unless otherwise noted, X, Y, Z, $R_1$, $R_2$, $R_2'$, $R_3$, $R_4$, $R_5$ and $R_6$ are as defined above, and L represents a leaving group. Variables designated with the subscript "a" or "b" have the same scope as, but are chosen independently of, their parent variable.

SCHEME 1

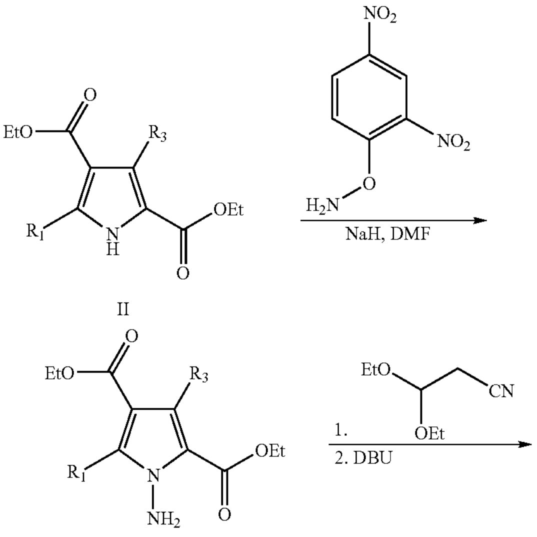

II

III

-continued

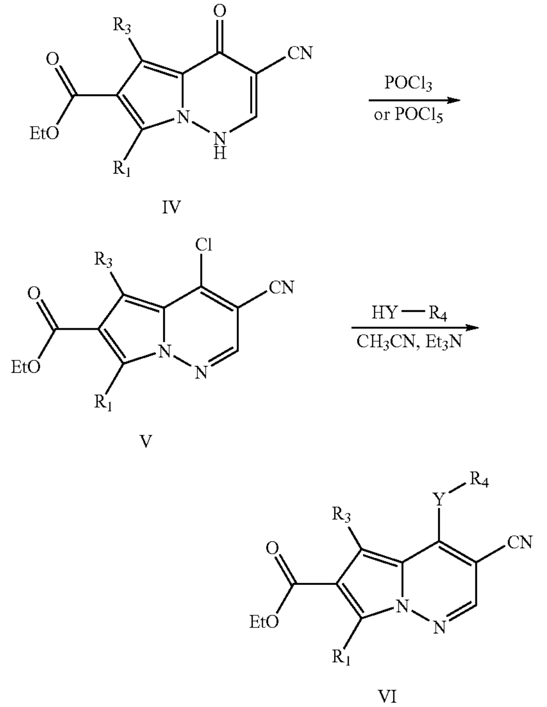

IV

V

VI

3-Cyanopyrrolopyridazines of formula VI may be prepared in accordance with Scheme 1. Pyrroles of formula II may be obtained by the processes described in Patent Cooperation Treaty (PCT) publication No. WO 00/71129, pending U.S. patent application Ser. No. 09/573,829, pending PCT Application No. US01/49982 and pending U.S. patent application Ser. No. 10/036,293 (all of which are herein incorporated by reference in their entirety).

Treatment of a pyrrole of formula II with a base such as sodium hydride in a reaction medium such as DMF followed by the addition of an aminating reagent such as 2,4-dinitroaminophenol generates an aminopyrrole of formula III. Condensation with an acetal such as 1,1-diethoxypropionitrile followed by base induced cyclization employing a base such as DBU or diisopropylethylamine, in a reaction medium such as toluene, provides the 3-cyanopyrrolopyridazine of formula IV. Conversion to the 4-chloro compounds of formula V can then be accomplished using a chlorinating reagent such as $POCl_3$ or $POCl_5$. Treatment of a compound of formula V with a reagent of formula $HY-R_4$ in the presence of a base such as triethylamine in a reaction medium such as acetonitrile provides compounds of formula VI, which are compounds of formula I wherein $XR_2$ is C(O)OEt, Z is a valence bond, $R_5$ is CN, and $R_6$ is H.

SCHEME 2

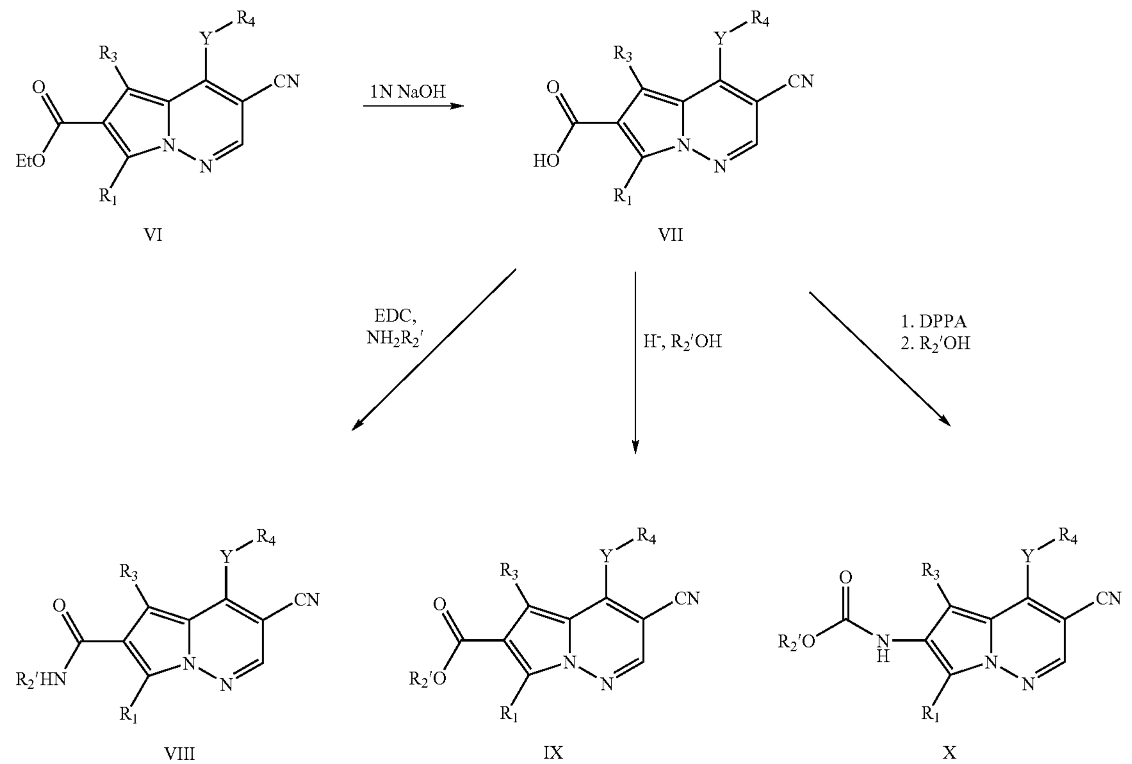

VI

VII

VIII

IX

X

Compounds of formula VI may be saponified with a base such as NaOH to prepare carboxylic acids of formula VII as shown above in Scheme 2. Compounds of formula VIII, which are compounds of formula I wherein $XR_2$ is C(O)$NHR_2'$, Z is a valence bond, $R_5$ is CN, and $R_6$ is H, may be prepared via treatment of compounds of formula VII with a coupling reagent such as EDC and an amine such as $NHR_{2a}'R_{2}a''$, in a reaction medium such as dichloromethane. Compounds of formula IX, which are compounds of formula I wherein $XR_2$ is C(O)$OR_2'$, Z is a valence bond, $R_5$ is CN, and $R_6$ is H, may be prepared via treatment of compound VII with an acid such as hydrochloric acid and an alcohol of formula $R_2'$OH. Compounds of formula X, which are compounds of formula I where $XR_2$ is NHC(O)$OR_2'$, Z is a valence bond, $R_5$ is CN, and $R_6$ is H, may be prepared via treatment of compounds of formula VII with a reagent such as DPPA followed by the addition of an alcohol of the formula $R_2'$OH.

SCHEME 3

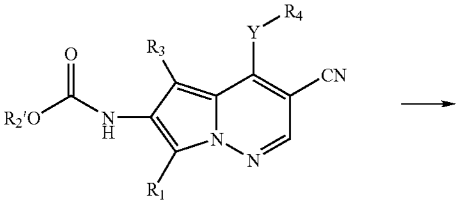

X

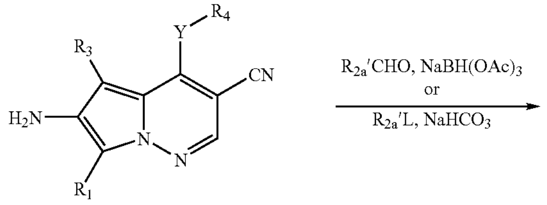

XI

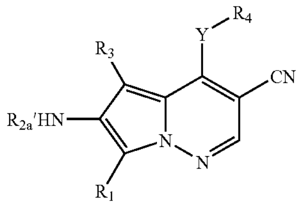

XII

As shown in Scheme 3, compounds of formula XII, which are compounds of formula I wherein $XR_2$ is $NHR_{2a}'$, Z is a valence bond, $R_5$ is CN, and $R_6$ is H, may be prepared from compounds of formula X where the carbalkoxy of the compound of formula X is a removable protecting group (e.g., $R_2'$ is t-butyl or benzyl). The compound of formula XI may be prepared by deprotection, i.e., acid cleavage or hydrogenation, respectively. Compounds of formula XII may then be prepared via reductive amination of compounds of formula XI using an aldehyde of formula $R_{2a}'$CHO and a reducing agent such as $NaBH(OAc)_3$ in a reaction medium such as 1,2-dichloroethane. Alternatively, preparation of compounds of formula XII may be accomplished via treatment of compounds of formula XI with a base such as $NaHCO_3$ and a reagent of formula $R_{2a}'$L.

SCHEME 4

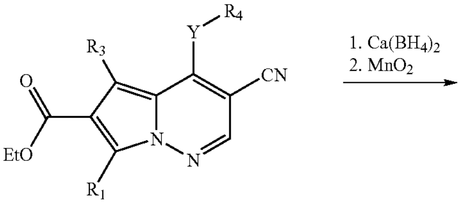

VI

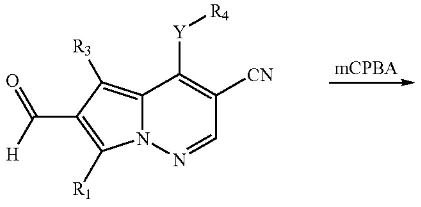

XIII

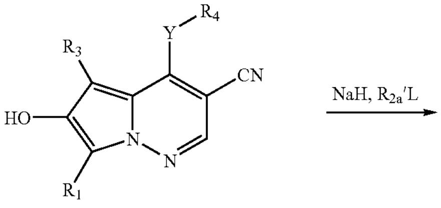

XIV

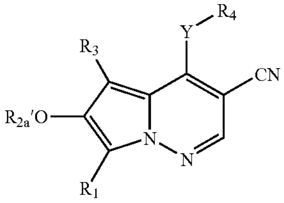

XV

Compounds of formula XV may be prepared via the method shown in Scheme 4. Reduction of compounds of formula VI with a reducing agent such as DIBAL-H in reaction media such as dichloromethane or toluene, followed by oxidation with an oxidizing agent such as $MnO_2$, provides aldehydes of formula XIII. Treatment of compounds of formula XIII with a peracid such as m-CPBA in a reaction medium such as dichloromethane followed by etherification using a base such as sodium hydride in reaction mediums such as tetrahydrofuran or DMF and a reagent of formula $R_{2a}'$L yields compounds of formula XV, which are compounds of formula I where $XR_2$ is $OR_{2a}'$, Z is a valence bond, $R_5$ is CN, and $R_6$ is H.

SCHEME 5

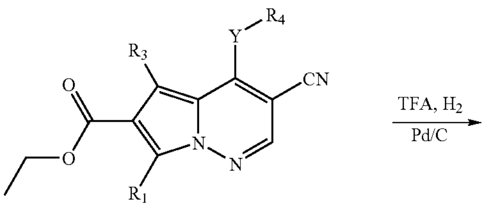

XXV

-continued

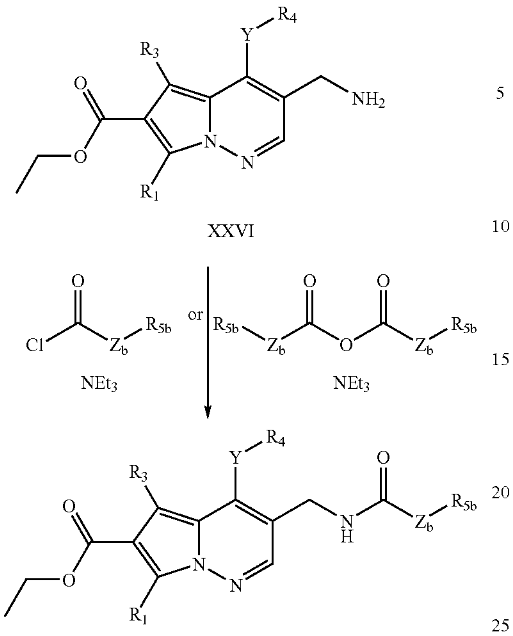

XXVI or

XXVIII

As shown in Scheme 5, an intermediate of formula XXV, which is a compound of formula I wherein $R_6$ is H and $ZR_5$ is a nitrile group, can be reduced in the presence of hydrogen, trifluoroacetic acid (TFA), and a catalyst such as Pd/C to yield an compound of formula XXVI. The compound of formula XXVI can be treated with intermediates of formula $R_{5b}$—$Z_b$—C(O)—Cl or ($R_{5b}$—$Z_b$—C(O)$)_2$O in the presence of a base such as triethylamine to yield the compound of formula XXVII. Intermediates of formula $R_{5b}$—$Z_b$—C(O)—Cl and ($R_{5b}$—$Z_b$—C(O)$)_2$) are readily available from commercial sources, or may be synthesized by those of skill in the art.

Solvates (e.g., hydrates) of the compounds of formula I are also within the scope of the present invention. Methods of solvation are generally known in the art. Accordingly, the compounds of the instant invention may be in the free or solvated form.

The compounds of formula I may be present as salts, in particular pharmaceutically acceptable salts. Compounds of formula I having, for example, at least one basic center can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methanesulfonic acid or p-toluenesulfonic acid. Corresponding acid addition salts can also be formed having, if desired, an additional basic center.

The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine thiomorpholine, piperidine, pyrrolidine, a mono-, di-, or tri-lower alkylamine, for example ethyl, t-butyl, diethyl, diisopropyl, triethyl, tributyl or dimethyl-propylamine, or a mono, di, or trihydroxy lower alkylamine, for example mono, di or triethanolamine.

Corresponding internal salts may furthermore be formed. Salts which are unsuitable for pharmaceutical uses but which can be employed, for example, for he isolation or purification of free compounds of formula I or their pharmaceutically acceptable salts, are also included within the scope of this invention.

Preferred salts of the compounds of formula I which include a basic group include monohydrochloride, hydrogen sulfate, methanesulfonate, phosphate or nitrate.

Preferred salts of the compounds of formula I which include an acid group include sodium, potassium and magnesium salts and pharmaceutically acceptable organic amines.

Methods of Using the Compounds

It has been discovered that pyrrolopyridazines of the invention are inhibitors of protein kinases. More specifically, certain pyrrolopyridazines inhibit the effects of receptor tyrosine kinases and serine/threonine kinases, a property of value in the treatment of disease states associated with hyperproliferation, angiogenesis, increased vascular permeability, and inflammation, such as cancer and inflammatory disease. In particular, the compounds of formula I and their salts, solvates, and stereoisomers are expected to inhibit the growth of primary and recurrent solid tumors by antiproliferative and/or antiangiogenic mechanisms. The solid tumors include, for example, cancers of the bladder, squamous cell, head, colorectal, oesophageal, gynecologocal (such as ovarian), pancreas, breast, prostate, lung, vulva, skin, brain, genitourinary tract, lymphatic system (such as thyroid), stomach, larynx and lung In some embodiments of the present invention, methods are provided for treating proliferative or inflammatory diseases comprising administering to a patient in need thereof a therapeutically effective amount of a compound having formula I, as described above.

The methods optionally comprise administering at least one other therapeutic agent such as angiogenesis inhibitors, antiestrogens, progestogens, aromatase inhibitors, antihormones, antiprogestogens, antiandrogens, LHRH agonists and antagonists, testoterone 5α-dihydroreductase inhibitors, farnesyl transferase inhibitors, anti-invasion agents, growth factor inhibitors, antimetabolites, intercalating antitumour antibiotics, platinum derivatives, alkylating agents, antimitotic agents, topoisomerase inhibitors, cell cycle inhibitors, and biological response modifiers, linomide, integrin αvβ3 function inhibitors, angiostatin, razoxin, tamoxifen, toremifen, raloxifene, droloxifene, iodoxyfene, megestrol acetate, anastrozole, letrazole, borazole, exemestane, flutamide, nilutamide, bicalutamide, cyproterone acetate, gosereline acetate, luprolide, finasteride, metalloproteinase inhibitors, urokinase plasminogen activator receptor function inhibitors, growth factor antibodies, growth factor receptor antibodies, tyrosine kinase inhibitors, serine/threonine kinase inhibitors, methotrexate, 5-fluorouracil, purine, adenosine analogues, cytosine arabinoside, doxorubicin, daunomycin, epirubicin, idarubicin, mitomycin-C, dactinomycin, mithramycin, cisplatin, carboplatin, nitrogen mustard, melphalan, chlorambucil, busulphan, cyclophosphamide, ifosfamide nitrosoureas, thiotephan, vincristine, taxol, taxotere, epothilone analogs, discodermolide anlogs, eleutherobin analogs, etoposide, teniposide, amsacrine, topotecan, flavopyridols, and biological response modifiers. In some preferred embodiments, the additional thereapeutic agent is selected from Erbitux™, taxol, paraplatin and Ifex.

More generally, the compounds of formula I are useful in the treatment of a variety of cancers, including, but not limited to, the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

The compounds of formula I are especially useful in treatment of tumors having a high incidence of protein kinase activity, such as colon, lung, prostate, breast and pancreatic tumors. By the administration of a composition comprising a compound of the invention, or a combination of such compounds, development of tumors in a mammalian host is reduced.

Compounds of formula I may also be useful in the treatment of diseases other than cancer that may be associated with signal transduction pathways operating through growth factor receptors. For example, due to the key role of kinases in the regulation of cellular proliferation in general, kinase inhibitors could act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

In addition, compounds of formula I may induce or inhibit apoptosis. The apoptotic response is aberrant in a variety of human diseases. Compounds of formula I, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

As inhibitors of protein kinases, compounds of the present invention have utility in treating conditions associated with inappropriate kinase activity. Such conditions also include diseases in which cytokine levels are modulated as a consequence of intracellular signaling, and in particular, diseases that are associated with an overproduction of such cytokines as IL-1, IL-4, IL-8 and TNF-α. For example, compounds of the present invention are useful in treating and preventing:

IL-1 mediated diseases such as, for example, rheumatoid arthritis, osteoarthritis, stroke, endotoxemia and/or toxic shock syndrome, inflammatory reaction induced by endotoxin, inflammatory bowel disease, tuberculosis, antherosclerosis, muscle degeneration, cachexia, psoriatic arthritis, Reiter's syndrome, gout, traumatic arthritis, rubella arthritis, acute synovitis, diabetes, pancreatic β-cell disease and Alzheimer's disease;

IL-4 mediated diseases or conditions such as, for example, allergic inflammatory processes including those that occur in asthma, IL-8 mediated diseases or conditions such as, for example, those characterized by massive neutrophil infiltration, such as psoriasis, inflammatory bowel disease, asthma, cardiac and renal reperfusion injury, adult respiratory distress syndrome, thrombosis and glomerulonephritis; and TNF-mediated diseases or conditions such as rheumatoid arthritis, rheumatoid spondylitis, osteoarthritis, gouty arthritis and other arthritic conditions, sepsis, septic shock syndrome, adult respiratory distress syndrome, cerebral malaria, chronic pulmonary inflammatory disease, silicosis, pulmonary sarcoisosis, bone resorption disease, reperfusion injury, graft vs. host reaction, allograft rejections, fever and myalgias due to infection, cachexia secondary to infection, AIDS, ARC or malignancy, meloid formation, scar tissue formation, Crohn's disease, ulcerative colitis, pyresis, viral infections, such as HIV, CMV, influenza and herpes; and veterinary viral infections, such as lentivirus infections, including, but not limited to equine infectious anemia virus; or retrovirus infections, including feline immunodeficiency virus, bovine immunodeficiency virus, or canine immunodeficiency virus.

Diseases mediated by p38 include rheumatoid arthritis (RA), chronic obstructive pulmonary disease (COPD), asthma, Crohn's disease, meurological diseases such as Alzheimer's disease and stroke, and inflammatory bone diseases. A further discussion of diseases mediated by p38 can be found in pending PCT Application No. US01/49982 and pending U.S. patent application Ser. No. 10/036,293 (both of which are herein incorporated by reference in their entirety).

Inhibitors of protein kinase activity, such as the compounds of the present invention, are useful in treating and preventing other conditions and classes of conditions including, but not limited to, inflammatory diseases, autoimmune diseases, destructive bone disorders, proliferative disorders, angiogenic disorders, infectious diseases, neurodegenerative diseases, viral diseases, allergies, myocardial ischemia, reperfusion/ischemia in stroke heart attacks, organ hyposia, vascular hyperplasia, cardiac hypertrophy, thrombin-induced platelet aggregation, and conditions associated with prostaglandin endoperoxidase synthase-2.

Inflammatory diseases which may be treated or prevented include, but are not limited to, acute pancreatitis, chronic pancreatitis, asthma, allergies and adult respiratory distress syndrome.

Autoimmune diseases which may be treated or prevented include, but are not limited to, glomerulonephritis, rheumatoid arthritis, systemic lupus erythematosis, scleroderma, chronic thyroiditis, Grave's disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, or graft vs. host diseases.

Destructive bone disorders which may be treated or prevented include, but are not limited to, osteoporosis, osteoarthritis and multiple myeloma-related bone disorder.

Proliferative diseases which may be treated or prevented include, but are not limited to, acute myelogenous leukemia, chronic myelogeneous leukemia, metastatic melanoma, Kaposi's sarcoma, and multiple myeloma.

Angiogenic disorders which may be treated or prevented include hemangiomas, psoriasis, Kaposi's sarcoma, ocular neovascularization, retinopathy of prematurity, macular degeneration, diabetic retinopathy, diabetic nephropathy, rheumatoid arthritis, endometriosis, atherosclerosis, tumor growth and metastasis, myocardial ischemia, peripheral ischemia, cerebral ischemia, impaired wound healing, certain female reproductive disorders, organ hypoxia, and impaired ulcer healing.

Infectious diseases which may be treated or prevented include, but are not limited to, sepsis, septic shock, and Shigellosis.

Neurodegenerative diseases which may be treated or prevented by the compounds of this invention include, but are not limited to, Alzheimer's disease, Parkinson's disease, cerebral ischemias or neurodegenerative disease caused by traumatic injury.

Viral diseases which may be treated or prevented include but are not limited to, acute hepatitis infection (including hepatitis A, hepatitis B and hepatitis C), HIV infection and CMV retinitis.

The compounds of formula I may also prevent blastocyte implantation, and, therefore, may be used as contraceptives in mammals.

In addition, protein kinase inhibitors of this invention also exhibit inhibition of the expression of inducible pro-inflammatory proteins such as prostaglandin endoperoxide synthase-2 (PGHS-2), also referred to as cyclooxygenase-2 (COX-2). Accordingly, additional conditions which may be treated or prevented by appropriate administration of compounds of the invention include edemia, analgesia, fever and pain, such as neuromuscular pain, headache, pain caused by cancer, dental pain and arthritis pain.

In the field of medical oncology, it is normal practice to combine different agents for treatment of patients with cancer. Thus, a compound of formula I may optionally be combined with other components, such as antiproliferative, antiangiogenic and/or vascular permeability reducing agents. Additionally, surgery, radiotherapy or chemotherapy may optionally be utilized in conjunction with administration of compounds of formula I. Accordingly, the compound of formula I may be administered alone or combined with the administration of one or more other therapeutic agents, substances and/or treatments.

Such conjoint treatment may be achieved by way of the simultaneous, sequential or separate administration of the individual components of the treatment. When not administered simultaneously, the component therapies may be administered in any order. If formulated as a fixed dose, such combination products employ the compounds of this invention within the dosage range described below and the other pharmaceutically active agent within its approved dosage range. Dosage ranges of many pharmaceutically active agents may be found in the Physician's Desk Reference, $55^{th}$ Edition, Medical Economics Company (2001). Compounds of formula I may also be used sequentially with known anticancer or cytotoxic agents and treatment, including radiation, when a combination formulation is appropriate.

In general, there are three main categories of chemotherapeutic agents:

(i) antiangiogenic agents, for example, linomide, inhibitors of integrin $\alpha v\beta 3$ function, angiostatin, and razoxin;

(ii) cytostatic agents such as antiestrogens (for example tamoxifen, toremifen, raloxifene, droloxifene, iodoxyfene), progestogens (for example megestrol acetate), aromatase inhibitors (for example anastrozole, letrazole, borazole, exemestane), antihormones, antiprogestogens, antiandrogens (for example, flutamide; nilutamide; bicalutamide; cyproterone acetate; (R)-2,3,4,5-tetrahydro-1-(1H-imidazole-4-ylmethyl)-3-(phenylmethyl)-4-(2-thienylsulfonyl)-1H-1,4-benzodiazepine-7-carbonitrile, mesylate salt; N-[5-[[[5-(1,1-Dimethylethyl)-2-oxazolyl]methyl]thio]-2-thiazolyl]-4-piperidinecarboxamide, hemi L-Tartaric acid salt; cetuximab; molecules disclosed in pending U.S. patent application Ser. No. 10/025,116 (herein incorporated by reference), LHRH agonists and antagonists (for example gosereline acetate, luprolide), inhibitors of testosterone 5α-dihydroreductase (for example finasteride), farnesyl transferase inhibitors, anti-invasion agents (for example metalloproteinase inhibitors like marimastat and inhibitors of urokinase plasminogen activator receptor function) and inhibitors of growth factor function, (such growth factors include for example EGF, FGF, platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); intercalating antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide nitrosoureas, thiotephan); antimitotic agents (for example vinca alkaloids like vincristine and taxoids like taxol, taxotere and newer microbtubule agents such as epothilone analogs, discodermolide analogs, and eleutherobin analogs); topoisomerase inhibitors (for example epipodophyllotoxins like etoposide and teniposide, amsacrine, topotecan); cell cycle inhibitors (for example flavopyridols); and biological response modifiers. Particular compounds could include N-[5-[[[5-(1,1-Dimethylethyl)-2-oxazolyl]methyl]thio]-2-thiazolyl]-4-piperidinecarboxamide, hemi L-Tartaric acid salt.

The compounds of formula I and the pharmaceutical compositions comprising compounds of formula I may be administered by any means suitable for the condition to be treated, which may depend on the need for site-specific treatment or quantity of drug to be delivered. The compounds may be administered in a dosage range of about 0.05 to 200 mg/kg/day, preferably less than 100 mg/kg/day, in a single dose or in 2 to 4 divided doses.

Topical administration is generally preferred for skin-related diseases, and systematic treatment is preferred for cancerous or pre-cancerous conditions, although other modes of delivery are contemplated. For example, the compounds and compositions may be delivered oraly, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aqueous or non-aqueous solutions or suspensions); nasally such as by inhalation spray; topically, such as in the form of a cream or ointment; rectally such as in the form of suppositories; or liposomally.

Dosage unit formulations containing non-toxic, pharmaceutically acceptable carriers, vehicles or diluents may be administered. The compounds and compositions may be administered in a form suitable for immediate release or extended release. Immediate release or extended release may be achieved with suitable pharmaceutical compositions or, particularly in the case of extended release, with devices such as subcutaneous implants or osmotic pumps. Further techniques for formulation and administration of the compounds and compositions of the instant application may be found in "Remington's Pharmaceutical Sciences," 18th Ed. (1990, Mack Publishing Co., Easton, Pa.).

Abbreviations

The following abbreviations are among those used herein:

Δ=heat

Ac=acetyl

AcOH=acetic acid aq.=aqueous

ATP=adenosine triphosphate

BOP=benzotriazol-1-yloxytris(dimethylamino)-phosphonium

BSA=Bovine serum albumin

DBU=1,8-diazabicyclo[5.4.0]undec-7-ene

DCC=Dicyclohexylcarbodiimide

DCE=dichloroethane

DEAD=diethyl azodicarboxylate

DIBAL-H=diisobutylaluminum hydride

DIPEA=N,N-diisopropylethylamine

DMA=dimethylacetamide

DME=1,2-dimethoxyethane

DMF=dimethylformamide

DMSO=dimethylsulfoxide

DPPA=Diphenylphosphoryl azide

DTT=Dithiothreitol

EDC=1-(3-dimethylaminopropyl)-3-ethylcarbodiimide hydrochloride

EDTA=ethylenediamine tetracetic acid

Et=ethyl $Et_2O$=diethyl ether

EtOAc=ethyl acetate

EtOH=ethanol

GST=gluetithione S-transferase h=hours

Hexafluorophosphate

HOAt=1-hydroxy-7-azabenzotriazole

HOBt=1-hydroxybenzotriazole

Hünig's Base=N,N-diisopropylethylamine

KOtBu=potassium tert-butoxide

LC=liquid chromatography

LDA=lithium diisopropylamide

MBP=Myelin basic protein mCPBA=m-chloropetroxybenzoic acid

Me=methyl

MeI=methyl iodide

MeOH=methanol

MS(ES)=Electro-Spray Mass Spectrometry n-BuLi=n-butyllithium

Pd/C=palladium on activated charcoal

Ph=phenyl $PhCH_3$=toluene pTSA=para-toluenesulfonic acid

RT=retention time rt=room temperature sat.=saturated t-Bu=tert.butyl

TCA=trichloroacetic acid

TEA=triethylamine

TFA=trifluoroactic acid

THF=tetrahydrofuran

TLC=thin layer chromatography

Tris-HCL=Tris[hydroxymethyl]aminomethane hydrochloride

Ts=tosyl

TsCl=tosyl chloride

TsOH=tosic acid

The following examples are provided to describe the invention in further detail. These examples are intended to illustrate and not to limit the invention. All temperatures are given in centigrade degrees (° C.) unless otherwise noted. The YMC Co., Ltd., a supplier of HPLC columns, is located in Kyoto, Japan, and may be reached through the Waters Co. in Milford, Mass.

EXAMPLE 1

Preparation of 3-Cyano-4-(cyclohexylamino)-5-methylpyrrolo[1,2-b]pyridazine-6-carboxylic acid ethyl ester (1E)

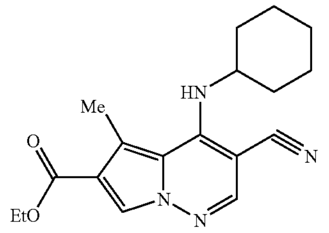

A. Preparation of 3-Methyl-1H-pyrrole-2,4-dicarboxylic acid diethyl ester (1A)

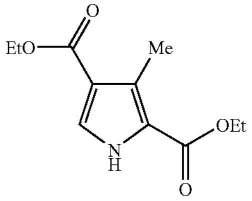

To a solution of ethyl isocyanoacetate (38.1 mL, 0.34 mol) and DBU (50.8 mL, 0.34 mol) in THF (400 mL) at 50° C. was added a solution of acetaldehyde (9.5 mL, 0.17 mol) in THF (100 mL) over 25 min. The reaction mixture was stirred at 55° C. for 17 h, cooled to 25° C. and acetic acid (20 mL) was slowly added. The resulting mixture was concentrated in vacuo and the resulting residue was dissolved in ethyl acetate (800 mL) and washed with HCl (1 N, 3x300 mL). The combined aqueous washes were extracted with ethyl acetate (3x200 mL) and the combined organic layer were washed with $NaHCO_3$ (sat. aq., 3x200 mL), water (100 mL) and brine (100 mL) and then concentrated in vacuo to afford a dark brown oil. Elution of this oil through a silica pad using ethyl acetate/hexanes (1:1) and the concentration in vacuo provided compound 1A (16 g, 42% yield) as a yellow solid. HPLC: 100% at 3.536 min (retention time) (YMC S5 ODS column, 4.6x═mm, eluting with 10–90% aqueous methanol over 4 min containing 0.2% phosphoric acid, 4 mL/min, monitoring at 220 nm). MS (ES): m/z 226.0 $[M+H]^+$.

B. Preparation of 1-Amino-3-methyl-1H-pyrrole-2,4-dicarboxylic acid diethyl ester (1B)

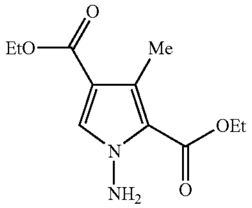

To a suspension of NaH (60% suspension in mineral oil, 213 mg, 5.33 mmol) in DMF (15 mL) at 0° C. was added compound 1A (1.0 g, 4.44 mmol), portionwise. The reaction mixture was stirred at 0° C. for 5 min and then warmed to 25° C. and stirred for an additional 1 h. The reaction mixture was then cooled to 10° C. and 2,4-dinitro-aminophenol (972 mg, 4.88 mmol) was added in two portions. The resulting mixture was warmed to 25° C., stirred for 12 h, poured onto water (40 mL) and dichloromethane (50 mL), and the layers were separated. The aqueous phase was extracted with dichloromethane (3x20 mL), and the combined organic extracts were washed with NaOH (1N, 3x20 mL), water (20 mL), and brine (20 mL) and then dried over $MgSO_4$, filtered, and concentrated in vacuo. The resulting reddish-brown residue was further concentrated for 12 h under high vacuum to yield 800 mg (75% yield) of compound 2B which was used without further purification. HPLC: 100% at 3.488 min (retention time) (YMC S5 ODS column, 4.6x50 mm, eluting with 10–90% aqueous methanol over 4 min containing 0.2% phosphoric acid, 4 mL/min, monitoring at 220 nm). MS (ES): m/z 241.17 $[M+H]^+$.

C. Preparation of 3-Cyano-1,4-dihydro-5-methyl-4-oxopyrrolo[1,2-b]pyridazine-6-carboxylic acid ethyl ester (1C)

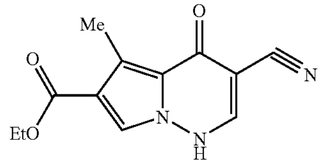

To a solution of 1-amino-3-methyl-1H-pyrrole-2,4-dicarboxylic acid diethyl ester (1.08 g, 4.50 mmol) in toluene (15 mL) were added 1,1-diethoxypropionitrile (2.02 mL, 1.93 g, 13.5 mmol) and TsOH-$H_2O$ (171 mg, 0.90 mmol). The reaction mixture was heated at reflux for 12 h and then cooled to 25° C. DBU (0.18 mL, 0.822 g, 5.40 mmol) was added and the resulting dark brown mixture was heated at 80° C. for 1 h and then coded to room temperature. The reaction mixture was poured onto dichloromethane (50 mL) and $NH_4Cl$ (sat. aq., 50 mL) and the layers were separated. The aqueous layer was extracted with dichloromethane (2x30 mL) and the combined organic extracts were washed with water (30 mL), dried over $MgSO_4$, filtered and concentrated in vacuo. The crude product was purified by silica gel column chromatography (10–30% methanol/dichloromethane) to provided 441 mg (40%) of compound 1C as a brown solid. HPLC: 100% at 3.383 min (retention time) (YMC S5 ODS column, 4.6x50 mm, eluting with 10–90% aqueous methanol over 4 min containing 0.2% phosphoric acid, 4 mL/min, monitoring at 220 nm). MS (ES): m/z 246.09 $[M+H]^+$.

D Preparation of 4-Chloro-3-cyano-5-methylpyrrolo[1,2-b]pyridazine-6-carboxylic acid ethyl ester (1D)

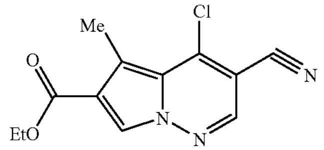

A 15 mL round bottom flask containing the compound 1C (370 mg, 1.51 mmol) was charged with $POCl_3$ (1 mL) and heated to 75° C. for 2 h. The reaction mixture was concentrated in vacuo and the resulting yellow residue was dissolved in dichloromethane (10 mL) and added, via pipette, to a saturated aqueous solution of $NaCHO_3$ with stirring at 0° C. The heterogeneous mixture was stirred for 10 min at 0° C. then warmed to room temperature and stirred for an additional 1h. The mixture was poured into a separatory funnel and the layers were separated. The aqueous phase was extracted with dichloromethane (2x20 mL) and the combined organic extracts were washed with $NaHCO_3$ (sat. aq., 1×20 mL), dried over $Na_2SO_4$, filtered and concentrated in vacuo. The resulting residue was dissolved in EtOAc (20 mL) and filtered through a pad of silica using EtOAc (100 mL) to wash the silica pad. The filtrate was concentrated in vacuo to afford compound 1D as a yellow solid which was used without further purification. HPLC: 100% at 4.160 min (retention time) (YMC S5 ODS column, 4.6×50 mm, eluting with 10–90% aqueous methanol over 4 min containing 0.2% phosphoric acid, 4 mL/min, monitoring at 220 nm).

E. Preparation of 3-Cyano-4-(cyclohexylamino)-5-methylpyrrolo[1,2-b]pyridazine-6-carboxylic acid ethyl ester (1E)

To a solution of compound 1D (20 mg, 0.076 mmol) in acetonitrile (1 mL) were added $Et_3N$ (32 μL, 0.228 mmol) and cyclohexylamine (10 μL, 0.084 mmol) and the reaction mixture was stirred at 25° C. After 24 h, an additional 10 μL of cyclohexylamine was added and the reaction mixture was stirred for an additional 1.5 h after which time it was poured onto $NaHCO_3$ (sat. aq., 20 mL) and dichloromethane. The layers were separated and the aqueous layer was extracted with dichloromethane (2×10 mL). The combined organic layers were washed with water (20 mL), dried over $MgSO_4$, filtered and concentrated in vacuo to yield 18 mg (75%) of compound 1E as a yellow solid, which was used without further purification. HPLC: 100% at 4.60 min (retention time) (YMC S5 ODS column, 4.6×50 mm, eluting with 10–90% aqueous methanol over 4 min containing 0.2% phosphoric acid, 4 mL/min, monitoring at 220 nm). MS (ES): m/z 327.2 $[M+H]^+$.

EXAMPLE 2

Preparation of 3-Cyano-5-methyl-4-phenoxypyrrolo[1,2-b]pyridazine-6-carboxylic acid ethyl ester

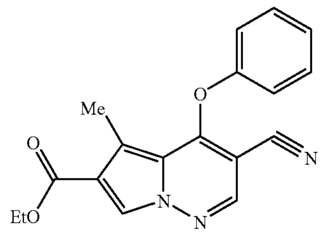

To a solution of compound 1D (18 mg, 0.068 mmol) in acetonitrile (0.5 mL) at room temperature was added $Et_3N$ (21 uL, 0.205 mmol) and phenol (7 mg, 0.075 mmol). The reaction mixture was stirred for 24 h and then poured onto dichloromethane (10 mL) and $NaHCO_3$ (sat. aq., 10 mL). The layers were separated, the aqueous phase was extracted with dichloromethane (3×5 mL), and the combined organic extracts were washed with water, dried over $MgSO_4$, filtered, and concentrated in vacuo to afford compound 2 (15 mg, 68%) as a yellow solid. HPLC: 100% at 4.35 min (retention time) (YMC S5 ODS column, 4.6×50 mm, eluting with 10–90% aqueous methanol over 4 min containing 0.2% phosphoric acid, 4 mL/min, monitoring at 220 nm). MS (ES): m/z 340.0 $[M+NH_4]^+$.

EXAMPLE 3

Preparation of 6-(Methoxymethyl)-5-methyl-4-[(4-phenoxyphenyl)amino]pyrrolo[1,2-b]pyridazine-3-carbonitrile (3C)

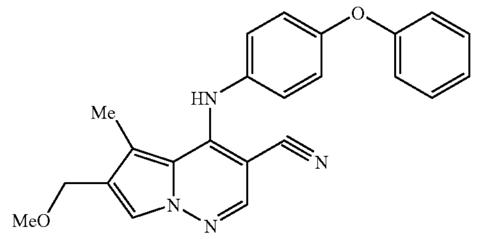

A. Preparation of 3-Cyano-5-methyl-4-[(4-phenoxyphenyl)amino]pyrrolo[1,2-b]pyridazine-6-carboxylic acid ethyl ester (3A)

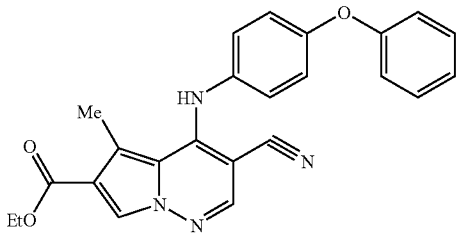

To a solution of compound 1D (26 mg, 0.10 mmol) in DMF (2 mL) were added $K_2CO_3$ (138 mg, 1.00 mmol) and p-phenoxyaniline (20 mg, 0.11 mmol) at 25° C. The reaction mixture was stirred for 12 h and then diluted with dichloromethane (15 mL) and washed with water (10 mL) and brine (10 mL). The organic phase was dried over $Na_2SO_4$ and concentrated and the resulting residue was triturated with methanol to afford 31 mg (76% yield) of the desired compound as a yellow solid. HPLC: 100% at 4.62 min (retention time) (YMC S5 ODS column, 4.6×50 mm, eluting with 10–90% aqueous methanol over 4 min containing 0.2% phosphoric acid, 4 mL/min, monitoring at 220 nm). MS (ES): m/z 413.12 $[M+H]^+$.

Compound 3A can also be prepared as follows: To a solution of 1D (1.00 g, 3.79 mmol) in THF (10 mL) were added 4-phenoxyaniline (0.84 g, 4.53 mmol) and triethylamine (1.06 mL, 7.58 mmol). The reaction mixture was heated at 60° C. for 3 days, after which time it was cooled to room temperature and diluted with MeOH (50 mL). The resulting solids were filtered, washed with MeOH and dried to yield 1.50 g (96% yield) of 3A as a yellow powder.

B. Preparation of 6-(Hydroxymethyl)-5-methyl-4-[(4-phenoxyphenyl)amino]pyrrolo[1,2-b]pyridazine-3-carbonitrile (3B)

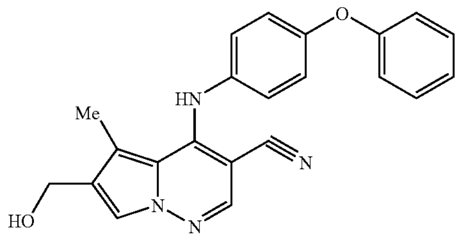

To a solution of compound 3A (41 mg, 0.10 mmol) in THF (2 mL) at −78° C. was added DIBAL-H (1.5 M in toluene, 0.13 mL, 0.20 mmol). The reaction mixture was stirred for 6 h at −78° C., warmed to 0° C. and stirred for an additional 2h. The reaction mixture was quenched by the addition of methanol (3 mL) and sat. aq. $Na_2CO_3$ (3 mL) and then poured onto dichloromethane (20 mL). The layers were separated, the aqueous phase was extracted with dichloromethane (2×15 mL), and the combined organic extracts were dried over $MgSO_4$, filtered, and concentrated in vacuo. Purification via preparative HPLC (YMC S5 ODS 20–100 mm, eluting with 30–100% aqueous methanol over 15 min containing 0.1% TFA, 20 mL/min) afforded 33 mg (90% yield) of compound 3B as a yellow solid. HPLC: 100% at 3.98 min (retention time) (YMC S5 ODS column, 4.6×50 mm, eluting with 10–90% aqueous methanol over 4 min containing 0.2% phosphoric acid, 4 mL/min, monitoring at 220 nm). MS (ES): m/z 371.19 $[M+H]^+$.

C. Preparation of 6-(Methoxymethyl)-5-methyl-4-[(4-phenoxyphenyl)amino]pyrrolo[1,2-b]pyridazine-3-carbonitrile (3C)

To a solution of compound 3B (9.0 mg, 0.025 mmol) in DMF:THF (1:1, 1 mL) at 0° C. was added KOtBu (1.5 M in THF, 0.025 mL, 0.038 mmol). After stirring for 45° min at 0° C., methyl iodide (2 μL, 0.025 mmol) was added and the reaction mixture was stirred for an additional 1h, warmed to 25° C., and stirred for 3h. No reaction was observed during this time. The reaction mixture was cooled once more to 0° C., additional KOtBu (1.5 M in THF, 0.25 mL, 0.38 mmol) was added and the reaction mixture was stirred for 30 min, after which time additional methyl iodide (20 μL, 0.25 mmol) was added. After stirring for an additional 2h at 0° C., the reaction was quenched by the addition of saturated aqueous $NH_4Cl$ (10 mL) and dichloromethane (10 mL). The layers were separated, the aqueous phase was extracted with dichloromethane (2×10 mL) and the combined organic extracts were dried over $MgSO_4$, filtered concentrated, and purified by preparative HPLC (YMC S5 ODS 20×100 mm, eluting with 30–100% aqueous methanol over 15 min containing 0.1% TFA, 20 mL/min) to afford the desired product as a yellow semi-solid. HPLC: 100% at 4.27 min (retention time) (YMC S5 ODS column, 4.6×50 mm, eluting with 10–90% aqueous methanol over 4 min containing 0.2% phosphoric acid, 4 mL/min, monitoring at 200 nm). MS (ES): m/z 385.21 $[M+H]^+$.

EXAMPLE 4

Preparation of 4-[(2-Chloro-4-iodophenyl)amino]-3-cyano-5-methylpyrrolo[1,2-b]pyridazine-6-carboxylic acid

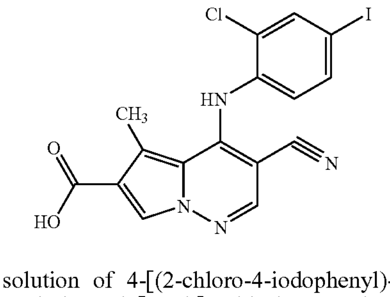

To a solution of 4-[(2-chloro-4-iodophenyl)-amino]-3-cyano-5-methylpyrrolo[1,2-b]pyridazine-6-carboxylic acid, ethyl ester (59 mg, 0.123 mmol, prepared as described in Example 1) in THF (1 mL) was added NaOH (1N, 1 mL). The reaction mixture was stirred at 25° C. for 72 h and then poured onto $NaHCO_3$ (30 mL) and EtOAc (30 mL). The layers were separated and the aqueous phase was acidified to pH=2 and extracted with dichloromethane (2×20 mL). The combined organic extracts were washed with brine, dried over $MgSO_4$, filtered and concentrated in vacuo to afford 20 mg (36% yield) of compound 4 which was used without further purification. $^1H$ NMR (DMSO-$d_6$) □8.99 (s, 1H), 8.18 (s, 1H), 8.03 (s, 1H), 7.97 (s, 1H), 7.75 (d, 1H), 7.29 (d, 1H), 2.78 (s, 3H). HPLC: 100% at 4.04 min (retention time) (YMC S5 ODS column, 4.6×50 mm, eluting with 10–90% aqueous methanol over 4 min containing 0.2% phosphoric acid, 4 mL/min, monitoring at 220 nm).

EXAMPLE 5

Preparation of 4-[(2-Chloro-4-iodophenyl)amino]-3-cyano-5-methyl-N-(2-methylpropoxy)pyrrolo[1,2-b]pyridazine-6-carboxamide

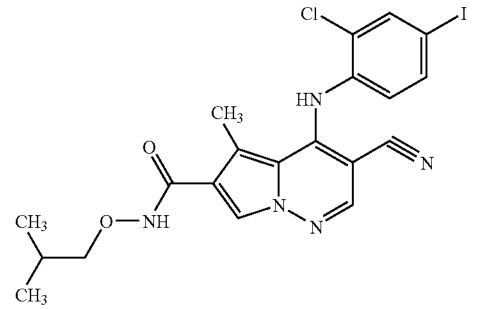

To a solution of compound 4 (20 mg, 0.442 mmol) in THF:dichloromethane (1:1, 1 mL) were added isopropylhydroxylamine (7 mg, 0.053 mmol), Hunig's base (18 □L, 0.106 mmol) and PyBOP (benzotriazol-1-yl oxytripyrrolidinophosphonium hexafluorophosphate) 28 mg, 0.531 mmol). The reaction mixture was stirred for 1h, concentrated in vacuo and diluted with 10% HCl (15 mL) and $Et_2O$ (15 mL). The layers were separated and the organic phase was washed with 1N NaOH (15 mL) and brine (15 mL), dried over $MgSO_4$, filtered and concentrated in vacuo. The aqueous phase was made basic by the addition of 1N NaOH and extracted with EtOAc (2×15 mL). The organic extracts were dried over $MgSO_4$, filtered, concentrated in vacuo, and added to the combined organic layers of the first extractions. Preparative HPLC (YMC S5 ODS 20×100 mm, eluting with 30–100% aqueous methanol over 15 min containing 0.1% TFA, 20 mL/min) provided 1.1 mg of the compound 5. HPLC: 100% at 3.68 min (retention time) (YMC S5 ODS column, 4.6×50 mm, eluting with 10–90% aqueous methanol over 4 min containing 0.1% TFA, 4 mL/min, monitoring at 220 nm). MS (ES): m/z 524.02 $[M+H]^+$.

EXAMPLE 6

Preparation of 3-Cyano-4-[[5-[(methoxyamino)carbonyl]-2-methylphenyl]amino]-5-methylpyrrolo[1,2-b]pyridazine-6-carboxylic acid

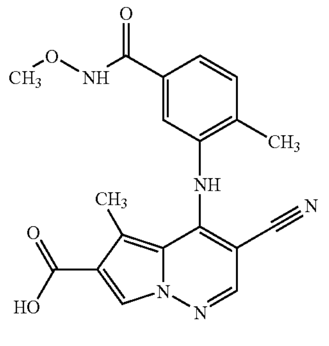

To a solution of 3-cyano-4-[[5-[(methoxyamino)carbonyl]-2-methylphenyl]amino]-5-methylpyrrolo[1,2-b]

pyridazine-6-carboxylic acid, ethyl ester (160 mg, 0.393 mmol, prepared as described in Example 1) in THF (2 mL) was added 1N NaOH (4 mL). The reaction mixture was stirred at 25° C. for 2 days and then neutralized with 1M citric acid and poured onto dichloromethane. The organic phase was separated and extracted with dichloromethane, and the combined organic extracts were dried over $Na_2SO_4$, filtered, and concentrated in vacuo. The resulting residue was purified via preparative HPLC (YMC S5 ODS 20'100 mm, eluting with 30–100% aqueous methanol over 15 min containing 0.1% TFA, 20 mL/min) to afford 36 mg (39% yield) of compound 6. HPLC: 100% at 3.33 min (retention time) (YMC S5 ODS column, 4.6×50 mm, eluting with 10–90% aqueous methanol over 4 min containing 0.2% phosphoric acid, 4 mL/min, monitoring at 220 nm). MS (ES): m/z 380.24 $[M+H]^+$.

EXAMPLE 7

Preparation of 3-Cyano-4-[[5-[(methoxyamino) carbonyl]-2-methylphenyl]amino]-5-methyl-N-[(1S)-1-phenylethyl]pyrrolo[1,2-b]pyridazine-6-carboxamide

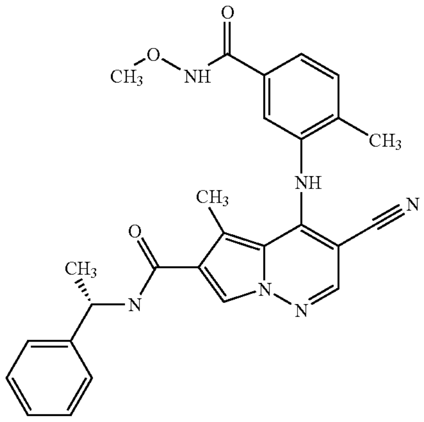

To a solution of compound 6 (19 mg, 0.05 mmol) in DMF (2 mL) were added EDC (14.4 mg, 0.075 mmol), HOBt (10.1 mg, 0.075 mmol) and DIPEA (12.9 mg, 0.10 mmol) and the reaction mixture was stirred for 30 min at 25° C. (S)-Methylbenzylamine (7.3 mg, 0.06 mmol) was then added and the reaction mixture was stirred for an additional 16h at 25° C. The reaction was then diluted with dichloromethane and poured into water. The layers were separated and the organic phase was dried over $Na_2SO_4$, filtered and concentrated in vacuo. The residue was purified via preparative HPLC (YMC S5 ODS 20×100 mm, eluting with 30–100% aqueous methanol over 15 min containing 0.1% TFA, 20 mL/min) to afford 21 mg (87% yield) of compound 7 as a yellow semi-solid. HPLC: 100% at 3.79 min (retention time) (YMC S5 ODS column, 4.6×50 mm, eluting with 10–90% aqueous methanol over 4 min containing 0.2% phosphoric acid, 4 mL/min, monitoring at 220 nm). MS (ES): m/z 483.36 $[M+H]^+$.

EXAMPLE 8

Preparation of 6-Formyl-5-methyl-4-[(4-phenoxyphenyl)amino]pyrrolo[1,2-b]pyridazine-3-carbonitrile

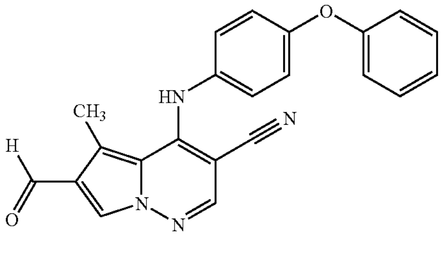

To a solution of compound 3B (266 mg, 0.72 mmol) in dichloromethane (30 mL) was added $MnO_2$ (200 mg, 2.0 mmol). The reaction mixture was heated at 60° C. for 3 h, cooled to 25° C., diluted with dichloromethane and filtered through Celite. The filtrate was concentrated in vacuo and purified by column chromatography on silica gel (0.5% $MeOH/CH_2Cl_2$) to afford 238 mg (90% yield) of compound 8 as a yellow solid. HPLC; 100% at 3.37 min (retention time) (YMC S5 ODS column, 4.6×50 mm, eluting with 10–90% aqueous methanol over 4 min containing 0.2% phosphoric acid, 4 mL/min, monitoring at 220 nm). MS (ES): m/z 369.08 $[M+H]^+$.

EXAMPLE 9

Preparation of 3-Cyano-5-methyl-4-[(4-phenoxyphenyl)amino]pyrrolo[1,2-b]pyridazine-6-carboxylic acid

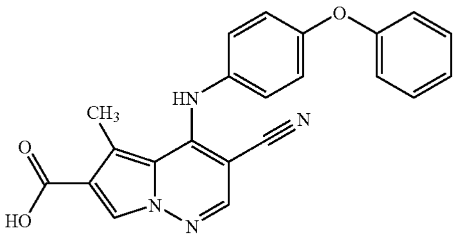

To a solution of compound 3A (1.50 g, 3.64 mmol) in THF (50 mL) were added NaOH (1 M, 20.0 mL) and EtOH (25 mL). The reaction was heated at 80° C., effectively evaporating the THF, and, after 1h, the reaction mixture became homogeneous. Heating was continued for an additional 6h, after which time the reaction was cooled to rt and neutralized with HCl (1 M, 20.0 mL). The resulting solids were filtered, washed with water and dried to afford compound 9 (1.33 g, 95% yield) as a yellow solid. HPLC: 100% at 1.84 min (retention time) (YMC S5 ODs column, 4.6×50 mm eluting with 10–90% $MeOH/H_2O$ over 2 minutes containing 0.1% TFA; 4 mL/min, monitoring at 220 nm). MS (ES): m/z 489.0 $[M+H]^+$.

EXAMPLE 10

Preparation of an Amide Library

Preparation of 3-Cyano-5-methyl-4-[(4-phenoxyphenyl)amino]-N-phenylpyrrolo[1,2-b]pyridazine-6-carboxamide

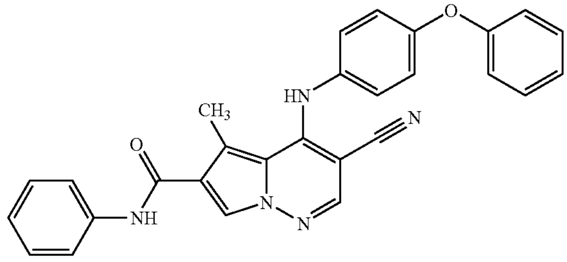

To a solution of compound 9 (11.5 mg, 0.030 mmol) and HOAt (6.1 mg, 0.045 mmol) in THF (0.60 mL) was added a solution of aniline (14 mg, 0.15 mmol) in THF (0.15 mL) followed by a solution of EDC (11.5 mg, 0.06 mmol) in chloroform (0.30 mL). The reaction mixture was heated at 60° C. overnight and then cooled to rt and diluted with MeOH (0.4 mL). The resulting mixture was purified by elution through a SCX/SAC cartridge (500 mg/500 mg) SCX SAX silica bound ionexchange cartridges supplied by United Chemical Technologies, Inc., Bristol, Pa., with MeOH, followed by concentration of the solvent in vacuo, to afford 13.2 mg (96% yield) of compound 10 as a yellow solid. HPLC: 100% at 2.05 min (retention time) (YMC S5 ODS column 4.6×50 mm eluting with 10–90% MeOH/$H_2O$ over 4 minutes containing 0.2% phosphoric acid, 4 mL/min, monitoring at 220 nm). MS (ES): m/z 460.0 $[M+H]^+$.

The above procedure was utilized to prepare a library of 68 amide compounds by substituting other amines for the aniline reactant. Compounds were purified using the above method or by preparative HPLC (Shimadzu VP-ODS 20.0×50.0 mm eluting with 25–90% MeOH/$H_2O$ over 7 minutes containing 0.1% TFA, 10 mL/min, monitoring at 220 nm).

EXAMPLE 11

Preparation of 6-Amino-5-methyl-4-[(4-phenoxyphenyl)amino]pyrrolo[1,2-b]pyridazine-3-carbonitrile (11B)

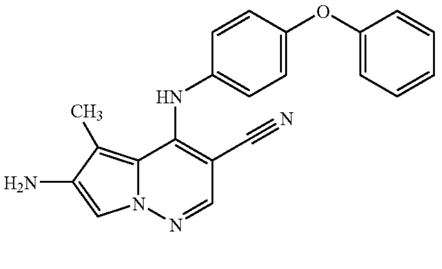

A. Preparation of [3-Cyano-5-methyl-4-[(4-phenoxyphenyl)amino]pyrrolo[1,2-b]pyridazin-6-yl]carbamic acid, phenylmethyl ester (11A)

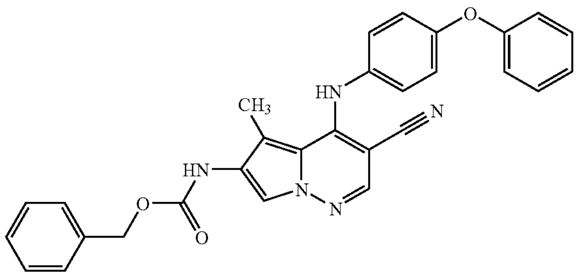

To a solution of compound 9 (192 mg, 0.50 mmol) in dioxane (anhydrous, 4 mL) under an $N_2$ atmosphere were added triethylamine (0.140 mL, 1.00 mmol) and DPPA (0.216 mL, 1.00 mmol), and the mixture was stirred overnight. Benzyl alcohol (0.310 mL, 3.00 mmol) was then added and the reaction mixture was heated at 75° C. for 4 h, concentrated in vacuo and purified by column chromatography on silica gel. (20 to 30% EtOAc/hexanes) to yield compound 11A as a yellow oil (172 mg, 70%). HPLC: 100% at 4.01 min (retention time) (YMC S5 ODS column, 4.6×50 mm eluting with 10–90% MeOH/$H_2O$ over 4 minutes containing 0.1% TFA; 4 mL/min, monitoring at 220 nm). MS (ES): m/z 490.0 $[M+H]^+$.

B. Preparation of 6-Amino-5-methyl-4-[(4-phenoxyphenyl)amino]pyrrolo[1,2-b]pyridazine-3-carbonitrile (11B)

To a solution of compound 11A (40 mg, 0.082 mmol) in MeOH (4 mL) was added Pd/C (12 mg), and the reaction mixture was stirred under hydrogen (1 atm) for 30 minutes, after which time HCl (4M in dioxane, 0.1 mL) was added. The reaction mixture was filtered and the filtrate concentrated in vacuo to provide 32 mg of compound 11B as an orange solid (quantitative yield as HCl salt). HPLC: 100% at 2.90 min (retention time) (YMC S5 ODS column, 4.6×50 mm eluting with 10–90% McOH/$H_2O$ over 4 minutes containing 0.1% TFA; 4 mL/min, monitoring at 220 nm). MS (ES): m/z 356.0 $[M+H]^+$.

EXAMPLE 12

Preparation of N-[3-Cyano-5-methyl-4-[(4-phenoxyphenyl)amino]pyrrolo[1,2-b]pyridazin-6-yl]acetamide

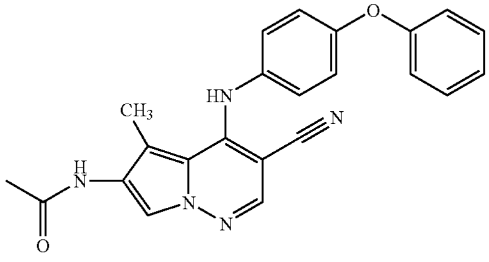

To a solution of compound 11B (HCl salt, 32 mg, 0.082 mmol) in THF (2 mL) was added acetic anhydride (11 mg, 0.11 mmol) followed by triethylamine (33 mg, 0.33 mmol) and the reaction was stirred at rt for 30 min. After quenching with MeOH, the reaction mixture was stirred for an additional 30 min, concentrated in vacuo and purified by flash chromatography on silica gel (40 to 50% EtOAc/dichloromethane) to furnish compound 12 as a yellow oil (30 mg, 92% yield). HPLC: 100% at 3.46 min (retention time) (YMC S5 ODS column, 4.6×50 mm eluting with 10–90% MeOH/$H_2O$ over 2 minutes containing 0.1% TFA; 4 mL/min, monitoring at 220 nm). MS (ES): m/z 398.0 $[M+H]^+$.

EXAMPLE 13

Preparation of 3-(Aminomethyl)-5-methyl-4-[(4-phenoxyphenyl)amino]pyrrolo[1,2-b]pyridazine-6-carboxylic acid

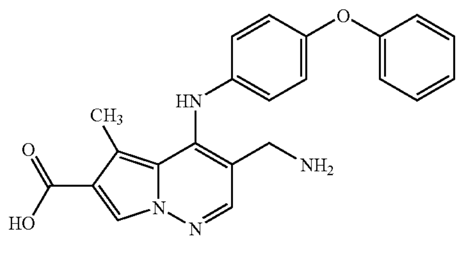

To a solution of compound 9 (27 mg, 0.070 mmol) in MeOH:THF (2:1 v/v, 6 ml) was added TFA (30 mg) followed by Pd/C (10 mg). The reaction mixture was stirred under hydrogen (1 atm) overnight and then filtered through a pad of Celite. The filtrate was concentrated in vacuo and the residue was purified by several azeotropic distillations with MeOH to remove excess TFA. This procedure afforded compound 13 as a yellow solid (35 mg, quantitative). HPLC: 100% at 2.96 min (retention time) (YMC S5 ODS column, 4.6x50 mm eluting with 10–90% MeOH/$H_2O$ over 4 minutes containing 0.1% TFA; mL/min, monitoring at 220 nm). MS (ES): m/z 389.0 $[M+H]^+$.

EXAMPLE 14

Preparation of 3-[(Acetylamino)methyl]-5-methyl-4-[(4-phenoxyphenyl)amino]pyrrolo[1,2-b]pyridazine-6-carboxylic acid

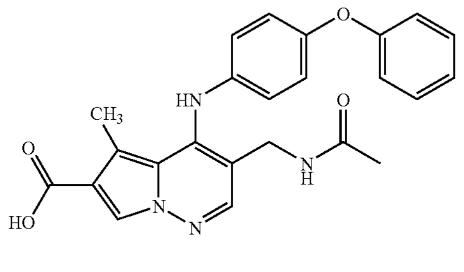

To a solution of compound 13 (10 mg, 0.02 mmol) in THF was added triethylamine (1 drop, ~10 mg) followed by acetic anhydride (1 drop, ~10 mg). The reaction was stirred at rt for 10 min and then concentrated in vacuo. The residue was redissolved in THF, and NaOH (1M, 2 drops) was added. The resulting mixture was stirred at rt for 2 hours, neutralized with HCl (1M) and purified by preparative HPLC (Shimadzu VP-ODS 20.0x50.0 mm eluting with 25–90% MeOH/$H_2O$ over 7 minutes containing 0.1% TFA, 10 mL/min, monitoring at 220 nm) to give compound 14 as a yellow solid (7 mg, 81% yield). HPLC: 100% at 3.46 min (retention time) (YMC S5 ODS column, 4.6x50 mm eluting with 10–90% MeOH/$H_2O$ over 4 minutes containing 0.1% TFA; 4 mL/min, monitoring at 220 nm). MS (ES): m/z 431.0 $[M+H]^+$.

EXAMPLE 15

Preparation of N-[3-Cyano-5-methyl-4-[(4-phenoxyphenyl)amino]pyrrolo[1,2-b]pyridazin-6-yl]-N'-methylurea

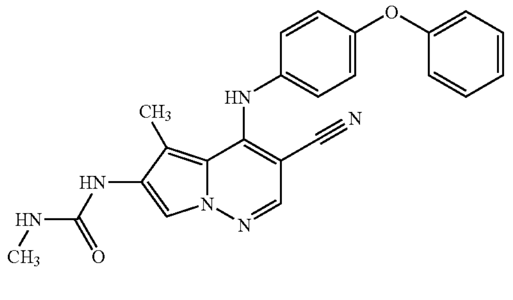

A solution of compound 9 (19 mg, 0.05 mmol), triethylamine (0.014 mL, 0.10 mmol) and DPPA (0.022 mL, 0.10 mmol) in dry dioxane (1 mL) was stirred under $N_2$ for 12h. The reaction was then heated to 80° C. for 1 h and then allowed to cool to 25° C. on standing. Methylamine (2.0 M THF solution, 0.30 mL, 0.60 mmol) was added and the reaction was stirred at 25° C. for 1 h, concentrated in vacuo and purified by flash chromatography on a silica gel column (50 to 70% EtOAc/dichloromethane) to give compound 15 (15 mg, 73%) as a yellow solid. HPLC: 100% at 3.44 min (retention time) (YMC S5 ODS column, 4.6x50 mm eluting with 10–90% MeOH/$H_2O$ over 4 minutes containing 0.1% TFA; 4 mL/min, monitoring at 220 nm). MS (ES): m/z 413.0 $[M+H]^+$.

EXAMPLE 16

Preparation of 3-Cyano-5-hydroxymethyl-4-(4-phenoxy-phenylamino)-pyrrolo[1,2-b]pyridazine-6-carboxylic acid ethyl ester (16C)

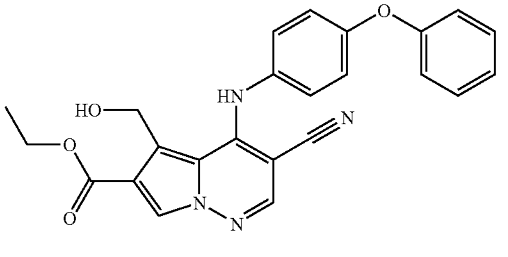

A. 5-Bromomethyl-4-chloro-3-cyano-pyrrolo[1,3-b]pyridazine-6-carboxylic acid ethyl ester (16A)

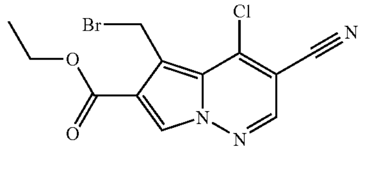

A suspension of compound 1D (79 mg, 0.30 mmol), NBS (59 mg, 0.33 mmol) and benzoyl peroxide (5 mg, 0.02 mmol) in $CCl_4$ (2 mL) was heated at 77° C. for 3 hours. After cooling to room temperature, the reaction was purified by a short silica gel column (eluted with $CH_2Cl_2$) to give compound 16A as a yellow solid (102 mg, 99%).

B. 4-Chloro-3-cyano-5-hydroxymethyl-pyrrolo[1,2-b]pyridazine-6-carboxylic acid ethyl ester (16B)

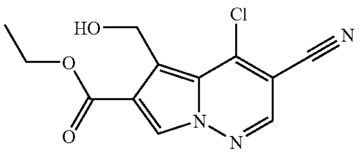

To a solution of compound 16A (102 mg, 0.30 mmol) in THF (12 mL) was added water (3 mL) dropwise. The reaction was kept at room temperature for 3 days and then heated to 50° C. for 3 hours. Upon cooling to room temperature, $NaHCO_3$ (70 mg) was added to the reaction mixture. The reaction was concentrated to dryness, redissolved in $CH_2Cl_2$ and filtered. The filtrate was concentrated to give compound 16B as a yellow solid (84 mg, 100%). This compound was used in the following steps without further purification.

C. 3-Cyano-5-hydroxymethyl-4-(4-phenoxy-phenylamino)-pyrrolo[1,2-b]pyridazine-6-carboxylic acid ethyl ester (16C)

A solution of compound 16B (84 mg, 0.30 mmol), 4-phenoxyaniline (72 mg, 0.39 mmol) and triethylamine (0.083 mL, 0.60 mmol) in THF (2.5 mL) was heated at 70° C. for 30 min. After cooled to room temperature, the reaction was concentrated to about 0.5 mL, diluted with MeOH (2 mL) and filtered. The solid was washed with MeOH and dried to give compound 16C as yellow solid (118 mg, 92%). HPLC: 92% at 2.12 min (retention time) (Prime Sphere 5u C18-HC column. 4.6x30 mm eluting with 10–90% MeOH/$H_2O$ over 2 minutes containing 0.1% TFA; 5 mL/min, monitoring at 220 nm). MS (ES): m/z 429.0 $[M+H]^+$.

EXAMPLE 17

Preparation of 3-Cyano-5-methoxymethyl-4-(4-phenoxy-phenylamino)-pyrrolo[1,2-b]pyridazine-6-carboxylic acid ethyl ester (17B)

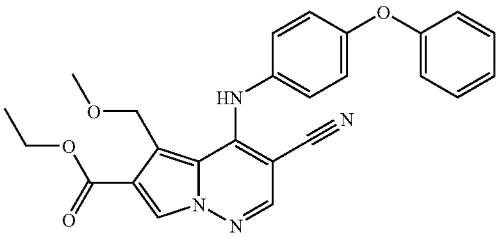

A. 4-Chloro-3-cyano-5-methoxymethyl-pyrrolo[1,2-b]pyridazine-6-carboxylic acid ethyl ester (17A)

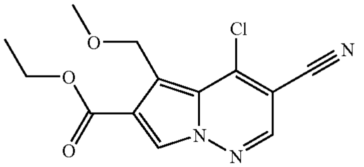

To a solution of compound 16A (31 mg, 0.09 mmol) in 1:1 MeOH:$CH_2Cl_2$ (2 mL) was added $NaHCO_3$ (30 mg, 0.36 mmol). The reaction was kept at room temperature for 3 h, heated to 70° C. for 1 h, cooled to room temperature, concentrated to dryness, redissolved in $CH_2Cl_2$ and filtered. The filtrate was concentrated to give compound 17A as a yellow solid (26 mg, 98%).

B. 3-Cyano-5-methoxymethyl-4-(4-phenoxy-phenylamino)-pyrrolo[1,2-b]pyridazine-6-carboxylic acid ethyl ester (17B)

Compound 17B was made in accordance with the procedure described in Example 16C. HPLC: 96% at 2.24 min (retention time) (PrimeSphere 5 u C18-HC column, 4.6x30 mm eluting with 10–90% MeOH/$H_2O$ over 2 minutes containing 0.1% TFA; 5 mL/min, monitoring at 220 nm). MS (ES): m/z 443.0 $[M+H]^+$.

EXAMPLE 18

Preparation of 3-Cyano-5-formyl-4-(4-phenoxy-phenylamino)-pyrrolo[1,2-b]pyridazine-6-carboxylic acid ethyl ester (18)

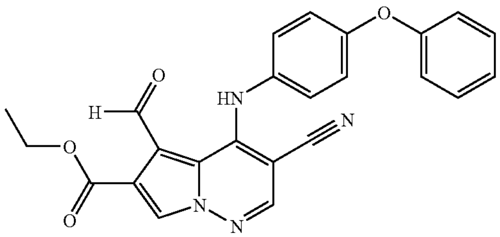

To a solution of compound 16C (21.4 mg, 0.05 mmol) in chloroform (1 mL) was added $MnO_2$ (<5 micron, activated, 17 mg, 0.20 mmol). The reaction was heated at 55° C. overnight, cooled to room temperature and purified by flash chromatography on a silica gel column (0–2% EtOAc/$CH_2Cl_2$) to give compound 18 as a yellow solid (20 mg, 94%). HPLC: 94% at 2.20 min (retention time) (PrimeSphere 5u C18-HC column, 4.6x30 mm eluting with 10–90% MeOH/$H_2O$ over 2 minutes containing 0.1% TFA; 5 mL/min, monitoring at 200 nm). MS (ES): m/z 427.0 $[M+H]^+$.

EXAMPLE 19

Preparation of 1-[3-Cyano-5-methyl-4-(4-phenoxy-phenylamino)-pyrrolo[1,2-b]pyridazin-6-yl]-3-(2-morpholin-4-yl-ethyl)-urea (19-1) & 5-Methyl-6-(5-oxo-4,5-dihydro-tetrazol-1-yl)-4-(4-phenoxy-phenylamino)-pyrrolo[1,2-b]pyridazine-3-carbonitrile (19-2)

19-1

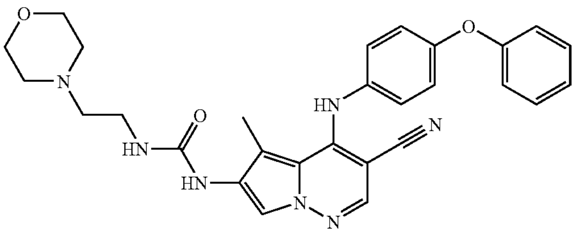

19-2

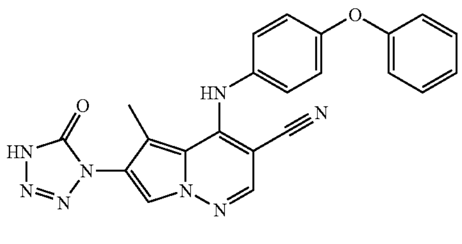

A solution of compound 9 (115 mg, 0.30 mmol), triethylamine (0.063 mL, 0.45 mmol) and DPPA (0.97 mL, 0.45 mmol) in dioxane (5 mL) was stirred overnight. The next day TMS-azide (0.08 mL, 0.60 mmol) was added and the reaction temperature was brought to 80° C. The reaction was heated at 80° C. for 2 hours, cooled to room temperature and 4-(2-aminoethyl)morpholine (0.079 mL, 0.06 mmol) was added. The reaction was stirred at room temperature for 1 h, concentrated and purified by flash chromatography on a sila gel column (3–6% MeOH/$CH_2Cl_2$) to give a mixture of compounds 19-1 and 19-2 as a yellow oil. This oil was recrystalized from MeOH to give compound 19-1 as a yellow solid (116 mg, 76%). 19-1: HPLC: 97% at 3.11 min (retention time) (YMC S5 ODS column, 4.6x50 mm eluting with 10–90% MeOH/$H_2O$ over 4 minutes containing 0.1% TFA, 4 mL/min, monitoring at 220 nm). MS (ES): m/z 512.0 $[M+H]^+$.

The mother liquor from the above recrystallization was passed through a SCX cartridge (500 mg) and eluted with MeOH (5 mL). The elutant was concentrated to give compound 19-2 as a yellow solid (9 mg, 7%). 19-2: HPLC: 94% at 1.93 min (retention time) (PrimeSphere 5u C18-HC column, 4.6x30 mm eluting with 10–90% MeOH/$H_2O$ over 2 minutes containing 0.1% TFA; 5 mL/min, monitoring at 220 nm). MS (ES): m/z 424.0 $[M+H]^+$.

EXAMPLES 20 TO 144

Further compounds of the present invention were prepared by procedures analogous to those described above. Table 1 provides the name and structure or representative compounds and their retention times, as well as the Example number of the procedure on which the preparation of the compound was based. The chromatography techniques used to determine the retention times of the compounds listed in Table 1 are as follows:

LCMS=YMC S5 ODS column, 4.6x50 mm eluting with 10–90% MeOH/$H_2O$ over 4 minutes containing 0.1% TFA; 4 mL/min, monitoring at 220 nm.

LCMS*=YMC S5 ODS column, 4.6x50 mm eluting with 10–90% MeOH/$H_2O$ over 2 minutes containing 0.1% TFA; 4 mL/min, monitoring at 220 nm.

LCMS-1=PrimeSphere 5u C18-HC column, 4.6x30 mm eluting with 10–90% MeOH/$H_2O$ over 2 minutes containing 0.1% TFA; 5 mL/min, monitoring at 220 nm.

LC=YMC S5 S5 ODS column 4.6x50 mm eluting with 10–90% MeOH/$H_2O$ over 4 minutes containing 0.2% phosphate acid, 4 mL/min, monitoring at 220 nm.

LC*=YMC S5 ODs column 4.6x50 mm eluting wiht 10–90% MeOH/$H_2O$ over 4 minutes containing 0.2% phosphoric acid, 4 mL/min, monitoring at 220 nm.

The molecular mass of the compounds listed in Table 1 were determined by MS (ES) by the formula m/z.

TABLE 1

| Ex. No. | Compound Structure | Compound Name | Retention Time Min./ Molecular Mass | Proc. of Ex. |
|---|---|---|---|---|
| 20 | 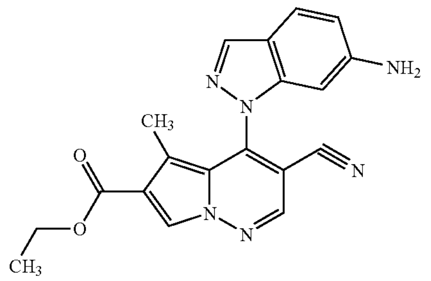 | 4-(6-Amino-1H-indazol-1-yl)-3-cyano-5-methylpyrrolo[1,2-b]pyridazine-6-carboxylic acid, ethyl ester | 3.42 LC $[M + H]^+$ = 361.0 | 1 |
| 21 | 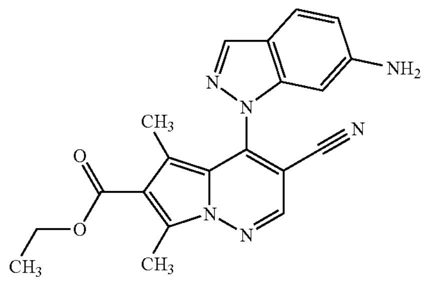 | 4-(6-Amino-1H-indazol-1-yl)-3-cyano-5,7-dimethylpyrrolo[1,2-b]pyridazine-6-carboxylic acid, ethyl ester | 3.59 LC $[M + H]^+$ = 375.0 | 1 |

TABLE 1-continued

| Ex. No. | Compound Structure | Compound Name | Retention Time Min./ Molecular Mass | Proc. of Ex. |
|---|---|---|---|---|
| 22 | 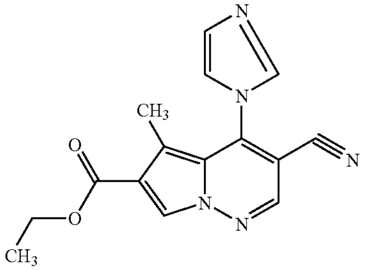 | 3-Cyano-4-(1-H-imidazol-1-yl)-5-methylpyrrolo]1,2-b]pyridazine-6-carboxylic acid, ethyl ester | 2.79 LC $[M + H]^+$ = 296.0 | 1 |
| 23 | 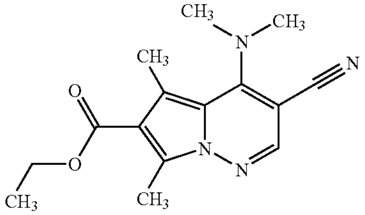 | 3-Cyano-4-(dimethylamino)-5,7-dimethylpyrrolo[1,2-b]pyridazine-6-carboxylic acid, ethyl ester | 4.27 LC $[M + H]^+$ = 287.0 | 1 |
| 24 | 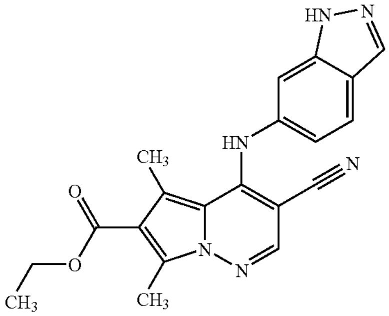 | 3-Cyano-4-(1-H-indazol-6-ylamino)-5,7-dimethylpyrrolo[1,2-b]pyridazine-6-carboxylic acid, ethyl ester | 4.06 LC $[M + H]^+$ = 375.0 | 1 |
| 25 | 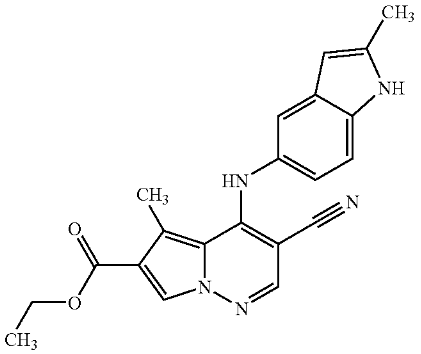 | 3-Cyano-5-methyl-4-[(2-methyl-1H-indol-5-yl)amino]pyrrolo[1,2-b]pyridazine-6-carboxylic acid, ethyl ester | 4.22 LC $[M + H]^+$ = 374.0 | 1 |
| 26 | 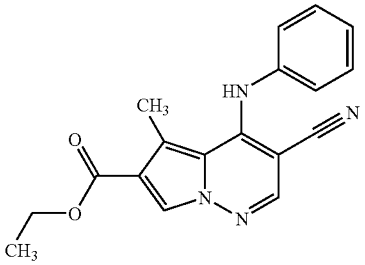 | 3-Cyano-5-methyl-4-(phenylamino)-pyrrolo[1,2-b]pyridazine-6-carboxylic acid, ethyl ester | 4.07 LC $[M + H]^+$ = 321.0 | 1 |

TABLE 1-continued

| Ex. No. | Compound Structure | Compound Name | Retention Time Min./ Molecular Mass | Proc. of Ex. |
|---|---|---|---|---|
| 27 | 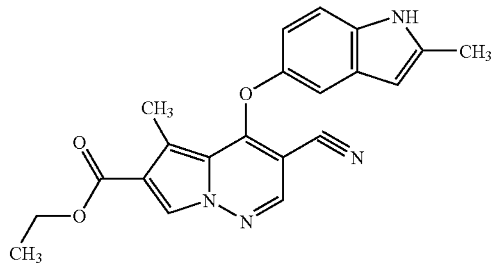 | 3-Cyano-5-methyl-4-[(2-methyl-1H-indol-5-yl)oxy]pyrrolo[1,2-b]pyridazine-6-carboxylic acid, ethyl ester | 3.80 LCMS $[M + H]^+$ = 375.0 | 2 |
| 28 | 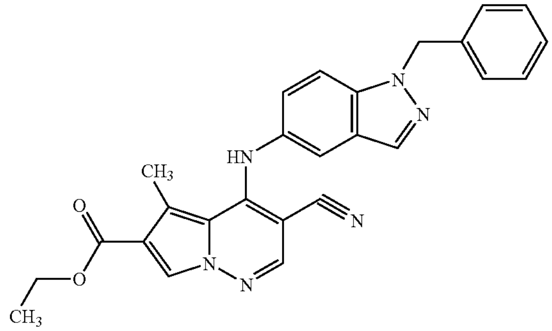 | 3-Cyano-5-methyl-4-[[1-(phenylmethyl)-1H-indazol-5-yl]amino]pyrrolo[1,2-b]pyridazine-6-carboxylic acid, ethyl ester | 4.31 LC $[M + H]^+$ = 451.0 | 1 |
| 29 | 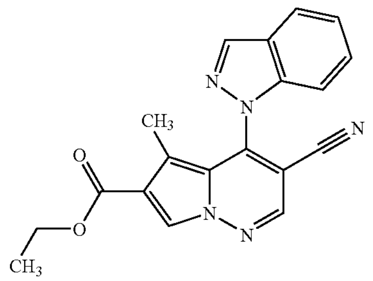 | 3-Cyano-5-methyl-4-(1H-indazol-1-yl)pyrrolo[1,2-b]pyridazine-6-carboxylic acid, ethyl ester | 4.04 LC $[M + H]^+$ = 346.0 | 1 |
| 30 | 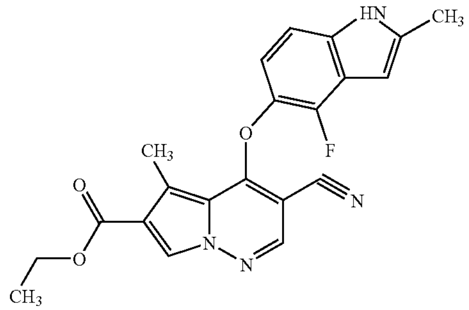 | 3-Cyano-4-[(4-fluoro-2-methyl-1H-indol-5-yl)oxy]-5-methylpyrrolo[1,2-b]pyridazine-6-carboxylic acid, ethyl ester | 3.86 LC $[M + H]^+$ = 393.0 | 1 |

TABLE 1-continued

| Ex. No. | Compound Structure | Compound Name | Retention Time Min./ Molecular Mass | Proc. of Ex. |
|---|---|---|---|---|
| 31 | 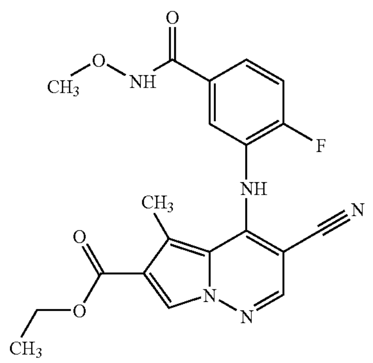 | 3-Cyano-4-[[2-fluoro-5-[(methyoxyamino)car-bonyl]phenyl]-amino]-5-methylpyrrolo[1,2-b]pyridazine-6-carboxylic acid, ethyl ester | 4.23 LC $[M + H]^+$ = 412.0 | 1 |
| 32 | 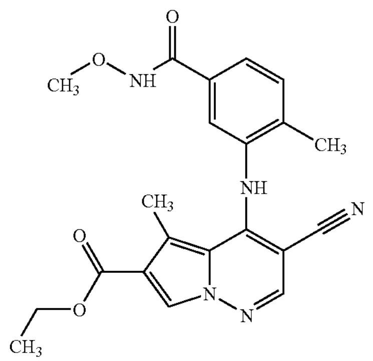 | 3-Cyano-4-[[5-[(methoxyamino)car-bonyl]-2-methylphenyl]-amino]-5-methylpyrrolo[1,2-b]pyridazine-6-carboxylic acid, ethyl ester | 4.19 LC $[M + H]^+$ = 408.0 | 1 |
| 33 | 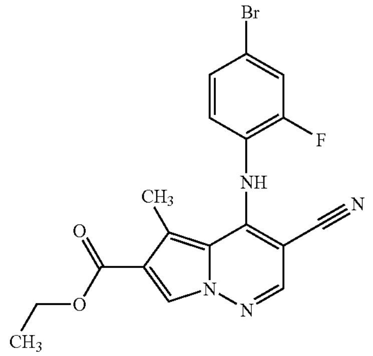 | 4-[(4-Bromo-2-fluorophenyl)amino]-3-cyano-5-methylpyrrolo[1,2-b]pyridazine-6-carboxylic acid, ethyl ester | 4.32 LC | 1 |
| 34 | 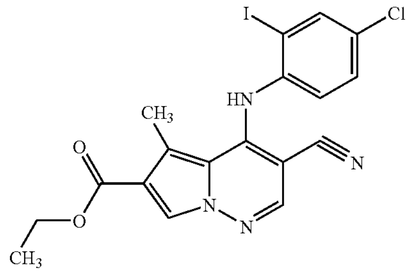 | 4-[(4-Chloro-2-iodophenyl)amino]-3-cyano-5-methylpyrrolo[1,2-b]pyridazine-6-carboxylic acid, ethyl ester | 4.37 LC $[M + H]^+$ = 481.0 | 1 |

TABLE 1-continued

| Ex. No. | Compound Structure | Compound Name | Retention Time Min./ Molecular Mass | Proc. of Ex. |
|---|---|---|---|---|
| 35 | 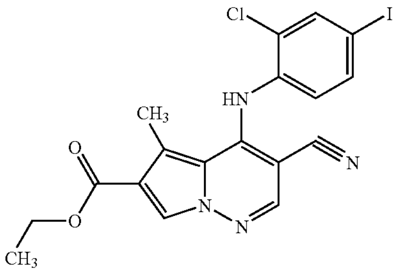 | 4-[(2-Chloro-4-iodophenyl)amino]-3-cyano-5-methylpyrrolo[1,2-b]pyridazine-6-carboxylic acid, ethyl ester | 4.51 LC $[M + Na^+]^+$ = 503.0 | |
| 36 | 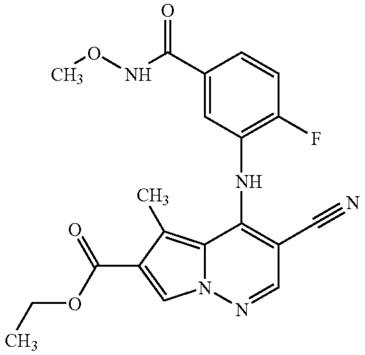 | 3-Cyano-4-[[2-fluoro-5-[(methoxyamino)carbonyl]phenyl]-amino]-5-methylpyrrolo[1,2-b]pyridazine-6-carboxylic acid, ethyl ester | 4.24 LC $[M + H]^+$ = 412.0 | 1 |
| 37 | 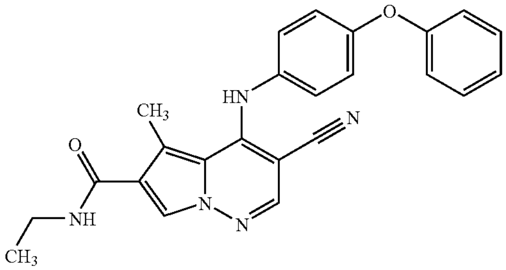 | 3-Cyano-N-ethyl-5-methyl-4-[(4-phenoxy-phenyl)amino] pyrrolo[1,2-b]pyridazine-6-carboxamide | 1.85 LC* $[M + H]^+$ = 412.0 | 10 |
| 38 | 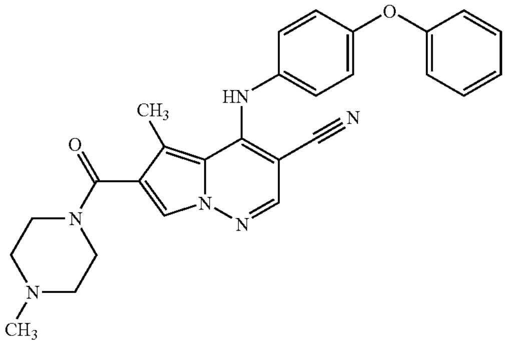 | 1-[[3-Cyano-5-methyl-4-[(4-phenoxy-phenyl)amino] pyrrolo[1,2-b]pyridazin-6-yl]carbonyl]-4-methylpiperazine | 1.53 LC* $[M + H]^+$ = 467.0 | 10 |
| 39 | 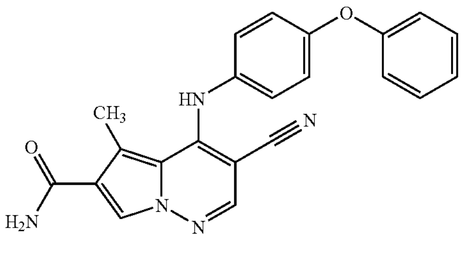 | 3-Cyano-5-methyl-4[(4-phenoxy-phenyl)amino] pyrrolo[1,2-b]pyridazine-6-carboxamide | 1.75 LC* [M + H] = 384.0 | 10 |

TABLE 1-continued

| Ex. No. | Compound Structure | Compound Name | Retention Time Min./ Molecular Mass | Proc. of Ex. |
|---|---|---|---|---|
| 40 | 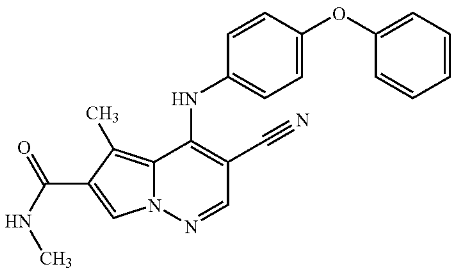 | 3-Cyano-N,5-dimethyl-4-[(4-phenoxy-phenyl)amino] pyrrolo[1,2-b]pyridazine-6-carboxamide | 1.79 LC* $[M + H]^+$ = 398.0 | 10 |
| 41 | 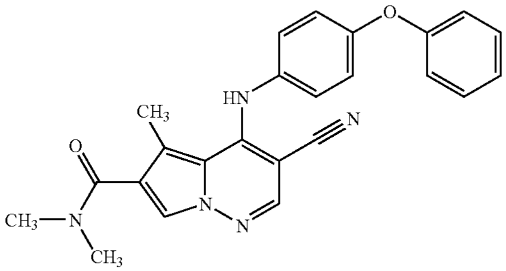 | 3-Cyano-N,N,5-trimethyl-4-[(4-phenoxy-phenyl)amino]pyrrolo [1,2-b]pyridazine-6-carboxamide | 1.78 LC* $[M + H]^+$ = 412.0 | 10 |
| 42 | 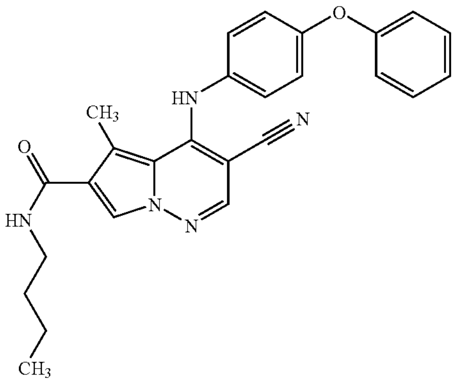 | N-Butyl-3-cyano-5-methyl-4-[(4-phenoxy-phenyl)amino] pyrrolo[1,2-b]pyridazine-6-carboxamide | 2.00 LC* $[M + H]^+$ = 440.0 | 10 |
| 43 | 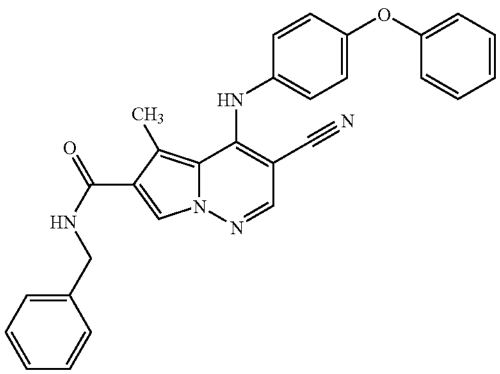 | 3-Cyano-5-methyl-4-[(4-phenoxy-phenyl)amino]-N-(phenylmethyl) pyrrolo [1,2-b]pyridazine-6-carboxamide | 2.00 LC* $[M + H]^+$ = 474.0 | 10 |

TABLE 1-continued

| Ex. No. | Compound Structure | Compound Name | Retention Time Min./ Molecular Mass | Proc. of Ex. |
|---|---|---|---|---|
| 44 | 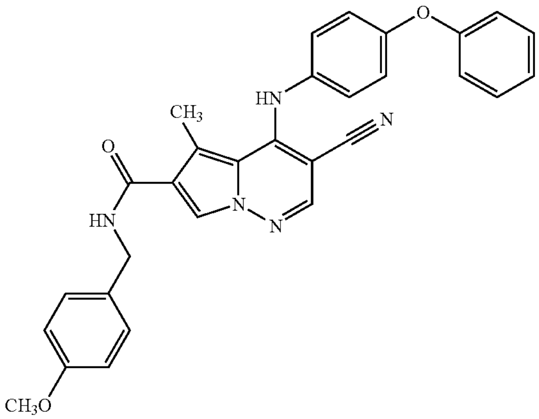 | 3-Cyano-N-[(4-methoxyphenyl) methyl]-5-methyl-4-[(4-phenoxyphenyl) amino]pyrrolo[1,2-b]pyridazine-6-carboxamide | 1.98 LC* $[M + H]^+$ = 504.0 | 10 |
| 45 | 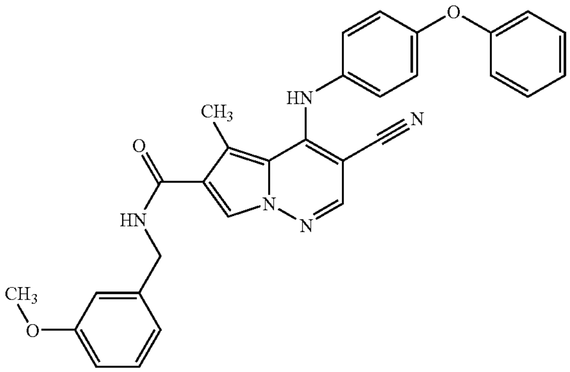 | 3-Cyano-N-[(3-methoxyphenyl) methyl -5-methyl-4-[(4-phenoxy-phenyl)amino] pyrrolo[1,2-b]pyridazine-6-carboxamide | 2.10 LC* $[M + H]^+$ = 504.0 | 10 |
| 46 | 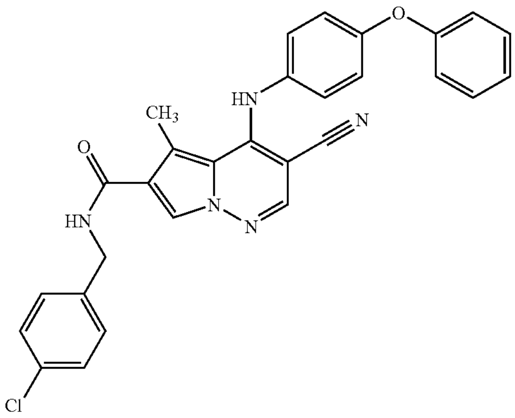 | N-[(4-Chlorophenyl) methyl]-3-cyano-5-methyl-4-[(4-phenoxy-phenyl)amino] pyrrolo[1,2-b]pyridazine-6-carboxamide | 2.09 LC* $[M + H]^+$ = 508.0 | 10 |

TABLE 1-continued

| Ex. No. | Compound Structure | Compound Name | Retention Time Min./ Molecular Mass | Proc. of Ex. |
|---|---|---|---|---|
| 47 | 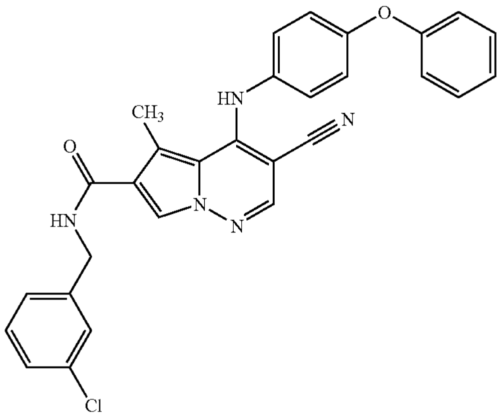 | N-[(3-Chlorophenyl) methyl]-3-cyano-5-methyl-4-[(4-phenoxy-phenyl)amino] pyrrolo[1,2-b]pyridazine-6-carboxamide | 2.08 LC* [M + H]+ = 508.0 | 10 |
| 48 | 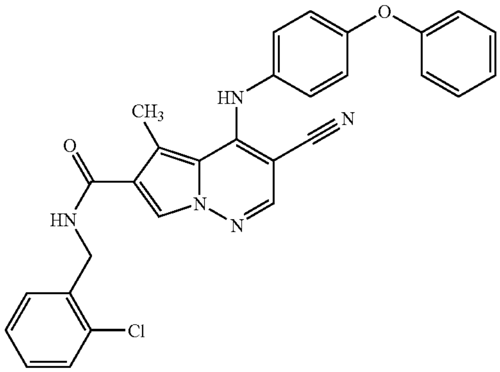 | N-[(2-Chlorophenyl) methyl]-3-cyano-5-methyl-4-[(4-phenoxy-phenyl)amino] pyrrolo[1,2-b]pyridazine-6-carboxamide | 2.06 LC* [M + H]+ = 508.0 | 10 |
| 49 | 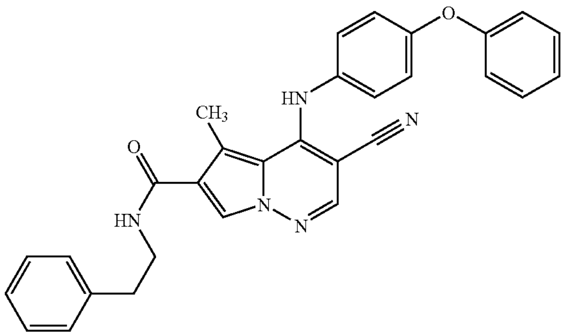 | 3-Cyano-5-methyl-4[(4-phenoxy-phenyl)amino]-N-(2-phenylethyl)pyrrolo [1,2-b]pyridazine-6-carboxamide | 2.04 LC* [M + H]+ = 488.0 | 10 |
| 50 | 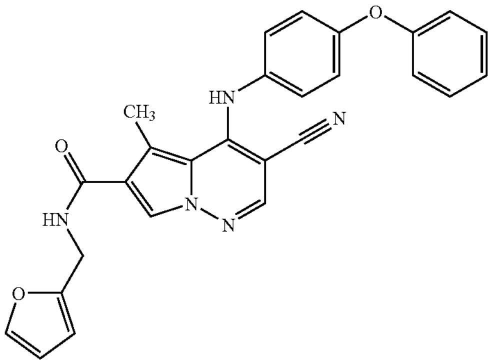 | 3-Cyano-N-(2-furanylmethyl)-5-methyl-4-[(4-phenoxy-phenyl)amino]pyrrolo [1,2-b]pyridazine-6-carboxamide | 1.92 LC* [M + H]+ = 464.0 | 10 |

TABLE 1-continued

| Ex. No. | Compound Structure | Compound Name | Retention Time Min./ Molecular Mass | Proc. of Ex. |
|---|---|---|---|---|
| 51 | 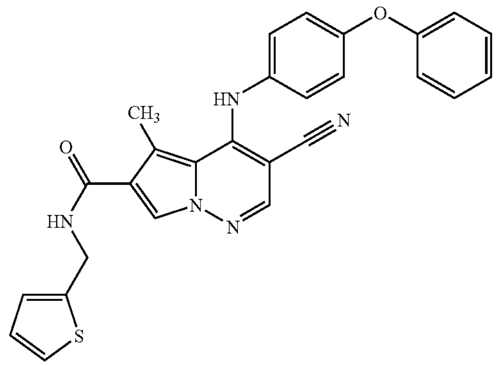 | 3-Cyano-5-methyl-4-[(4-phenoxy-phenyl)amino]-N-(2-thienylmethyl)pyrrolo[1,2-b]pyridazine-6-carboxamide | 1.97 LC* $[M + H]^+$ = 480.0 | 10 |
| 52 | 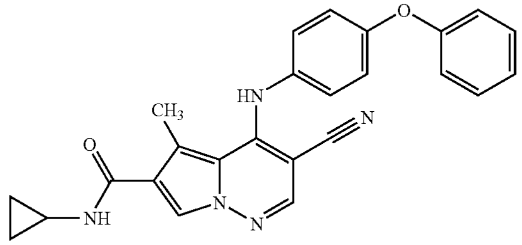 | 3-Cyano-N-cyclopropyl-5-methyl-4-[(4-phenoxy-phenyl)amino]pyrrolo[1,2-b]pyridazine-6-carboxamide | 1.86 LC* $[M + H]^+$ = 424.0 | 10 |
| 53 | 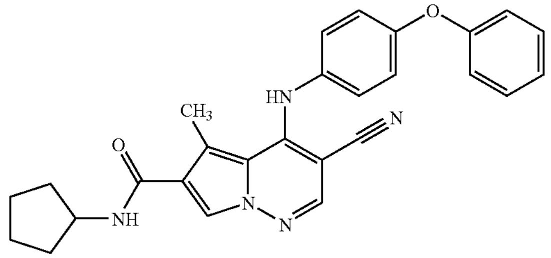 | 3-Cyano-N-cyclopentyl-5-methyl-4-[(4-phenoxy-phenyl)amino]pyrrolo[1,2-b]pyridazine-6-carboxamide | 1.99 LC* $[M + H]^+$ = 452.0 | 10 |
| 54 | 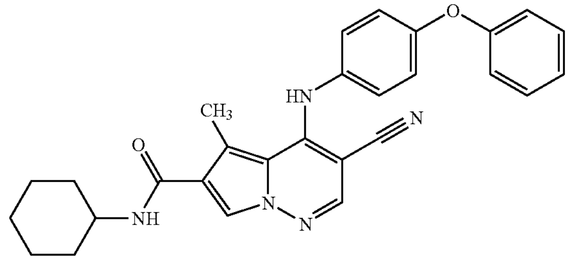 | 3-Cyano-N-cyclohexyl-5-methyl-4-[(4-phenoxy-phenyl)amino]pyrrolo[1,2-b]pyridazine-6-carboxamide | 2.07 LC* $[M + H]^+$ = 466.0 | 10 |
| 55 | 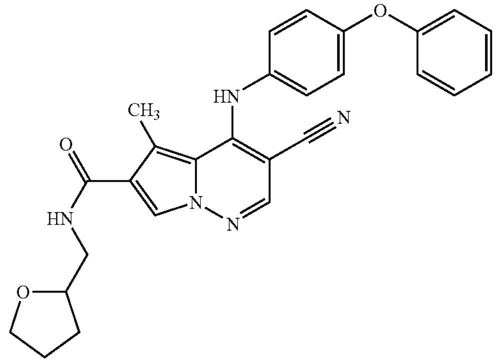 | 3-Cyano-5-methyl-4-[(4-phenoxy-phenyl)amino]-N-[(tetrahydro-2-furanyl)methyl]pyrr-olo[1,2-b]pyridazine-6-carboxamide | 1.89 LC* $[M + H]^+$ = 468.0 | 10 |

TABLE 1-continued

| Ex. No. | Compound Structure | Compound Name | Retention Time Min./ Molecular Mass | Proc. of Ex. |
|---|---|---|---|---|
| 56 | 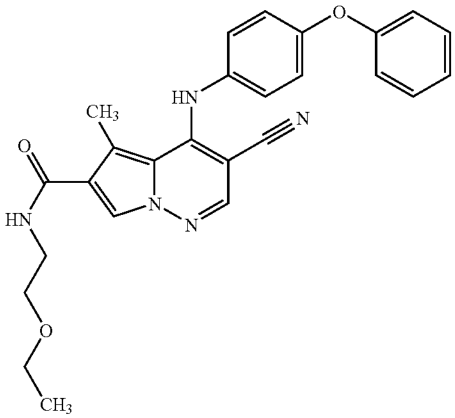 | 3-Cyano-N-(2-ethoxyethyl)-5-methyl-4-[(4-phenoxy-phenyl)amino] pyrrolo[1,2-b]pyridazine-6-carboxamide | 1.90 LC* $[M + H]^+$ = 456.0 | 10 |
| 57 | 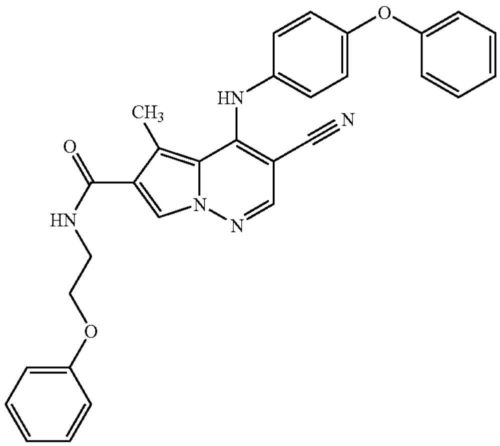 | 3-Cyano-5-methyl-N-(2-phenoxyethyl)-4-[(4-phenoxy-phenyl)amino]pyrrolo [1,2-b]pyridazine-6-carboxamide | 2.05 LC* $[M + H]^+$ = 504.0 | 10 |
| 58 | 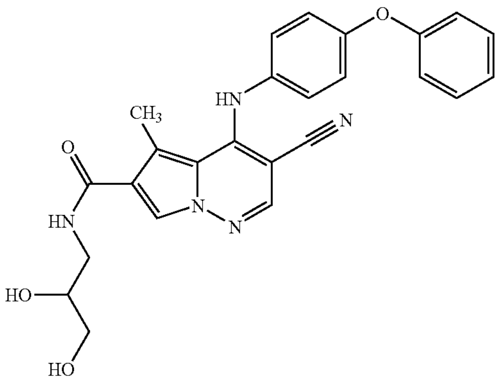 | 3-Cyano-N-(2,3-dihydroxypropyl)-5-methyl-4-[(4-phenoxy-phenyl)amino] pyrrolo[1,2-b]pyridazine-6-carboxamide | 1.69 LC* $[M + H]^+$ = 458.0 | 10 |

TABLE 1-continued

| Ex. No. | Compound Structure | Compound Name | Retention Time Min./ Molecular Mass | Proc. of Ex. |
|---|---|---|---|---|
| 59 | 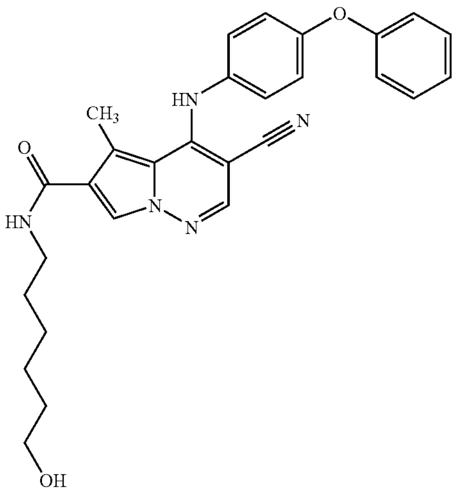 | 3-Cyano-N-(6-hydroxyhexyl)-5-methyl-4-[(4-phenoxy-phenyl)amino] pyrrolo[1,2-b]pyridazine-6-carboxamide | 1.87 LC* $[M + H]^+$ = 484.0 | 10 |
| 60 | 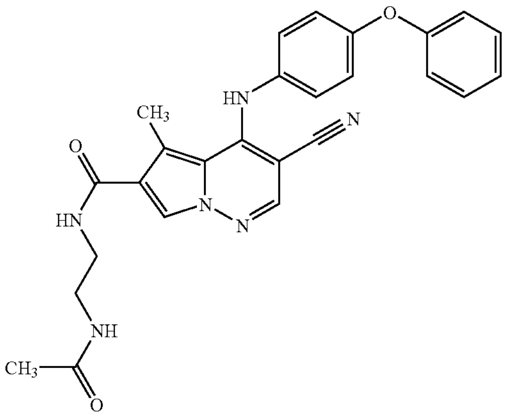 | N-[2-(Acetylamino)ethyl]-3-cyano-5-methyl-4-[(4-phenoxy-phenyl)amino] pyrrolo[1,2-b]pyridazine-6-carboxamide | 1.74 LC* $[M + H]^+$ = 469.0 | 10 |
| 61 | 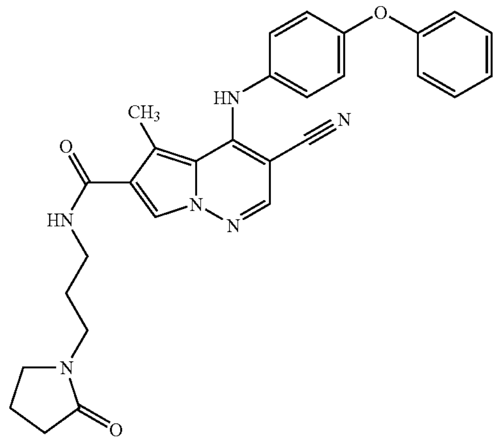 | 3-Cyano-5-methyl-N-[3-(2-oxo-1-pyrrolidinyl)propyl]-4-[(4-phenoxy-phenyl)amino] pyrrolo[1,2-b]pyridazine-6-carboxamide | 1.81 LC* $[M + H]^+$ = 509.0 | 10 |

TABLE 1-continued

| Ex. No. | Compound Structure | Compound Name | Retention Time Min./ Molecular Mass | Proc. of Ex. |
|---|---|---|---|---|
| 62 | 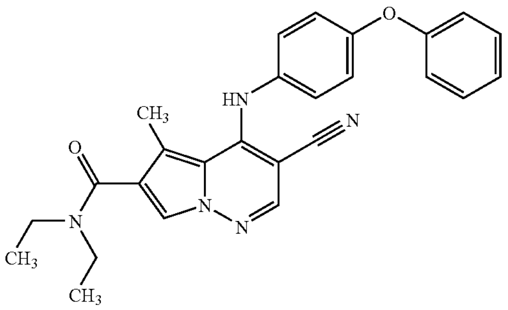 | 3-Cyano-N,N-diethyl-5-methyl-4-[(4-phenoxy-phenyl)amino] pyrrolo[1,2-b]pyridazine-6-carboxamide | 1.90 LC* [M + H]+ = 440.0 | 10 |
| 63 | 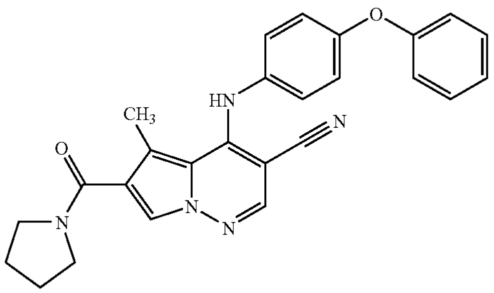 | 1-[[3-Cyano-5-methyl-4-[(4-phenoxy-phenyl)amino] pyrrolo[1,2-b]pyridazin-6-yl]carbonyl] pyrrolidine | 1.88 LC* [M + H]+ = 438.0 | 10 |
| 64 | 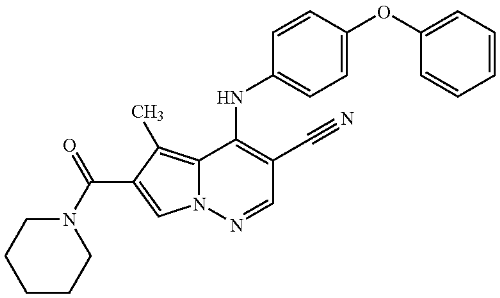 | 1-[[3-Cyano-5-methyl-4-[(4-phenoxy-phenyl)amino] pyrrolo[1,2-b]pyridazin-6-yl]carbonyl]piperidine | 1.96 LC* [M + H]+ = 452.0 | 10 |
| 65 | 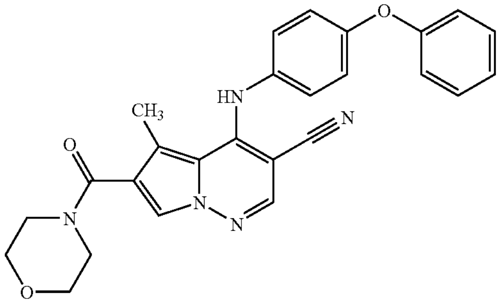 | 4-[[3-Cyano-5-methyl-4-[(4-phenoxy-phenyl)amino] pyrrolo[1,2-b]pyridazin-6-yl]carbonyl] morpholine | 1.76 LC* [M + H]+ = 454.0 | 10 |

TABLE 1-continued

| Ex. No. | Compound Structure | Compound Name | Retention Time Min./ Molecular Mass | Proc. of Ex. |
|---|---|---|---|---|
| 66 | 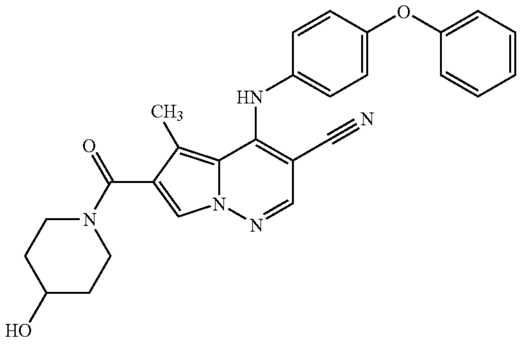 | 1-[[3-Cyano-5-methyl-4-[(4-phenoxy-phenyl)amino] pyrrolo[1,2-b]pyridazin-6-yl]carbonyl]-4-hydroxypiperidine | 1.74 LC* $[M + H]^+$ = 468.0 | 10 |
| 67 | 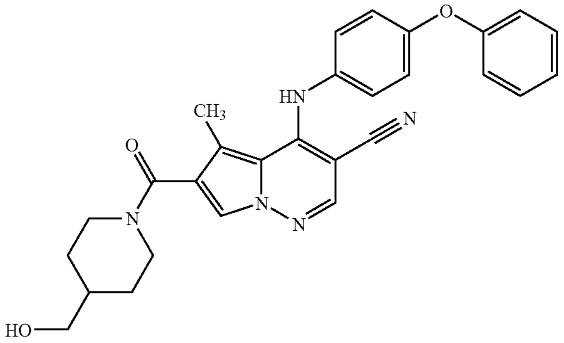 | 1-[[3-Cyano-5-methyl-4-[(4-phenoxy-phenyl)amino] pyrrolo[1,2-b]pyridazin-6-yl]carbonyl]-4-(hydroxymethyl) piper-idine | 1.76 LC* $[M + H]^+$ = 482.0 | 10 |
| 68 | 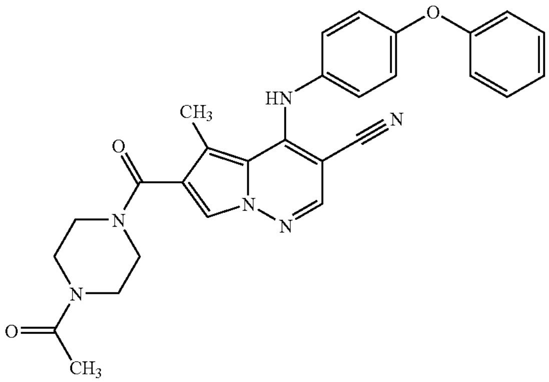 | 1-Acetyl-4-[[3-cyano-5-methyl-4-[(4-phenoxy-phenyl)amino] pyrrolo[1,2-b]pyridazin-6-yl]carbonyl]piper-azine | 1.69 LC* $[M + H]^+$ = 495.0 | 10 |
| 69 | 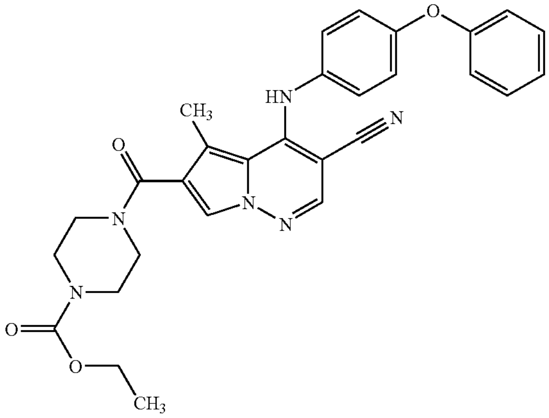 | 4-[[3-Cyano-5-methyl-4-[(4-phenoxy-phenyl)amino] pyrrolo[1,2-b]pyridazin-6-yl]carbonyl]-1-piperiazinecarboxylic acid, ethyl ester | 1.85 LC* $[M + H]^+$ = 525.0 | 10 |

TABLE 1-continued

| Ex. No. | Compound Structure | Compound Name | Retention Time Min./ Molecular Mass | Proc. of Ex. |
|---|---|---|---|---|
| 70 | 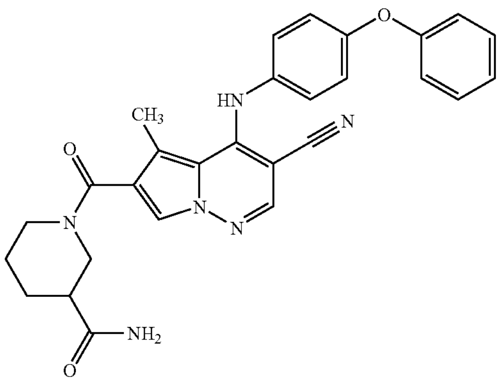 | 1-[[3-Cyano-5-methyl-4-[(4-phenoxy-phenyl)amino]pyrrolo[1,2-b]pyridazin-6-yl]carbonyl]-3-piperidinecarbox-amide | 1.72 LC* $[M + H]^+$ = 495.0 | 10 |
| 71 | 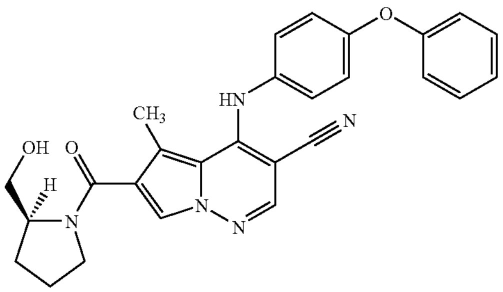 | (2S)-1-[[3-Cyano-5-methyl-4-[(4-phenoxy-phenyl)amino] pyrrolo[1,2-b]pyridazin-6-yl]carbonyl]-2-(hydroxymethyl)pyrr-olidone | 1.79 LC* $[M + H]^+$ = 468.0 | 10 |
| 72 | 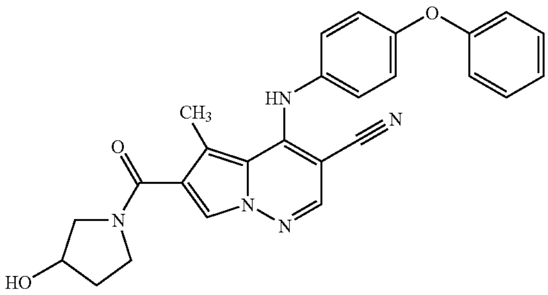 | 1-[[3-Cyano-6-methyl-4-[(4-phenoxy-phenyl)amino] pyrrolo[1,2-b]pyridazin-6-yl]carbonyl]-3-hydroxypyrrolidine | 1.70 LC* $[M + H]^+$ = 454.0 | 10 |
| 73 | 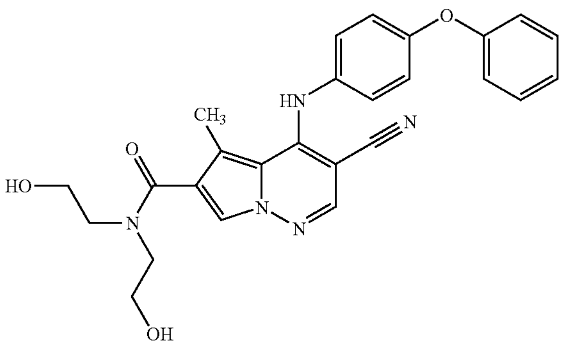 | 3-Cyano-N,N-bis(2-hydroxyethyl)-5-methyl-4-[(4-phenoxy-phenyl)amino] pyrrolo[1,2-b]pyridazine-6-carboxamide | 1.62 LC* $[M + H]^+$ = 472.0 | 10 |

TABLE 1-continued

| Ex. No. | Compound Structure | Compound Name | Retention Time Min./ Molecular Mass | Proc. of Ex. |
|---|---|---|---|---|
| 74 | 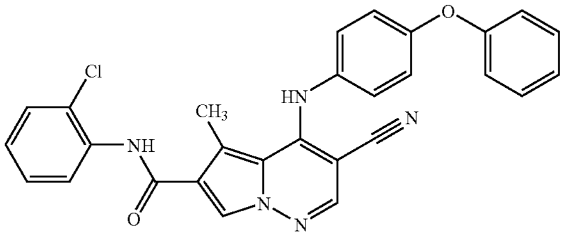 | N-(2-Chlorophenyl)-3-cyano-5-methyl-4-[(4-phenoxy-phenyl)amino] pyrrolo[1,2-b]pyridazine-6-carboxamide | 2.09 LC* $[M + H]^+$ = 494.0 | 10 |
| 75 | 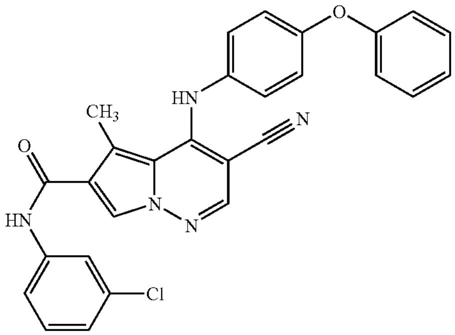 | N-(3-Chlorophenyl)-3-cyano-5-methyl-4-[(4-phenoxy-phenyl)amino] pyrrolo[1,2-b]pyridazine-6-carboxamide | 2.18 LC* $[M + H]^+$ = 494.0 | 10 |
| 76 | 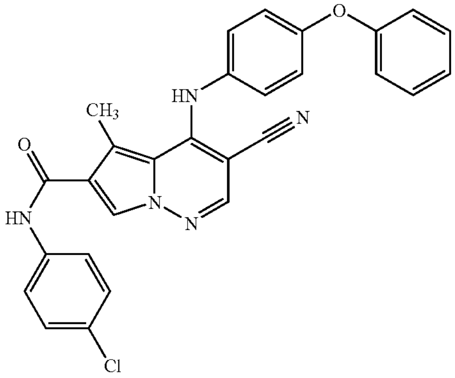 | N-(4-Chlorophenyl)-3-cyano-5-methyl-4-[(4-phenoxy-phenyl)amino] pyrrolo[1,2-b]pyridazine-6-carboxamide | 2.17 LC* $[M + H]^+$ = 494.0 | 10 |
| 77 | 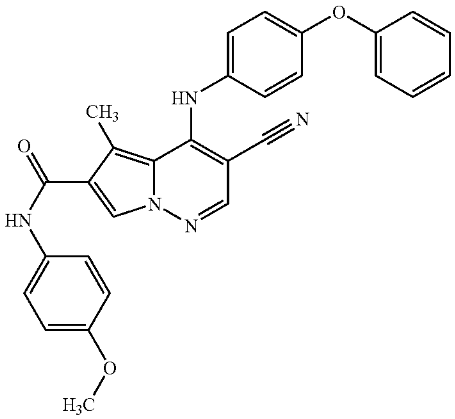 | 3-Cyano-N-(4-methoxyphenyl)-5-methyl-4-[(4-phenoxyphentl) amino] pyrrolo[1,2-b]pyridazine-6-carboxamide | 2.03 LC* $[M + H]^+$ = 490.0 | 10 |

TABLE 1-continued

| Ex. No. | Compound Structure | Compound Name | Retention Time Min./ Molecular Mass | Proc. of Ex. |
|---|---|---|---|---|
| 78 | 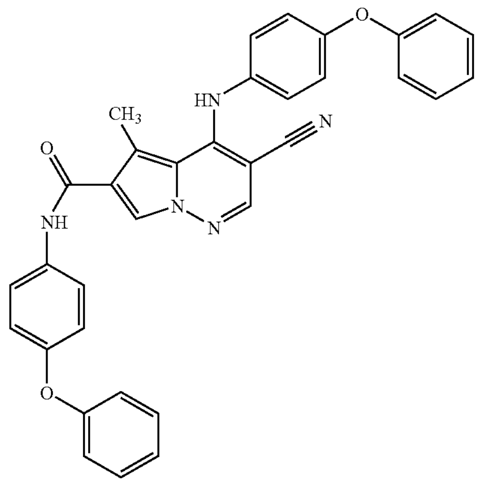 | 3-Cyano-5-methyl-N-(4-phenoxyphenyl)-4-[(4-phenoxy-phenyl)amino] pyrrolo[1,2-b]pyridazine-6-carboxamide | 2.26 LC* [M + H]+ = 552.0 | 10 |
| 79 | 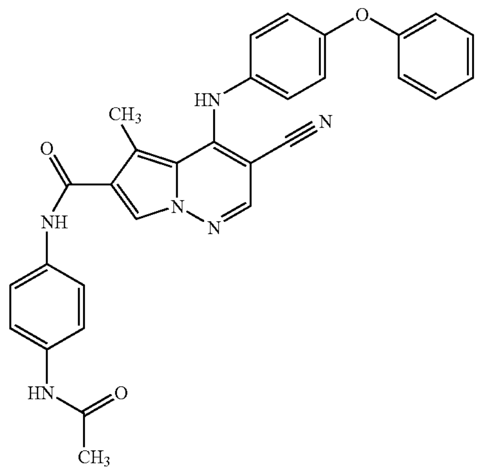 | N-[4-(Acetylamino)-phenyl]-3-cyano-5-methyl-4-[(4-phenoxy-phenyl)amino] pyrrolo[1,2-b]pyridazine-6-carboxamide | 1.91 LC* [M + H]+ = 517.0 | 10 |
| 80 | 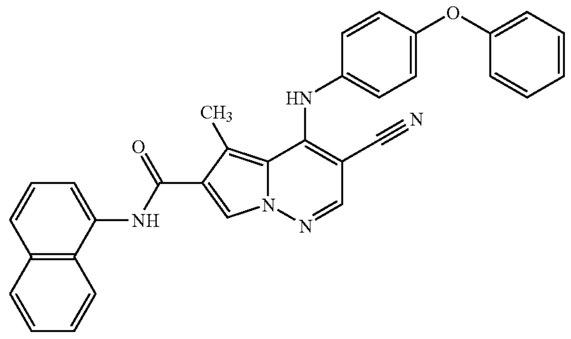 | 3-Cyano-5-methyl-N-1-naphthalenyl-4-[(4-phenoxy-phenyl)amino]pyrrolo [1,2-b]pyridazine-6-carboxamide | 2.09 LC* [M + H]+ = 510.0 | 10 |

TABLE 1-continued

| Ex. No. | Compound Structure | Compound Name | Retention Time Min./ Molecular Mass | Proc. of Ex. |
|---|---|---|---|---|
| 81 | 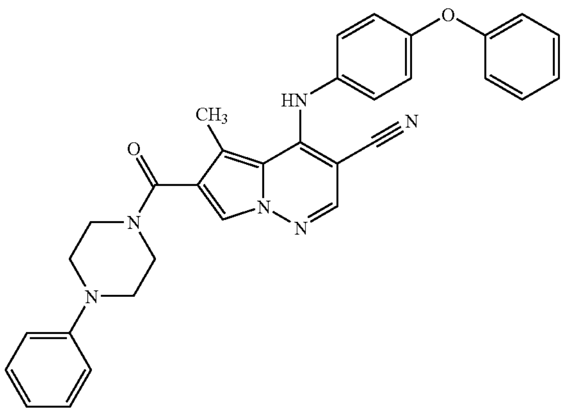 | 1-[[3-Cyano-5-methyl-4-[(4-phenoxy-phenyl)amino] pyrrolo[1,2-b]pyridazin-6-yl]carbonyl]-4-phenylpiperazine | 2.02 LC* $[M + H]^+$ = 529.0 | 10 |
| 82 | 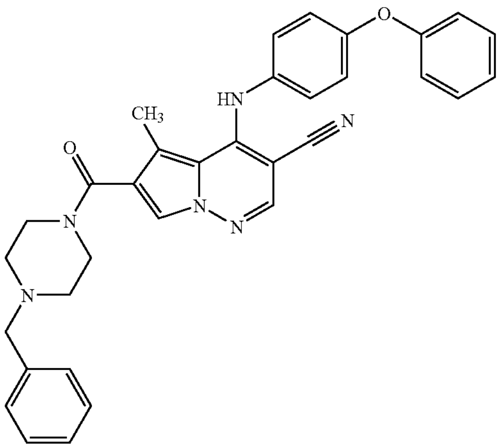 | 1-[[3-Cyano-5-methyl-4-[(4-phenoxy-phenyl)amino] pyrrolo[1,2-b]pyridazin-6-yl]carbonyl]-4-(phenylmethyl)piper-azine | 1.64 LC* $[M + H]^+$ = 543.0 | 10 |
| 83 | 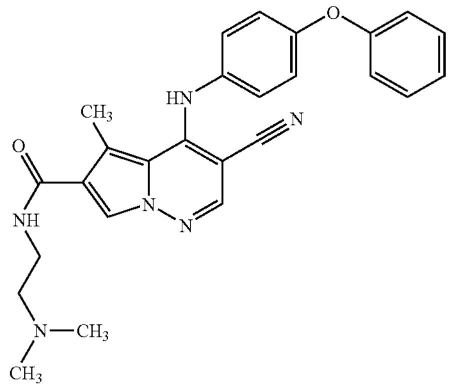 | 3-Cyano-N-[2-(dimethylamino) ethyl]-5-methyl-4-[(4-phenoxy-phenyl)amino] pyrrolo[1,2-b]pyridazine-6-carboxamide | 1.60 LC* $[M + H]^+$ = 455.0 | 10 |

TABLE 1-continued

| Ex. No. | Compound Structure | Compound Name | Retention Time Min./ Molecular Mass | Proc. of Ex. |
|---|---|---|---|---|
| 84 | 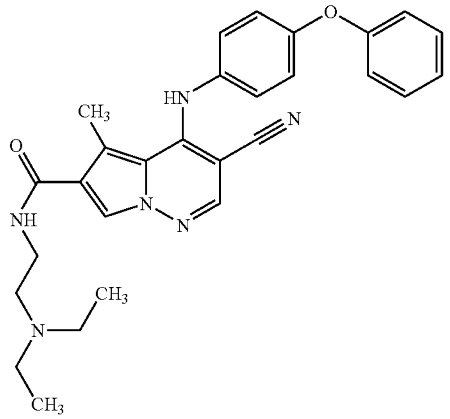 | 3-Cyano-N-[2-(diethylamino)ethyl]-5-methyl-4-[(4-phenoxy-phenyl)amino] pyrrolo[1,2-b]pyridazine-6-carfboxamide | 1.62 LC* [M + H]$^+$ = 483.0 | 10 |
| 85 | 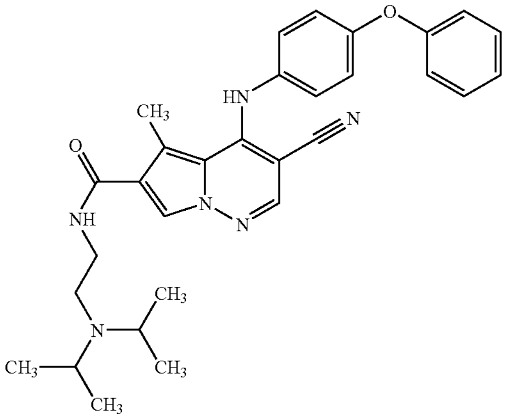 | N-[2-[Bis(1-methylethyl)amino] ethyl]-3-cyano-5-methyl-4-[(4-phenoxy-phenyl)amino] pyrrolo[1,2-b]pyridazine-6-carboxamide | 1.66 LC* [M + H]$^+$ = 511.0 | 10 |
| 86 | 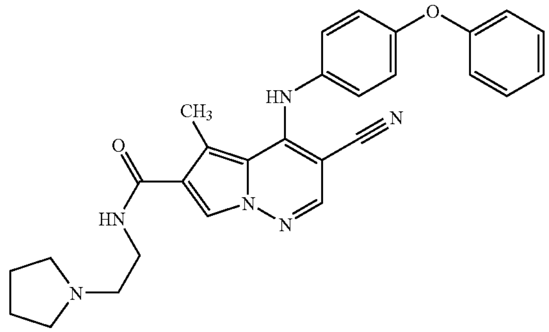 | 3-Cyano-5-methyl-4-[(4-phenoxy-phenyl)amino]-N-[2-(1-pyrrolidinyl)ethyl] pyrrolo[1,2-b]pyridazine-6-carboxamide | 1.62 LC* [M + H]$^+$ = 481.0 | 10 |
| 87 | 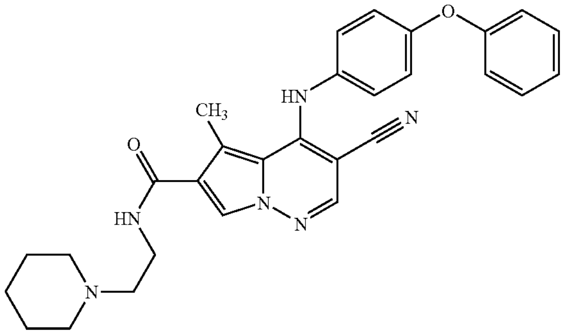 | 3-Cyano-5-methyl-4-[(4-phenoxy-phenyl)amino]-N-[2-(1-piperidinyl)ethyl] pyrrolo[1,2-b]pyridazine-6-carboxamide | 1.64 LC* [M + H]$^+$ = 495.0 | 10 |

TABLE 1-continued

| Ex. No. | Compound Structure | Compound Name | Retention Time Min./ Molecular Mass | Proc. of Ex. |
| --- | --- | --- | --- | --- |
| 88 | 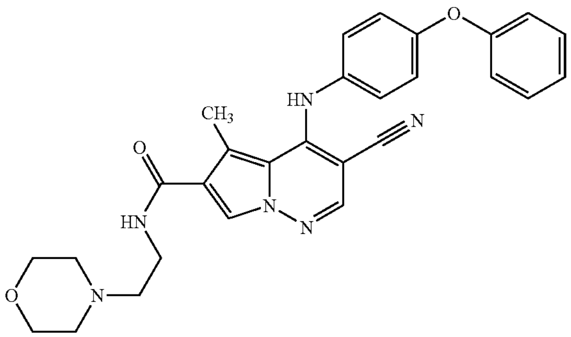 | 3-Cyano-5-mnethyl-4-[(4-phenoxy-phenyl)amino]-N-[2-(4-morpholinyl)ethyl] pyrrolo[1,2-b]pyridazine-6-carboxamide | 1.60 LC* $[M + H]^+$ = 497.0 | 10 |
| 89 | 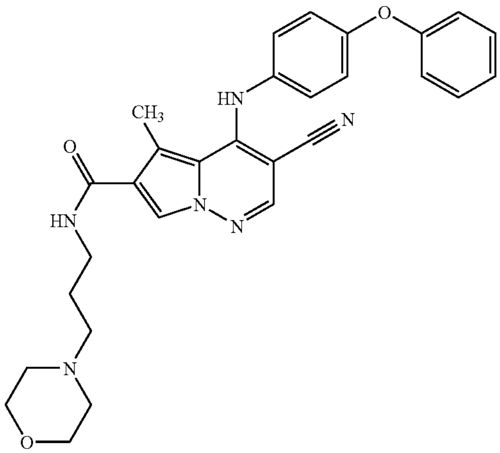 | 3-Cyano-5-methyl-N-[3-(4-morpholinyl)propyl]-4-[(4-phenopxyphenyl) amino] pyrrolo[1,2-b]pyridazine-6-carboxamide | 1.60 LC* $[M + H]^+$ = 511.0 | 10 |
| 90 | 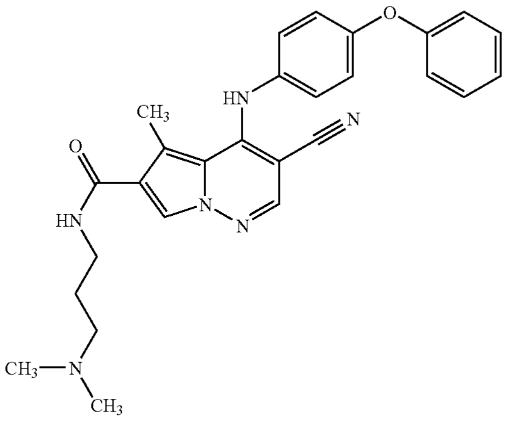 | 3-Cyano-N-[3-(dimethylamino)pro-pyl]-5-methyl-4-[(4-phenoxy-phenyl)amino] pyrrolo[1,2-b]pyridazine-6-carboxamide | 1.62 LC* $[M + H]^+$ = 469.0 | 10 |

TABLE 1-continued

| Ex. No. | Compound Structure | Compound Name | Retention Time Min./ Molecular Mass | Proc. of Ex. |
|---|---|---|---|---|
| 91 | 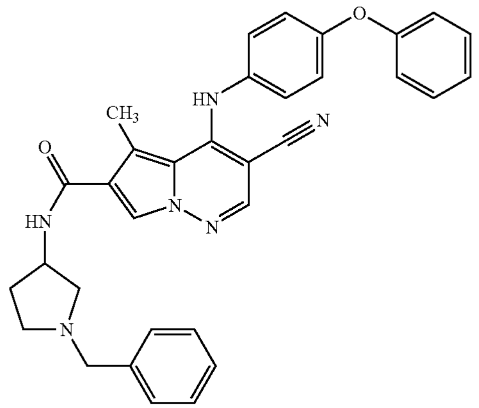 | 3-Cyano-5-methyl-4-[(4-phenoxy-phenyl)amino]-N-[1-(phenylmethyl)-34-pyrrolidinyl]pyrrolo[1,2-b]pyridazine-6-carboxamide | 1.71 LC* $[M + H]^+$ = 543.0 | 10 |
| 92 | 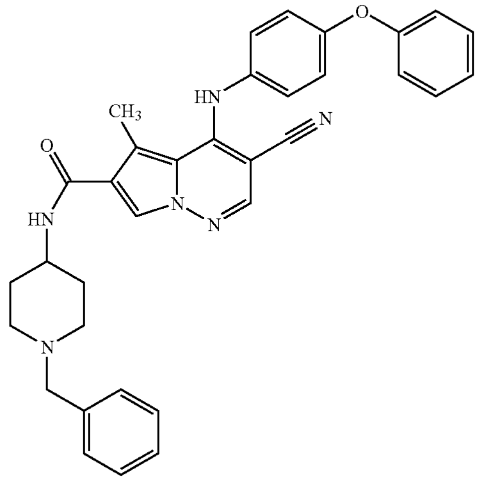 | 3-Cyano-5-methyl-4-[(4-phenoxy-phenyl)amino]-N-[1-(phenylmethyl)-4-piperidinyl]pyrrolo[1,2-b]pyridazine-6-carboxamide | 1.71 LC* $[M + H]^+$ = 557.0 | 10 |
| 93 | 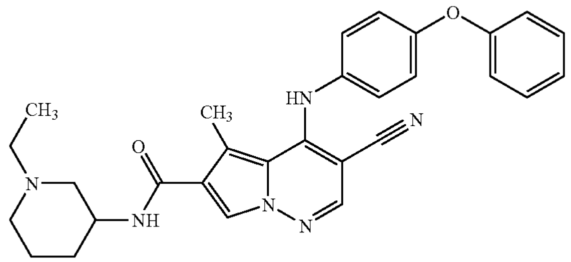 | 3-Cyano-N-(1-ethyl-3-piperidinyl)-5-methyl-4-[(4-phenoxy-phenyl)amino] pyrrolo[1,2-b]pyridazine-6-carboxamide | 1.65 LC* $[M + H]^+$ = 495.0 | 10 |
| 94 | 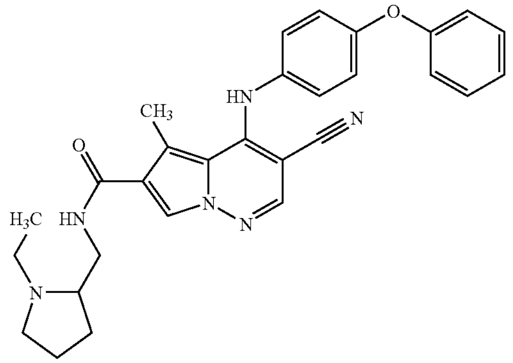 | 3-Cyano-N-[(1-ethyl-2-pyrrolidinyl)methyl]-5-methyl-4-[(4-phenoxyphenyl (amino] pyrrolo[1,2-b]pyridazine-6-carboxamide | 1.65 LC* $[M + H]^+$ = 495.0 | 10 |

TABLE 1-continued

| Ex. No. | Compound Structure | Compound Name | Retention Time Min./ Molecular Mass | Proc. of Ex. |
|---|---|---|---|---|
| 95 | 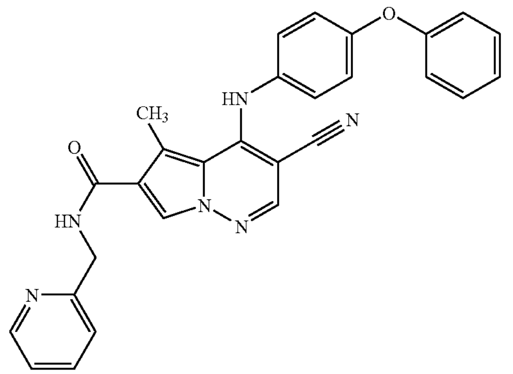 | 3-Cyano-5-methyl-4-[(4-phenopxyphenyl) amino]-N-(2-pyridinylmethyl) pyrrolo[1,2-b]pyridazine-6-carboxamide | 1.63 LC* $[M + H]^+$ = 475.0 | 10 |
| 96 | 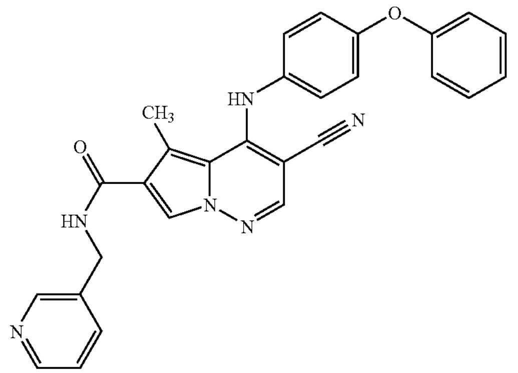 | 3-Cyano-5-methyl-4-[(4-phenoxy-phenyl)amino]-N-(3-pyridinylmethyl) pyrrolo[1,2-b]pyridazine-6-carboxamide | 1.61 LC* $[M + H]^+$ = 475.0 | 10 |
| 97 | 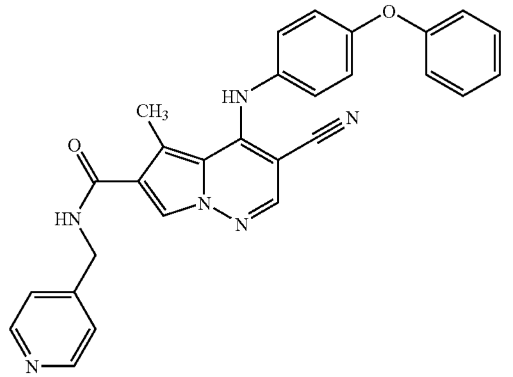 | 3-Cyano-5-methyl-4-[(4-phenoxy-phenyl)amino]-N-(4-pyridinylmethyl) pyrrolo[1,2-b]pyridazine-6-carboxamide | 1.61 LC* $[M + H]^+$ = 475.0 | 10 |
| 98 | 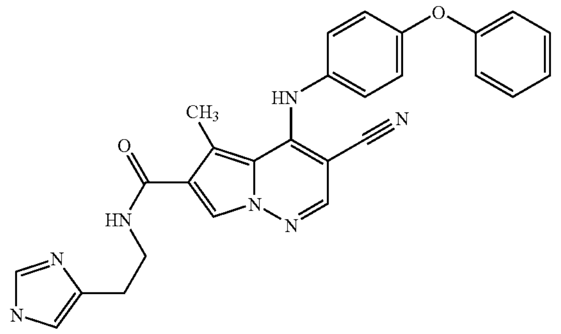 | 3-Cyano-N-[2-(1H-imidazol-4-yl)ethyl]-5-methyl-4-[(4-phenoxy-phenyl)amino] pyrrolo[1,2-b]pyridazine-6-carboxamide | 1.61 LC* $[M + H]^+$ = 478.0 | 10 |

TABLE 1-continued

| Ex. No. | Compound Structure | Compound Name | Retention Time Min./ Molecular Mass | Proc. of Ex. |
|---|---|---|---|---|
| 99 | 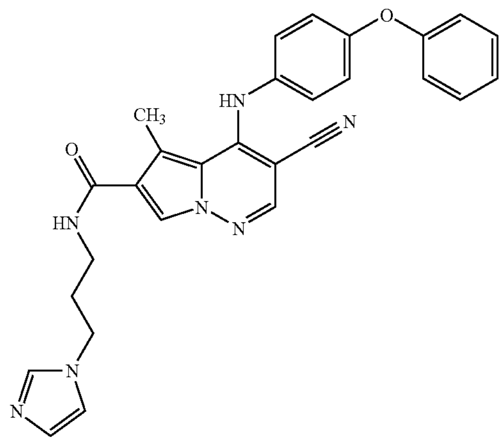 | 3-Cyano-N-[3-(1H-imidazol-1-yl)propyl]-5-methyl-4-[(4-phenoxy-phenyl)amino] pyrrolo[1,2-b]pyridazine-6-carboxamide | 1.62 LC* $[M + H]^+$ = 492.0 | 10 |
| 100 | 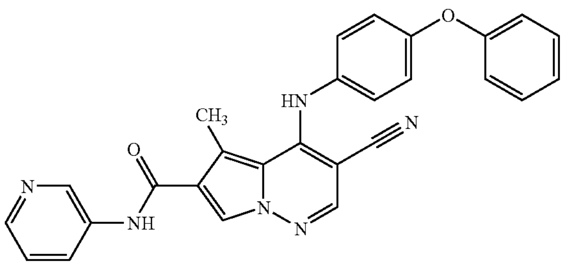 | 3-Cyano-5-methyl-4-[(4-phenoxy-phenyl)amino]-N-3-pyridinylpyrrolo[1,2-b]pyridazine-6-carboxamide | 1.70 LC* $[M + H]^+$ = 461.0 | 10 |
| 101 | 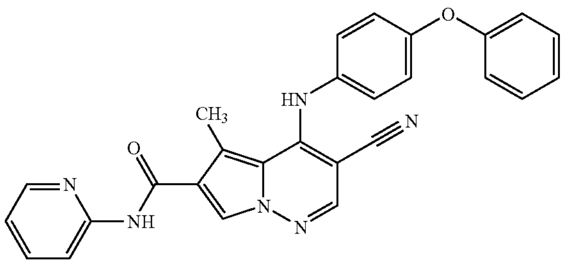 | 3-Cyano-5-methyl-4-[(4-phenoxy-phenyl)amino]-N-2-pyridinylpyrrolo[1,2-b]pyridazine-6-carboxamide | 1.74 LC* $[M + H]^+$ = 461.0 | 10 |
| 102 | 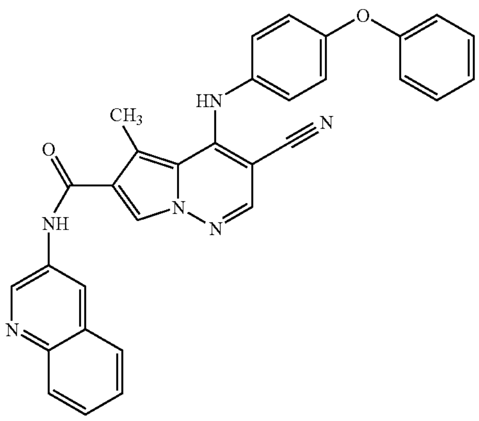 | 3-Cyano-5-methyl-4-[(4-phenoxy-phenyl)amino]-N-3-quinolinylpyrrolo[1,2-b]pyridazine-6-carboxamide | 1.96 LC* $[M + H]^+$ = 511.0 | 10 |

TABLE 1-continued

| Ex. No. | Compound Structure | Compound Name | Retention Time Min./ Molecular Mass | Proc. of Ex. |
|---|---|---|---|---|
| 103 | 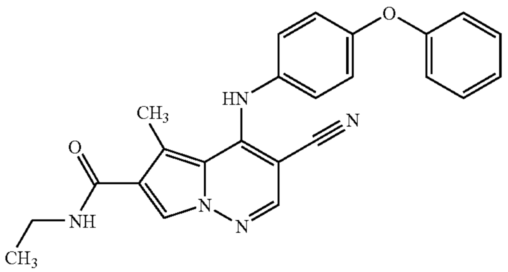 | 3-Cyano-N-ethyl-5-methyl-4-[(4-phenoxyphenyl) amino] pyrrolo[1,2-b]pyridazine-6-carboxamide | 1.85 LC* $[M + H]^+$ = 412.0 | 10 |
| 104 | 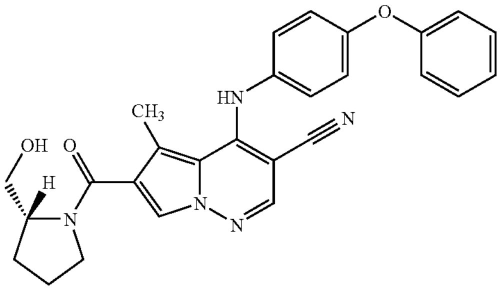 | (2R)-1-[[3-Cyano-5-methyl-4-[(4-phenoxy-phenyl)amino] pyrrolo[1,2-b]pyridazin-6-yl]carbonyl]-2-(hydroxymethyl) pyrrolidine | 1.79 LC* $[M + H]^+$ = 468.0 | 10 |
| 105 | 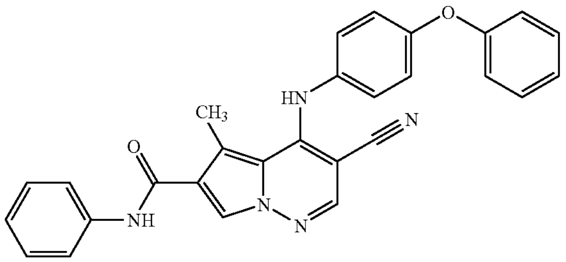 | 3-Cyano-5-methyl-4-[(4-phenoxy-phenyl)amino]-N-phenylpyrrolo[1,2-b]pyridazine-6-carboxamide | 2.05 LC* $[M + H]^+$ = 460.0 | 10 |
| 106 | 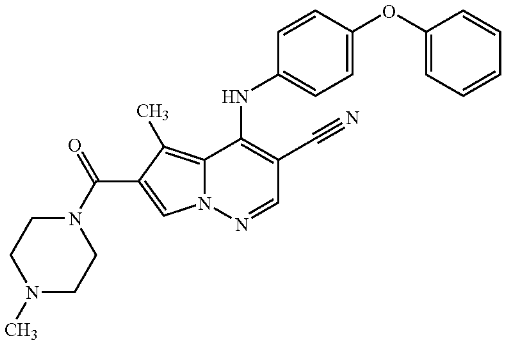 | 1-[[3-Cyano-5-methyl-4-[(4-phenoxy-phenyl)amino] pyrrolo[1,2-b]pyridazin-6-yl]carbonyl]-4-methylpiperazine | 1.53 LC* $[M + H]^+$ = 467.0 | 10 |
| 107 | 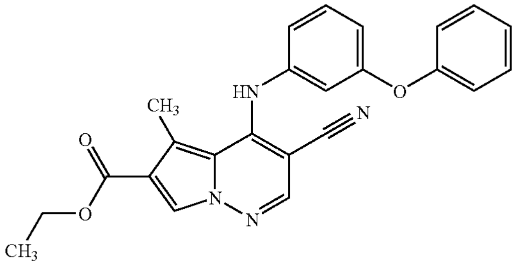 | 3-Cyano-5-methyl-4-[(3-phenoxy-phenyl)amino] pyrrolo[1,2-b]pyridazine-6-carboxylic acid, ethyl ester | 2.01 LCMS* $[M + H]^+$ = 413.0 | 10 |

TABLE 1-continued

| Ex. No. | Compound Structure | Compound Name | Retention Time Min./ Molecular Mass | Proc. of Ex. |
|---|---|---|---|---|
| 108 | 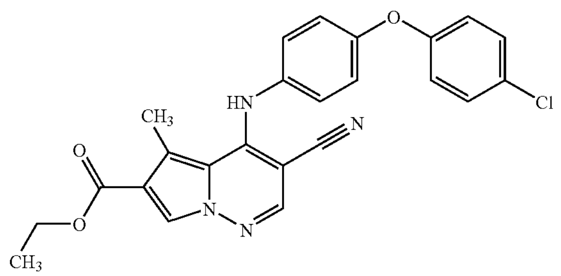 | 4-[[4-(4-Chlorophenoxy) phenyl] amino]-3-cyano-5-methylpyrrolo[1,2-b]pyridazine-6-carboxylic acid, ethyl ester | 2.13 LCMS* $[M + H]^+$ = 447.0 | 10 |
| 109 | 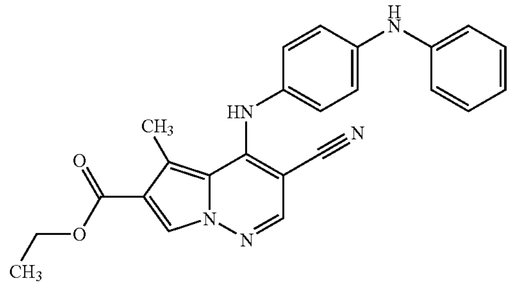 | 3-Cyano-5-methyl-4-[[4-(phenyl-amino)phenyl] amino]pyrrolo[1,2-b]pyridazine-6-carboxylic acid, ethyl ester | 1.95 LCMS* $[M + H]^+$ = 412.0 | 10 |
| 110 | 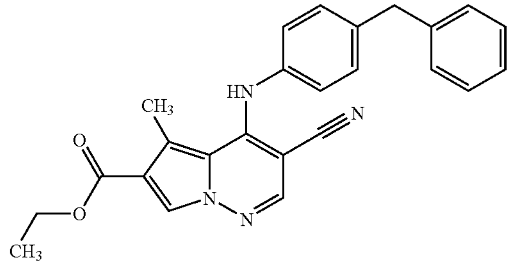 | 3-Cyano-5-methyl-4-[[4-(phenylmethyl) phenyl] amino]pyrrolo[1,2-b]pyridazine-6-carboxylic acid, ethyl ester | 2.05 LCMS* $[M + H]^+$ = 411.0 | 10 |
| 111 | 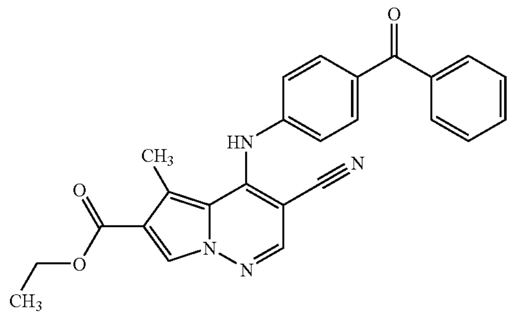 | 4-[(4-Benzoylphenyl) amino]-3-cyano-5-methylpyrrolo[1,2-b]pyridazine-6-carboxylic acid, ethyl ester | 1.91 LCMS* $[M + H]^+$ = 425.0 | 10 |
| 112 | 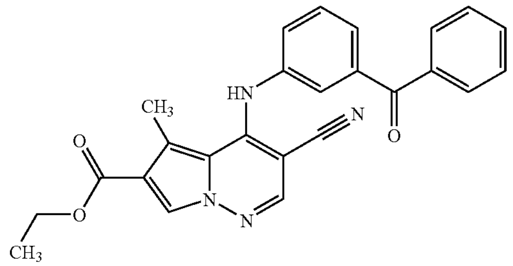 | 4-[(3-Benzoylphenyl) amino]-3-cyano-5-methyl-pyrrolo[1,2-b]pyridazine-6-carboxlylic acid, ethyl ester | 1.92 LCMS* $[M + H]^+$ = 425.0 | 10 |

TABLE 1-continued

| Ex. No. | Compound Structure | Compound Name | Retention Time Min./ Molecular Mass | Proc. of Ex. |
|---|---|---|---|---|
| 113 | 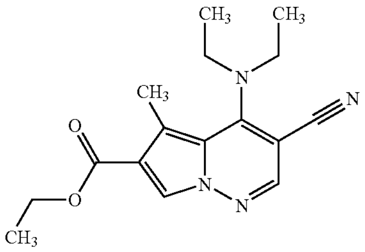 | 3-Cyano-4-(diethylamino)-5-methylpyrrolo[1,2-b]pyridazine-6-carboxylic acid, ethyl ester | 1.85 LCMS* $[M + H]^+$ = 301.0 | 10 |
| 114 | 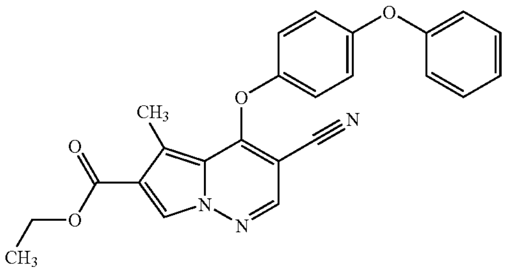 | 3-Cyano-5-methyl-4-(4-phenoxyphenoxy) pyrr-olo[1,2-b]pyridazine-6-carboxylic acid, ethyl ester | 2.19 LCMS* $[M + H]^+$ = 414.0 | 10 |
| 115 | 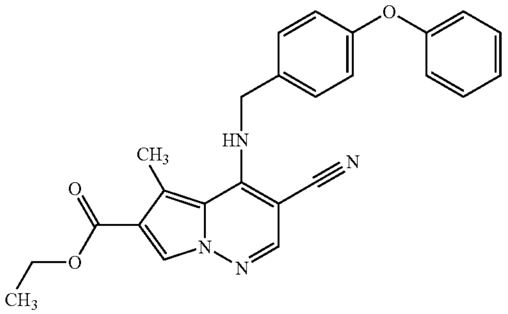 | 3-Cyano-5-methyl-4-[[(4-phenoxyphenyl) methyl] amino]pyrrolo[1,2-b]pyridazine-6-carboxylic acid, ethyl ester | 4.20 LCMS $[M + H]^+$ = 427.0 | 10 |
| 116 | 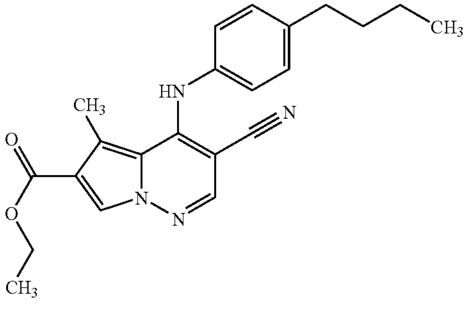 | 4-[(4-Butylphenyl)amino]-3-cyano-5-methylpyrrolo[1,2-b]pyridazine-6-carboxylic acid, ethyl ester | 2.10 LCMS* $[M + H]^+$ = 377.0 | 10 |
| 117 | 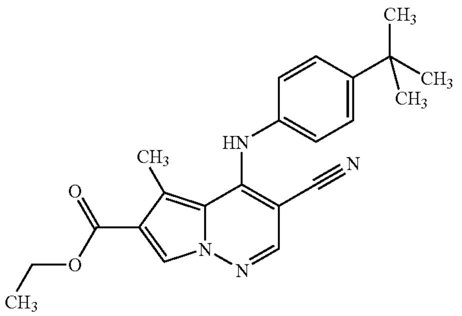 | 3-Cyano-4-[[4-(1,1-dimethylethyl)-phenyl]amino]-5-methylpyrrolo[1,2-b]pyridazine-6-carboxylic acid, ethyl ester | 2.07 LCMS* $[M + H]^+$ = 377.0 | 10 |

TABLE 1-continued

| Ex. No. | Compound Structure | Compound Name | Retention Time Min./ Molecular Mass | Proc. of Ex. |
|---|---|---|---|---|
| 118 | 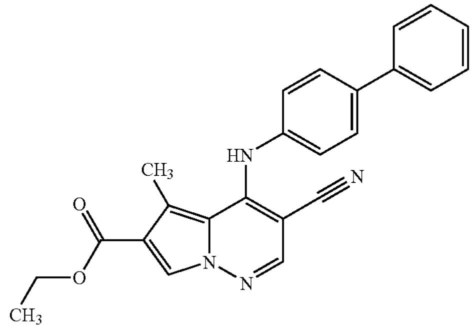 | 4-([1,1'-Biphenyl]-4-ylamino)-3-cyano-5-methylpyrrolo[1,2-b]pyridazine-6-carboxylic acid, ethyl ester | 2.04 LCMS* $[M + H]^+$ = 397.0 | 10 |
| 119 | 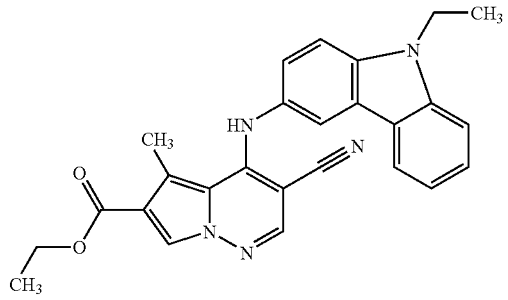 | 3-Cyano-4-[(9-ethyl-9H-carbazol-3-yl)amino]-5-methylpyrrolo[1,2-b]pyridazine-6-carboxylic acid, ethyl ester | 2.05 LCMS* $[M + H]^+$ = 438.0 | 10 |
| 120 | 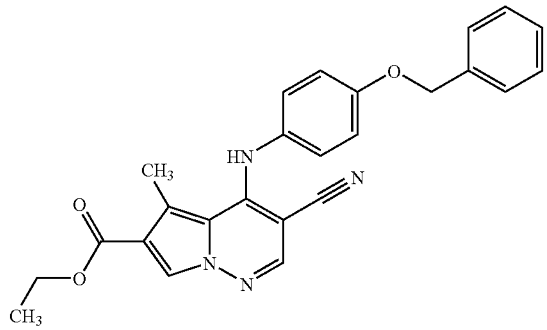 | 3-Cyano-5-methyl-4-[[4-(phenylmethoxy) phenyl] amino]-pyrrolo[1,2-b]pyridazine-6-carboxylic acid, ethyl ester | 2.03 LCMS* $[M + H]^+$ = 427.0 | 10 |
| 121 | 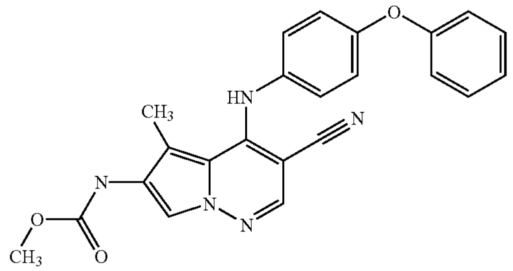 | [3-Cyano-5-methyl-4-[(4-phenoxy-phenyl)amino] pyrrolo[1,2-b]pyridazin-6-yl]carbamic acid, methyl ester | 3.65 LCMS* $[M + H]^+$ = 414.0 | 11A |

TABLE 1-continued

| Ex. No. | Compound Structure | Compound Name | Retention Time Min./ Molecular Mass | Proc. of Ex. |
|---|---|---|---|---|
| 122 | 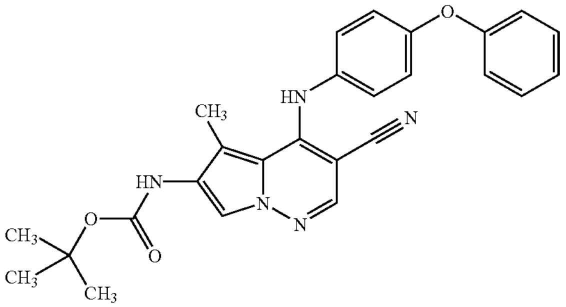 | [3-Cyano-5-methyl-4-[(4-phenoxy-phenyl)amino] pyrrolo[1,2-b]pyridazin-6-yl]carbamic acid, 1,1-dimethyl ester | 3.99 LCMS [M + H]+ = 456.0 | 11A |
| 123 | 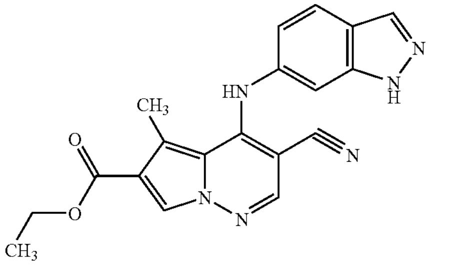 | 3-Cyano-4-(1H-indazol-6-ylamino)-5-methylpyrrolo[1,2-b]pyridazine-6-carboxylic acid, ethyl ester | 3.79 LC [M + H]+= 361.13 | 1 |
| 124 | 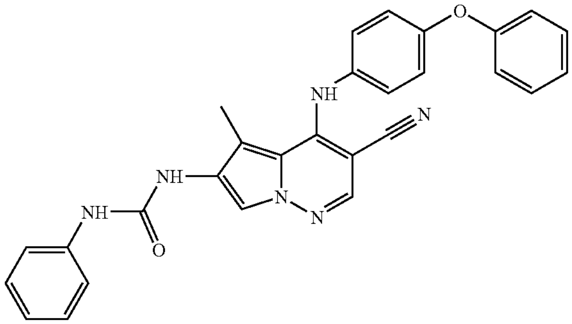 | 1-[3-Cyano-5-methyl-4-(4-phenoxy-phenylamino) pyrrolo[1,2-b]pyridazin-6-yl]-3-phenyl-urea | 3.90 LCMS [M + H]+ = 475.0 | 19 |
| 125 | 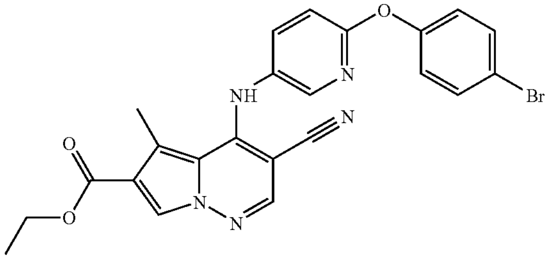 | 4-[6-(4-Bromo-phenoxy)-pyridin-3-ylamino]-3-cyano-5-methyl-pyrrolo[1,2-b]pyridazine-6-carboxylic acid ethyl ester | 4.01 LCMS [M + H]+ = 492.0 | 1 |
| 126 | 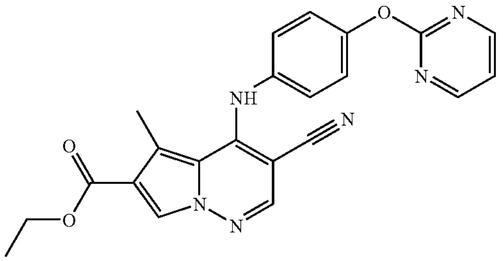 | 3-Cyano-5-methyl-4-[4-(pyrimidin-2-yloxy)-phenylamino]-pyrrolo[1,2-b]pyridazine-6-carboxylic acid ethyl ester | 3.38 LC [M + H]+ = 415.0 | 1 |

TABLE 1-continued

| Ex. No. | Compound Structure | Compound Name | Retention Time Min./ Molecular Mass | Proc. of Ex. |
|---|---|---|---|---|
| 127 | 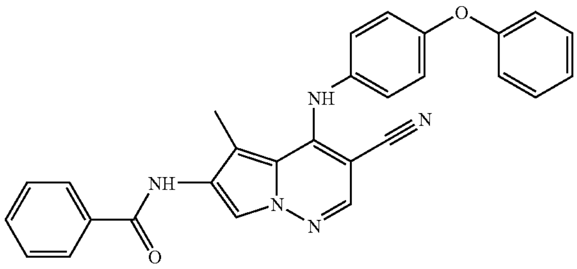 | N-[3-Cyano-5-methyl-4-(4-phenoxy-phenylamino)-pyrrolo[1,2-b]pyridazin-6-yl]-benzamide | 1.94 LCMS-1 $[M + H]^+$ = 460.0 | 12 |
| 128 | 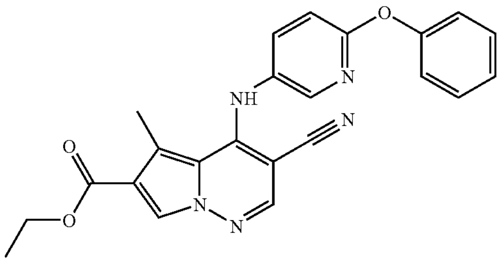 | 3-Cyano-5-methyl-4-(6-phenoxy-pyridin-3-ylamino)-pyrrolo[1,2-b]pyridazine-6-carboxylic acid ethyl ester | 3.72 LCMS $[M + H]^+$ = 414.0 | 1 |
| 129 | 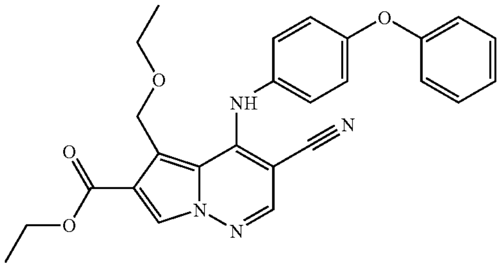 | 3-Cyano-5-ethoxymethyl-4-(4-phenoxy-phenylamino)-pyrrolo[1,2-b]pyridazine-6-carboxylic acid ethyl ester | 2.30 LCMS-1 $[M + H]^+$ = 457.0 | 17 |
| 130 | 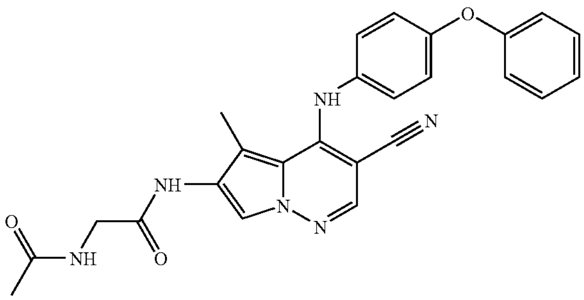 | 2-Acetylamino-N-[3-cyano-5-methyl-4-(4-phenoxy-phenylamino)-pyrrolo[1,2-b]pyridazin-6-yl]-acetamide | 1.70 LCMS-1 $[M + H]^+$ = 455.0 | 12 |
| 131 | 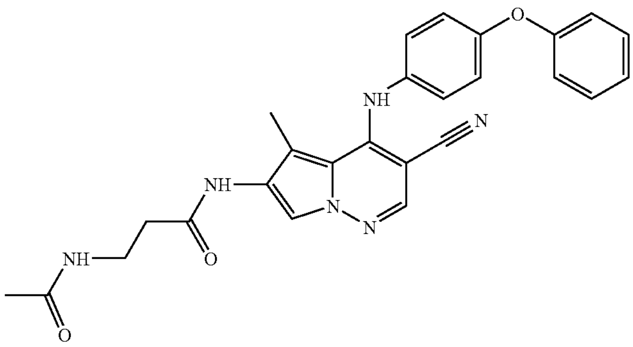 | 3-Acetylamino-N-[3-cyano-5-methyl-4-(4-phenoxy-phenylamino) pyrrolo[1,2-b]pyridazin-6-yl]-propionamide | 1.73 LCMS-1 $[M + H]^+$ = 469.0 | 12 |

TABLE 1-continued

| Ex. No. | Compound Structure | Compound Name | Retention Time Min./ Molecular Mass | Proc. of Ex. |
|---|---|---|---|---|
| 132 | 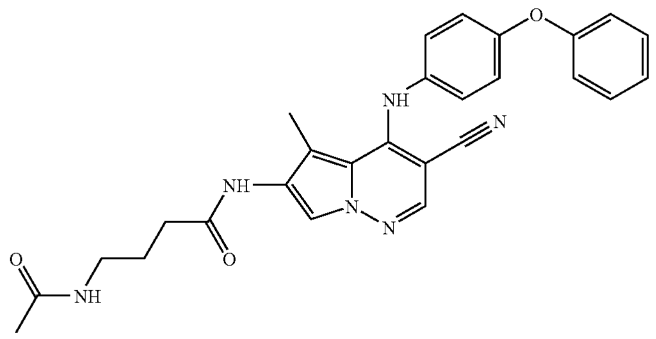 | 4-Acetylamino-N-[3-cyano-5-methyl-4-(4-phenoxy-phenylamino)-pyrrolo[1,2-b]pyridazin-6-yl]-butyramide | 1.76 LCMS-1 $[M + H]^+$ = 483.0 | 12 |
| 133 | 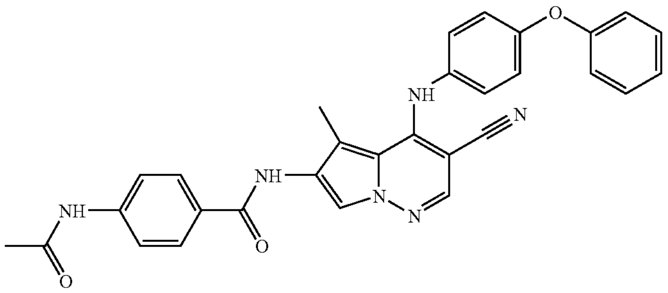 | 4-Acetylamino-N-[3-cyano-5-methyl-4-(4-phenoxy-phenylamino)-pyrrolo[1,2-b]pyridazin-6-yl]-benzamide | 1.85 LCMS-1 $[M + H]^+$ = 517.0 | 12 |
| 134 | 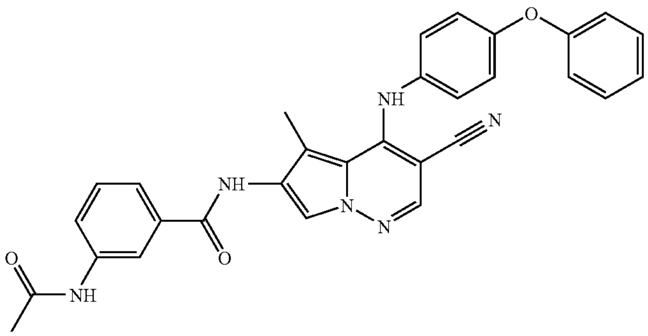 | 3-Acetylamino-N-[3-cyano-5-methyl-4-(4-phenoxy-phenylamino)-pyrrolo[1,2-b]pyridain-6-yl]-benzamide | 1.87 LCMS-1 $[M + H]^+$ = 517.0 | 12 |
| 135 | 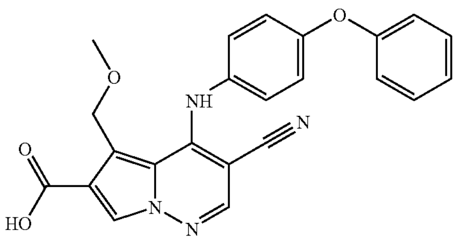 | 3-Cyano-5-methoxymethyl-4-(4-phenoxy-phenylamino)-pyrrolo[1,2-b]pyridazine-6-carboxylic acid | 3.86 LCMS $[M + H]^+$ = 415.0 | 4, 17 |
| 136 | 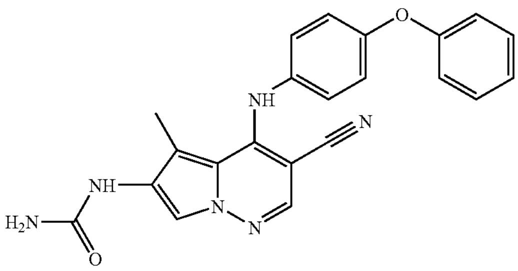 | [3-Cyano-5-methyl-4-(4-phenoxy-phenylamino)-pyrrolo[1,2-b]pyridazin-6-yl]-urea | 3.31 LCMS $[M + H]^+$ = 399.0 | 19 |

TABLE 1-continued

| Ex. No. | Compound Structure | Compound Name | Retention Time Min./ Molecular Mass | Proc. of Ex. |
|---|---|---|---|---|
| 137 | 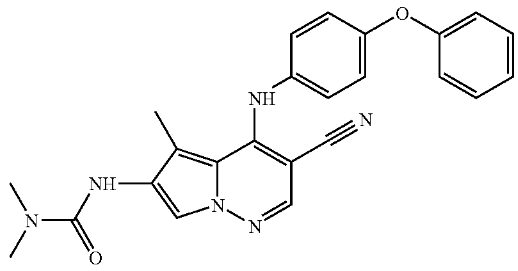 | 3-[3-Cyano-5-methyl-4-(4-phenoxy-phenylamino)-pyrrolo[1,2-b]pyridazin-6-yl]-1,1-dimethyl-urea | 3.38 LCMS $[M + H]^+$ = 427.0 | 19 |
| 138 | 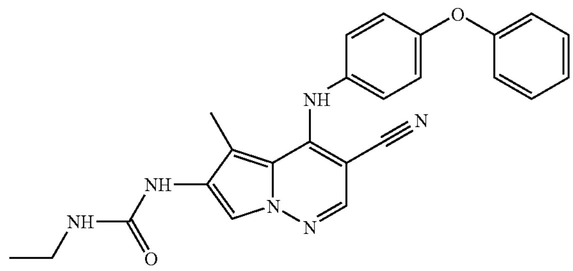 | 1-[3-Cyano-5-methyl-4-(4-phenoxy-phenylamino)-pyrrolo[1,2-b]pyridazin-6-yl]-3-ethyl-urea | 3.54 LCMS $[M + H]^+$ = 427.0 | 19 |
| 139 | 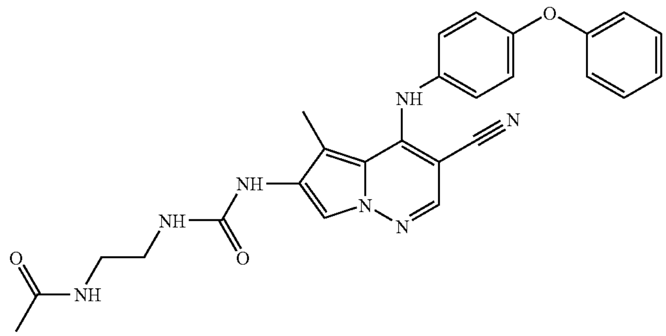 | N-(2-{3-[3-Cyano-5-methyl-4-(4-phenoxy-phenylamino)-pyrrolo[1,2-b]pyridazin-6-yl]-ureido}-ethyl)-acetamide | 3.35 LCMS $[M + H]^+$ = 484.0 | 19 |
| 140 | 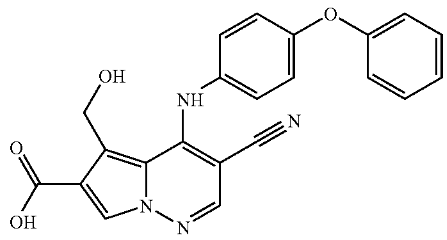 | 3-Cyano-5-hydroxymethyl-4-(4-phenoxy-phenylamino)-pyrrolo[1,2-b]pyridazine-6-carboxylic acid | 3.66 LCMS $[M + H]^+$ = 401.0 | 4, 16 |
| 141 | 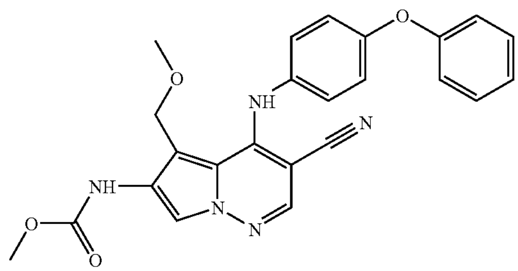 | [3-Cyano-5-methoxymethyl-4-(4-phenoxy-phenylamino)-pyrrolo[1,2-b]pyridazin-6-yl]-carbamic acid methyl ester | 1.99 LCMS-1 $[M + H]^+$ = 444.0 | 11, 17 |

TABLE 1-continued

| Ex. No. | Compound Structure | Compound Name | Retention Time Min./ Molecular Mass | Proc. of Ex. |
|---|---|---|---|---|
| 142 | 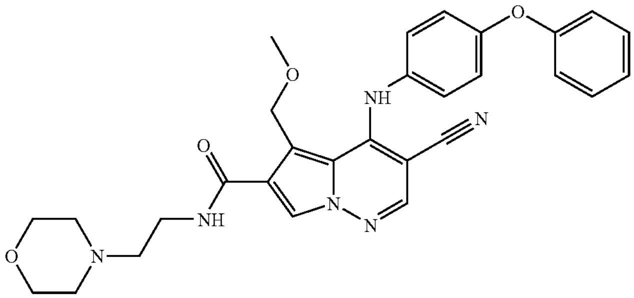 | 3-Cyano-5-methoxymethyl-4-(4-phenoxy-phenylamino)-pyrrolo[1,2-b]pyridazine-6-carboxylic acid (2-morph-olin-4-yl-ethyl)-amide | 1.78 LCMS-1 $[M + H]^+$ = 527.0 | 12, 17 |
| 143 | 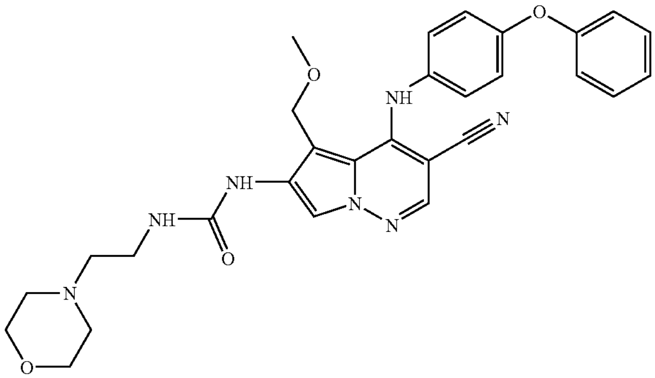 | 1-[3-Cyano-5-methoxymethyl-4-(4-phenoxy-phenylamino)-pyrrolo[1,2-b]pyridazin-6-yl]-3-(2-morpholin-4-yl-ethyl)-urea | 1.73 LCMS-1 $[M + H]^+$ = 542.0 | 17, 19 |
| 144 | 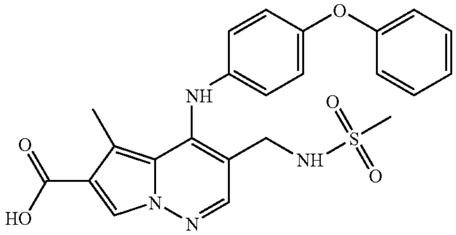 | 3-(Methanesulfonyl-amino-methyl)-5-methyl-4-(4-phenoxy-phenylamino)-pyrrolo[1,2-b]pyridazine-6-car-boxylic acid | 3.35 LCMS $[M + H]^+$ = 467.0 | 14 |

EXAMPLE 145

6-(1-Hydroxy-1-methyl-ethyl)-5-methyl-4-(4-phenoxy-phenylamino)-pyrrolo[1,2-b]pyridazine-3-carbonitrile (145)

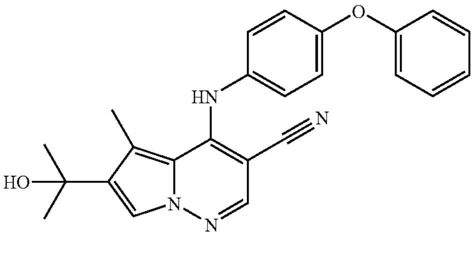

To a solution of compound 3A (124 mg, 0.30 mmol) in THF (5 mL) at 0° C. was slowly added a 3.0 M solution of MeMgBr in ether (0.40 mL, 1.20 mmol. The reaction was warmed to room temperature and then heated at 50° C. for 1 h. After cooling to room temperature, the reaction was quenched with EtOAc (20 mL) and saturated aqueous $NH_4Cl$ (20 mL) was added. The resulting two layers were separated and the organic layer washed with brine, dried over $Na_2SO_4$ and concentrated to an orange oil. This crude oil was purified by silica gel flash chromatography (eluted with 14–17% EtOAc/$CH_2Cl_2$) to give compound 145 as a yellow solid (76 mg, 64%). HPLC: 97% at 1.97 min (retention time) (Phenom-Prime S5 C18 column, 4.6×30 mm, eluting with 10–90% aqueous methanol over 2 min containing 0.1% TFA, 5 mL/min, monitoring at 220 nm). MS (ES): m/z 399 $[M+H]^+$.

EXAMPLE 146

6-Hydroxy-5-methyl-4-(4-phenoxy-phenylamino)-pyrrolo[1,2-b]pyridazine-3-carbonitrile (146)

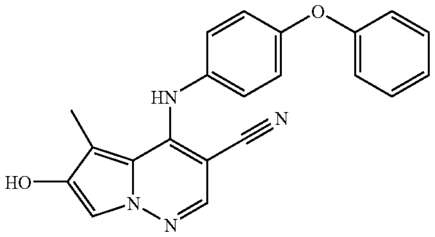

To a mixture of $H_2O_2$ (50% wt in $H_2O$, 0.0115 mL, 0.20 mmol) and $CH_2Cl_2$ (2 mL) at −5° C. was added $BF_3.OEt_2$. The reaction was stirred at −5° C. for 40 min before a solution of compound 145 (56 mg, 0.14 mmol) in $CH_2Cl_2$ (3 mL) was added. The reaction was kept at −5° C. for 10 min and quenched with an aqueous solution of $Na_2SO_3$ (2 g, 10 mL). The reaction was diluted with $CH_2Cl_2$ and the two layers were separated. The aqueous layer was extracted with $CH_2Cl_2$ (2×10 mL). The $CH_2Cl_2$ layers were combined and concentrated in vacuo to give a brown oil. This crude oil was purified by silica gel flash chromatography (eluted with 10% EtOAc/$CH_2Cl_2$) to give compound 146 as a yellow solid (32 mg, 64%). HPLC: 90% at 1.89 min (retention time) (Phenom-Prime S5 C18 column, 4.6×30 mm, eluting with 10–90% aqueous methanol over 2 min containing 0.1% TFA, 5 mL/min, monitoring at 220 nm). MS (ES): m/z 357 $[M+H]^+$.

EXAMPLE 147

5-Methyl-6-(2-morpholin-4-yl-ethoxy)-4-(4-phenoxy-phenylamino)-pyrrolo[1,2-b]pyridazine-3-carbonitrile (154)

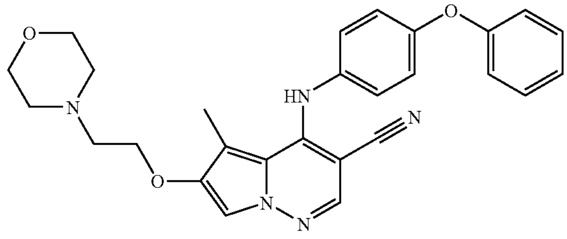

To a solution of compound 146 (8.9 mg, 0.025 mmol) $PPh_3$ (13.1 mg, 0.05 mmol) and 4-(2-hydroxyethyl)-morpholine (6.6 mg, 0.05 mmol) in dry THF (0.3 mL) under $N_2$ at 0° C. was added DEAD (8.7 mg, 0.05 mmol). The reaction was stirred at 0° C. for 5 min, warmed to room temperature for 2 h, concentrated to dryness, and purified by silica gel flash chromatography (eluted within 1–5% MeOH/$CH_2Cl_2$) to give compound 147 as a yellow oil (10 mg, 85%). HPLC: 96% at 1.69 min (retention time) (Phenom-Prime SS C18 column, 4.6×30 mm, eluting with 10–90% aqueous methanol over 2 min containing 0.1% TFA, 5 mL/min, monitoring at 220 nm). MS (ES): m/z 470 $[M+H]^+$.

EXAMPLE 148

5-Cyano-7-oxo-6-(4-phenoxy-phenyl)-6.7-dihydro-9H-8-oxa-2a,3,6-triaza-benzo[cd]azulene-1-carboxylic acid ethyl ester (148)

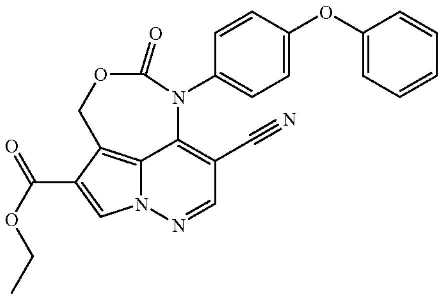

To a solution of compound 16C (26 mg, 0.061 mmol) and DIPEA (63 mg, 0.485 mmol) in $CH_2Cl_2$ (6 mL) at −50° C. was added triphosgene (30 mg, 0.101 mmol). The reaction was slowly warmed up to 10° C. over 1 h, quenched with MeOH (1 mL) concentrated to dryness in vacuo and purified by silica gel flash chromatography (eluted with 1–2% EtOAc/$CH_2Cl_2$) to give compound 148 as a yellow solid (16 mg, 58%). HPLC: 91% at 2.09 min (retention time) (Phenom-Prime S5 C18 column, 4.6×30 mm, eluting with 10–90% aqueous methanol over 2 min containing 0.1% TFA, 5 mL/min, monitoring at 220 nm). MS (ES): m/z 455 $[M+H]^+$.

EXAMPLE 149

5-Azidemethyl-3-cyano-4-(4-phenoxy-phenylamino)-pyrrolo[1,2-b]pyridazine-6-carboxylic acid ethyl ester (149)

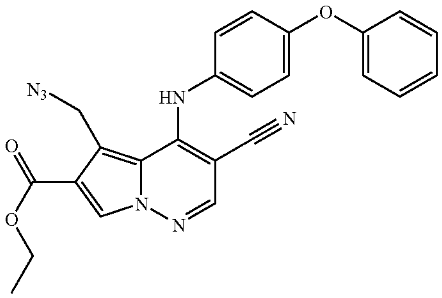

To a solution of compound 148 (21 mg, 0.05 mmol) in THF (0.6 mL) was added DPPA (22 mg, 0.08 mmol) followed by DBU (9 mg, 0.06 mmol). The reaction was stirred at room temperature for 4 h; concentrated and purified by flash chromatography on a silica gel column (0.5–1% EtOAc/$CH_2Cl_2$) to give compound 149 as a yellow oil (14 mg, 63%). HPLC: 99% at 2.16 min (retention time)

(PrimeSphere 5u C18-HC column, 4.6×30 mm, eluting with 10–90% aqueous methanol over 2 min containing 0.1% TFA, 5 mL/min, monitoring at 220 nm). MS (ES): m/z 454 $[M+H]^+$.

EXAMPLE 150

5-Aminomethyl-3-cyano-4-(4-phenoxy-phenylamino)-pyrrolo[1,2-b]pyridazine-6-carboxylic acid ethyl ester (150)

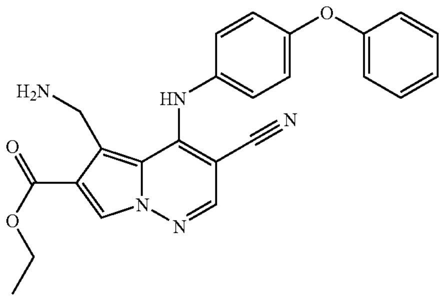

To a solution of compound 149 (12 mg, 0.026 mmol) in a mixture of 1:2 THF: MeOH (3 mL) was added Pd/C (5 mg). The reaction was hydrogenated under a hydrogen balloon at room temperature for 30 min and filtered. The filtrate was concentrated to give 8 as a yellow solid (9 mg, 80%). No further purification was required. HPLC: 92% at 1.71 min (retention time) (PrimeSphere 5u C18-HC column, 4.6×30 mm, eluting with 10–90% aqueous methanol over 2 min containing 0.1% TFA, 5 mL/min, monitoring at 220 nm). MS (ES): m/z 428 $[M+H]^+$.

EXAMPLE 151

5-Cyano-7-oxo-6-(4-phenoxy-phenyl)-6,7,8,9-tetrahydro-2a,3,6,8-tetraazabenzo[cd]azulene-1-carboxylic acid ethyl ester (151)

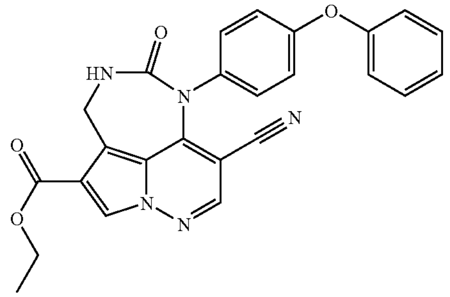

To a solution of compound 150 (7 mg, 0.016 mmol) and DIPEA (17 mg, 0.13 mmol) in $CH_2Cl_2$ (1.5 mL) at −70° C. was added triphosegene (9.5 mg, 0.032 mmol). The reaction was slowly warmed up to −5° C. over 1 h, quenched with MeOH (0.5 mL), concentrated to dryness and purified by silica gel flash chromatography (eluted with 6–8% EtOAc/$CH_2Cl_2$) to give 9 as a yellow solid (6 mg, 81%). HPLC: 98% at 1.97 min (retention time) (PrimeSphere 5u (C18-HC column, 4.6×30 mm, eluting with 10–90% aqueous methanol over 2 min containing 0.1% TFA, 5 mL/min, monitoring at 220 nm). MS (ES): m/z 454 $[M+H]^+$.

EXAMPLES 152 TO 367

Further compounds of the present invention were prepared by procedures analogous to those described. Table 2 provides the name and structure of representative compounds and their retention times, as well as the Example number of the procedure on which the preparation of the compound was based. The chromatography techniques used to determine the retention times of the compounds listed in Table 2 are as follows:

LC=YMC S5 ODS column, 3.6×50 mm, eluting with 10–90% aqueous methanol over 2 min containing 0.1% TFA, 5 mL/min, monitoring at 220 nm LC*=YMC S5 ODS column 4.6×50 mm eluting with 10–90% $MeOH/H_2O$ over 4 minutes containing 0.2% phosphoric acid, 4 mL/min, monitoring at 220 nm.

The molecular mass of the compounds listed in Table 2 were determined by MS (ES) by the formula m/z.

TABLE 2

| Ex. No. | Structure | Compound Name | Retention Time Min./ Molecular Mass | Proc. of Ex. |
|---|---|---|---|---|
| 152 | 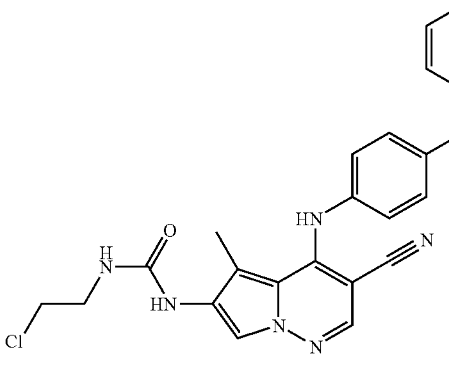 | 1-(2-Chloro-ethyl)-3[3-cyano-5-methyl-4-(4-phenoxy-phenylamino)-pyrrolo[1,2-b]pyridazin-6-yl]-urea | 1.74 LC $[M + H]^+$ = 416.2 | 19 |

TABLE 2-continued

| Ex. No. | Structure | Compound Name | Retention Time Min./ Molecular Mass | Proc. of Ex. |
|---|---|---|---|---|
| 153 | 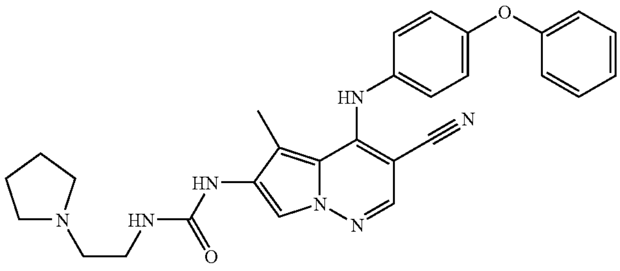 | 1-[3-Cyano-5-methyl-4-(4-phenoxy-phenylamino)-pyrrolo[1,2-b]pyridazin-6-yl]-3-(2-pyrrolidin-1-yl-ethyl)-urea | 1.51 LC $[M + H]^+$ = 496.2 | 19 |
| 154 | 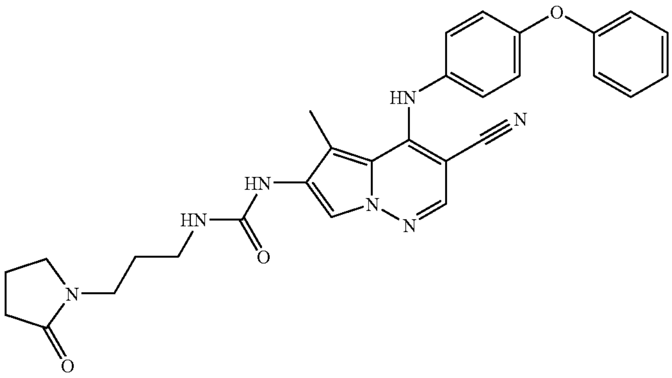 | 1-[3-Cyano-5-methyl-4-(4-phenoxy-phenylamino)-pyrrolo[1,2-b]pyridazin-6-yl]-3-[3-(2-oxo-pyrrolidin-1-yl)-propyl]-urea | 1.67 LC $[M + H]^+$ = 524.2 | 19 |
| 155 | 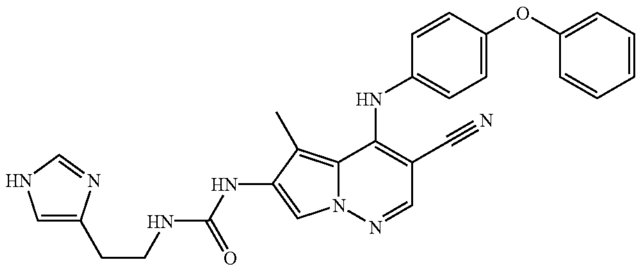 | 1-[3-Cyano-5-methyl-4-(4-phenoxy-phenylamino)-pyrrolo[1,2-b]pyridazin-6-yl]-3-[2-(1H-imidazol-4-yl)-ethyl]-urea | 1.51 LC $[M + H]^+$ = 493.2 | 19 |
| 156 | 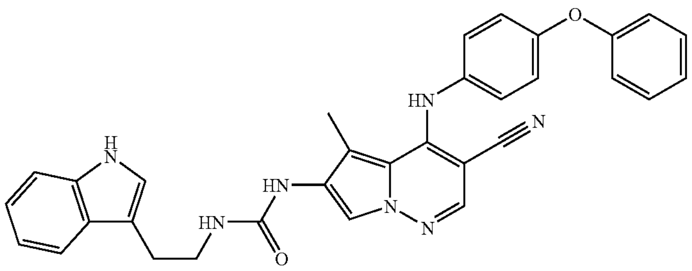 | 1-[3-Cyano-5-methyl-4-(4-phenoxy-phenylamino)-pyrrolo[1,2-b]pyridazin-6-yl]-3-[2-(1H-indol-3-yl)-ethyl]-urea | 1.86 LC $[M + H]^+$ = 542.2 | 19 |

TABLE 2-continued

| Ex. No. | Structure | Compound Name | Retention Time Min./ Molecular Mass | Proc. of Ex. |
|---|---|---|---|---|
| 157 | 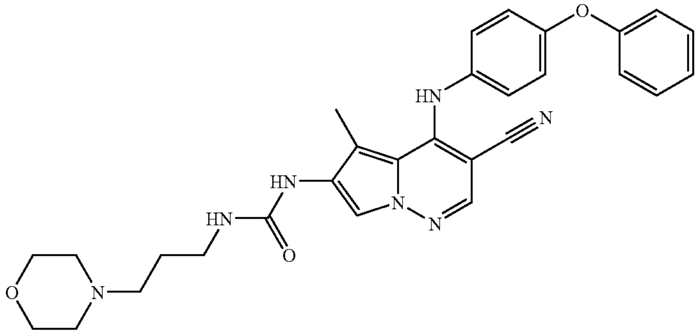 | 1-[3-Cyano-5-methyl-4-(4-phenoxy-phenylamino)-pyrrolo[1,2-b]pyridazin-6-yl]-3-(3-morpholin-4-yl-propyl)-urea | 1.51 LC $[M + H]^+$ = 526.2 | 19 |
| 158 | 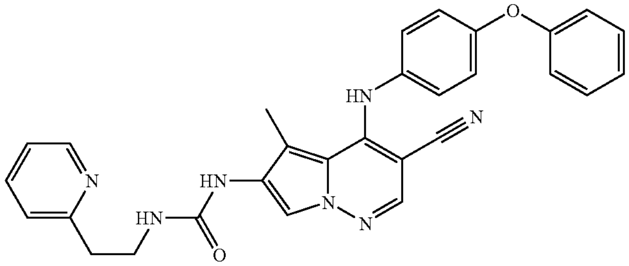 | 1-[3-Cyano-5-methyl-4-(4-phenoxy-phenylamino)-pyrrolo[1,2-b]pyridazin-6-yl]-3-(2-pyridin-2-yl-ethyl)-urea | 1.53 LC $[M + H]^+$ = 504.2 | 19 |
| 159 | 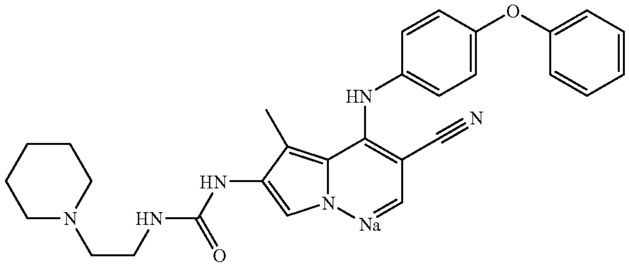 | 1-[3-Cyano-5-methyl-4-(4-phenoxy-phenylamino)-pyrrolo[1,2-b]pyridazin-6-yl]-3-(2-piperidin-1-yl-ethyl)-urea | 1.55 LC $[M + H]^+$ = 510.2 | 19 |
| 160 | 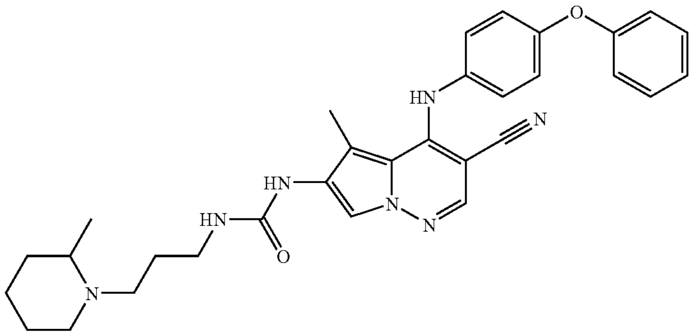 | 1-[3-Cyano-5-methyl-4-(4-phenoxy-phenylamino)-pyrrolo[1,2-b]pyridazin-6-yl]-3-[3-(2-methyl-piper-idin-1-yl)-propyl]-urea | 1.57 LC $[M + H]^+$ = 538.3 | 19 |

TABLE 2-continued

| Ex. No. | Structure | Compound Name | Retention Time Min./ Molecular Mass | Proc. of Ex. |
|---|---|---|---|---|
| 161 | 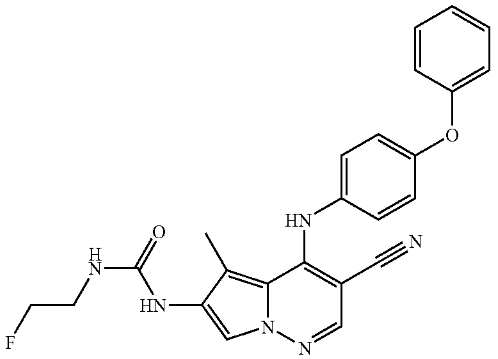 | 1-[3-Cyano-5-methyl-4-(4-phenoxy-phenylamino)-pyrrolo[1,2-b]pyridazin-6-yl]-3-(2-fluoro-ethyl)-urea | 1.69 LC $[M + H]^+$ = 455.2 | 19 |
| 162 | 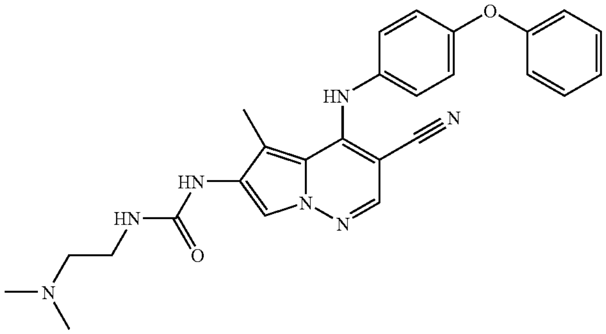 | 1-[3-Cyano-5-methyl-4-(4-phenoxy-phenylamino)-pyrrolo[1,2-b]pyridazin-6-yl]-3-(2-dimethylamino-ethyl)-urea | 1.5 LC $[M + H]^+$ = 470.2 | 19 |
| 163 | 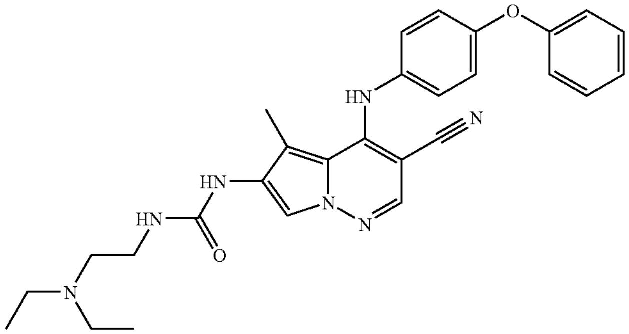 | 1-[3-Cyano-5-methyl-4-(4-phenoxy-phenylamino)-pyrrolo[1,2-b]pyridazin-6-yl]-3-(2-diethylamino-ethyl)-urea | 1.54 LC $[M + H]^+$ = 498.2 | 19 |
| 164 | 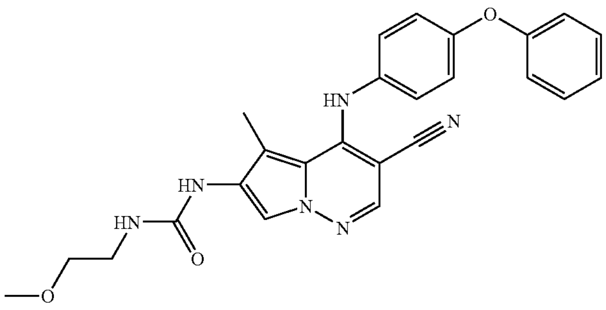 | 1-[3-Cyano-5-methyl-4-(4-phenoxy-phenylamino)-pyrrolo[1,2-b]pyridazin-6-yl]-3-(2-methoxy-ethyl)-urea | 1.7 LC $[M + H]^+$ = 457.2 | 19 |

TABLE 2-continued

| Ex. No. | Structure | Compound Name | Retention Time Min./ Molecular Mass | Proc. of Ex. |
|---|---|---|---|---|
| 165 | 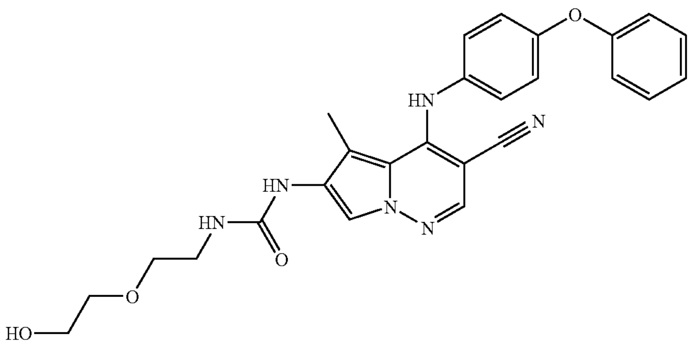 | 1-[3-Cyano-5-methyl-4-(4-phenoxy-phenylamino)-pyrrolo[1,2-b]pyridazin-6-yl]-3-[2-(2-hydroxy-ethoxy)-ethyl]-urea | 1.64 LC $[M + H]^+$ = 487.2 | 19 |
| 166 | 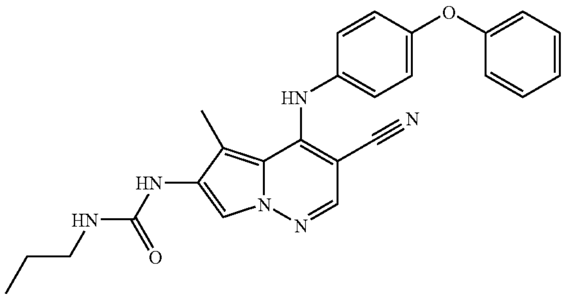 | 1-[3-Cyano-5-methyl-4-(4-phenoxy-phenylamino)-pyrrolo[1,2-b]pyridazin-6-yl]-3-propyl-urea | 1.78 LC $[M + H]^+$ = 441.2 | 19 |
| 167 | 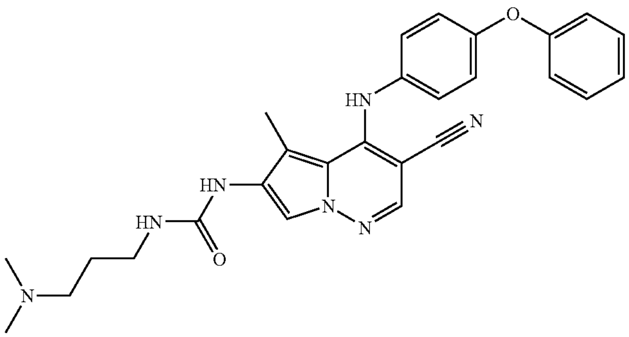 | 1-[3-Cyano-5-methyl-4-(4-phenoxy-phenylamino)-pyrrolo[1,2-b]pyridazin-6-yl]-3-(3-dimethylamino-propyl)-urea | 1.52 LC $[M + H]^+$ = 484.2 | 19 |
| 168 | 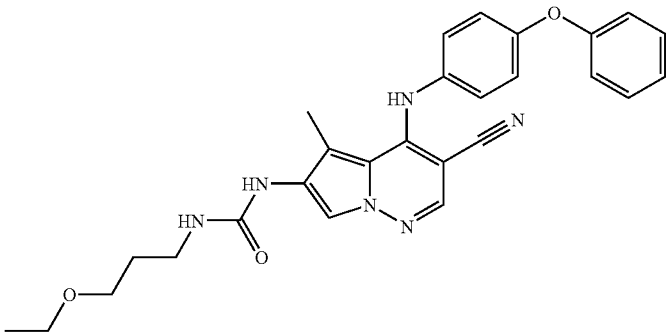 | 1-[3-Cyano-5-methyl-4-(4-phenoxy-phenylamino)-pyrrolo[1,2-b]pyridazin-6-yl]-3-(3-ethoxy-propyl)-urea | 1.79 LC $[M + H]^+$ = 485.2 | 19 |

TABLE 2-continued

| Ex. No. | Structure | Compound Name | Retention Time Min./ Molecular Mass | Proc. of Ex. |
|---|---|---|---|---|
| 169 | 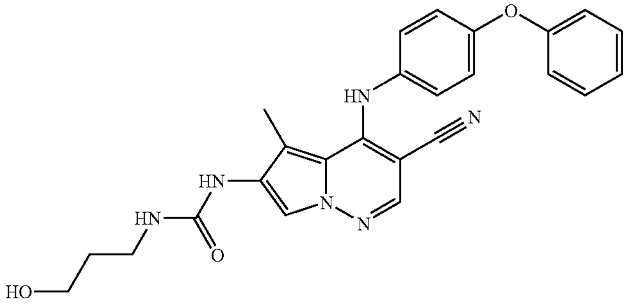 | 1-[3-Cyano-5-methyl-4-(4-phenoxy-phenylamino)-pyrrolo[1,2-b]pyridazin-6-yl]-3-(3-hydroxy-propyl)-urea | 1.62 LC $[M + H]^+$ = 457.2 | 19 |
| 170 | 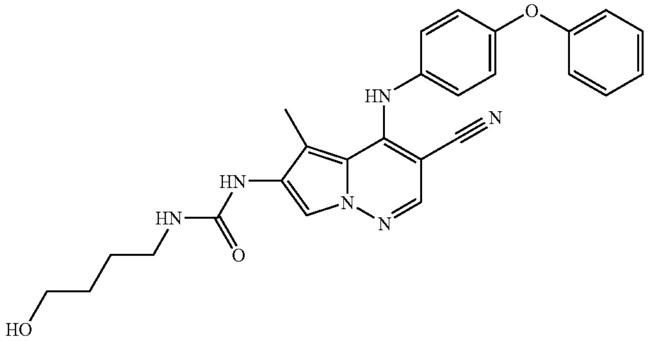 | 1-[3-Cyano-5-methyl-4-(4-phenoxy-phenylamino)-pyrrolo[1,2-b]pyridazin-6-yl]-3-(4-hydroxy-butyl)-urea | 1.63 LC $[M + H]^+$ = 471.3 | 19 |
| 171 | 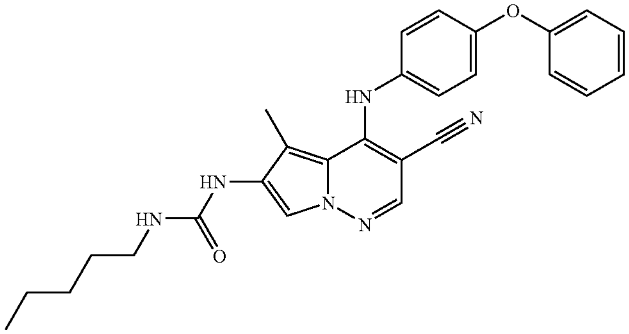 | 1-[3-Cyano-5-methyl-4-(4-phenoxy-phenylamino)-pyrrolo[1,2-b]pyridazin-6-yl]-3-pentyl-urea | 1.92 LC $[M + H]^+$ = 467.2 | 19 |
| 172 | 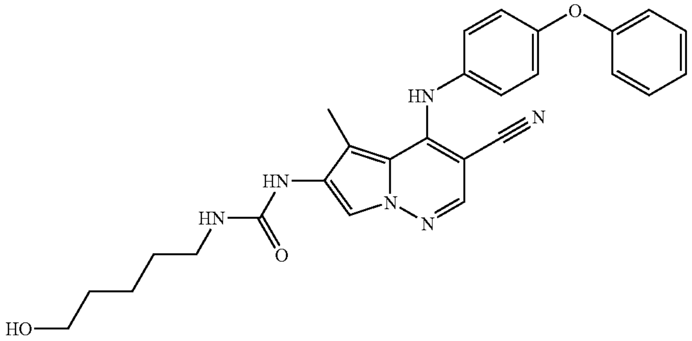 | 1-[3-Cyano-5-methyl-4-(4-phenoxy-phenylamino)-pyrrolo[1,2-b]pyridazin-6-yl]-3-(5-hydroxy-pentyl)-urea | 1.7 LC $[M + H]^+$ = 485.2 | 19 |

TABLE 2-continued

| Ex. No. | Structure | Compound Name | Retention Time Min./ Molecular Mass | Proc. of Ex. |
|---|---|---|---|---|
| 173 | 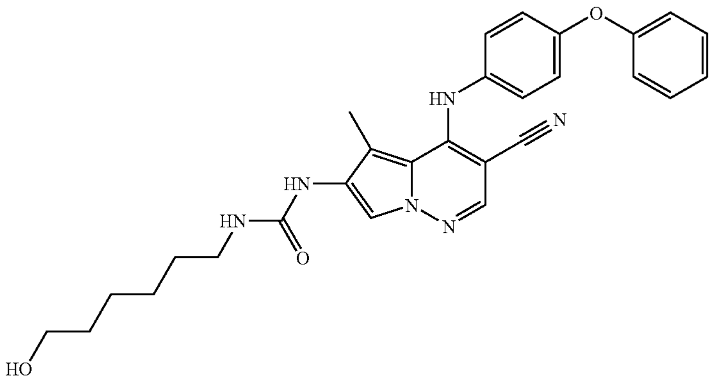 | 1-[3-Cyano-5-methyl-4-(4-phenoxy-phenylamino)-pyrrolo[1,2-b]pyridazin-6-yl]-3-(6-hydroxy-hexyl)-urea | 1.75 LC $[M + H]^+$ = 499.2 | 19 |
| 174 | 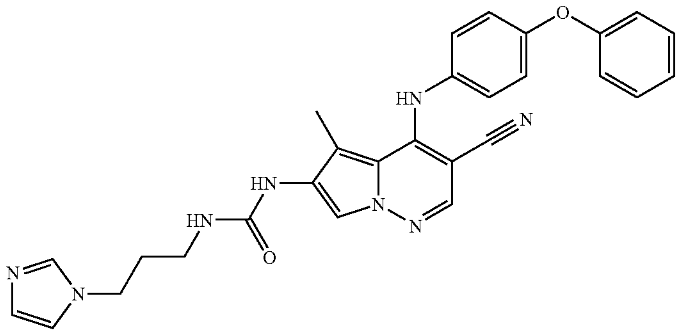 | 1-[3-Cyano-5-methyl-4-(4-phenoxy-phenylamino)-pyrrolo[1,2-b]pyridazin-6-yl]-3-(3-imidazol-1-yl-propyl)-urea | 1.53 LC $[M + H]^+$ = 507.2 | 19 |
| 175 | 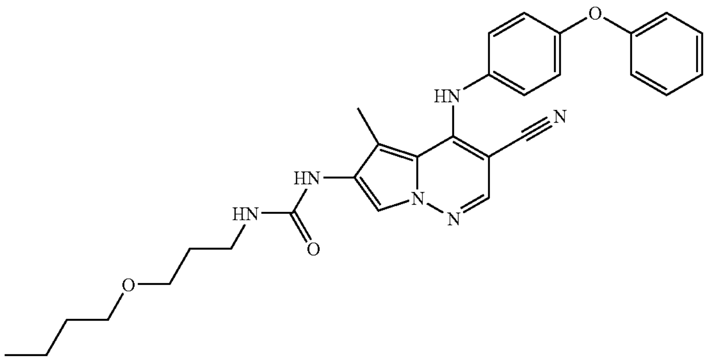 | 1-(3-Butoxy-propyl)-3-[3-cyano-5-methyl-4-(4-phenoxy-phenylamino)-pyrrolo[1,2-b]pyridazin-6-yl]-urea | 1.91 LC $[M + H]^+$ = 513.2 | 19 |
| 176 | 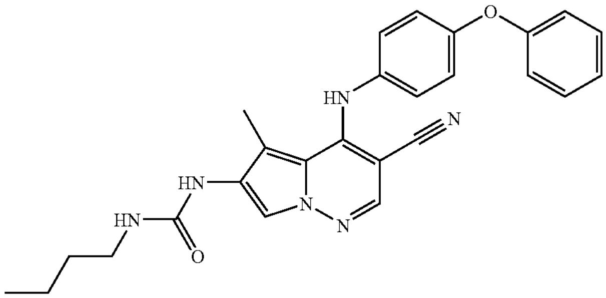 | 1-Butyl-3-[3-cyano-5-methyl-4-(4-phenoxy-phenylamino)-pyrrolo[1,2-b]pyridazin-6-yl]-urea | 1.85 LC $[M + H]^+$ = 455.2 | 19 |

TABLE 2-continued

| Ex. No. | Structure | Compound Name | Retention Time Min./ Molecular Mass | Proc. of Ex. |
|---|---|---|---|---|
| 177 | 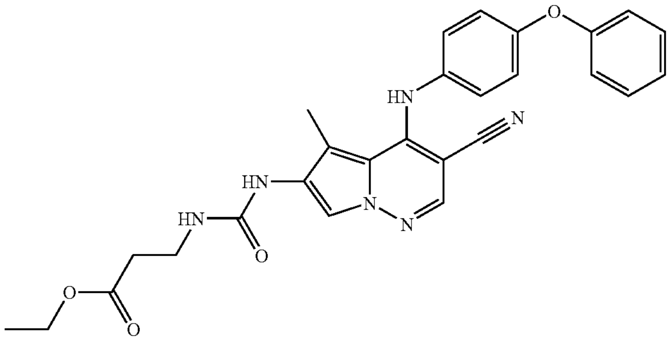 | 3-{3-[3-Cyano-5-methyl-4-(4-phenoxy-phenylamino)-pyrrolo[1,2-b]pyridazin-6-yl]-ureido}-propionic acid ethyl ester | 1.77 LC $[M + H]^+$ = 499.2 | 19 |
| 178 | 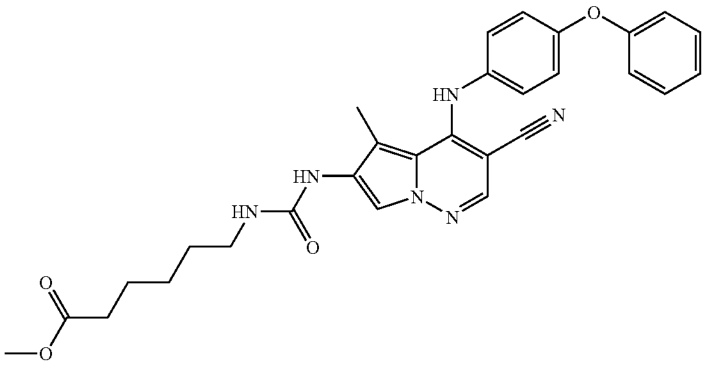 | 6-{3-[3-Cyano-5-methyl-4-(4-phenoxy-phenylamino)-pyrrolo[1,2-b]pyridazin-6-yl]-ureido}-hexanoic acid methyl ester | 1.81 LC $[M + H]^+$ = 527.2 | 19 |
| 179 | 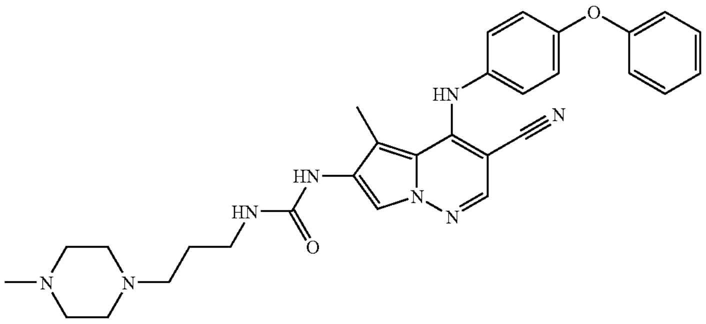 | 1-[3-Cyano-5-methyl-4-(4-phenoxy-phenylamino)-pyrrolo[1,2-b]pyridazin-6-yl]-3-[3-(4-methyl-piperazin-1-yl)-propyl]-urea | 1.44 LC $[M + H]^+$ = 539.2 | 19 |
| 180 | 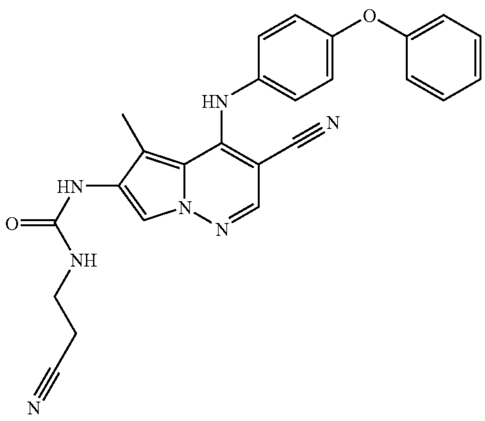 | 1-(2-Cyano-ethyl)-3-[3-cyano-5-methyl-4-(4-phenoxy-phenylamino)-pyrrolo[1,2-b]pyridazin-6-yl]-urea | 1.64 LC $[M + H]^+$ = 452.2 | 19 |

TABLE 2-continued

| Ex. No. | Structure | Compound Name | Retention Time Min./ Molecular Mass | Proc. of Ex. |
|---|---|---|---|---|
| 181 | 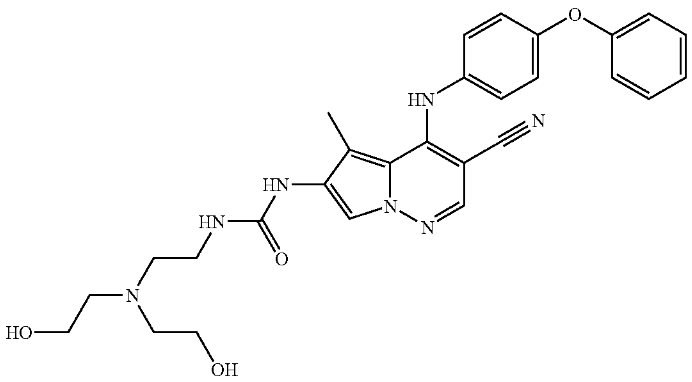 | 1-{2-[Bis-(2-hydroxy-ethyl)-amino]-ethyl}-3-[3-cyano-5-methyl-4-(4-phenoxy-phenylamino)-pyrrolo[1,2-b]pyridazin-6-yl]-urea | 1.46 LC $[M + H]^+$ = 530.2 | 19 |
| 182 | 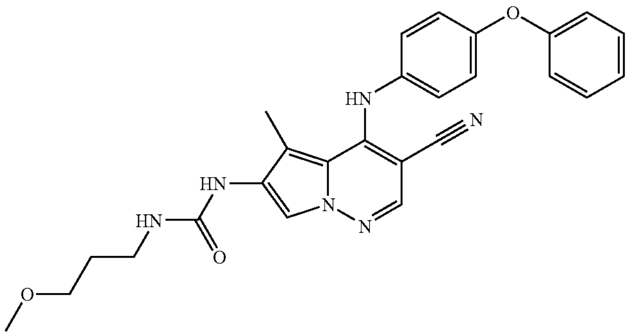 | 1-[3-Cyano-5-methyl-4-(4-phenoxy-phenylamino)-pyrrolo[1,2-b]pyridazin-6-yl]-3-(3-methoxy-propyl)-urea | 1.71 LC $[M + H]^+$ = 471.2 | 19 |
| 183 | 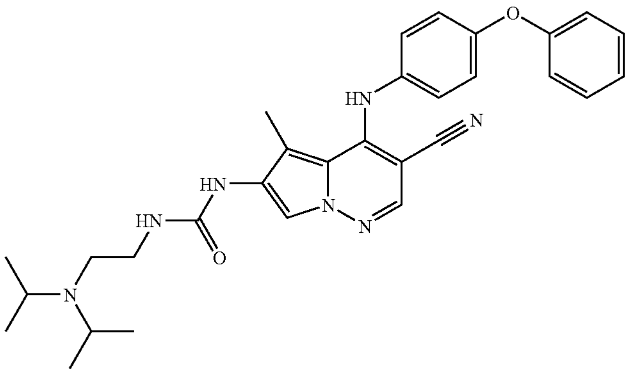 | 1-[3-Cyano-5-methyl-4-(4-phenoxy-phenylamino)-pyrrolo[1,2-b]-pyridazin-6-yl]-3-(2-diisopropyl-aminoethyl)-urea | 1.58 LC $[M + H]^+$ = 526.2 | 19 |
| 184 | 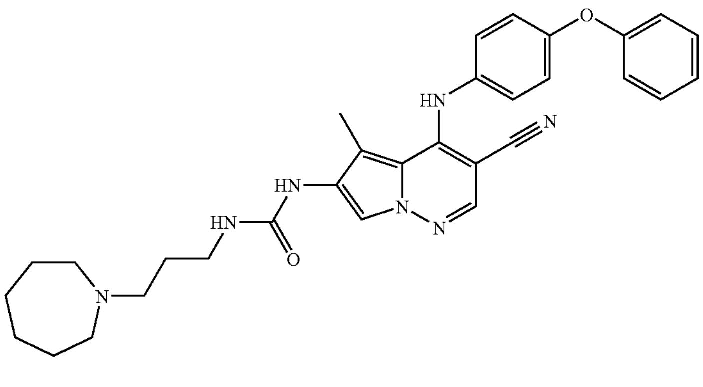 | 1-(3-Azepan-1-yl-propyl)-3-[3-cyano-5-methyl-4-(4-phenoxy-phenylamino)-pyrrolo[1,2-b]pyridazin-6-yl]-urea | 1.59 LC $[M + H]^+$ = 538.2 | 19 |

TABLE 2-continued

| Ex. No. | Structure | Compound Name | Retention Time Min./ Molecular Mass | Proc. of Ex. |
| --- | --- | --- | --- | --- |
| 185 | 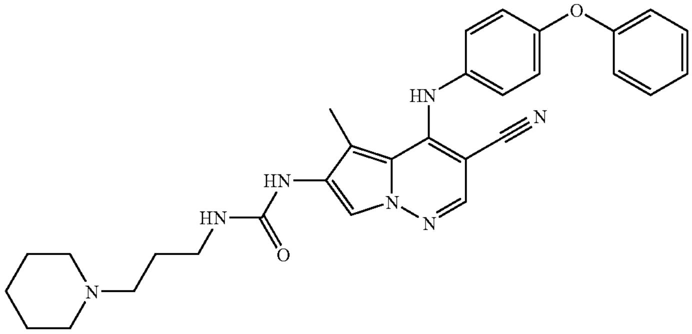 | 1-[3-Cyano-5-methyl-4-(4-phenoxy-phenylamino)-pyrrolo[1,2-b]pyridazin-6-yl]-3-(3-piperidin-1-yl-propyl)-urea | 1.57 LC $[M + H]^+$ = 524.2 | 19 |
| 186 | 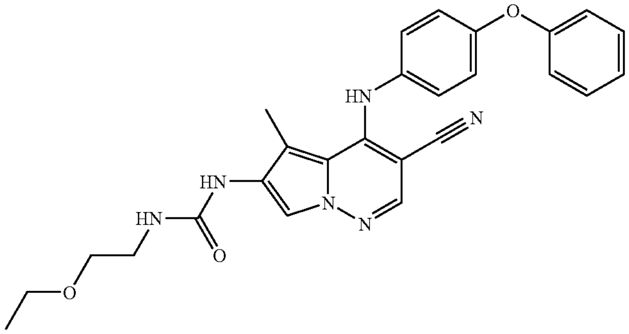 | 1-[3-Cyano-5-methyl-4-(4-phenoxy-phenylamino)-pyrrolo[1,2-b]pyridazin-6-yl]-3-(2-ethoxy-ethyl)-urea | 1.76 LC $[M + H]^+$ = 471.2 | 19 |
| 187 | 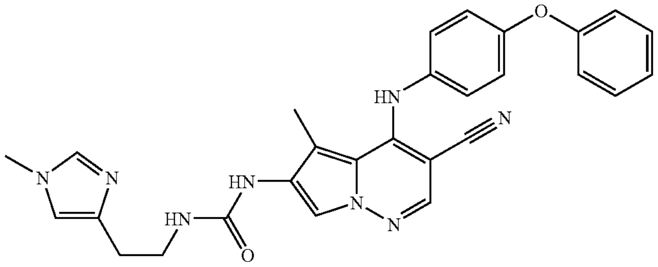 | 1-[3-Cyano-5-methyl-4-(4-phenoxy-phenylamino)-pyrrolo[1,2-b]pyridazin-6-yl]-3-[2-(1-methyl-1H-imid-azol-4-yl)-ethyl]-urea | 1.52 LC $[M + H]^+$ = 507.2 | 19 |
| 188 | 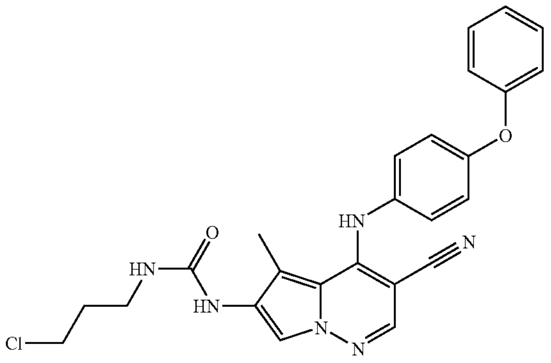 | 1-(3-Chloro-propyl)-3-[3-cyano-5-methyl-4-(4-phenoxy-phenylamino)-pyrrolo[1,2-b]pyridazin-6-yl]-urea | 1.8 LC $[M + H]^+$ = 475.2 | 19 |

TABLE 2-continued

| Ex. No. | Structure | Compound Name | Retention Time Min./ Molecular Mass | Proc. of Ex. |
|---|---|---|---|---|
| 189 | 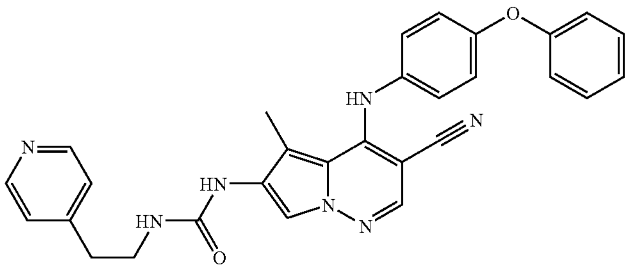 | 1-[3-Cyano-5-methyl-4-(4-phenoxy-phenylamino)-pyrrolo[1,2-b]pyridazin-6-yl]-3-(2-pyridin-4-yl-ethyl)-urea | 1.53 LC $[M + H]^+$ = 504.2 | 19 |
| 190 | 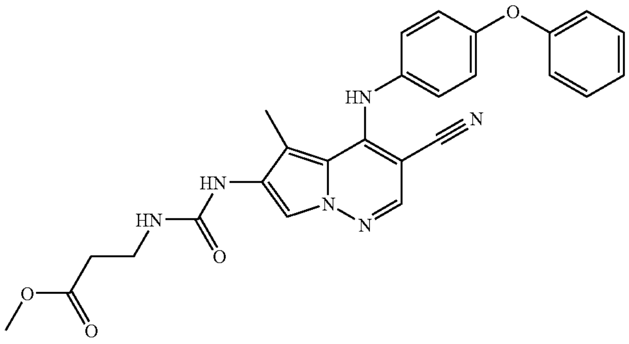 | 3-{3-[3-Cyano-5-methyl-4-(4-phenoxy-phenylamino)-pyrrolo[1,2-b]pyridazin-6-yl]-ureido}-propionic acid methyl ester | 1.7 LC $[M + H]^+$ = 485.2 | 19 |
| 191 | 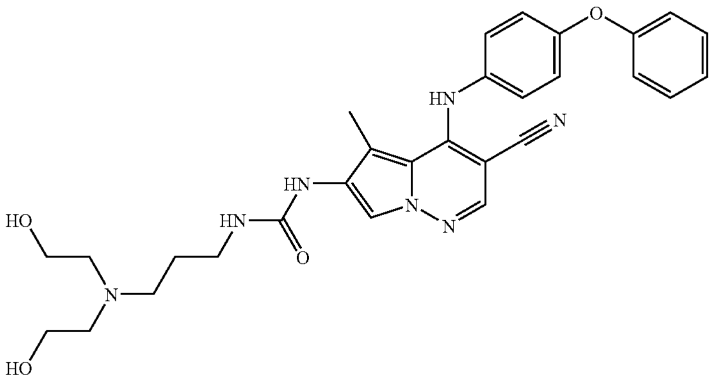 | 1-{3-[Bis-(2-hydroxy-ethyl)-amino]-propyl}-3-[3-cyano-5-methyl-4-(4-phenoxy-phenylamino)-pyrrolo[1-2-b]pyridazin-6-yl]-urea | 1.48 LC $]M + H]^+$ = 544.2 | 19 |
| 192 | 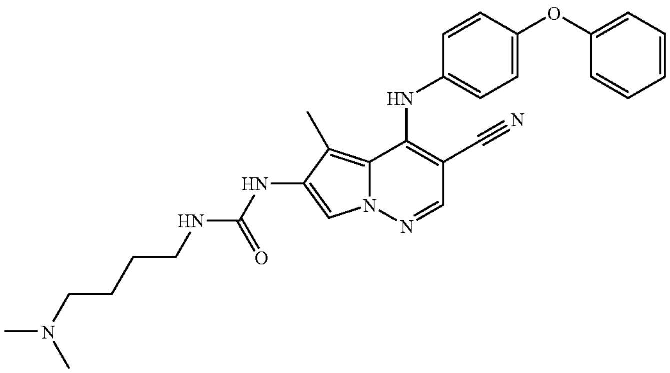 | 1-[3-Cyano-5-methyl-4-(4-phenoxy-phenylamino)-pyrrolo[1-2-b]pyridazin-6-yl]-3-(4-dimethylamino-butyl)-urea | 1.53 LC $[M + H]^+$ = 498.2 | 19 |

TABLE 2-continued

| Ex. No. | Structure | Compound Name | Retention Time Min./ Molecular Mass | Proc. of Ex. |
|---|---|---|---|---|
| 193 | 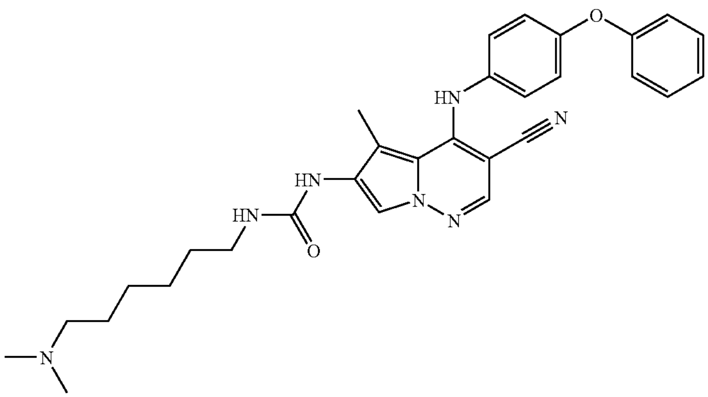 | 1-[3-Cyano-5-methyl-4-(4-phenoxy-phenylamino)-pyrrolo[1,2-b]pyridazin-6-yl]-3-(6-dimethylamino-hexyl)-urea | 1.6 LC $[M + H]^+$ = 526.2 | 19 |
| 194 | 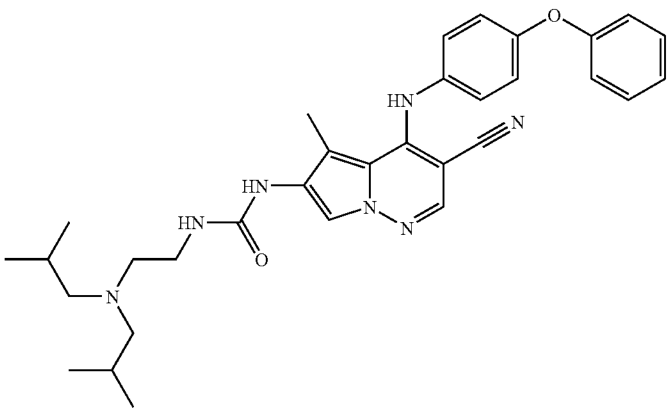 | 1-[3-Cyano-5-methyl-4-(4-phenoxy-phenylamino)-pyrrolo[1,2-b]pyridazin-6-yl]-3-(2-diisobutylamino-ethyl)-urea | 1.73 LC $[M + H]^+$ = 552.1 | 19 |
| 195 | 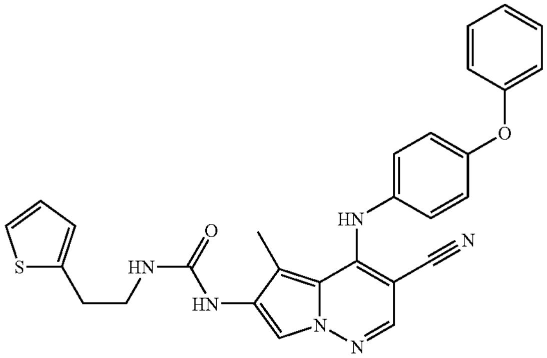 | 1-[3-Cyano-5-methyl-4-(4-phenoxy-phenylamino)-pyrrolo[1,2-b]pyridazin-6-yl]-3-(2-thiophen-2-yl-ethyl)-urea | 1.87 LC $[M + H]^+$ = 509.1 | 19 |

TABLE 2-continued

| Ex. No. | Structure | Compound Name | Retention Time Min./ Molecular Mass | Proc. of Ex. |
|---|---|---|---|---|
| 196 | 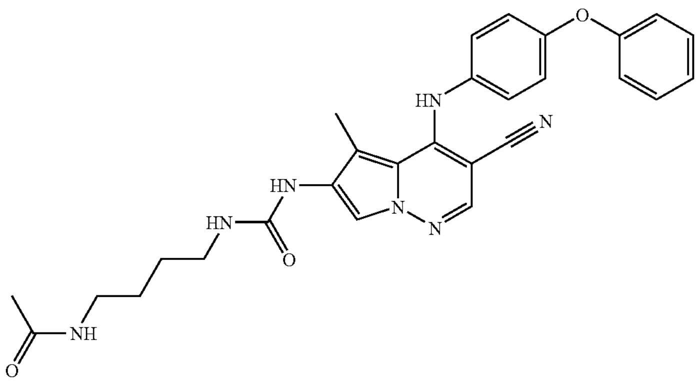 | N-(4-{3-[3-Cyano-5-methyl-4-(4-phenoxy-phenylamino)-pyrrolo[1,2-b]pyridazin-6-yl]-ureido}-butyl)-acetamide | 1.66 LC $[M + H]^+$ = 512.2 | 19 |
| 197 | 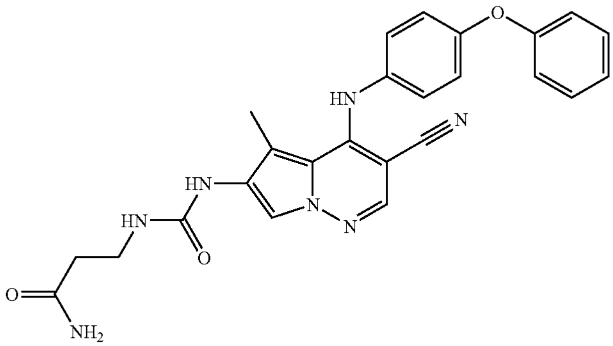 | 3-{3-[3-Cyano-5-methyl-4-(4-phenoxy-phenylamino)-pyrrolo[1,2-b]pyridazin-6-yl]-ureido}-propionamide | 1.59 LC $[M + H]^+$ = 470.2 | 19 |
| 198 | 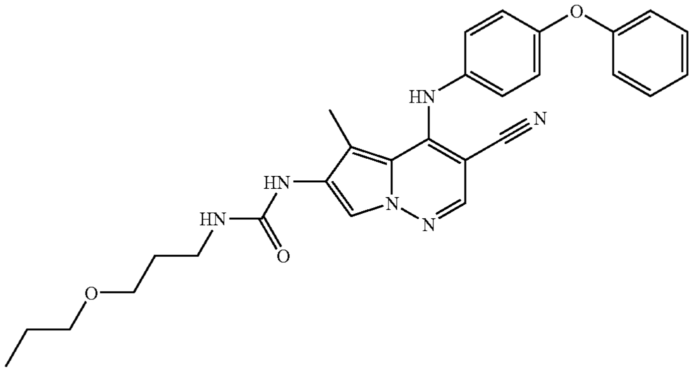 | 1-[3-Cyano-5-methyl-4-(4-phenoxy-phenylamnino)-pyrrolo[1,2-b]pyridazin-6-yl]-3-(3-propoxy-propyl)-urea | 1.85 LC $[M + H]^+$ = 499.2 | 19 |
| 199 | 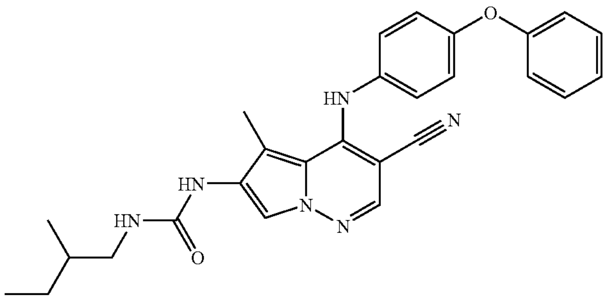 | 1-[3-Cyano-5-methyl-4-(4-phenoxy-phenylamino)-pyrrolo[1,2-b]pyridazin-6-yl]-3-(2-methyl-butyl)-urea | 1.9 LC $[M + H]^+$ = 469.2 | 19 |

TABLE 2-continued

| Ex. No. | Structure | Compound Name | Retention Time Min./ Molecular Mass | Proc. of Ex. |
|---|---|---|---|---|
| 200 | 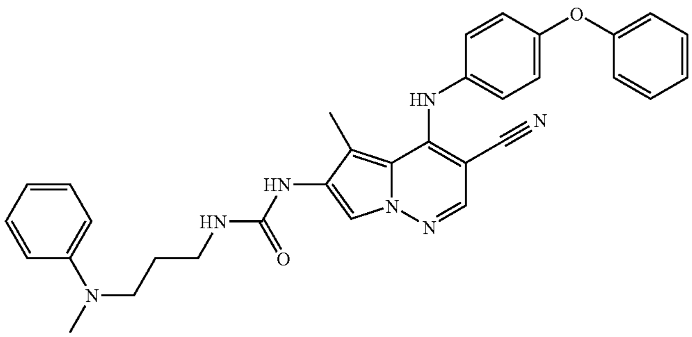 | 1-[3-Cyano-5-methyl-4-(4-phenoxy-phenylamino)-pyrrolo[1,2-b]pyridazin-6-yl]-3-[3-(methyl-phenyl-amino)-propyl]-urea | 1.61 LC $[M + H]^+$ = 546.2 | 19 |
| 201 | 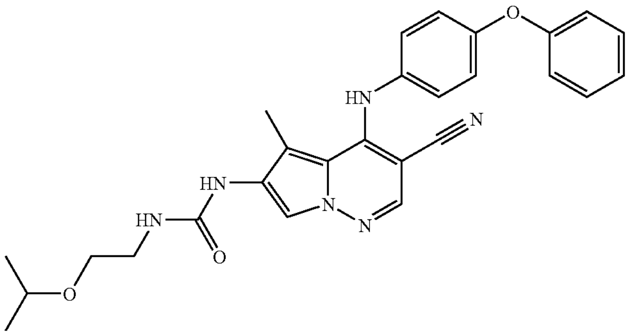 | 1-[3-Cyano-5-methyl-4-(4-phenoxy-phenylamino)-pyrrolo[1,2-b]pyridazin-6-yl]-3-(2-isopropoxy-ethyl)-urea | 1.82 LC $[M + H]^+$ = 485.2 | 19 |
| 202 | 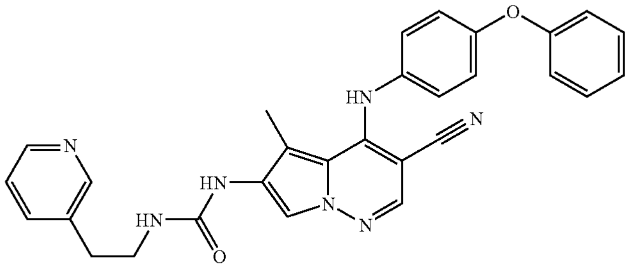 | 1-[3-Cyano-5-methyl-4-(4-phenoxy-phenylamino)-pyrrolo[1,2-b]pyridazin-6-yl]-3-(2-pyridin-3-yl-ethyl)-urea | 1.53 LC $[M + H]^+$ = 504.2 | 19 |
| 203 | 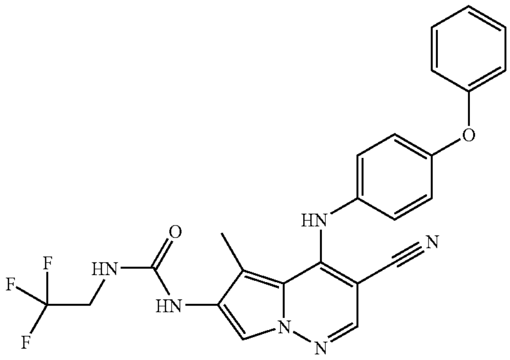 | 1-[3-Cyano-5-methyl-4-(4-phenoxy-phenylamino)-pyrrolo[1,2-b]pyridazin-6-yl]-3-(2,2,2-trifluoro-ethyl)-urea | 1.76 LC $[M + H]^+$ = 481.1 | 19 |

TABLE 2-continued

| Ex. No. | Structure | Compound Name | Retention Time Min./ Molecular Mass | Proc. of Ex. |
|---|---|---|---|---|
| 204 | 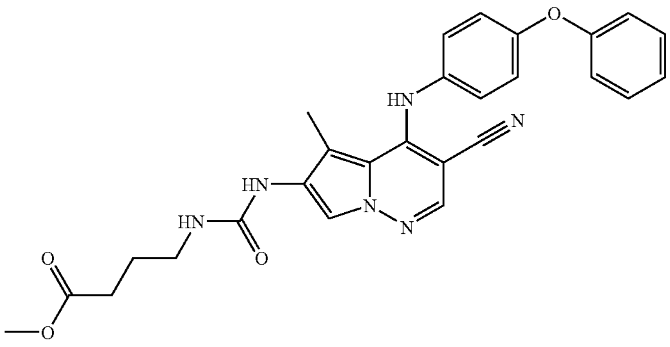 | 4-{3-[3-Cyano-5-methyl-4-(4-phenoxy-phenylamino)-pyrrolo[1,2-b]pyridazin-6-yl]-ureido}-butyric acid methyl ester | 1.71 LC [M + H]$^+$ = 499.2 | 19 |
| 205 | 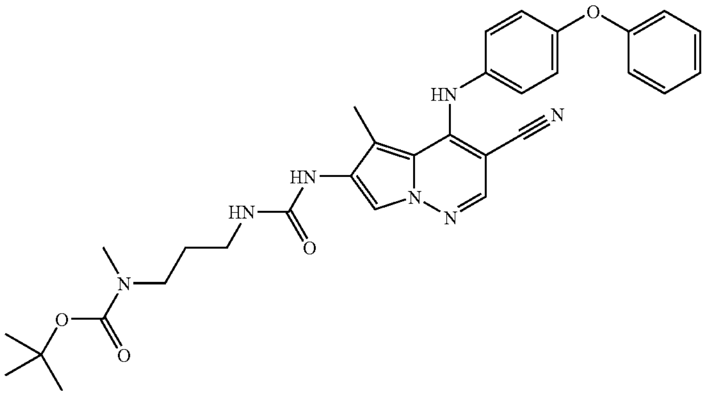 | (3-{3-[3-Cyano-5-methyl-4-(4-phenoxy-phenylamino)-pyrrolo[1,2-b]pyridazin--yl]-ureido}-propyl)-methyl-carbamic acid tert-butyl ester | 1.9 LC [M + H]$^+$ = 570.3 | 19 |
| 206 | 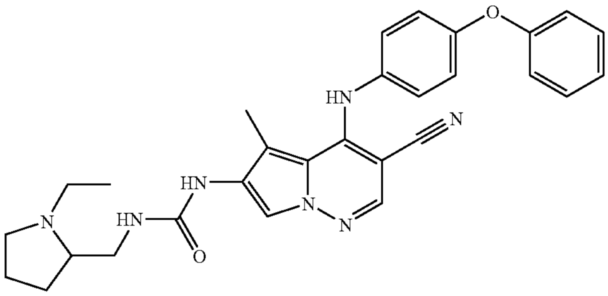 | 1-[3-Cyano-5-methyl-4-(4-phenoxy-phenylamino)-pyrrolo[1,2-b]pyridazin-6-yl]-3-(1-ethyl-pyrrolidin-2-ylmethyl)-urea | 1.55 LC [M + H]$^+$ = 510.2 | 19 |
| 207 | 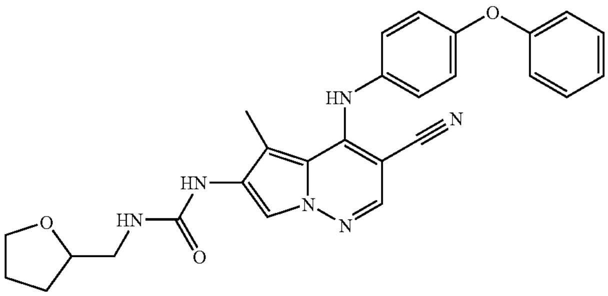 | 1-[3-Cyano-5-methyl-4-(4-phenoxy-phenylamino)-pyrrolo[1,2-b]pyridazin-6-yl]-3-(tetrahydro-furan-2-ylmethyl)-urea | 1.77 LC [M + H]$^+$ = 483.2 | 19 |

TABLE 2-continued

| Ex. No. | Structure | Compound Name | Retention Time Min./ Molecular Mass | Proc. of Ex. |
|---|---|---|---|---|
| 208 | 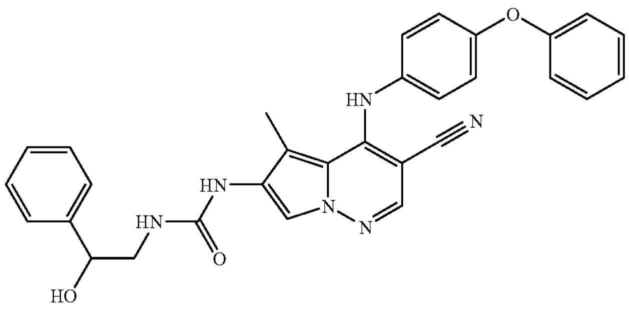 | 1-[3-Cyano-5-methyl-4-(4-phenoxy-phenylamino)-pyrrolo[1,2-b]pyridazin-6-yl]-3-(2-hydroxy-2-phenyl-ethyl)-urea | 1.79 LC $[M + H]^+$ = 519.2 | 19 |
| 209 | 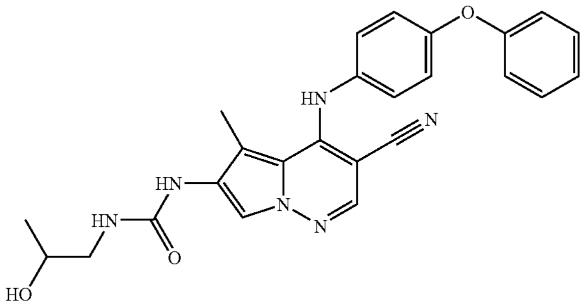 | 1-[3-Cyano-5-methyl-4-(4-phenoxy-phenylamino)-pyrrolo[1,2-b]pyridazin-6-yl]-3-(2-hydroxy-propyl)-urea | 1.66 LC $[M + H]^+$ = 457.2 | 19 |
| 210 | 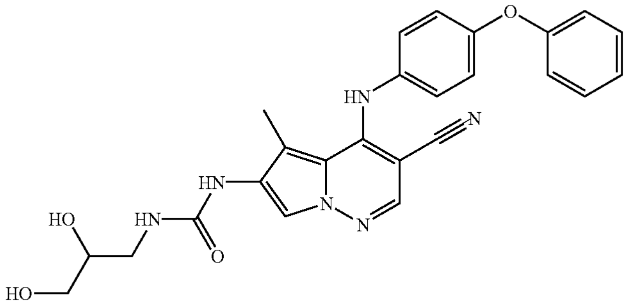 | 1-[3-Cyano-5-methyl-4-(4-phenoxy-phenylamino)-pyrrolo[1,2-b]pyridazin-6-yl]-3-(2,3-dihydroxy-propyl)-urea | 1.58 LC $[M + H]^+$ = 473.2 | 19 |
| 211 | 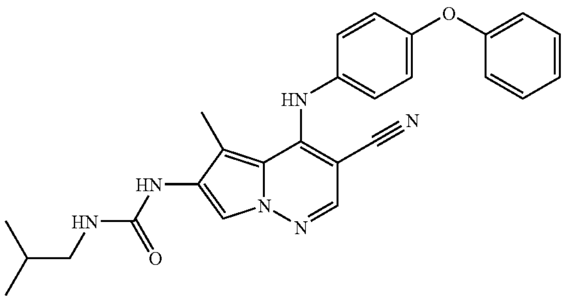 | 1-[3-Cyano-5-methyl-4-(4-phenoxy-phenylamino)-pyrrolo[1,2-b]pyridazin-6-yl]-3-isobutyl-urea | 1.85 LC $[M + H]^+$ = 455.2 | 19 |

TABLE 2-continued

| Ex. No. | Structure | Compound Name | Retention Time Min./ Molecular Mass | Proc. of Ex. |
|---|---|---|---|---|
| 212 | 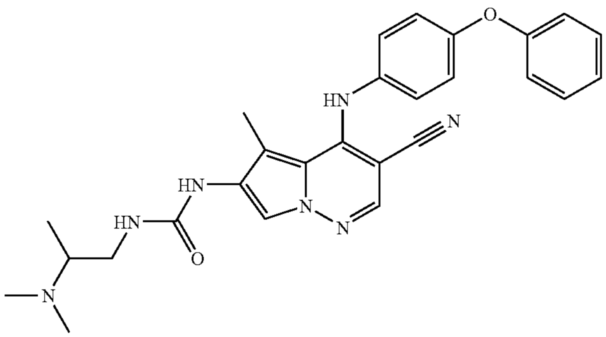 | 1-[3-Cyano-5-methyl-4-(4-phenoxy-phenylamino)-pyrrolo[1,2-b]pyridazin-6-yl]-3-(2-dimethylamino-propyl)-urea | 1.52 LC $[M + H]^+$ = 484.2 | 19 |
| 213 | 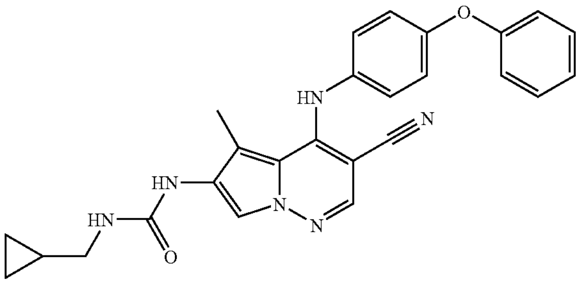 | 1-[3-Cyano-5-methyl-4-(4-phenoxy-phenylamino)-pyrrolo[1,2-b]pyridazin-6-yl]-3-cyclopropylmethyl-urea | 1.8 LC $[M + H]^+$ = 453.2 | 19 |
| 214 | 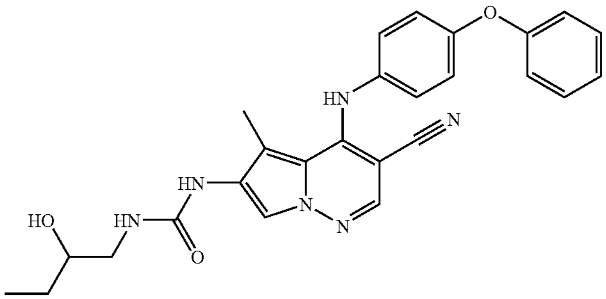 | 1-[3-Cyano-5-methyl-4-(4-phenoxy-phenylamino)-pyrrolo[1,2-b]pyridazin-6-yl]-3-(2-hydroxy-butyl)-urea | 1.73 LC $[M + H]^+$ = 471.2 | 19 |
| 215 | 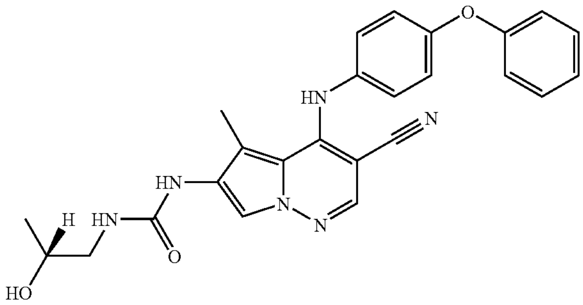 | 1-[3-Cyano-5-methyl-4-(4-phenoxy-phenylamino)-pyrrolo[1,2-b]pyridazin-6-yl]-3-(2-hydroxy-propyl)-urea | 1.66 LC $[M + H]^+$ = 457.2 | 19 |

TABLE 2-continued

| Ex. No. | Structure | Compound Name | Retention Time Min./ Molecular Mass | Proc. of Ex. |
|---|---|---|---|---|
| 216 | 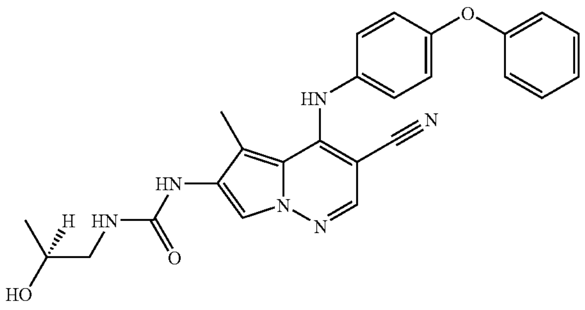 | 1-[3-Cyano-5-methyl-4-(4-phenoxy-phenylamino)-pyrrolo[1,2-b]pyridazin-6-yl]-3-(2-hydroxy-propyl)-urea | 1.66 LC $[M + H]^+$ = 457.2 | 19 |
| 217 | 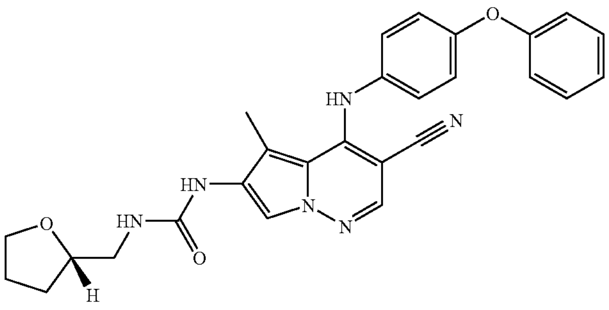 | 1-[3-Cyano-5-methyl-4-(4-phenoxy-phenylamino)-pyrrolo[1,2-b]pyridazin-6-yl]-3-(tetrahydro-furan-2-ylmethyl)-urea | 1.77 LC $[M + H]^+$ = 483.2 | 19 |
| 218 | 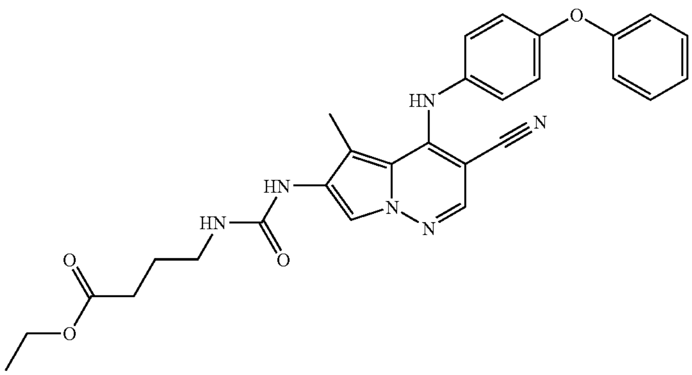 | 4-{3-[3-Cyano-5-methyl-4-(4-phenoxy-phenylamino)-pyrrolo[1,2-b]pyridazin-6-yl]-ureido}-butyric acid ethyl ester | 1.79 LC $[M + H]^+$ = 513.2 | 19 |
| 219 | 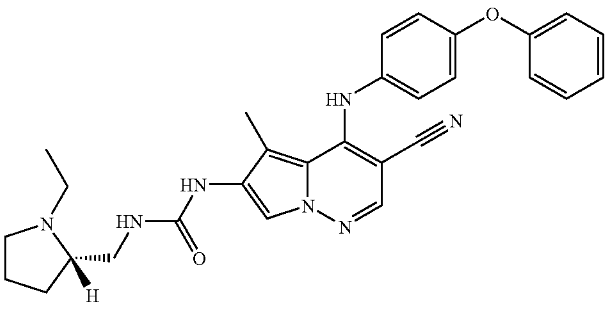 | 1-[3-Cyano-5-methyl-4-(4-phenoxy-phenylamino)-pyrrolo[1,2-b]pyridazin-6-yl]-3-(1-ethyl-pyrrolidin-2-ylmethyl)-urea | 1.56 LC $[M + H]^+$ = 510.2 | 19 |

TABLE 2-continued

| Ex. No. | Structure | Compound Name | Retention Time Min./ Molecular Mass | Proc. of Ex. |
|---|---|---|---|---|
| 220 | 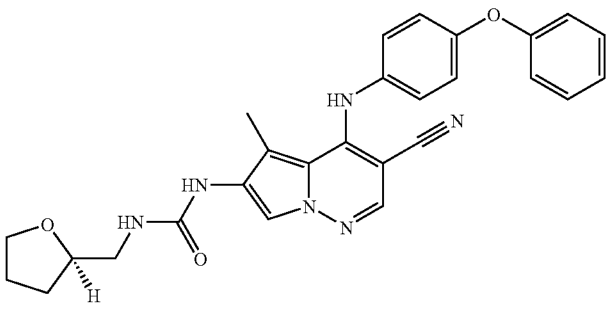 | 1-[3-Cyano-5-methyl-4-(4-phenoxy-phenylamino)-pyrrolo[1,2-b]pyridazin-6-yl]-3-(tetrahydro-furan-2-ylmethyl)-urea | 1.77 LC $[M + H]^+$ = 483.2 | 19 |
| 221 | 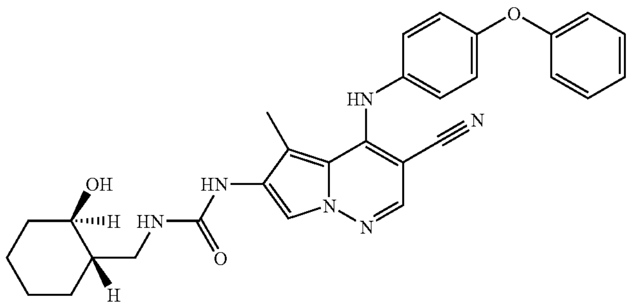 | 1-[3-Cyano-5-methyl-4-(4-phenoxy-phenylamino)-pyrrolo[1,2-b]pyridazin-6-yl]-3-(2-hydroxy-cyclohexylmethyl)-urea | 1.83 LC $[M + H]^+$ = 511.2 | 19 |
| 222 | 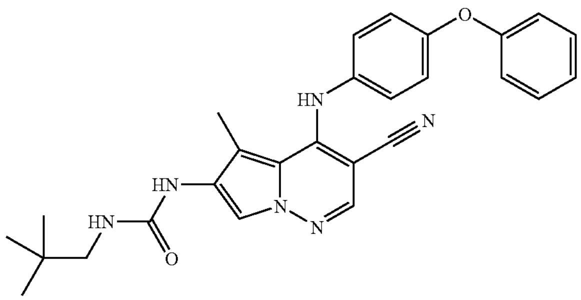 | 1-[3-Cyano-5-methyl-4-(4-phenoxy-phenylamino)-pyrrolo[1,2-b]pyridazin-6-yl]-3-(2,2-dimethyl-propyl)-urea | 1.9 LC $[M + H]^+$ = 469.2 | 19 |
| 223 | 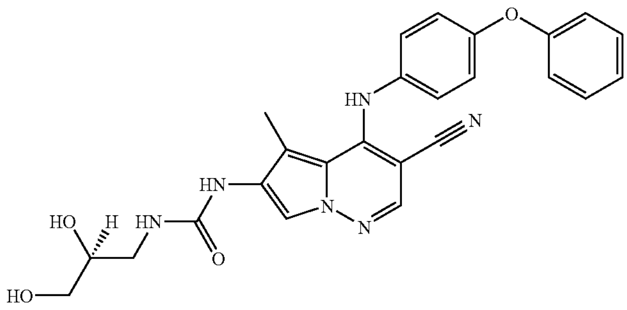 | 1-[3-Cyano-5-methyl-4-(4-phenoxy-phenylamino)-pyrrolo[1,2-b]pyridazin-6-yl]-3-(2,3-dihydroxy-propyl)-urea | 1.59 LC $[M + H]^+$ = 473.2 | 19 |

TABLE 2-continued

| Ex. No. | Structure | Compound Name | Retention Time Min./ Molecular Mass | Proc. of Ex. |
|---|---|---|---|---|
| 224 | 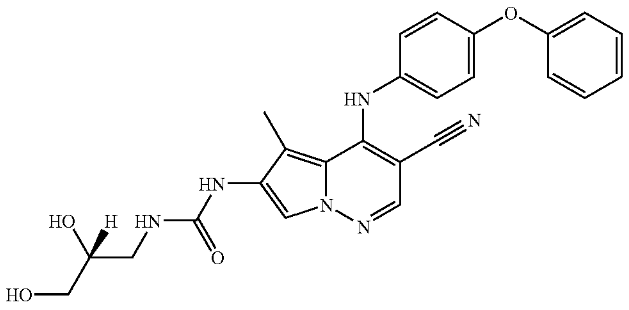 | 1-[3-Cyano-5-methyl-4-(4-phenoxy-phenylamino)-pyrrolo[1,2-b]pyridazin-6-yl]-3-(2,3-dihydroxy-propyl)-urea | 1.59 LC $[M + H]^+$ = 473.2 | 19 |
| 225 | 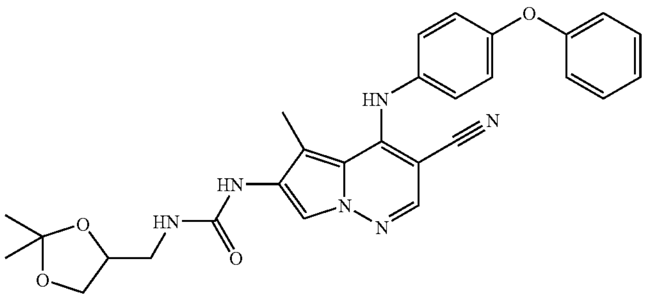 | 1-[3-Cyano-5-methyl-4-(4-phenoxy-phenylamino)-pyrrolo[1,2-b]pyridazin-6-yl]-3-(2,2-dimethyl-[1,3] dioxolan-4-ylmethyl)-urea | 1.58 LC $[M + H]^+$ = 511.2 | 19 |
| 226 | 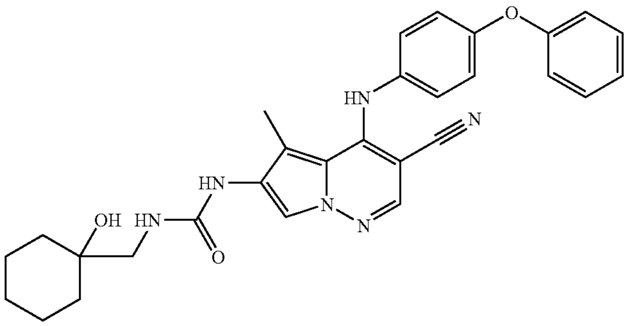 | 1-[3-Cyano-5-methyl-4-(4-phenoxy-phenylamino)-pyrrolo[1,2-b]pyridazin-6-yl]-3-(1-hydroxy-cyclohexylmethyl)-urea | 1.84 LC $[M + H]^+$ = 511.2 | 19 |
| 227 | 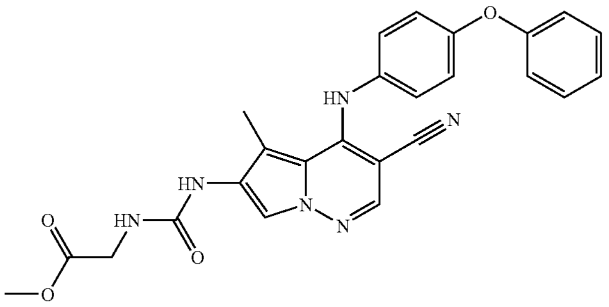 | {3-[3-Cyano-5-methyl-4-(4-phenoxy-phenylamino)-pyrrolo[1,2-b]pyridazin-6-yl]-ureido}-acetic acid methyl ester | 1.66 LC $[M + H]^+$ = 471.2 | 19 |

TABLE 2-continued

| Ex. No. | Structure | Compound Name | Retention Time Min./ Molecular Mass | Proc. of Ex. |
|---|---|---|---|---|
| 228 | 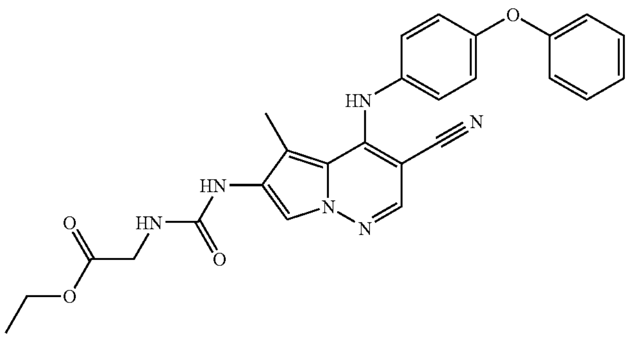 | {3-[3-Cyano-5-methyl-4-(4-phenoxy-phenylamino)-pyrrolo[1,2-b]pyridazin-6-yl]-ureido}-acetic acid ethyl ester | 1.72 LC $[M + H]^+$ = 485.2 | 19 |
| 229 | 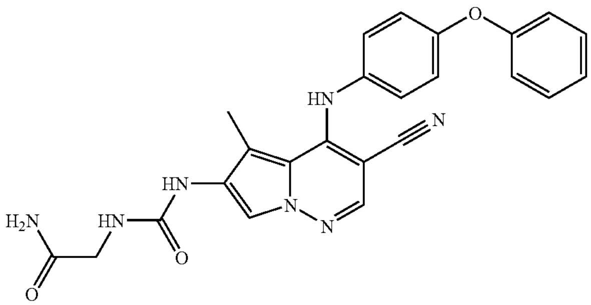 | 2-{3-[3-Cyano-5-methyl-4-(4-phenoxy-phenylamino)-pyrrolo[1,2-b]pyridazin-6-yl]-ureido-acetamide | 1.58 LC $[M + H]^+$ = 456.2 | 19 |
| 230 | 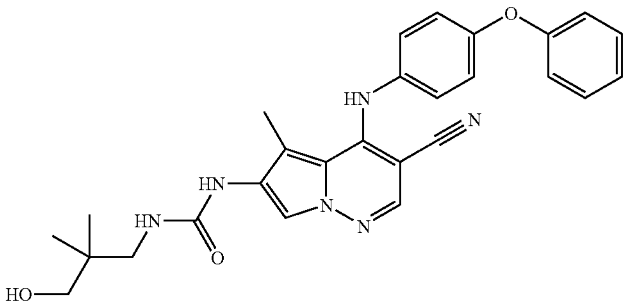 | 1-[3-Cyano-5-methyl-4-(4-phenoxy-phenylamino)-pyrrolo[1,2-b]pyridazin-6-yl]-3-(3-hydroxy-2,2-dimethyl-propyl)-urea | 1.77 LC $[M + H]^+$ = 485.2 | 19 |
| 231 | 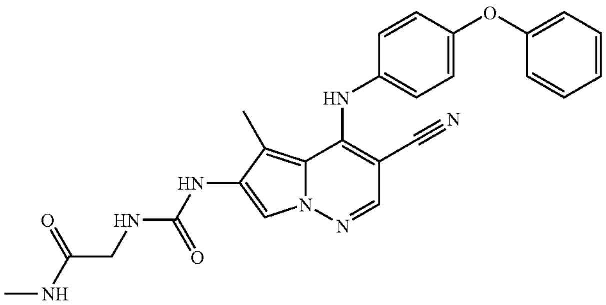 | 2-{3-[3-Cyano-5-methyl-4-(4-phenoxy-phenylamino)-pyrrolo[1,2-b]pyridazin-6-yl]-ureido}-N-methyl-acetamide | 1.59 LC $[M + H]^+$ = 470.2 | 19 |

TABLE 2-continued

| Ex. No. | Structure | Compound Name | Retention Time Min./ Molecular Mass | Proc. of Ex. |
|---|---|---|---|---|
| 232 | 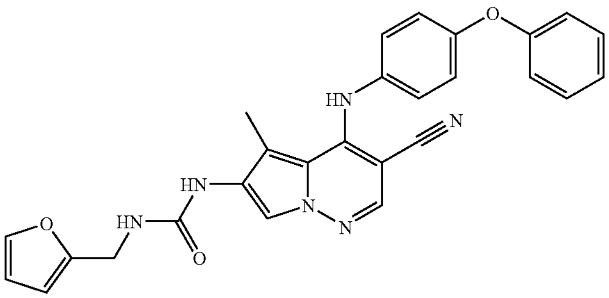 | 1-[3-Cyano-5-methyl-4-(4-phenoxy-phenylamino)-pyrrolo[1,2-b]pyridazin-6-yl]-3-furan-2-ylmethyl-urea | 1.79 LC $[M + H]^+$ = 479.2 | 19 |
| 233 | 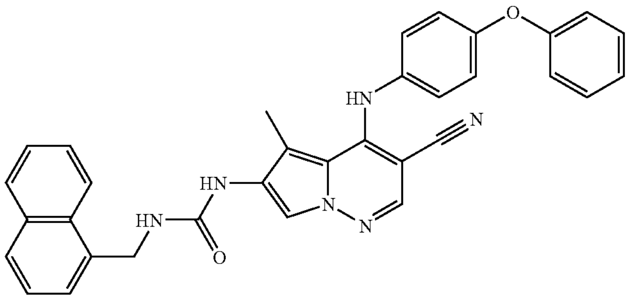 | 1-[3-Cyano-5-methyl-4-(4-phenoxy-phenylamino)-pyrrolo[1,2-b]pyridazin-6-yl]-3-naphthalen-1-ylmethyl-urea | 1.94 LC $[M + H]^+$ = 539.1 | 19 |
| 234 | 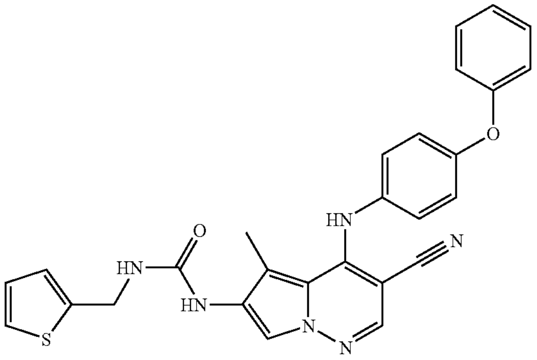 | 1-[3-Cyano-5-methyl-4-(4-phenoxy-phenylamino)-pyrrolo[1,2-b]pyridazin-6-yl]-3-thiophen-2-ylmethyl-urea | 1.83 LC $[M + H]^+$ = 495.2 | 19 |
| 235 | 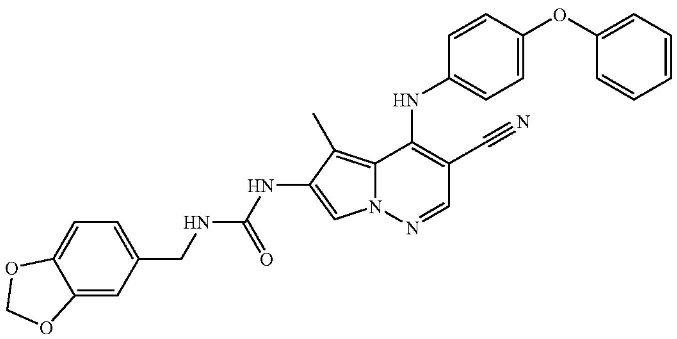 | 1-Benzo[1,3]dioxol-5-ylmethyl-3-[3-cyano-5-methyl-4-(4-phenoxy-phenylamino)-pyrrolo[1,2-b]pyridazin-6-yl]-urea | 1.84 LC $[M + H]^+$ = 533.1 | 19 |

TABLE 2-continued

| Ex. No. | Structure | Compound Name | Retention Time Min./ Molecular Mass | Proc. of Ex. |
|---|---|---|---|---|
| 236 | 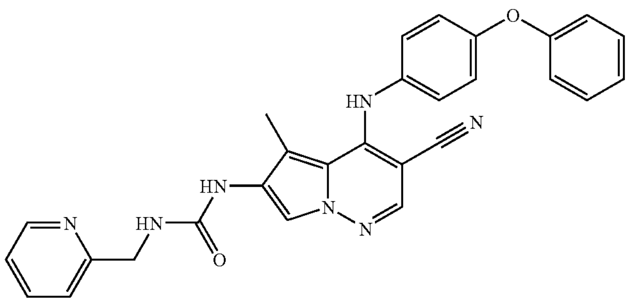 | 1-[3-Cyano-5-methyl-4-(4-phenoxy-phenylamino)-pyrrolo[1,2-b]pyridazin-6-yl]-3-pyridin-2-ylmethyl-urea | 1.53 LC $[M + H]^+$ = 490.2 | 19 |
| 237 | 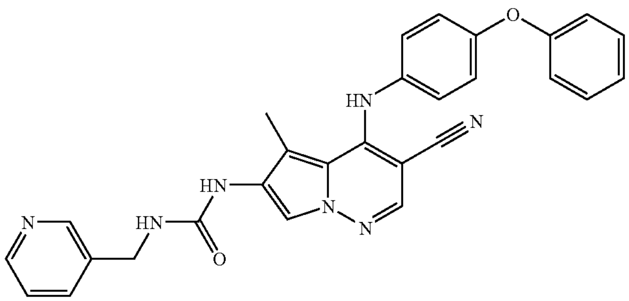 | 1-[3-Cyano-5-methyl-4-(4-phenoxy-phenylamino)-pyrrolo[1,2-b]pyridazin-6-yl]-3-pyridin-3-ylmethyl-urea | 1.52 LC $[M + H]^+$ = 490.2 | 19 |
| 238 | 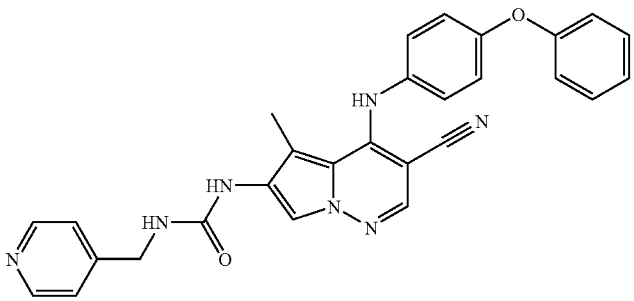 | 1-[3-Cyano-5-methyl-4-(4-phenoxy-phenylamino)-pyrrolo[1,2-b]pyridazin-6-yl]-3-pyridin-4-ylmethyl-urea | 1.52 LC $[M + H]^+$ = 490.2 | 19 |
| 239 | 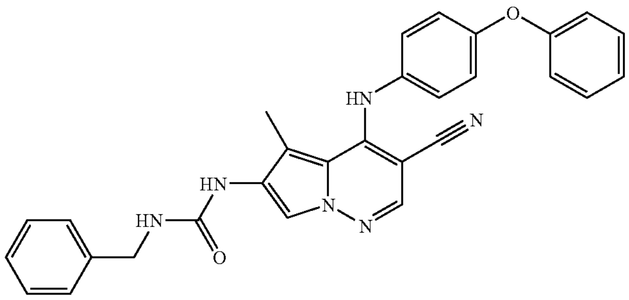 | 1-Benzyl-3-[3-cyano-5-methyl-4-(4-phenoxy-phenylamino)-pyrrolo[1,2-b]pyridazin-6-yl]-urea | 1.85 LC $[M + H]^+$ = 489.2 | 19 |

TABLE 2-continued

| Ex. No. | Structure | Compound Name | Retention Time Min./ Molecular Mass | Proc. of Ex. |
|---|---|---|---|---|
| 240 | 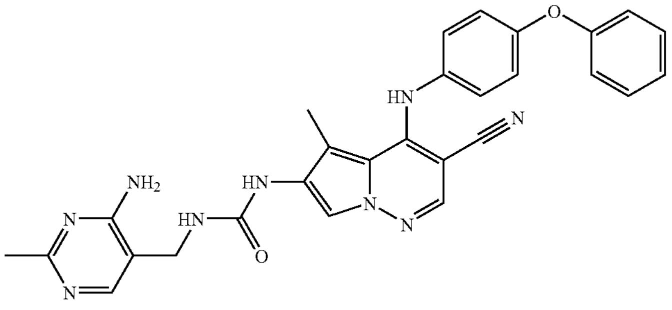 | 1-(4-Amino-2-methyl-pyrimidin-5-ylmethyl)-3-[3-cyano-5-methyl-4-(4-phenoxy-phenylamino)-pyrrolo[1,2-b]pyridazin-6-yl]-urea | 1.53 LC $[M + H]^+$ = 520.1 | 19 |
| 241 | 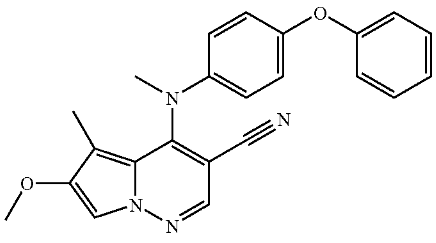 | 6-Methoxy-5-methyl-4-[methyl-(4-phenoxy-phenyl)-amino]-pyrrolo[1,2-b]pyridazine-3-carbonitrile | 2.17 LC $[M + H]^+$ = 385.2 | 154 |
| 242 | 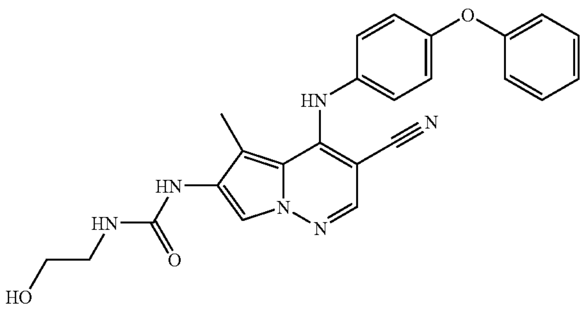 | 1-[3-Cyano-5-methyl-4-(4-phenoxy-phenylamino)-pyrrolo[1,2-b]pyridazin-6-yl]-3-(2-hydroxy-ethyl)-urea | 1.77 LC $[M + H]^+$ = 443.2 | 19 |
| 243 | 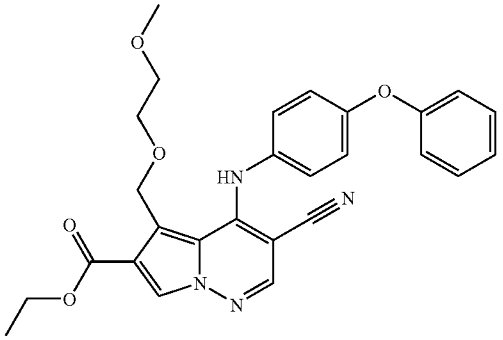 | 3-Cyano-5-(2-methoxy-ethoxymethyl)-4-(4-phenoxy-phenylamino)-pyrrolo[1,2-b]pyridazine-6-carboxylic acid ethyl ester | 2.19 LC $[M + H]^+$ = 487.2 | 17B |

TABLE 2-continued

| Ex. No. | Structure | Compound Name | Retention Time Min./ Molecular Mass | Proc. of Ex. |
|---|---|---|---|---|
| 244 | 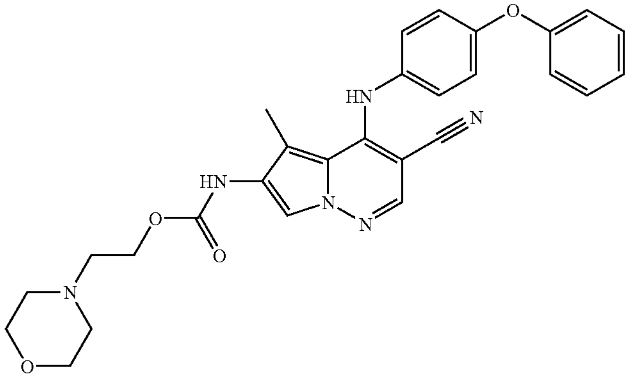 | [3-Cyano-5-methyl-4-(4-phenoxy-phenylamino)-pyrrolo[1,2-b]pyridazin-6-yl]-carbamic acid 2-morpholin-4-yl-ethyl ester | 1.50 LC $[M + H]^+$ = 513.2 | 11A |
| 245 | 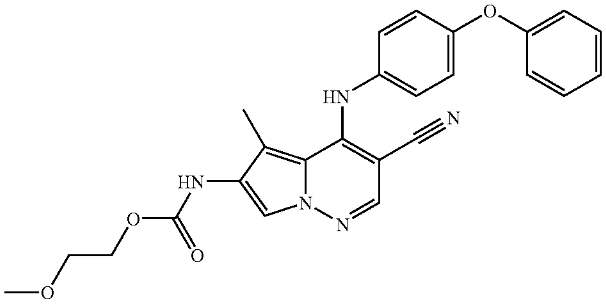 | [3-Cyano-5-methyl-4-(4-phenoxy-phenylamino)-pyrrolo[1,2-b]pyridazin-6-yl]-carbamic acid 2-methoxy-ethyl ester | 1.71 LC $[M + H]^+$ = 458.2 | 11A |
| 246 | 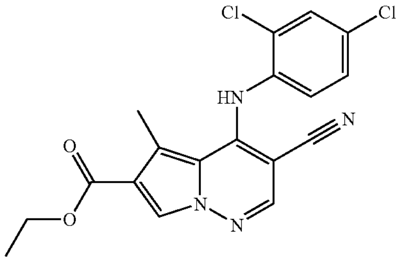 | 3-Cyano-4-(2,4-dichloro-phenylamino)-5-methyl-pyrrolo[1,2-b]pyridazine-6-carboxylic acid ethyl ester | 4.39 LC* $[M + H]^+$ = 390.0 | 1E |
| 247 | 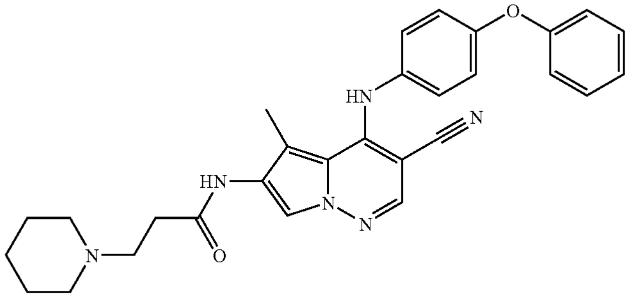 | N-[3-Cyano-5-methyl-4-(4-phenoxy-phenylamino)-pyrrolo[1,2-b]pyridazin-6-yl]-3-piperidin-1-yl-propionamide | 1.52 LC $[M + H]^+$ = 495.2 | 12 |

TABLE 2-continued

| Ex. No. | Structure | Compound Name | Retention Time Min./ Molecular Mass | Proc. of Ex. |
|---|---|---|---|---|
| 248 | 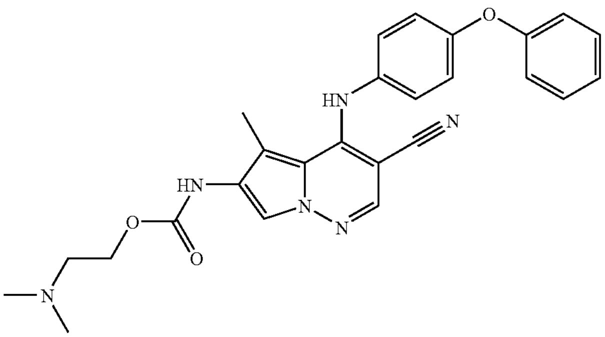 | [3-Cyano-5-methyl-4-(4-phenoxy-phenylamino)-pyrrolo[1,2-b]pyridiazin-6-yl]-carbamic acid 2-dimethyl amino-ethyl ester | 1.55 LC $[M + H]^+$ = 471.2 | 11A |
| 249 | 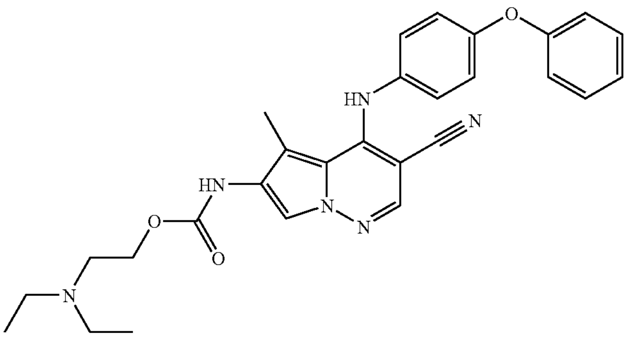 | [3-Cyano-5-methyl-4-(4-phenoxy-phenylamino)-pyrrolo[1,2-b]pyridazin-6-yl]-carbamic acid 2-diethyl-amino-ethyl ester | 1.52 LC $[M + H]^+$ = 499.2 | 11A |
| 250 | 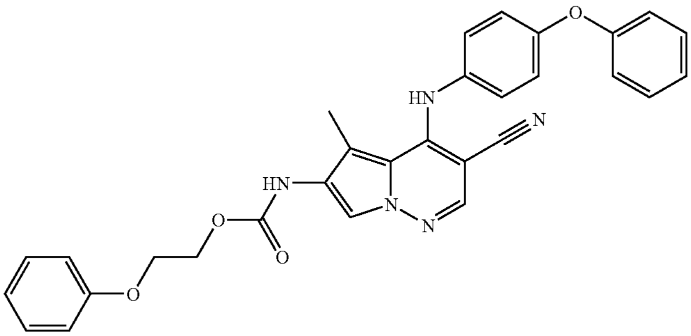 | [3-Cyano-5-methyl-4-(4-phenoxy-phenylamino)-pyrrolo[1,2-b]pyridazin-6-yl]-carbamic acid 2-phenoxy-ethyl ester | 1.90 LC $[M + H]^+$ = 520.1 | 11A |
| 251 | 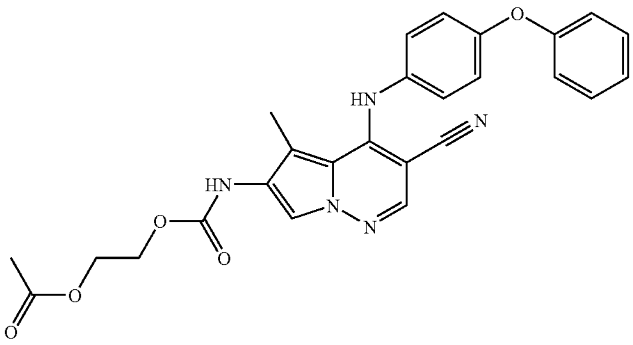 | Acetic acid 2-[3-cyano-5-methyl-4-(4-phenoxy-phenylamino)-pyrrolo[1,2-b]pyridazin-6-ylcarbamoyloxy]-ethyl ester | 1.72 LC $[M + H]^+$ = 486.2 | 11A |

TABLE 2-continued

| Ex. No. | Structure | Compound Name | Retention Time Min./ Molecular Mass | Proc. of Ex. |
|---|---|---|---|---|
| 252 | 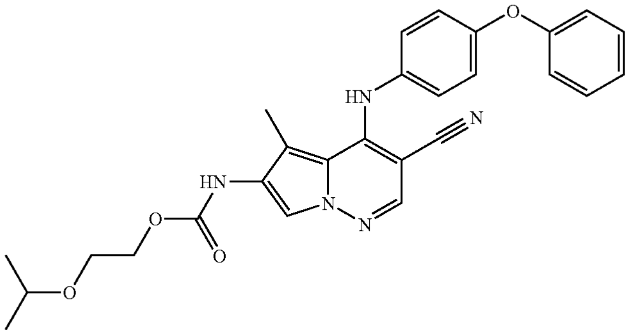 | [3-Cyano-5-methyl-4-(4-phenoxy-phenylamino)-pyrrolo[1,2-b]pyridazin-6-yl]-carbamic acid 2-isopropoxy-ethyl ester | 1.74 LC $[M + H]^+$ = 486.4 | 11A |
| 253 | 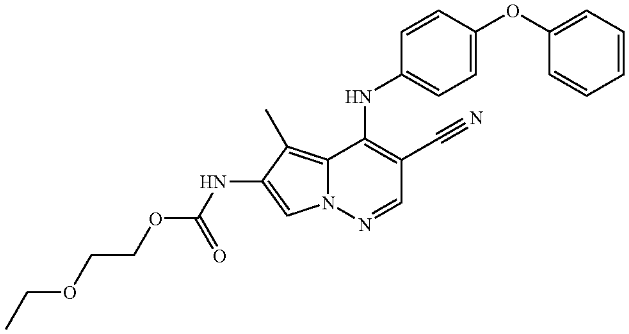 | [3-Cyano-5-methyl-4-(4-phenoxy-phenylamino)-pyrrolo[1,2-b]pyridazin-6-yl]-carbamic acid 2-ethoxy-ethyl ester | 1.77 LC $[M + H]^+$ = 472.2 | 11A |
| 254 | 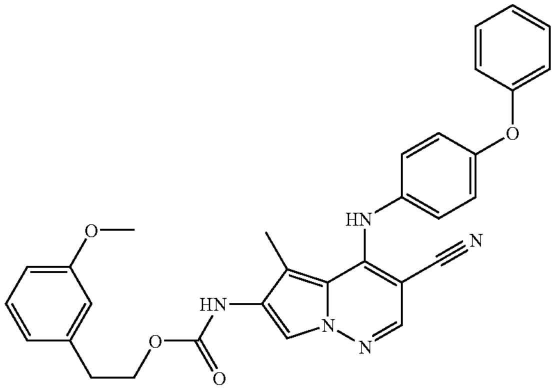 | [3-Cyano-5-methyl-4-(4-phenoxy-phenylamino)-pyrrolo[1,2-b]pyridazin-6-yl]-carbamic acid 2-(3-methoxy-phenyl)-ethyl ester | 1.92 LC $[M + H]^+$ = 534.2 | 11A |
| 255 | 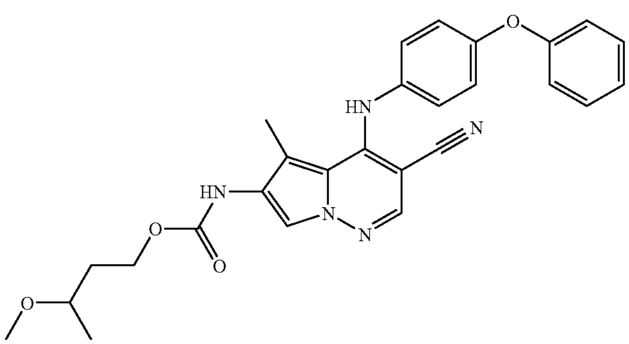 | [3-Cyano-5-methyl-4-(4-phenoxy-phenylamino)-pyrrolo[1,2-b]pyridazin-6-yl]-carbamic acid 3-methoxy-butyl ester | 1.81 LC $[M + H]^+$ = 486.2 | 11A |

TABLE 2-continued

| Ex. No. | Structure | Compound Name | Retention Time Min./ Molecular Mass | Proc. of Ex. |
|---|---|---|---|---|
| 256 | 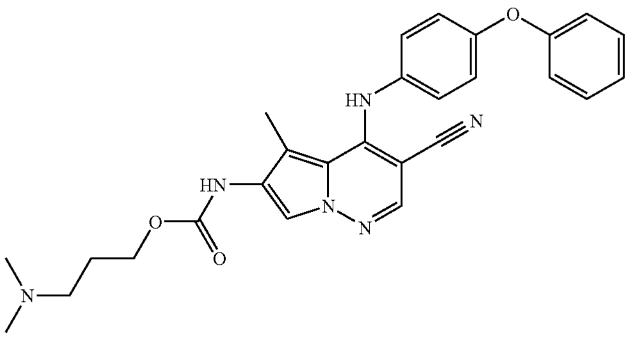 | [3-Cyano-5-methyl-4-(4-phenoxy-phenylamino)-pyrrolo[1,2-b]pyridazin-6-yl]-carbamic acid 3-dimethylamino-propyl ester | 1.56 LC $[M + H]^+$ = 485.2 | 11A |
| 257 | 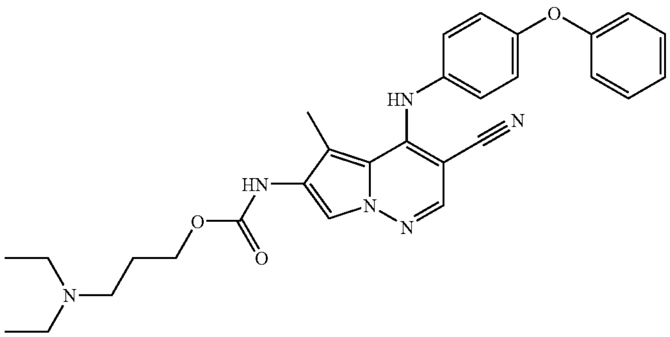 | [3-Cyano-5-methyl-4-(4-phenoxy-phenylamino)-pyrrolo[1,2-b]pyridazin-6-yl]-carbamic acid 3-diethylamino-propyl ester | 1.58 LC $[M + H]^+$ = 513.2 | 11A |
| 258 | 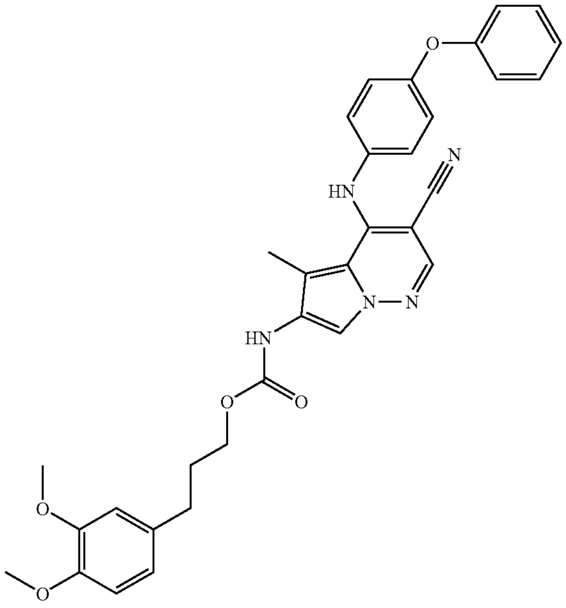 | [3-Cyano-5-methyl-4-(4-phenoxy-phenylamino)-pyrrolo[1,2-b]pyridazin-6-yl]-carbamic acid 3-(3,4-dimethoxy-phenyl)-propyl ester | 1.90 LC $[M + H]^+$ = 578.2 | 11A |

TABLE 2-continued

| Ex. No. | Structure | Compound Name | Retention Time Min./ Molecular Mass | Proc. of Ex. |
|---|---|---|---|---|
| 259 | 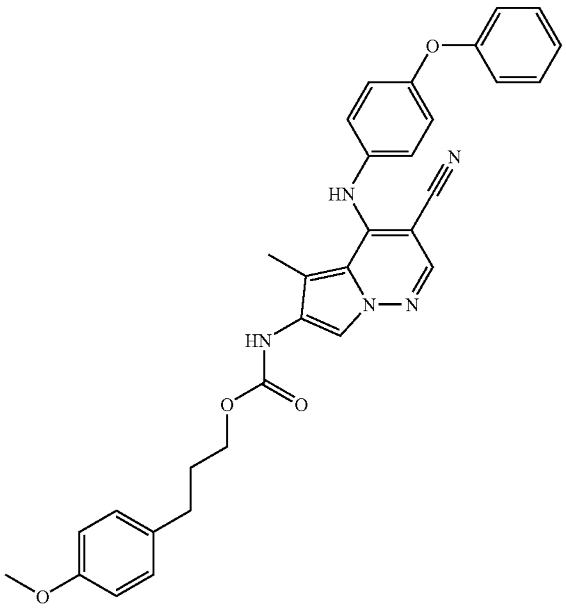 | [3-Cyano-5-methyl-4-(4-phenoxy-phenylamino)-pyrrolo[1,2-b]pyridazin-6-yl]-carbamic acid 3-(4-methoxy-phenyl)-propyl ester | 1.96 LC $[M + H]^+$ = 548.2 | 11A |
| 260 | 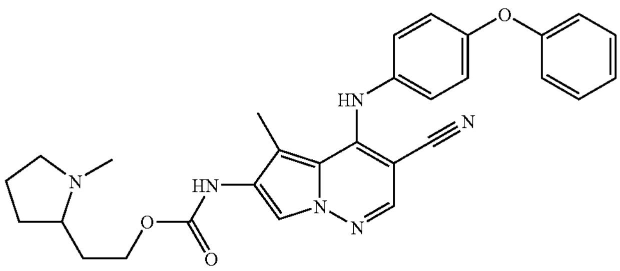 | [3-Cyano-5-methyl-4-(4-phenoxy-phenylamino)-pyrrolo[1,2-b]pyridazin-6-yl]-carbamic acid 2-(1-methyl-pyrrolidin-2-yl)-ethyl ester | 1.59 LC $[M + H]^+$ = 511.2 | 11A |
| 261 | 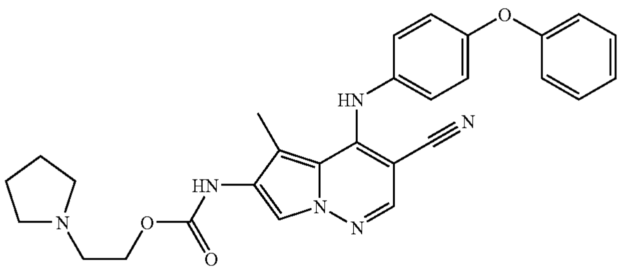 | [3-Cyano-5-methyl-4-(4-phenoxy-phenylamino)-pyrrolo[1,2-b]pyridazin-6-yl]-carbamic acid 2-pyrrolidin-1-yl-ethyl ester | 1.56 LC $[M + H]^+$ = 497.2 | 11A |
| 262 | 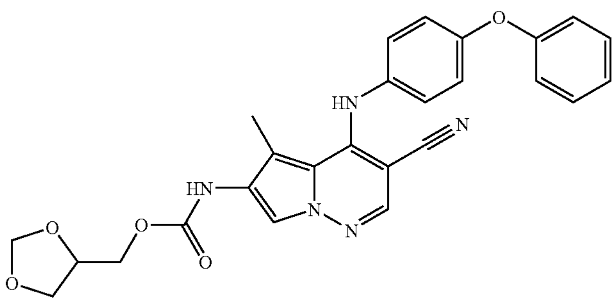 | [3-Cyano-5-methyl-4-(4-phenoxy-phenylamino)-pyrrolo[1,2-b]pyridazin-6-yl]-carbamic acid [1,3]dioxolan-4-ylmethyl ester | 1.70 LC $[M + H]^+$ = 486.2 | 11A |

TABLE 2-continued

| Ex. No. | Structure | Compound Name | Retention Time Min./ Molecular Mass | Proc. of Ex. |
|---|---|---|---|---|
| 263 | 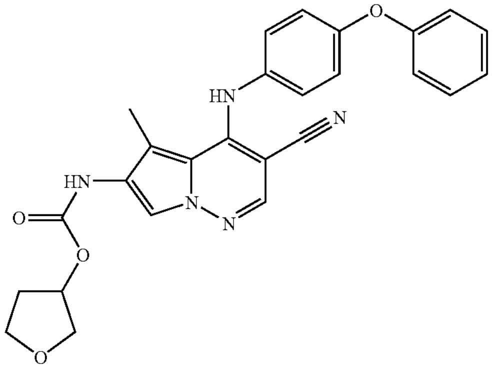 | [3-Cyano-5-methyl-4-(4-phenoxy-phenylamino)-pyrrolo[1,2-b]pyridazin-6-yl]-carbamic acid tetrahydro-furan-3-yl ester | 1.72 LC $[M + H]^+$ = 470.2 | 11A |
| 264 | 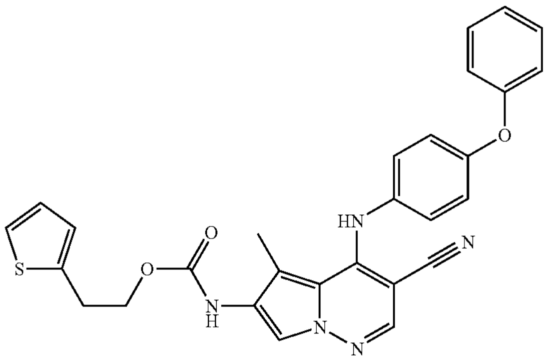 | [3-Cyano-5-methyl-4-(4-phenoxy-phenylamino)-pyrrolo[1,2-b]pyridazin-6-yl]-carbamic acid 2-thiophen-2-yl-ethyl ester | 1.90 LC $[M + H]^+$ = 510.1 | 11A |
| 265 | 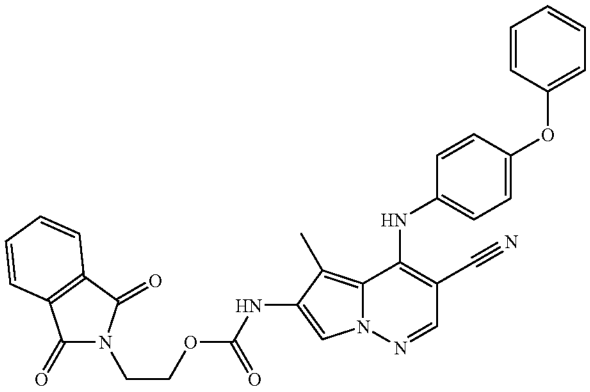 | [3-Cyano-5-methyl-4-(4-phenoxy-phenylamino)-pyrrolo[1,2-b]pyridazin-6-yl]-carbamic acid 2-(1,3-dioxo-1,3-dihydro-isoindol-2-yl)-ethyl ester | 1.80 LC $[M + H]^+$ = 573.2 | 11A |
| 266 | 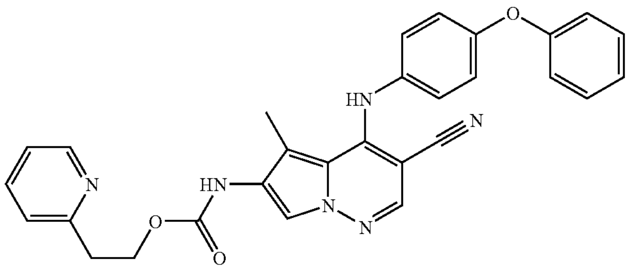 | [3-Cyano-5-methyl-4-(4-phenoxy-phenylamino)-pyrrolo[1,2-b]pyridazin-6-yl]-carbamic acid 2-pyridin-2-yl-ethyl ester | 1.57 LC $[M + H]^+$ = 505.2 | 11A |

TABLE 2-continued

| Ex. No. | Structure | Compound Name | Retention Time Min./ Molecular Mass | Proc. of Ex. |
|---|---|---|---|---|
| 267 | 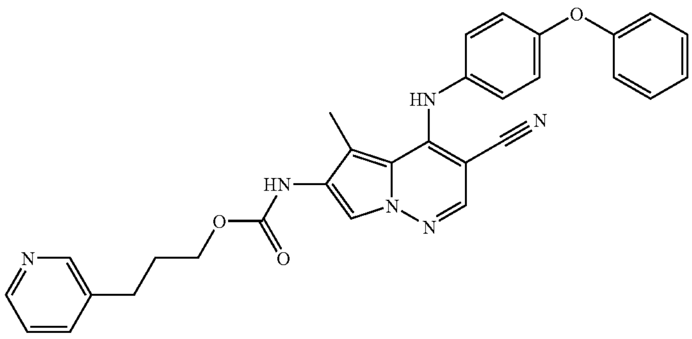 | [3-Cyano-5-methyl-4-(4-phenoxy-phenylamino)-pyrrolo[1,2-b]pyridazin-6-yl]-carbamic acid 3-pyridin-3-yl-propyl ester | 1.61 LC $[M + H]^+$ = 519.2 | 11A |
| 268 | 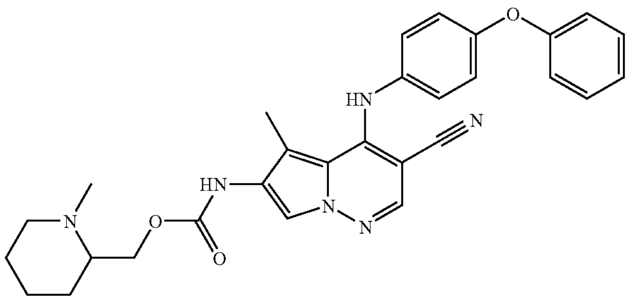 | [3-Cyano-5-methyl-4-(4-phenoxy-phenylamino)-pyrrolo[1,2-b]pyridazin-6-yl]-carbamic acid 1-methyl-piperidin-2-ylmethyl ester | 1.60 LC $[M + H]^+$ = 511.2 | 11A |
| 269 | 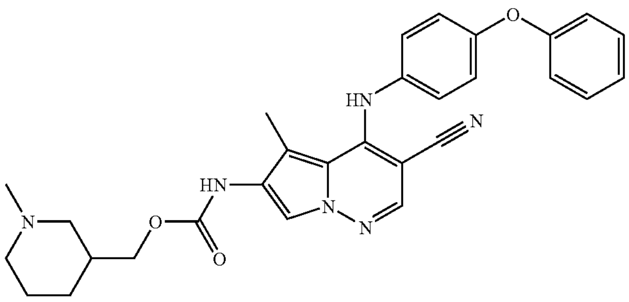 | [3-Cyano-5-methyl-4-(4-phenoxy-phenylamino)-pyrrolo[1,2-b]pyridazin-6-yl]-carbamic acid 1-methyl-piperidin-3-ylmethyl ester | 1.60 LC $[M + H]^+$ = 511.2 | 11A |
| 270 | 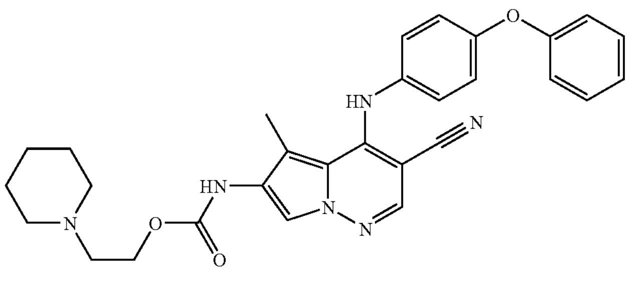 | [3-Cyano-5-methyl-4-(4-phenoxy-phenylamino)-pyrrolo[1,2-b]pyridazin-6-yl]-carbamic acid 2-piperidin-1-yl-ethyl ester | 1.54 LC $[M + H]^+$ = 511.2 | 11A |

TABLE 2-continued

| Ex. No. | Structure | Compound Name | Retention Time Min./ Molecular Mass | Proc. of Ex. |
|---|---|---|---|---|
| 271 | 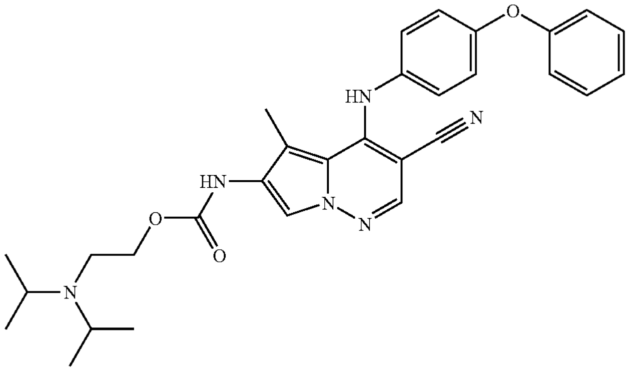 | [3-Cyano-5-methyl-4-(4-phenoxy-phenylamino)-pyrrolo[1,2-b]pyridazin-6-yl]-carbamic acid 2-diisopropylamino-ethyl ester | 1.59 LC $[M + H]^+$ = 527.2 | 11A |
| 272 | 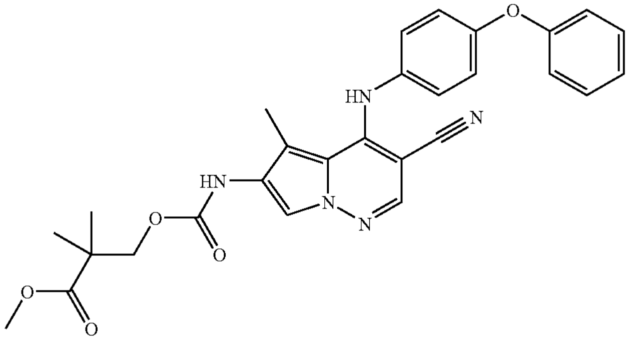 | 3-[3-Cyano-5-methyl-4-(4-phenoxy-phenylamino)-pyrrolo[1,2-b]pyridazin-6-ylcarbamoyloxy]-2,2-dimethyl-propionic acid methyl ester | 1.83 LC $[M + H]^+$ = 514.2 | 11A |
| 273 | 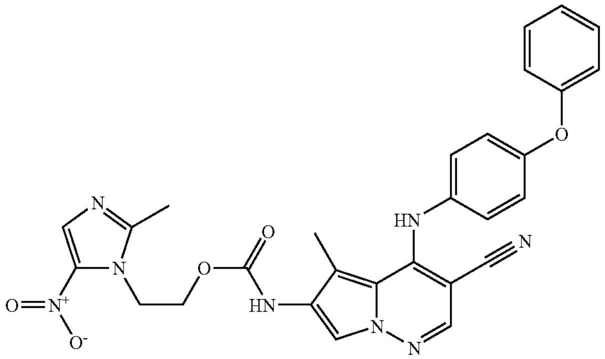 | [3-Cyano-5-methyl-4-(4-phenoxy-phenylamino)-pyrrolo[1,2-b]pyridazin-6-yl]-carbamic acid 2-(2-methyl-5-nitro-imidazol-1-yl)-ethyl ester | 1.70 LC $[M + H]^+$ = 553.2 | 11A |
| 274 | 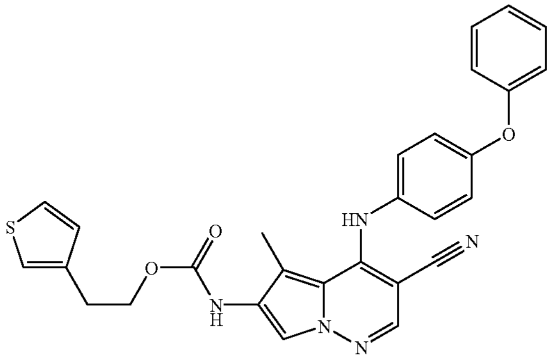 | [3-Cyano-5-methyl-4-(4-phenoxy-phenylamino)-pyrrolo[1,2-b]pyridazin-6-yl]-carbamic acid 2-thiophen-3-yl-ethyl ester | 1.95 LC $[M + H]^+$ = 510.2 | 11A |

TABLE 2-continued

| Ex. No. | Structure | Compound Name | Retention Time Min./ Molecular Mass | Proc. of Ex. |
|---|---|---|---|---|
| 275 | 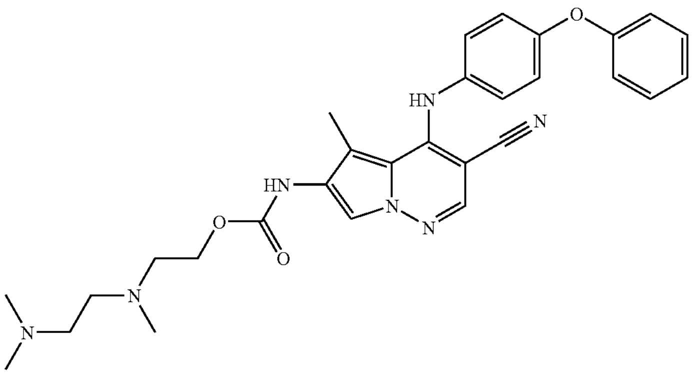 | [3-Cyano-5-methyl-4-(4-phenoxy-phenylamino)-pyrrolo[1,2-b]pyridazin-6-yl]-carbamic acid 2-[(2-dimethylamino-ethyl)-methyl-amino]-ethyl ester | 1.43 LC $[M + H]^+$ = 528.2 | 11A |
| 276 | 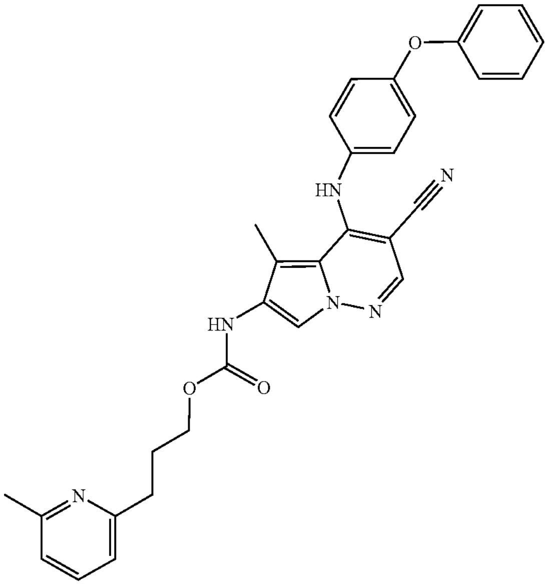 | [3-Cyano-5-methyl-4-(4-phenoxy-phenylamino)-pyrrolo[1,2-b]pyridazin-6-yl]-carbamic acid 3-(6-methyl-pyridin-2-yl)-propyl ester | 1.61 LC $[M + H]^+$ = 533.2 | 11A |
| 277 | 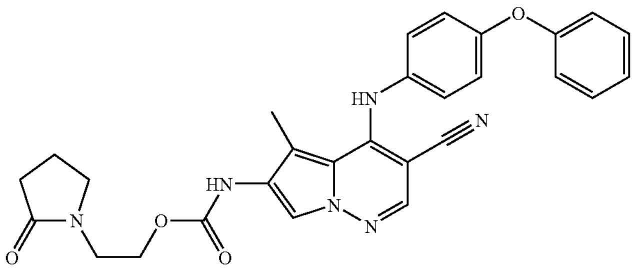 | [3-Cyano-5-methyl-4-(4-phenoxy-phenylamino)-pyrrolo[1,2-b]pyridazin-6-yl]-carbamic acid 2-(2-oxo-pyrrolidin-1-yl)-ethyl ester | 1.68 LC $[M + H]^+$ = 511.2 | 11A |

TABLE 2-continued

| Ex. No. | Structure | Compound Name | Retention Time Min./ Molecular Mass | Proc. of Ex. |
|---|---|---|---|---|
| 278 | 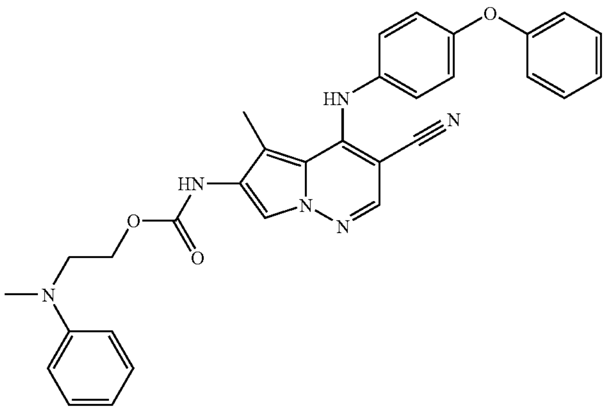 | [3-Cyano-5-methyl-4-(4-phenoxy-phenylamino)-pyrrolo[1,2-b]pyridazin-6-yl]-carbamic acid 2-(methylphenyl-amino)-ethyl ester | 1.72 LC $[M + H]^+$ = 533.2 | 11A |
| 279 | 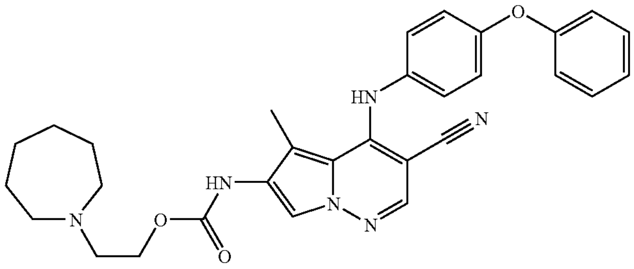 | [3-Cyano-5-methyl-4-(4-phenoxy-phenylamino)-pyrrolo[1,2-b]pyridazin-6-yl]-carbamic acid 2-azepan-1-yl-ethyl ester | 1.56 LC $[M + H]^+$ = 525.2 | 11A |
| 280 | 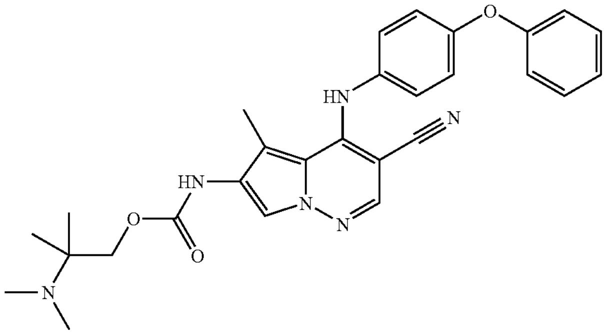 | [3-Cyano-5-methyl-4-(4-phenoxy-phenylamino)-pyrrolo[1,2-b]pyridazin-6-yl]-carbamic acid 2-dimethylamino-2-methyl-propyl ester | 1.57 LC $[M + H]^+$ = 499.2 | 11A |
| 281 | 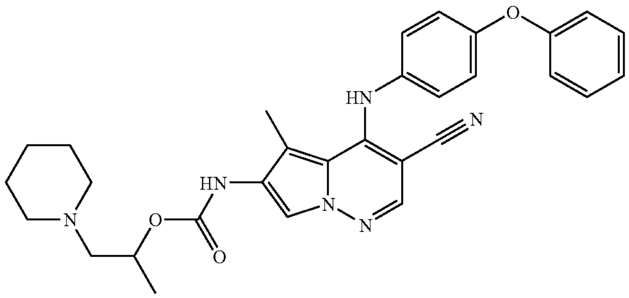 | [3-Cyano-5-methyl-4-(4-phenoxy-phenylamino)-pyrrolo[1,2-b]pyridazin-6-yl]-carbamic acid 1-methyl-2-piperidin-1-yl-ethyl ester | 1.58 LC $[M + H]^+$ = 525.2 | 11A |

TABLE 2-continued

| Ex. No. | Structure | Compound Name | Retention Time Min./ Molecular Mass | Proc. of Ex. |
|---|---|---|---|---|
| 282 | 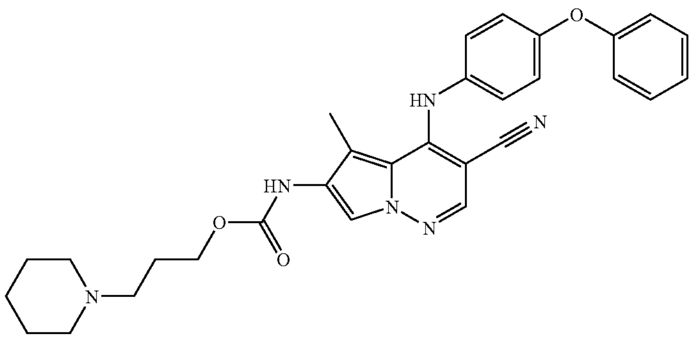 | [3-Cyano-5-methyl-4-(4-phenoxy-phenylamino)-pyrrolo[1,2-b]pyridazin-6-yl]-carbamic acid 3-piperidin-1-yl-propyl ester | 1.60 LC $[M + H]^+$ = 525.2 | 11A |
| 283 | 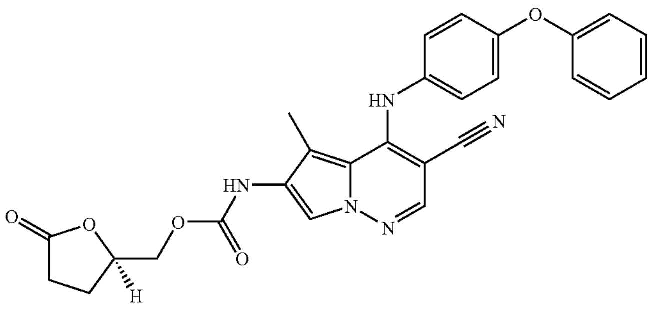 | [3-Cyano-5-methyl-4-(4-phenoxy-phenylamino)-pyrrolo[1,2-b]pyridazin-6-yl]-carbamic acid 5-oxo-tetrahydro-furan-2-ylmethyl ester | 1.70 LC $[M + H]^+$ = 498.2 | 11A |
| 284 | 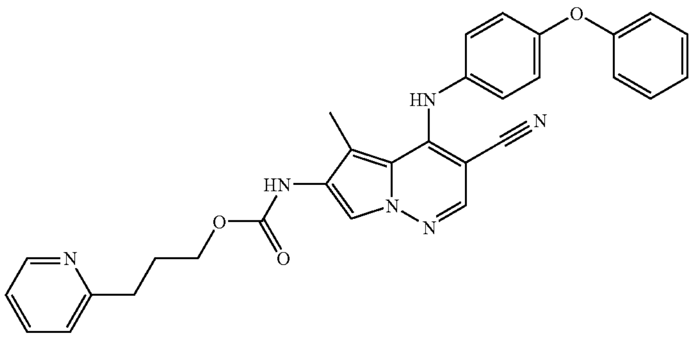 | [3-Cyano-5-methyl-4-(4-phenoxy-phenylamino)-pyrrolo[1,2-b]pyridazin-6-yl]-carbamic acid 3-pyridin-2-yl-propyl ester | 1.60 LC $[M + H]^+$ = 519.2 | 11A |
| 285 | 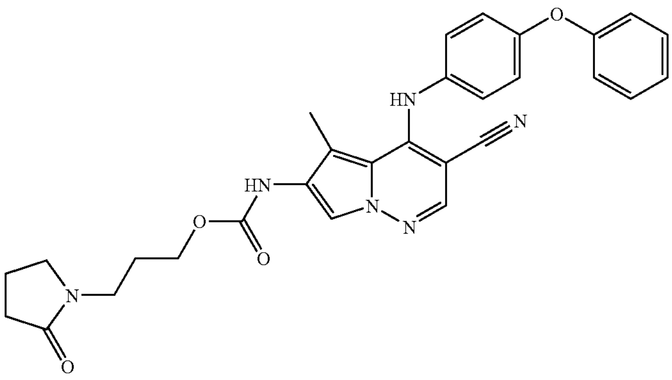 | [3-Cyano-5-methyl-4-(4-phenoxy-phenylamino)-pyrrolo[1,2-b]pyridazin-6-yl]-carbamic acid 3-(2-oxo-pyrrolidin-1-yl)-propyl ester | 1.72 LC $[M + H]^+$ = 525.2 | 11A |

TABLE 2-continued

| Ex. No. | Structure | Compound Name | Retention Time Min./ Molecular Mass | Proc. of Ex. |
|---|---|---|---|---|
| 286 | 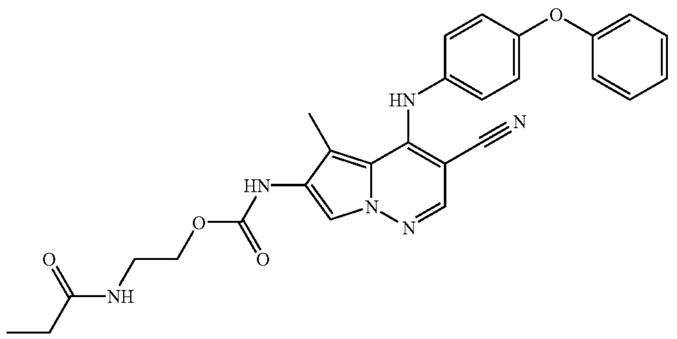 | [3-Cyano-5-methyl-4-(4-phenoxy-phenylamino)-pyrrolo[1,2-b]pyridazin-6-yl]-carbamic acid 2-propionylamino-ethyl ester | 1.68 LC $[M + H]^+$ = 499.2 | 11A |
| 287 | 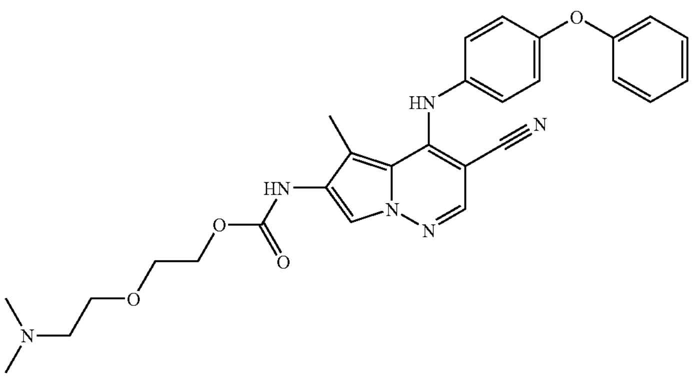 | [3-Cyano-5-methyl-4-(4-phenoxy-phenylamino)-pyrrolo[1,2-b]pyridazin-6-yl]-carbamic acid 2-(2-dimethylamino-ethoxy)-ethyl ester | 1.58 LC $[M + H]^+$ = 515.2 | 11A |
| 288 | 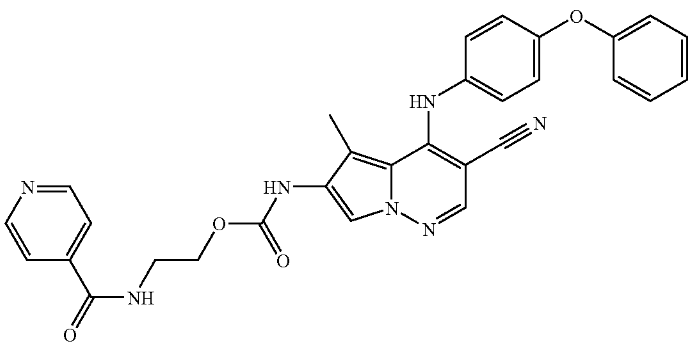 | [3-Cyano-5-methyl-4-(4-phenoxy-phenylamino)-pyrrolo[1,2-b]pyridazin-6-yl]-carbamic acid 2-[(pyridine-4-carbonyl)-amino]-ethyl ester | 1.58 LC $[M + H]^+$ = 548.2 | 11A |
| 289 | 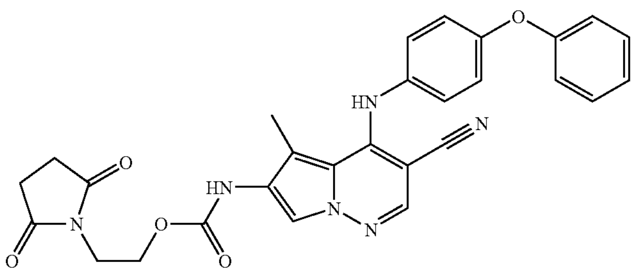 | [3-Cyano-5-methyl-4-(4-phenoxy-phenylamino)-pyrrolo[1,2-b]pyridazin-6-yl]-carbamic acid 2-(2,5-dioxo-pyrrolidin-1-yl)-ethyl ester | 1.64 LC $[M + H]^+$ = 523.2 | 11A |

TABLE 2-continued

| Ex. No. | Structure | Compound Name | Retention Time Min./ Molecular Mass | Proc. of Ex. |
|---|---|---|---|---|
| 290 | 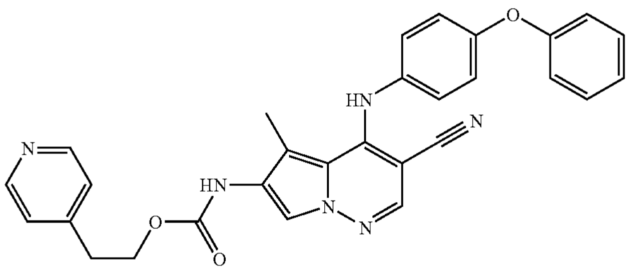 | [3-Cyano-5-methyl-4-(4-phenoxy-phenylamino)-pyrrolo[1,2-b]pyridazin-6-yl] carbamic acid 2-pyridin-4-yl-ethyl ester | 1.57 LC $[M + H]^+$ = 505.2 | 11A |
| 291 | 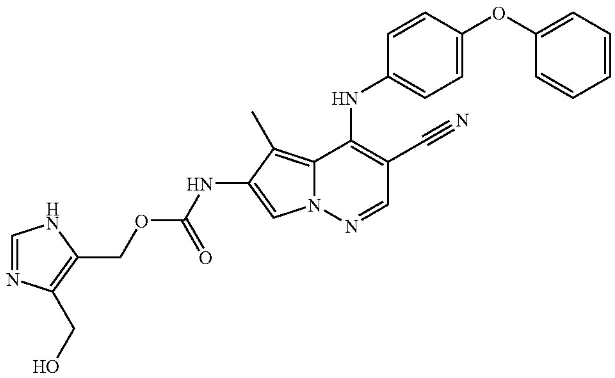 | [3-Cyano-5-methyl-4-(4-phenoxy-phenylamino)-pyrrolo[1,2-b]pyridazin-6-yl]-carbamic acid 5-hydroxymethyl-3H-imidazol-4-ylmethyl ester | 1.49 LC $[M + H]^+$ = 510.2 | 11A |
| 292 | 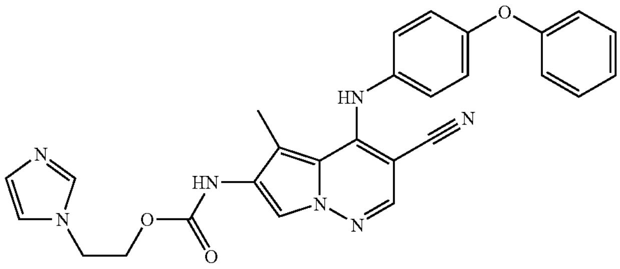 | [3-Cyano-5-methyl-4-(4-phenoxy-phenylamino)-pyrrolo[1,2-b]pyridazin-6-yl]-carbamic acid 2-imidazol-1-yl-ethyl ester | 1.55 LC $[M + H]^+$ = 494.2 | 11A |
| 293 | 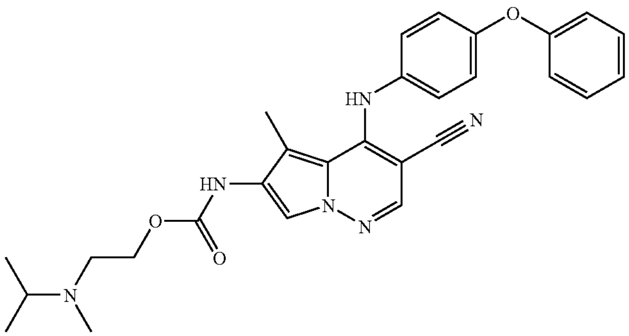 | [3-Cyano-5-methyl-4-(4-phenoxy-phenylamino)-pyrrolo[1,2-b]pyridazin-6-yl]-carbamic acid 2-(isopropyl-methyl-amino)-ethyl ester | 1.58 LC $[M + H]^+$ = 499.2 | 11A |

TABLE 2-continued

| Ex. No. | Structure | Compound Name | Retention Time Min./ Molecular Mass | Proc. of Ex. |
|---|---|---|---|---|
| 294 | 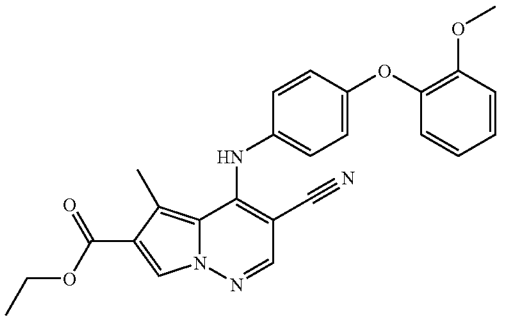 | 3-Cyano-4-[4-(2-methoxy-phenoxy)-phenylamino]-5-methyl-pyrrolo[1,2-b]pyridazine-6-carboxylic acid ethyl ester | 1.86 LC $[M + H]^+$ = 443.2 | 1E |
| 295 | 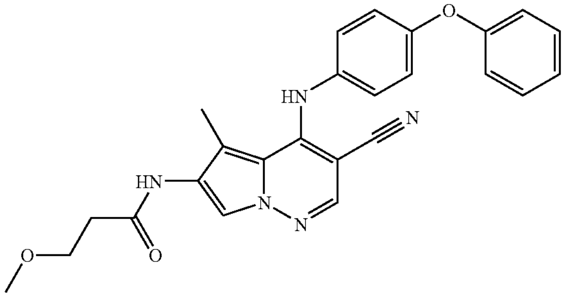 | N-[3-Cyano-5-methyl-4-(4-phenoxy-phenylamino)-pyrrolo[1,2-b]pyridazin-6-yl]-3-methoxy-propionamide | 1.64 LC $[M + H]^+$ = 442.2 | 12 |
| 296 | 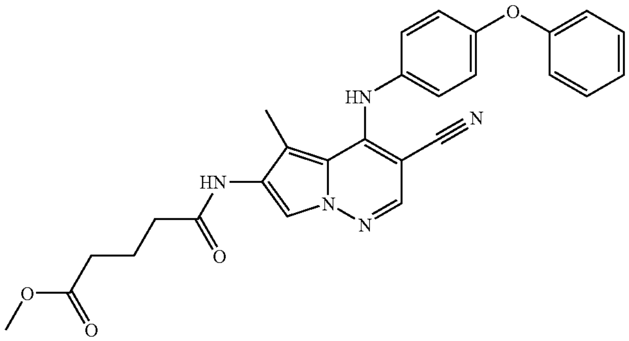 | 4-[3-Cyano-5-methyl-4-(4-phenoxy-phenylamino)-pyrrolo[1,2-b]pyridazin-6-ylcarbamoyl]-butyric acid methyl ester | 1.69 LC $[M + H]^+$ = 484.2 | 12 |
| 297 | 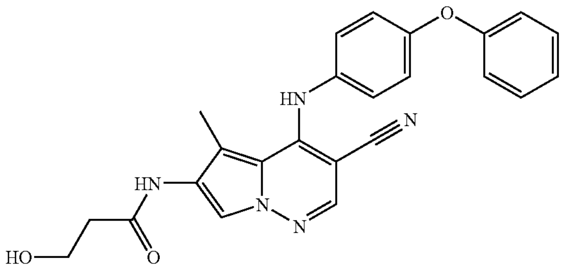 | N-[3-Cyano-5-methyl-4-(4-phenoxy-phenylamino)-pyrrolo[1,2-b]pyridazin-6-yl]-3-hydroxy-propionamide | 1.55 LC $[M + H]^+$ = 428.2 | 12 |

TABLE 2-continued

| Ex. No. | Structure | Compound Name | Retention Time Min./ Molecular Mass | Proc. of Ex. |
|---|---|---|---|---|
| 298 | 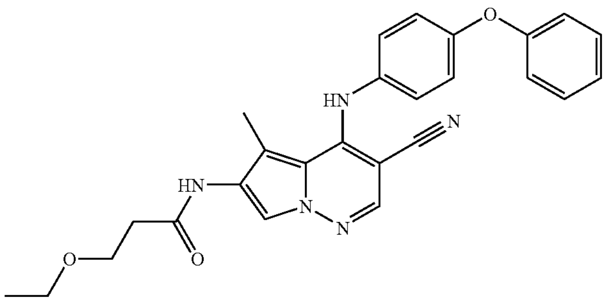 | N-[3-Cyano-5-methyl-4-(4-phenoxy-phenylamino)-pyrrolo[1,2-b]pyridazin-6-yl]-3-ethoxy-propionamide | 1.71 LC $[M + H]^+$ = 456.2 | 12 |
| 299 | 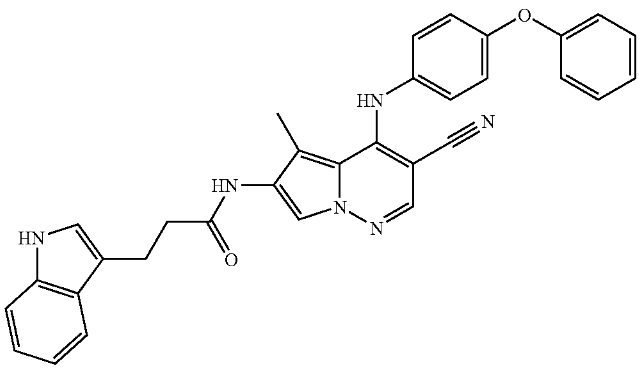 | N-[3-Cyano-5-methyl-4-(4-phenoxy-phenylamino)-pyrrolo[1,2-b]pyridazin-6-yl]-3-(1H-indol-3-yl)-propionamide | 1.8 LC $[M + H]^+$ = 527.2 | 12 |
| 300 | 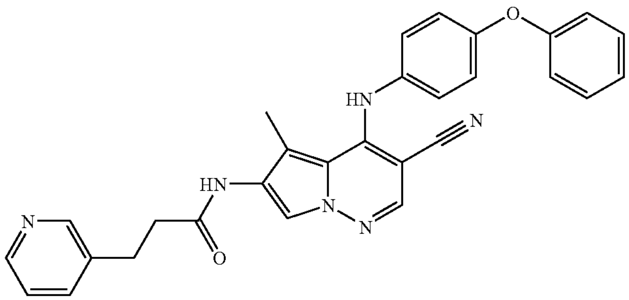 | N-[3-Cyano-5-methyl-4-(4-phenoxy-phenylamino)-pyrrolo[1,2-b]pyridazin-6-yl]-3-pyridin-3-yl-propionamide | 1.49 LC $[M + H]^+$ = 489.2 | 12 |
| 301 | 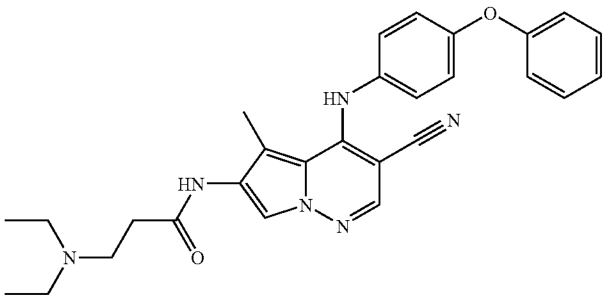 | N-[3-Cyano-5-methyl-4-(4-phenoxy-phenylamino)-pyrrolo[1,2-b]pyridazin-6-yl]-3-diethylamino-propionamide | 1.54 LC $[M + H]^+$ = 483.3 | 12 |

TABLE 2-continued

| Ex. No. | Structure | Compound Name | Retention Time Min./ Molecular Mass | Proc. of Ex. |
|---|---|---|---|---|
| 302 | 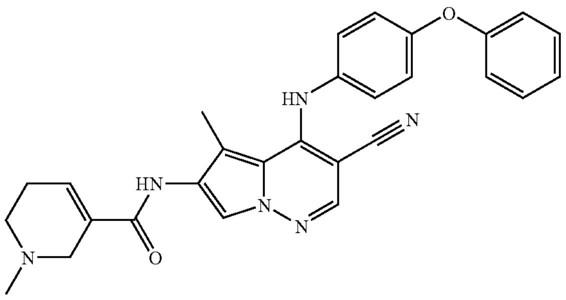 | 1-Methyl-1,2,5,6-tetrahydro-pyridine-3-carboxylic acid [3-cyano-5-methyl-4-(4-phenoxy-phenylamino)-pyrrolo[1,2-b]pyridazin-6-yl]-amide | 1.51 LC $[M + H]^+$ = 479.3 | 12 |
| 303 | 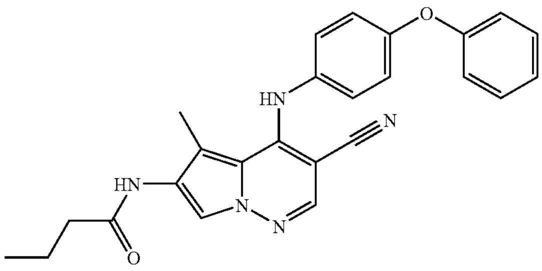 | N-[3-Cyano-5-methyl-4-(4-phenoxy-phenylamino)-pyrrolo[1,2-b]pyridazin-6-yl]-butyramide | 1.73 LC $[M + H]^+$ = 426.2 | 12 |
| 304 | 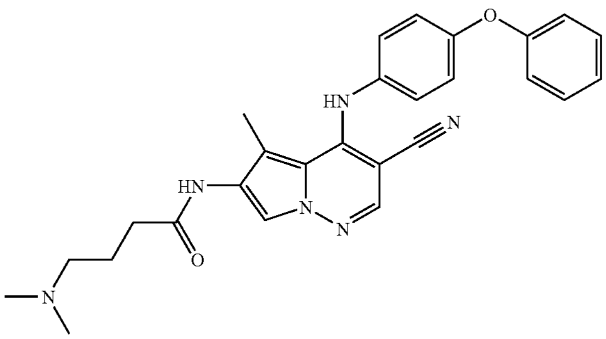 | N-[3-Cyano-5-methyl-4-(4-phenoxy-phenylamino)-pyrrolo[1,2-b]pyridazin-6-yl]-4-dimethylamino-butyramide | 1.55 LC $[M + H]^+$ = 469.3 | 12 |
| 305 | 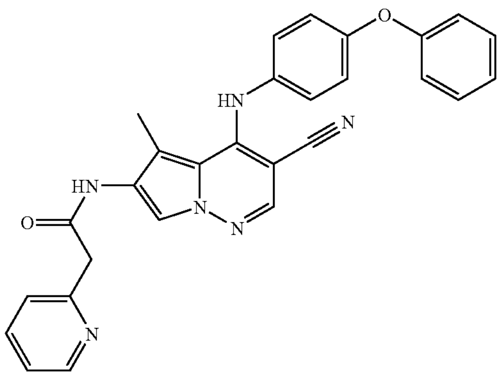 | N-[3-Cyano-5-methyl-4-(4-phenoxy-phenylamino)-pyrrolo[1,2-b]pyridazin-6-yl]-2-pyridin-2-yl-acetamide | 1.5 LC $[M + H]^+$ = 475.3 | 12 |

TABLE 2-continued

| Ex. No. | Structure | Compound Name | Retention Time Min./ Molecular Mass | Proc. of Ex. |
|---|---|---|---|---|
| 306 | 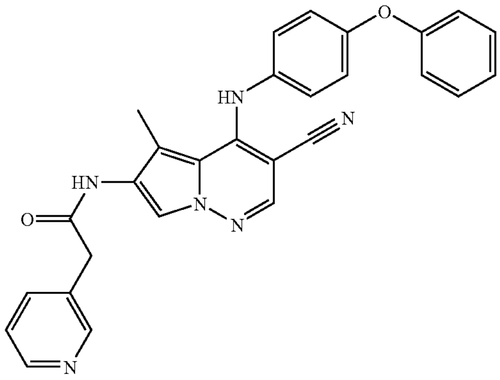 | N-[3-Cyano-5-methyl-4-(4-phenoxy-phenylamino) pyrrolo[1,2-b]pyridazin-6-yl]-2-pyridin-3-yl-acetamide | 1.48 LC $[M + H]^+$ = 475.3 | 12 |
| 307 | 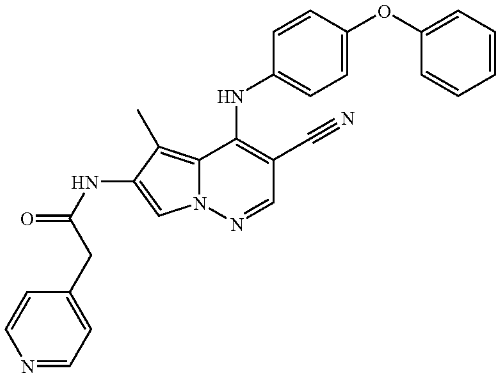 | N-[3-Cyano-5-methyl-4-(4-phenoxy-phenylamino)-pyrrolo[1,2-b]pyridazin-6-yl]-2-pyridin-4-yl-acetamide | 1.47 LC $[M + H]^+$ = 475.3 | 12 |
| 308 | 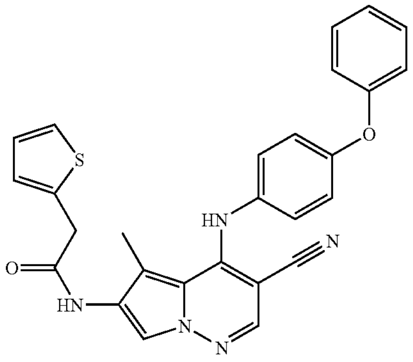 | N-[3-Cyano-5-methyl-4-(4-phenoxy-phenylamino)-pyrrolo[1,2-b]pyridazin-6-yl]-2-thiophen-2-yl-acetamide | 1.76 LC $[M + H]^+$ = 480.2 | 12 |
| 309 | 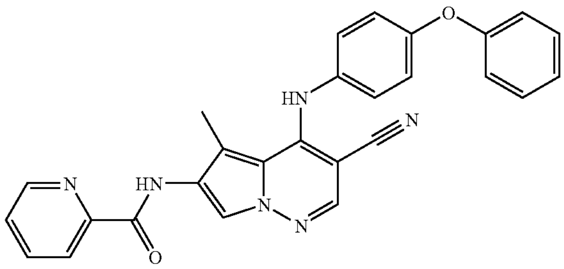 | Pyridine-2-carboxylic acid [3-cyano-5-methyl-4-(4-phenoxy-phenylamino)-pyrrolo[1,2-b]pyridazin-6-yl]-amide | 1.87 LC $[M + H]^+$ = 461.2 | 12 |

TABLE 2-continued

| Ex. No. | Structure | Compound Name | Retention Time Min./ Molecular Mass | Proc. of Ex. |
|---|---|---|---|---|
| 310 | 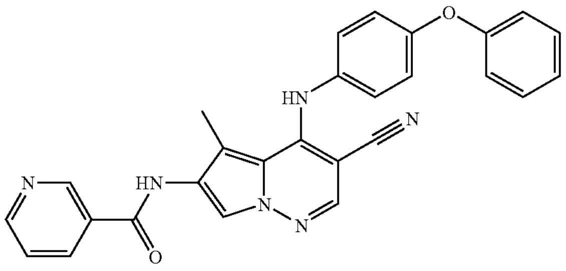 | N-[3-Cyano-5-methyl-4-(4-phenoxy-phenylamino)-pyrrolo[1,2-b]pyridazin-6-yl]-nicotinamide | 1.59 LC $[M + H]^+$ = 461.2 | 12 |
| 311 | 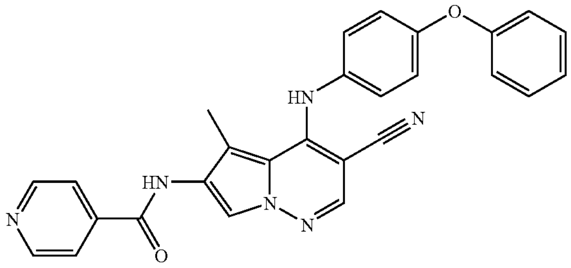 | N-[3-Cyano-5-methyl-4-(4-phenoxy-phenylamino)-pyrrolo[1,2-b]pyridazin-6-yl]-isonicotinamide | 1.57 LC $[M + H]^+$ = 461.2 | 12 |
| 312 | 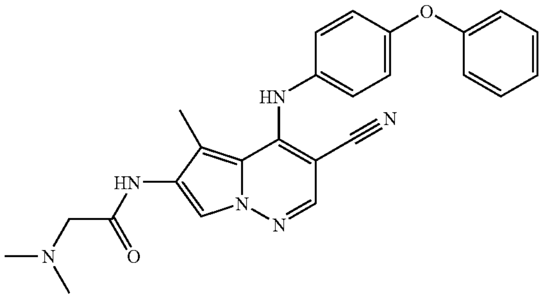 | N-[3-Cyano-5-methyl-4-(4-phenoxy-phenylamino)-pyrrolo[1,2-b]pyridazin-6-yl]-2-dimethylamino-acetamide | 1.5 LC $[M + H]^+$ = 441.2 | 12 |
| 313 | 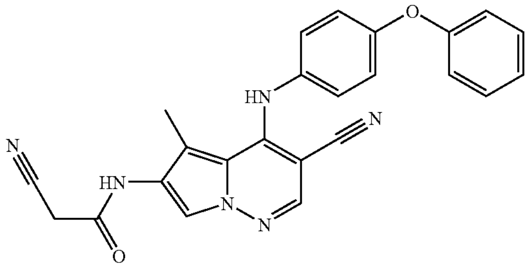 | 2-Cyano-N-[3-cyano-5-methyl-4-(4-phenoxy-phenylamino)-pyrrolo[1,2-b]pyridazin-6-yl]-acetamide | 1.64 LC $[M + H]^+$ = 423.2 | 12 |
| 314 | 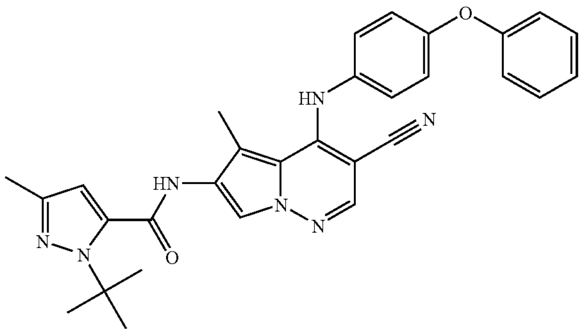 | 2-tert-Butyl-5-methyl-2H-pyrazole 3-carboxylic acid [3-cyano-5-methyl-4-(4-phenoxy-phenylamino)-pyrrolo[1,2-b]pyridazin-6-yl]-amide | 1.85 LC $[M + H]^+$ = 520.2 | 12 |

TABLE 2-continued

| Ex. No. | Structure | Compound Name | Retention Time Min./ Molecular Mass | Proc. of Ex. |
|---|---|---|---|---|
| 315 | 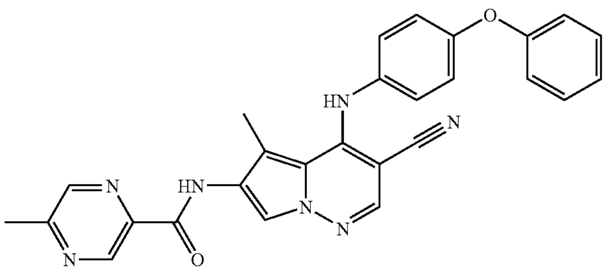 | 5-Methyl-pyrazine-2-carboxylic acid [3-cyano-5-methyl-4-(4-phenoxy-phenylamino)-pyrrolo[1,2-b]pyrid-azin-6-yl]-amide | 1.83 LC $[M + H]^+$ = 476.3 | 12 |
| 316 | 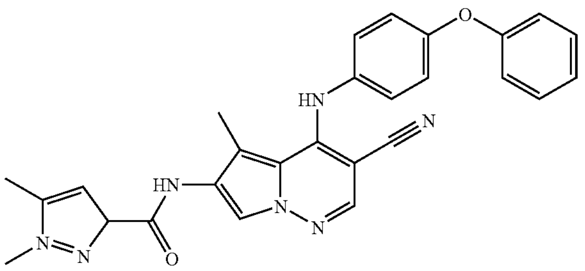 | 1,5-Dimethyl-1H-pyrazole-3-carboxylic acid [3-cyano-5-methyl-4-(4-phenoxy-phenylamino)-pyrrolo[1,2-b]pyridazin-6-yl]-amide | 1.78 LC $[M + H]^+$ = 478.3 | 12 |
| 317 | 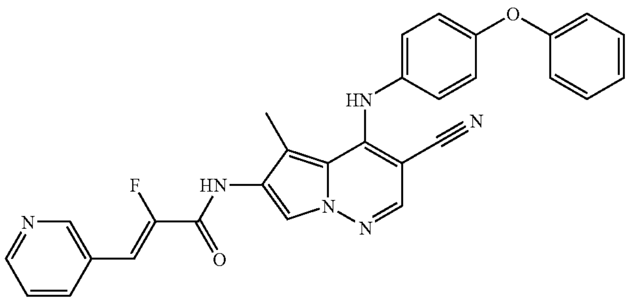 | N-[3-Cyano-5-methyl-4-(4-phenoxy-phenylamino)-pyrrolo[1,2-b]pyridazin-6-yl]-2-fluoro-3-pyridin-3-yl-acrylamide | 1.6 LC $[M + H]^+$ = 505.2 | 12 |
| 318 | 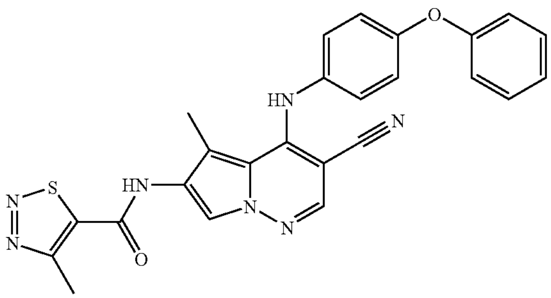 | 4-Methyl-[1,2,3]thiadiazole-5-carboxylic acid [3-cyano-5-methyl-4-(4-phenoxy-phenylamino)-pyrrolo[1,2-b]pyridazin-6-yl]-amide | 1.74 LC $[M + H]^+$ = 482.2 | 12 |
| 319 | 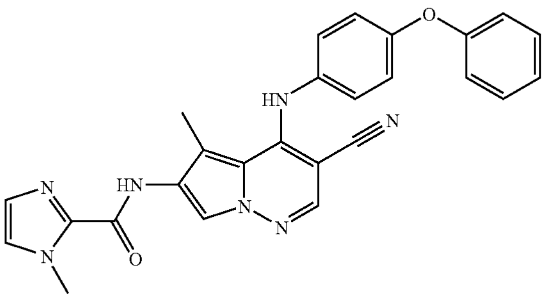 | 1-Methyl-1H-imidazole-2-carboxylic acid [3-cyano-5-methyl-4-(4-phenoxy-phenylamino)-pyrrolo[1,2-b]pyridazin-6-yl]-amide | 1.7 LC $[M + H]^+$ = 464.3 | 12 |

TABLE 2-continued

| Ex. No. | Structure | Compound Name | Retention Time Min./ Molecular Mass | Proc. of Ex. |
|---|---|---|---|---|
| 320 | 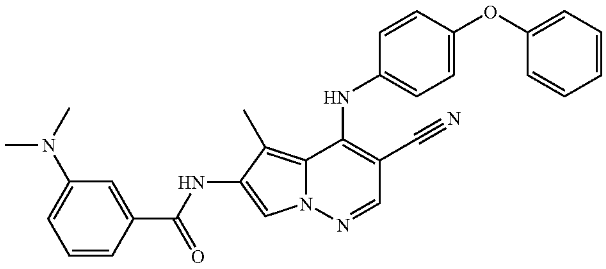 | N-[3-Cyano-5-methyl-4-(4-phenoxy-phenylamino)-pyrrolo[1,2-b]pyridazin-6-yl]-3-dimethylamino-benzamide | 1.62 LC [M + H]+ = 503.3 | 12 |
| 321 | 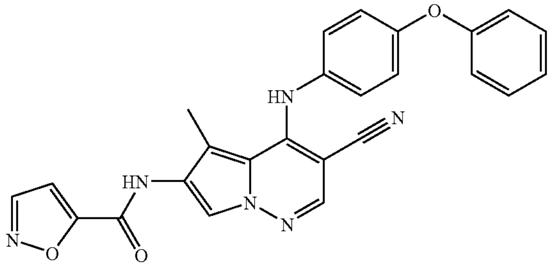 | Isoxazole-5-carboxylic acid [3-cyano-5-methyl-4-(4-phenoxy-phenylamino)-pyrrolo[1,2-b]pyridazin-6-yl]-amide | 1.67 LC [M + H]+ = 451.2 | 12 |
| 322 | 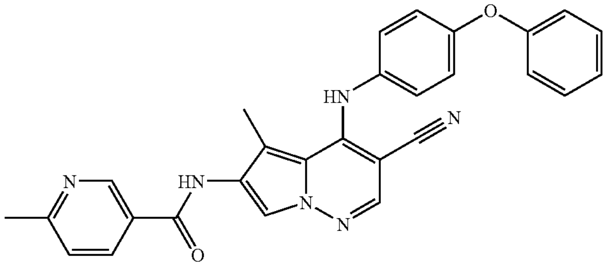 | N-[3-Cyano-5-methyl-4-(4-phenoxy-phenylamino)-pyrrolo[1,2-b]pyridazin-6-yl]-6-methyl-nicotinamide | 1.52 LC [M + H]+ = 475.3 | 12 |
| 323 | 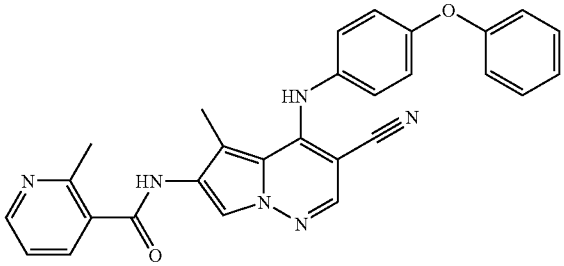 | N-[3-Cyano-5-methyl-4-(4-phenoxy-phenylamino)-pyrrolo[1,2-b]pyridazin-6-yl]-2-methyl-nicotinamide | 1.5 LC [M + H]+ = 475.3 | 12 |
| 324 | 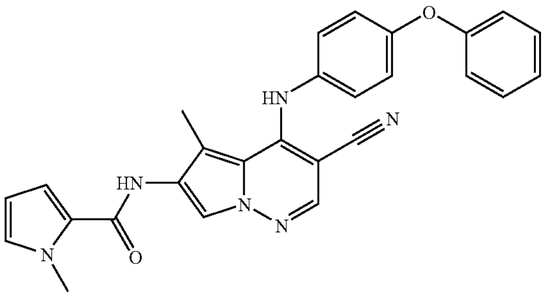 | 1-Methyl-1H-pyrrole-2-carboxylic acid [3-cyano-5-methyl-4-(4-phenoxy-phenylamino)-pyrrolo[1,2-b]pyridazin-6-yl]-amide | 1.76 LC [M + H]+ = 463.3 | 12 |

TABLE 2-continued

| Ex. No. | Structure | Compound Name | Retention Time Min./ Molecular Mass | Proc. of Ex. |
|---|---|---|---|---|
| 325 | 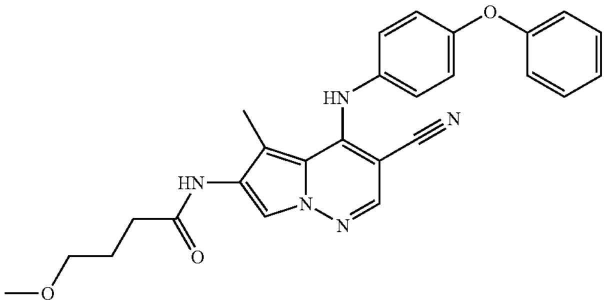 | N-[3-Cyano-5-methyl-4-(4-phenoxy-phenylamino)-pyrrolo[1,2-b]pyridazin-6-yl]-4-methoxy-butyramide | 1.67 LC $[M + H]^+$ = 456.2 | 12 |
| 326 | 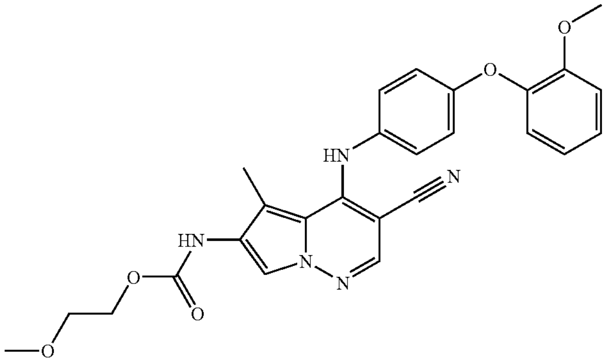 | {3-Cyano-4-[4-(2-methoxy-phenoxy)-phenylamino]-5-methyl-pyrrolo[1,2-b]pyridazin-6-yl}-carbamic acid 2-methoxy-ethyl ester | 1.64 LC $[M + H]^+$ = 488.4 | 11A |
| 327 | 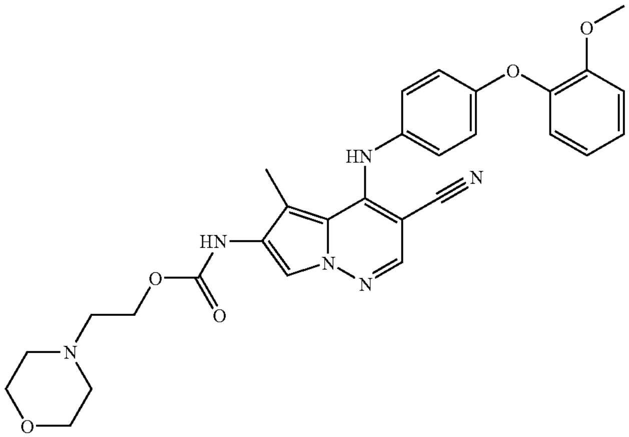 | {3-Cyano-4-[4-(2-methoxy-phenoxy)-phenylamino]-5-methyl-pyrrolo[1,2-b]pyridazin-6-yl}-carbamic acid 2-morpholin-4-yl-ethyl ester | 1.42 LC $[M + H]^+$ = 543.4 | 11A |
| 328 | 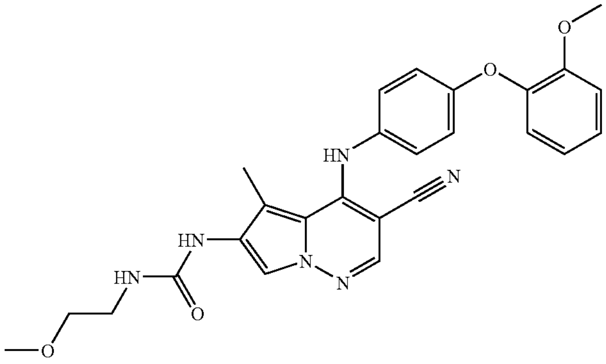 | 1-{3-Cyano-4-[4-(2-methoxy-phenoxy)-phenylamino]-5-methyl-pyrrolo[1,2-b]pyridazin-6-yl}-3-(2-methoxy-ethyl)-urea | 1.39 LC $[M + H]^+$ = 542.4 | 19 |

TABLE 2-continued

| Ex. No. | Structure | Compound Name | Retention Time Min./ Molecular Mass | Proc. of Ex. |
|---|---|---|---|---|
| 329 | 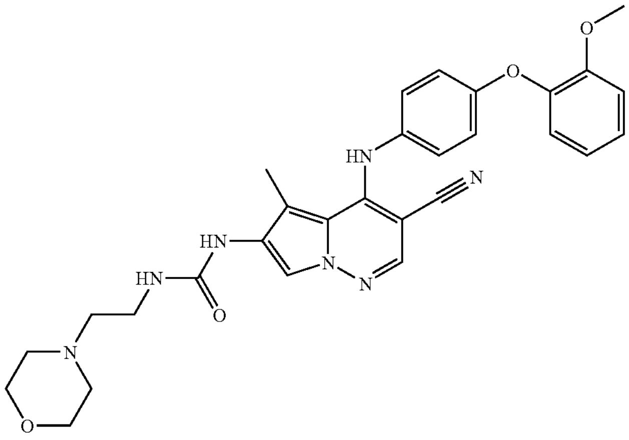 | 1-{3-Cyano-4-[4-(2-methoxy-phenyl)-phenylamino]-5-methyl-pyrrolo[1,2-b]pyridazin-6-yl}-3-(2-morpholin-4-yl-ethyl)-urea | 1.58 LC $[M + H]^+$ = 487.2 | 19 |
| 330 | 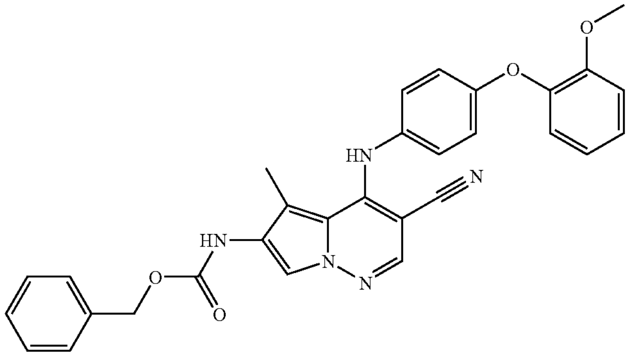 | {3-Cyano-4-[4-(2-methoxy-phenoxy)-phenylamino]-5-methyl-pyrrolo[1,2-b]pyridazin-6-yl}-carbamic acid benzyl ester | 1.83 LC $[M + H]^+$ = 520.2 | 11A |
| 331 | 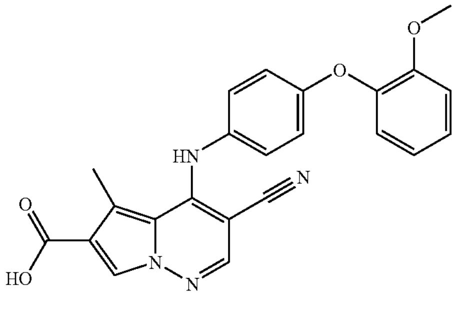 | 3-Cyano-4-[4-(2-methoxy-phenoxy)-phenylamino]-2-methyl-pyrrolo[1,2-b]pyridazine-6-carboxylic acid | 1.66 LC $[M + H]^+$ = 415.2 | 9 |
| 332 | 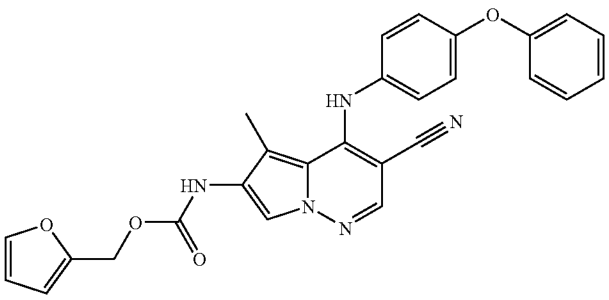 | [3-Cyano-5-methyl-4-(4-phenoxy-phenylamino)-pyrrolo[1,2-b]pyridazin-6-yl]-carbamic acid furan-2-ylmethyl ester | 1.80 LC $[M + H]^+$ = 480.2 | 11A |

TABLE 2-continued

| Ex. No. | Structure | Compound Name | Retention Time Min./ Molecular Mass | Proc. of Ex. |
|---|---|---|---|---|
| 333 | 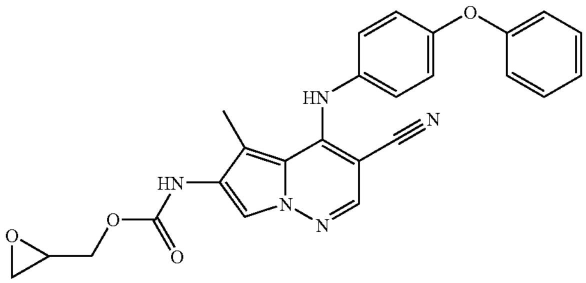 | [3-Cyano-5-methyl-4-(4-phenoxy-phenylamino)-pyrrolo[1,2-b]pyridazin-6-yl]-carbamic acid oxiranylmethyl ester | 1.67 LC [M + H]$^+$ = 456.3 | 11A |
| 334 | 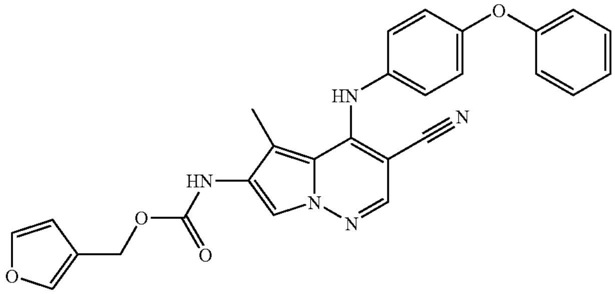 | [3-Cyano-5-methyl-4-(4-phenoxy-phenylamino)-pyrrolo[1,2-b]pyridazin-6-yl]-carbamic acid furan-3-ylmethyl ester | 1.84 LC [M + H]$^+$ = 480.3 | 11A |
| 335 | 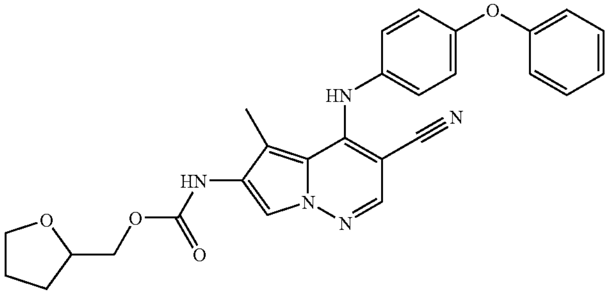 | [3-Cyano-5-methyl-4-(4-phenoxy-phenylamino)-pyrrolo[1,2-b]pyridazin-6-yl]-carbamic acid tetrahydro-furan-2-ylmethyl ester | 1.76 LC [M + H]$^+$ = 484.3 | 11A |
| 336 | 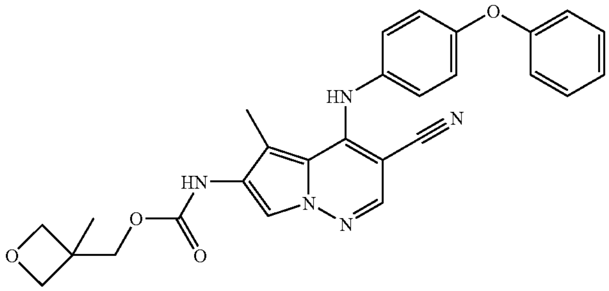 | [3-Cyano-5-methyl-4-(4-phenoxy-phenylamino)-pyrrolo[1,2-b]pyridazin-6-yl]-carbamic acid 3-methyl-oxetan-3-ylmethyl ester | 1.75 LC [M + H]$^+$ = 484.2 | 11A |
| 337 | 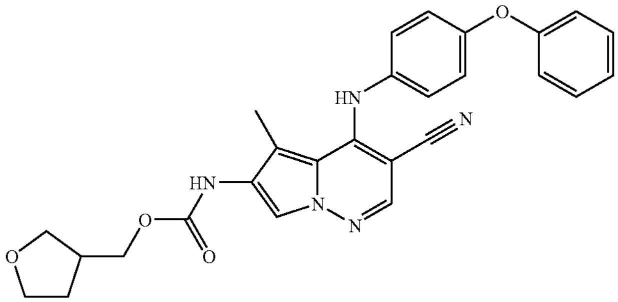 | [3-Cyano-5-methyl-4-(4-phenoxy-phenylamino)-pyrrolo[1,2-b]pyridazin-6-yl]-carbamic acid tetrahydro-furan-3-ylmethyl ester | 1.75 LC [M + H]$^+$ = 484.3 | 11A |

TABLE 2-continued

| Ex. No. | Structure | Compound Name | Retention Time Min./ Molecular Mass | Proc. of Ex. |
| --- | --- | --- | --- | --- |
| 338 | 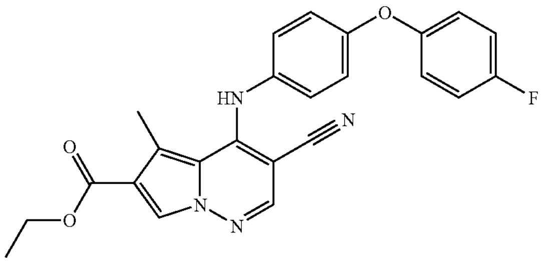 | 3-Cyano-4-[4-(4-fluoro-phenoxy)-phenylamino]-5-methyl-pyrrolo[1,2-b]pyridazine-6-carboxylic acid ethyl ester | 1.93 LC $[M + H]^+$ = 431.2 | 1E |
| 339 | 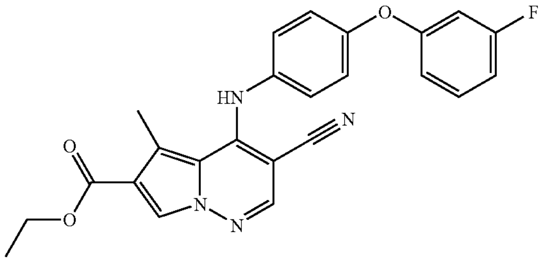 | 3-Cyano-4-[4-(3-fluoro-phenoxy)-phenylamino]-5-methyl-pyrrolo[1,2-b]pyridazine-6-carboxylic acid ethyl ester | 1.92 LC $[M + H]^+$ = 431.2 | 1E |
| 340 | 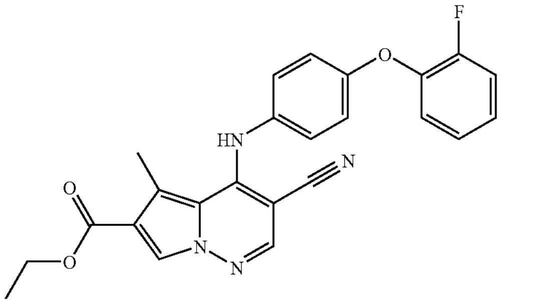 | 3-Cyano-4-[4-(2-fluoro-phenoxy)-phenylamino]-5-methyl-pyrrolo[1,2-b]pyridazine-6-carboxylic acid ethyl ester | 1.86 LC $[M + H]^+$ = 431.2 | 1E |
| 341 | 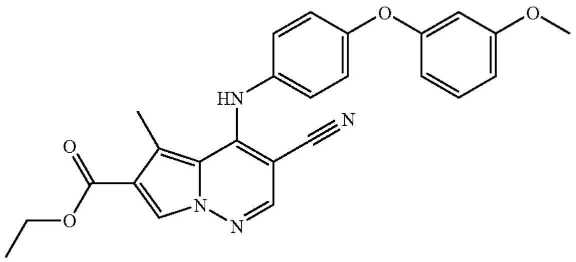 | 3-Cyano-4-[4-(3-methoxy-phenoxy)-phenylamino]-5-methyl-pyrrolo[1,2-b]pyridazine-6-carboxylic acid ethyl ester | 1.96 LC $[M + H]^+$ = 443.3 | 1E |
| 342 | 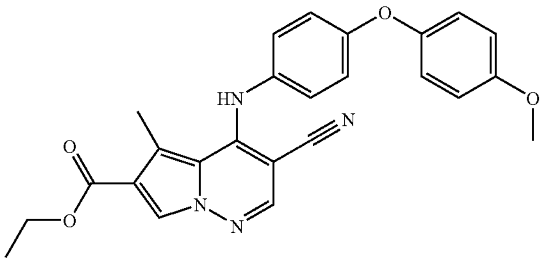 | 3-Cyano-4-[4-(4-methoxy-phenoxy)-phenylamino]-5-methyl-pyrrolo[1,2-b]pyridazine-6-carboxylic acid ethyl ester | 1.89 LC $[M + H]^+$ = 443.2 | 1E |

TABLE 2-continued

| Ex. No. | Structure | Compound Name | Retention Time Min./ Molecular Mass | Proc. of Ex. |
|---|---|---|---|---|
| 343 | 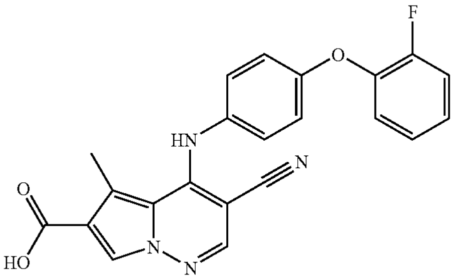 | 3-Cyano-4-[4-(2-fluoro-phenoxy)-phenylamino]-5-methyl-pyrrolo[1,2-b]pyridazine-6-carboxylic acid | 1.65 LC $[M + H]^+$ = 403.3 | 9 |
| 344 | 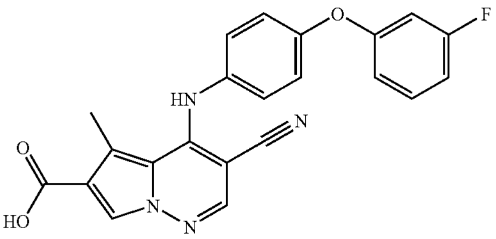 | 3-Cyano-4-[4-(3-fluoro-phenoxy)-phenylamino]-5-methyl-pyrrolo[1,2-b]pyridazine-6-carboxylic acid | 1.70 LC $[M + H]^+$ = 403.3 | 9 |
| 345 | 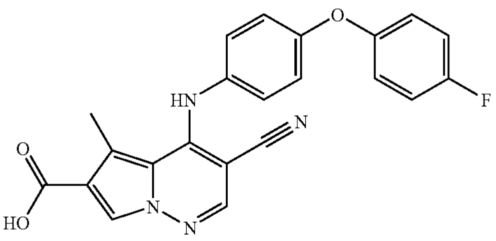 | 3-Cyano-4-[4-(4-fluoro-phenoxy)-phenylamino]-5-methyl-pyrrolo[1,2-b]pyridazine-6-carboxylic acid | 1.69 LC $[M + H]^+$ = 403.3 | 9 |
| 346 | 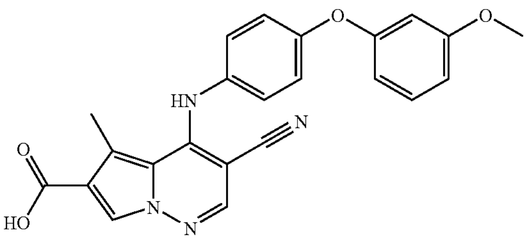 | 3-Cyano-4-[4-(3-methoxy-phenoxy)-phenylamino]-5-methyl-pyrrolo[1,2-b]pyridazine-6-carboxylic acid | 1.74 LC $[M + H]^+$ = 415.2 | 9 |
| 347 | 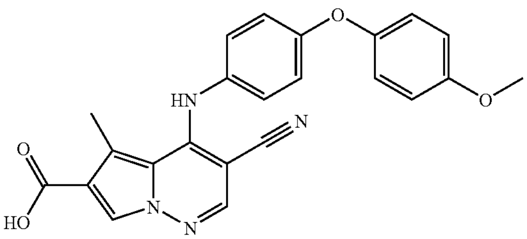 | 3-Cyano-4-[4-(4-methoxy-phenoxy)-phenylamino]-5-methyl-pyrrolo[1,2-b]pyridiazine-6-carboxylic acid | 1.66 LC $[M + H]^+$ = 415.2 | 9 |

TABLE 2-continued

| Ex. No. | Structure | Compound Name | Retention Time Min./ Molecular Mass | Proc. of Ex. |
|---|---|---|---|---|
| 348 | 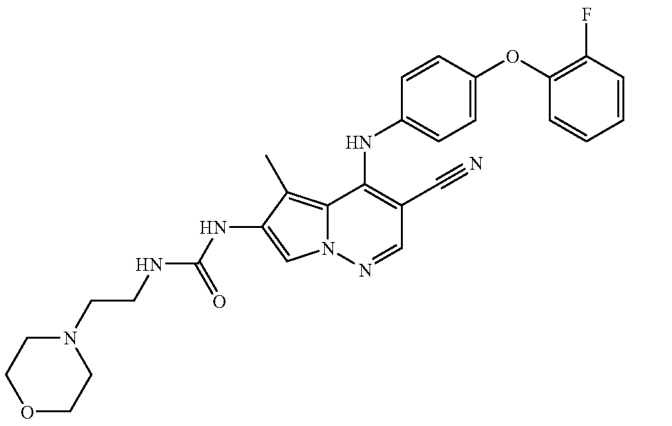 | 1-{3-Cyano-4-[4-(2-fluoro-phenoxy)-phenylamino]-5-methyl-pyrrolo[1,2-b]pyridazin-6-yl}-3-(2-morpholin-4-yl-ethyl)-urea | 1.46 LC $[M + H]^+$ = 530.3 | 19 |
| 349 | 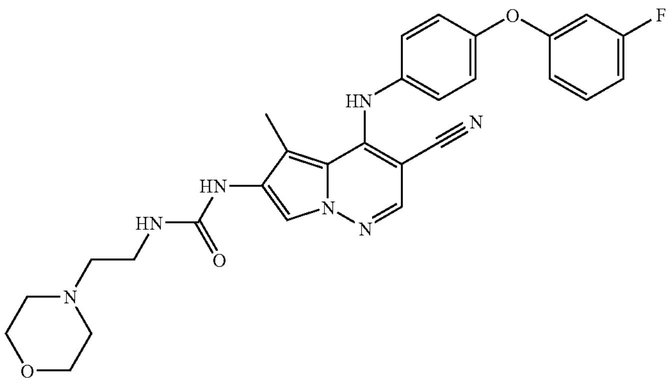 | 1-{3-Cyano-4-[4-(3-fluoro-phenoxy)-phenylamino]-5-methyl-pyrrolo[1,2-b]pyridazin-6-yl}-3-(2-morpholin-4-yl-ethyl)-urea | 1.53 LC $[M + H]^+$ = 530.3 | 19 |
| 350 | 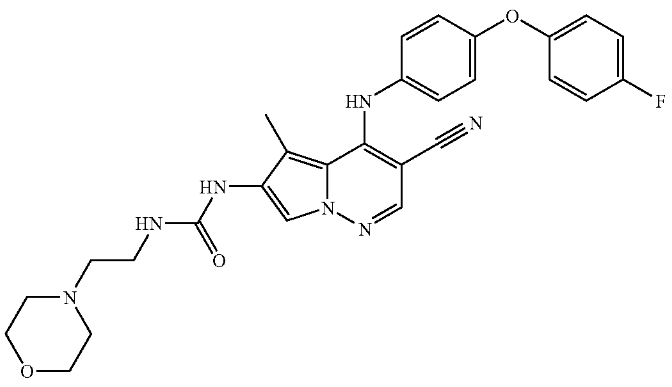 | 1-{3-Cyano-4-[4-(4-fluoro-phenoxy)-phenylamino]-5-methyl-pyrrolo[1,2-b]pyridazin-6-yl}-3-(2-morpholin-4-yl-ethyl)-urea | 1.50 LC $[M + H]^+$ = 530.3 | 19 |

TABLE 2-continued

| Ex. No. | Structure | Compound Name | Retention Time Min./ Molecular Mass | Proc. of Ex. |
|---|---|---|---|---|
| 351 | 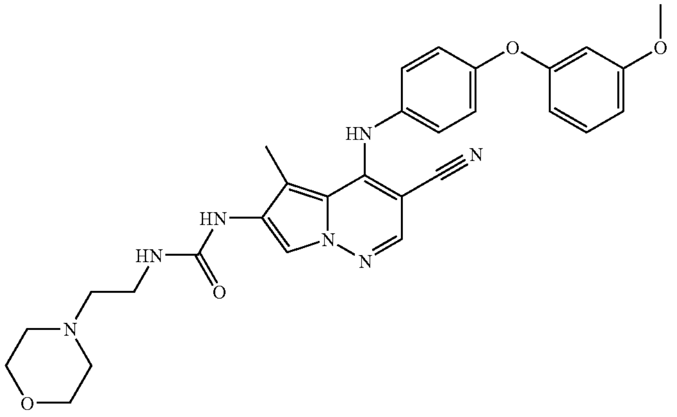 | 1-{3-Cyano-4-[4-(3-methoxy-phenoxy)-phenylamino]-5-methyl-pyrrolo[1,2-b]pyridazin-6-yl}-3-(2-morpholin-4-yl-ethyl)-urea | 1.51 LC $[M + H]^+$ = 542.4 | 19 |
| 352 | 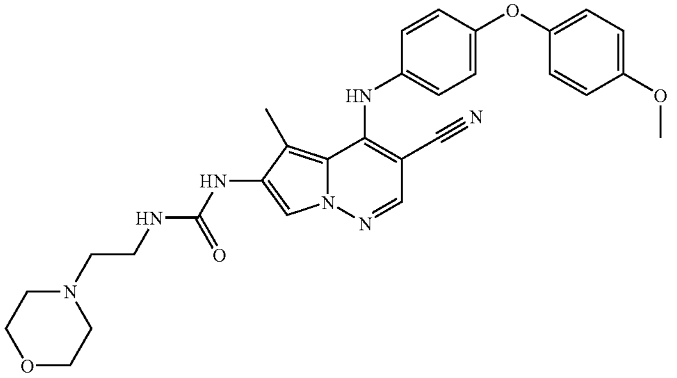 | 1-{3-Cyano-4-[4-(4-methoxy-phenoxy)-phenylamino]-5-methyl-pyrrolo[1,2-b]pyridazin-6-yl}-3-(2-morpholin-4-yl-ethyl)-urea | 1.49 LC $[M + H]^+$ = 542.4 | 19 |
| 353 | 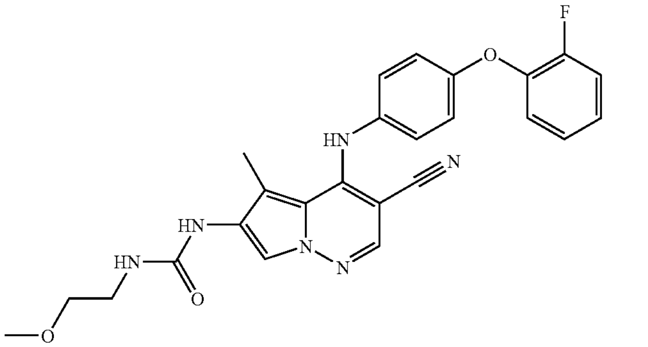 | 1-{3-Cyano-4-[4-(2-fluoro-phenoxy)-phenylamino]-5-methyl-pyrrolo[1,2-b]pyridazin-6-yl}-3-(2-methoxy-ethyl)-urea | 1.64 LC $[M + H]^+$ = 475.3 | 19 |
| 354 | 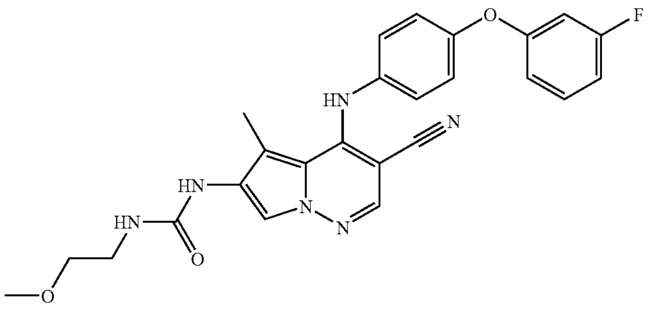 | 1-{3-Cyano-4-[4-(3-fluoro-phenoxy)-phenylamino]-5-methyl-pyrrolo[1,2-b]pyridazin-6-yl}-3-(2-methoxy-ethyl)-urea | 1.69 LC $[M + H]^+$ = 475.3 | 19 |

TABLE 2-continued

| Ex. No. | Structure | Compound Name | Retention Time Min./ Molecular Mass | Proc. of Ex. |
|---|---|---|---|---|
| 355 | 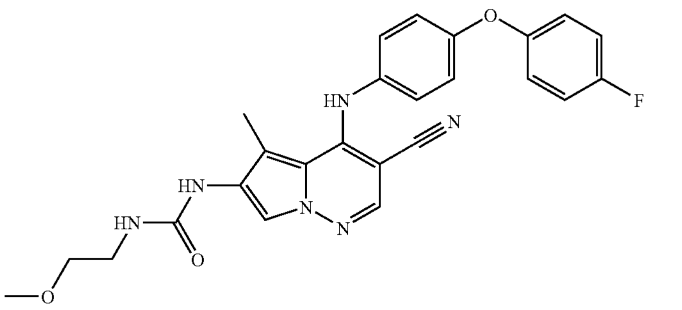 | 1-{3-Cyano-4-[4-(4-fluoro-phenoxy)-phenylamino]-5-methyl-pyrrolo[1,2-b]pyridazin-6-yl}-3-(2-methoxy-ethyl)-urea | 1.68 LC $[M + H]^+$ = 475.3 | 19 |
| 356 | 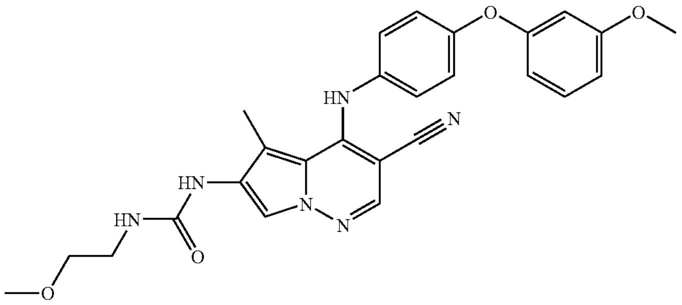 | 1-{3-Cyano-4-[4-(3-methoxy-phenoxy)-phenylamino]-5-methyl-pyrrolo[1,2-b]pyridazin-6-yl}-3-(2-methoxy-ethyl)-urea | 1.68 LC $[M + H]^+$ = 487.3 | 19 |
| 357 | 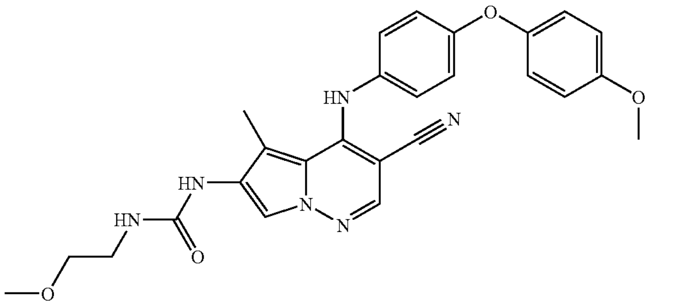 | 1-{3-Cyano-4-[4-(4-methoxy-phenoxy)-phenylamino]-5-methyl-pyrrolo[1,2-b]pyridazin-6-yl}-3-(2-methoxy-ethyl)-urea | 1.64 LC $[M + H]^+$ = 487.4 | 19 |
| 358 | 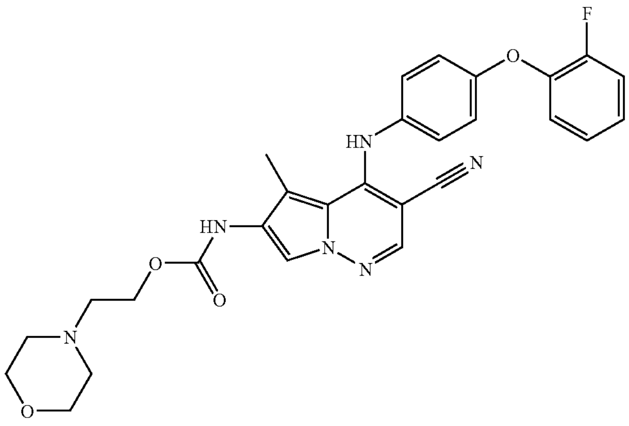 | {3-Cyano-4-[4-(2-fluoro-phenoxy)-phenylanmino]-5-methyl-pyrrolo[1,2-b]pyridazin-6-yl}-carbamic acid 2-morpholin-4-yl-ethyl ester | 1.47 LC $[M + H]^+$ = 531.3 | 11A |

TABLE 2-continued

| Ex. No. | Structure | Compound Name | Retention Time Min./ Molecular Mass | Proc. of Ex. |
|---|---|---|---|---|
| 359 | 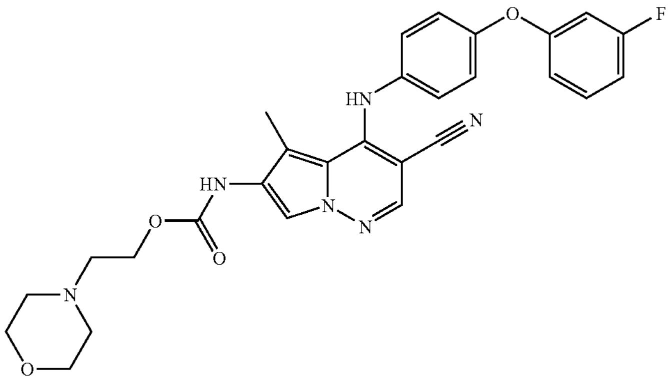 | {3-Cyano-4-[4-(3-fluoro-phenoxy)-phenylamino]-5-methyl-pyrrolo[1,2-b]pyridazin-6-yl}-carbamic acid 2-morpholin-4-yl-ethyl ester | 1.53 LC $[M + H]^+$ = 531.3 | 11A |
| 360 | 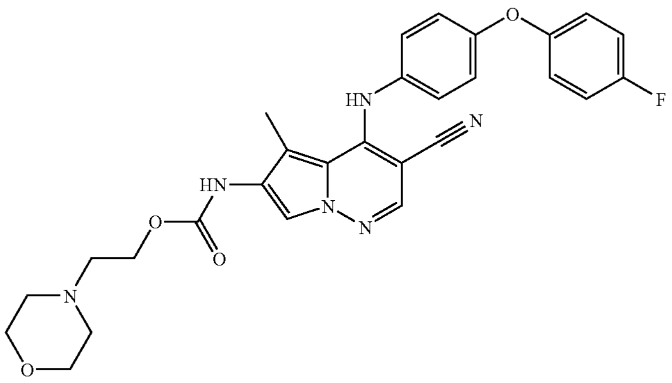 | {3-Cyano-4-[4-(4-fluoro-phenoxy)-phenylamino]-5-methyl-pyrrolo[1,2-b]pyridazin-6-yl}-carbamic acid 2-morpholin-4-yl-ethyl ester | 1.51 LC $[M + H]^+$ = 531.3 | 11A |
| 361 | 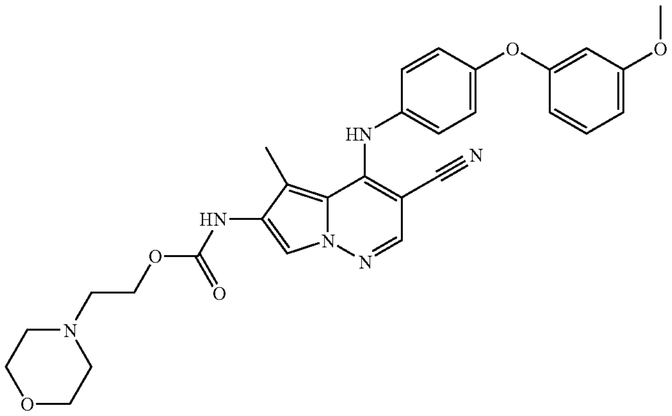 | {3-Cyano-4-[4-(3-methoxy-phenoxy)-phenylamino]-5-methyl-pyrrolo[1,2-b]pyridazin-6-yl}-carbamic acid 2-morpholin-4-yl-ethyl-ester | 1.52 CL $[M + H]^+$ = 543.4 | 11A |

TABLE 2-continued

| Ex. No. | Structure | Compound Name | Retention Time Min./ Molecular Mass | Proc. of Ex. |
|---|---|---|---|---|
| 362 | 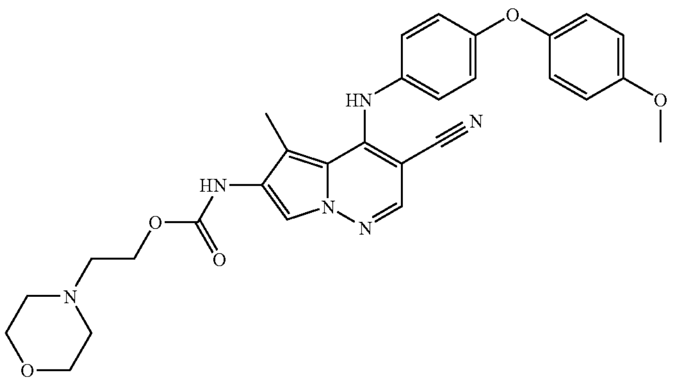 | {3-Cyano-4-[4-(4-methoxy-phenoxy)-phenylamino]-5-methyl-pyrrolo[1,2-b]pyridazin-6-yl}-carbamic acid 2-morpholin-4-yl-ethyl-ester | 1.48 LC [M + H]+ = 543.4 | 11A |
| 363 | 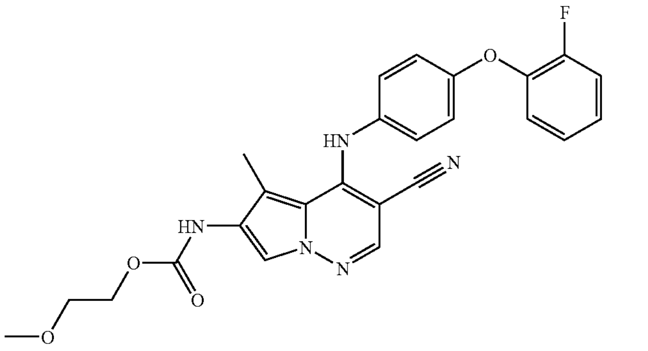 | {3-Cyano-4-[4-(2-fluoro-phenoxy)-phenylamino]-5-methyl-pyrrolo[1,2-b]pyridazin-6-yl}-carbamic acid 2-methoxy-ethyl ester | 1.68 LC [M + H]+ = 476.3 | 11A |
| 364 | 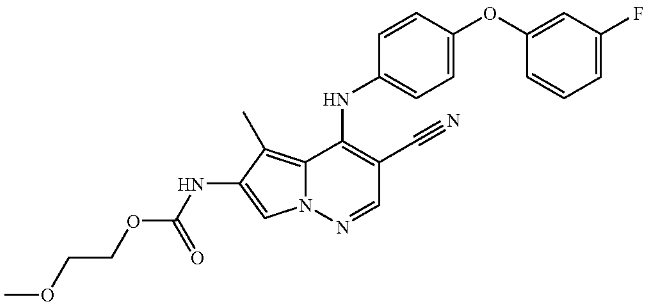 | {3-Cyano-4-[4-(3-fluoro-phenoxy)-phenylamino]-5-methyl-pyrrolo[1,2-b]pyridazin-6-yl}-carbamic acid 2-methoxy-ethyl ester | 1.68 LC [M + H]+ = 476.3 | 11A |
| 365 | 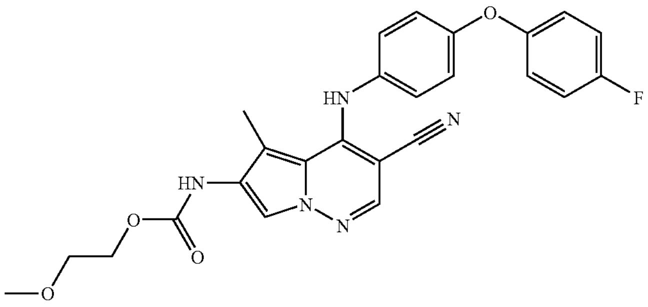 | {3-Cyano-4-[4-(4-fluoro-phenoxy)-phenylamino]-5-methyl-pyrrolo[1,2-b]pyridazin-6-yl}-carbamic acid 2-methoxy-ethyl ester | 1.72 LC [M + H]+ = 476.3 | 11A |

TABLE 2-continued

| Ex. No. | Structure | Compound Name | Retention Time Min./ Molecular Mass | Proc. of Ex. |
|---|---|---|---|---|
| 366 | 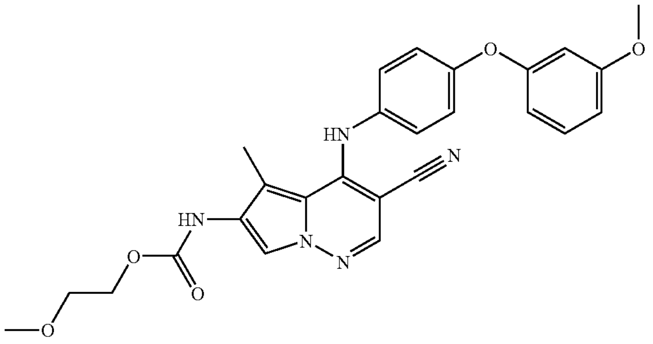 | {3-Cyano-4-[4-(3-methoxy-phenoxy)-phenylamino]-5-methyl-pyrrolo[1,2-b]pyridazin-6-yl}-carbamic acid 2-methoxy-ethyl ester | 1.78 LC $[M + H]^+$ = 488.3 | 11A |
| 367 | 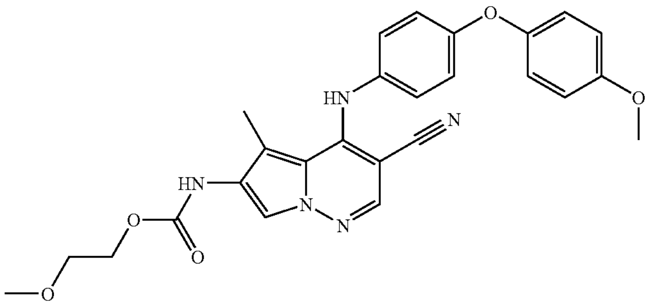 | {3-Cyano-4-[4-(4-methoxy-phenoxy)-phenylamino]-5-methyl-pyrrolo[1,2-b]pyridazin-6-yl}-carbamic acid 2-methoxy-ethyl ester | 1.68 LC $[M + H]^+$ = 488.3 | 11A |

EXAMPLE 368

Preparation of 3-Cyano-4-[4-(cyano-phenyl-methyl)-phenylamino]-5-methyl-pyrrolo[1,2-b]pyridazine-6-carboxylic acid ethyl ester (368)

368

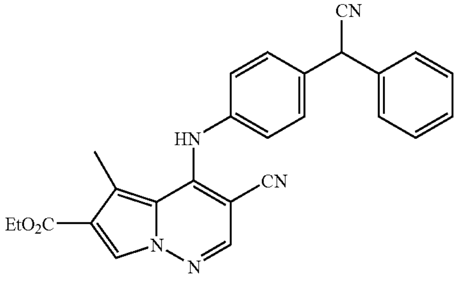

4-Chloro-3-cyano-5-methyl-pyrrolo[1,2-b]pyridazine-6-carboxylic acid ethyl ester (5 mg, 0.019 mmol) and (4-Amino-phenol)-phenyl-acetonitrile (8 mg, 0.016 mmol) in DMF (0.5 ml) were heated at 110° C. for 3 hrs. The reaction mixture was purified by silica gel flash chromatography to isolate 3-cyano-4-[4-cyano-phenyl-methyl) phenylamino]-5-methyl-pyrrolo[1,2-b]pyridazine-6-carboxylic acid ethyl ester 368 as yellow film (4.3 mg, 52%). $[M+H]^+$=436.1.

EXAMPLE 369

Preparation of 2-[3-Cyano-6-ethoxycarbonyl-4-(4-phenoxy-phenylamino)-pyrrolo[1,2-b]pyridazin-5-ylmethyl]-malonic acid diethyl ester (369)

369

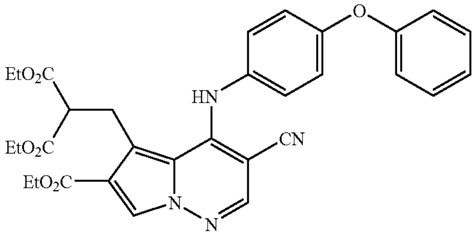

369B—Synthesis of 1-(4-Chloro-3-cyano-6-ethoxycarbonyl-pyrrolo[1,2-b]pyridazin-5-ylmethyl)-malonic acid diethyl ester)

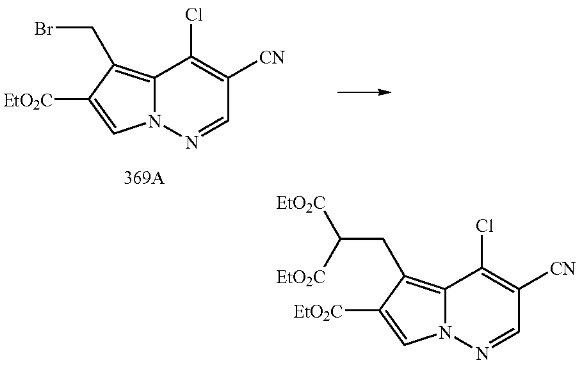

369A

369B

LDA (0.084 mmol, 2.0 M solution in heptane/THF) was added to diethyl malonate (0.096 mmol, 15.3 mg) in THF (0.5 ml) at 0° C. After 5 min, 5-bromomethyl-4-chloro-3-cyano-pyrrolo[1,2-b]pyridazine-6-carboxylic acid ethyl ester 369A (0.048 mmol, 16.2 mg) in THF (0.5 ml) was added. After 10 min, the reaction mixture was placed at RT and stirred for 1 hr, quenched with pH 7 phosphate buffer (5 ml) and extracted with dichloromethane (3×5 ml), dried over $Na_2SO_4$, concentrated and purified by silica gel flash chromatography to isolate 369B as a yellow film (6.5 mg, 31%). $[M+H]^+$=443.

(2) Preparation of 2-[3-Cyano-6-ethoxycarbonyl-4-(4-phenoxy-phenylamino)-pyrrolo[1,2-b]pyridazin-5-ylmethyl]-malonic acid diethyl ester

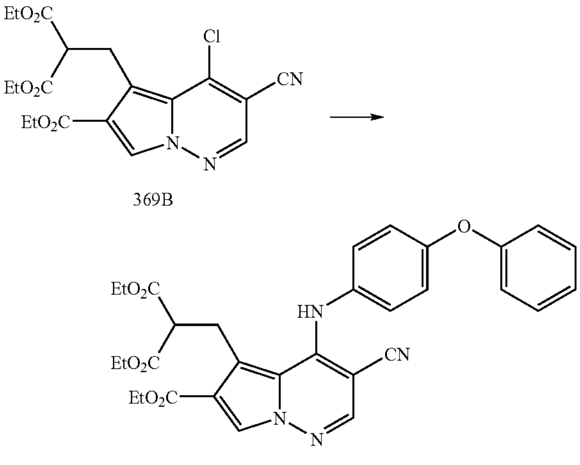

369B

369

A solution of 2-(4-Chloro-3-cyano-6-ethoxycarbonyl-pyrrolo[1,2-b]pyridazin-5-ylmethyl)-malonic acid diethyl ester 369B (6.5 mg, 0.015 mmol) and 4-phenoxyphenylamine (4.2 mg, 0.023 mmol) in DMF (0.5 ml) was heated at 110° C. for 4 hrs. The reaction mixture was purified by silica gel flash chromatography to isolate 369 as a yellow film (1.7 mg, 20%). $[M+H]^+$32 571.

EXAMPLE 370

Preparation of 5-Methyl-4-(4-phenoxy-phenylamino)-6-phenylamino-pyrrolo-[1,2-b]pyridazine-3-carbonitrile (370)

370

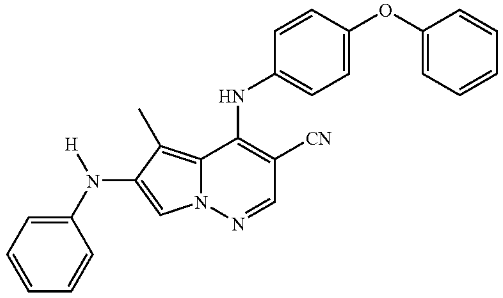

6-Amino-5-methyl-4-(4-phenoxy-phenylamino)-pyrrolo[1,2-b]pyridazine-3-carbonitrile hydrochloride (10.3 mg, 0.026 mmol), benzeneboronic acid (4.7 mg, 0.039 mmol), $Cu(OAc)_2$ (0.039 mmol, 7 mg) and TEA (0.13 mmol, 13 mg) in dichloromethane (1 ml) were stirred at RT for 16 hrs. The reaction mixture was purified by silica gel flash chromatography to isolate 370 as a yellow film (1.4 mg, 15%). $[M+H]^+$=432.1.

EXAMPLE 371

Preparation of 3-Cyano-5-methyl-4-(4-phenoxy-phenylamino)-pyrrolo[1,2-b]pyridazine-6-carboxylic acid (2-amino-phenyl)-amide (371)

371

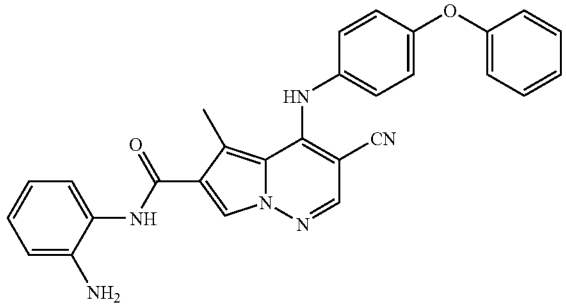

3-Cyano-5-methyl-4-(4-phenoxy-phenylamino)-pyrrolo[1,2-b]pyridazine-6-carboyxlic acid (40 mg, 0.1 mmol), phenylenediamine (16 mg, 0.15 mmol), PyBOP (78 mg, 0.15 mmol) and DIEA (19.4 mg, 0.15 mmol) in 1,2-dichloroethane (1.5 ml) were stirred at RT for 48 hrs. The reaction mixture was concentrated and purified by silica gel flash chromatography to isolate 371 as a yellow film (17.6 mg, 37%). $[M+H]^+$=475.11.

EXAMPLE 372

Preparation of {3-cyano-5-methyl-4-[(4-phenoxyphenyl)amino](7a-hydropyrrolo[1,2-e]pyridazin-6-yl)}-N-[2-({3-cyano-5-methyl-4-[(4-phenoxyphenyl)amino](7a-hydropyrrole[1,2-e]pyridazin-6-yl)}carbonylamino)phenyl]carboxamide (372)

372

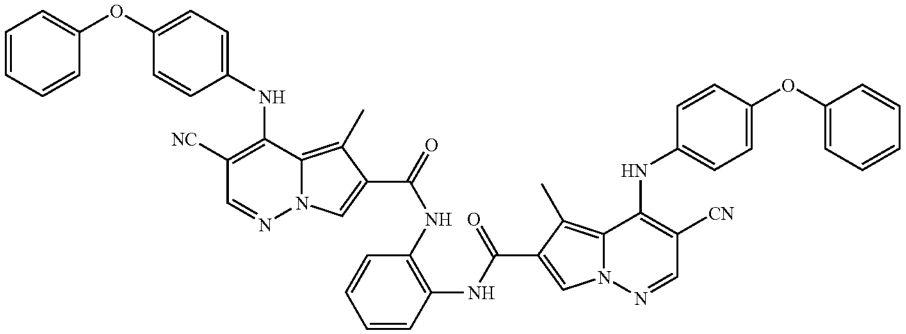

Compound 372 was the second product isolated from example 371 as a yellow film (10.6 mg, 12%). $[M+H]^+$=841.

EXAMPLE 373

Preparation of 6-(1H-Benzoimidazol-2-yl)-5-methyl-4-(4-phenoxy-phenylamino)-pyrrolo[1,2-b]pyridazine-3-carbonitrile (373)

373

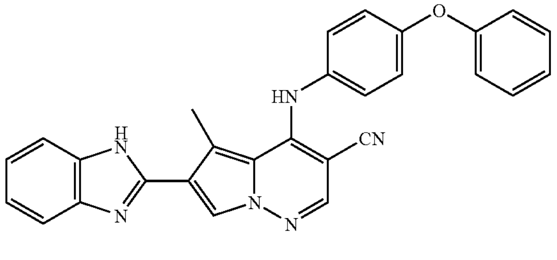

3-Cyano-5-methyl-4-(4-phenoxy-phenylamino)-pyrrolo[1,2-b]pyridazine-6-carboxylic acid (2-amino-phenyl)-amide 371 (4 mg, 0.008 mmol) and a small pinch of 10-camphorsulfonic acid was heated in toluene (1.0 ml) at 110° C. for 5 hrs. The reaction mixture was purified by silica gel flash chromatography to isolate 373 as yellow film (1.9 mg, 33%). $[M+H]^+$=436.1.

EXAMPLE 374

Preparation of N-[3-Cyano-5-methyl-4-(4-phenoxy-phenylamino)-pyrrolo[1,2-b]pyridazin-6-yl]-2-fluoro-benzamide (374)

374

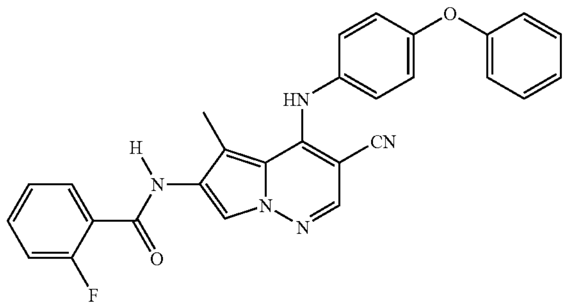

6-Amino-5-methyl-4-(4-phenoxy-phenylamino)-pyrrolo[1,2-b]pyridazine-3-carbonitrile hydrochloride (8 mg, 0.02 mmol), 2-fluorobenzoic acid (4.2 mg, 0.03 mmol), PyBOP (16 mg, 0.03 mmol) and DIEA (6.5 mg, 0.05 mmol) in 1,2-dichloroethane (0.5 ml) were stirred at RT for 16 hrs. The reaction mixture was concentrated and purified by silica gel flash chromatography to isolate 374 as a white solid (4 mg, 42%). $[M+H]^+$=478.

EXAMPLES 375

Preparation of 5-Methyl-6-(2-methyl-4-oxo-4H-quinazolin-3-yl)-4-(4-phenoxy-phenylamino)-pyrrolo[1,2-b]pyridazine-3-carbonitrile (375)

375

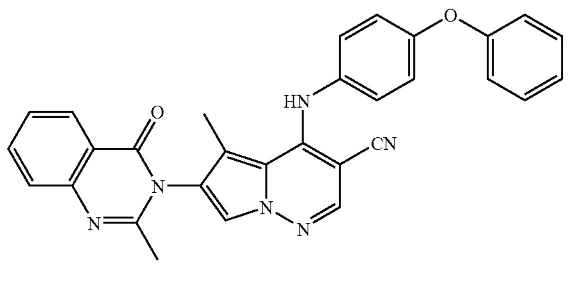

6-Amino-5-methyl-4-(4-phenoxy-phenylamino)-pyrrolo[1,2-b]pyridazine-3-carbonitrile hydrochloride (10.4 mg, 0.027 mmol), 2-acetylamino benzoic acid (7 mg, 0.04 mmol), PyBOP (21 mg, 0.04 mmol) and DIEA (8.6 mg, 0.067 mmol) in 1.2-dichloroethane (0.5 ml) were stirred at RT for 16 hrs. The reaction mixture was concentrated and purified by silica gel flash chromatography to isolate 375 as a yellow film (5.8 mg, 42%). $[M+H]^+=498$.

EXAMPLE 376

Preparation of 6-Benzylamino-5-methyl-4-(4-phenoxy-phenylamino)-pyrrolo-[1,2-b]pyridazine-3-carbonitrile (376)

376

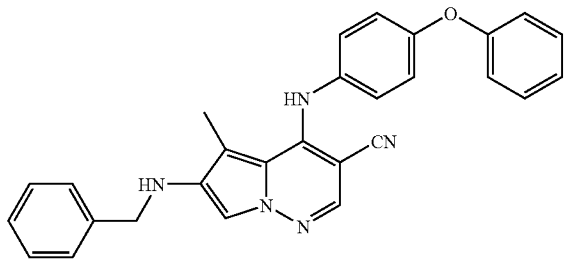

6-Amino-5-methyl-4-(4-phenoxy-phenylamino)-pyrrolo[1,2-b]pyridazine-3-carbonitrile hydrochloride (10 mg, 0.026 mmol), benzaldehyde (2.8 mg, 0.026 mmol) and acetic acid (0.5 ml) in 1,2-dichloroethane (1.0 ml) were stirred at RT. After 20 minutes, $NaBH(OAc)_3$ was added and the reaction mixture was stirred for additional 15 minutes, quenched with saturated $NH_4OH$ (4.0 ml), extracted with dichloromethane (3×3 ml), dried over $Na_2SO_4$, concentrated and purified by silica gel flash chromatography to isolate 376 as a yellow film (1.3 mg, 11%). $[M+H]^+=446.2$.

EXAMPLE 377

Preparation of N-[3-Cyano-5-methyl-4-(4-phenoxy-phenylamino)-pyrrolo[1,2-b]pyridazin-6-yl]-benzenesulfonamide (377)

377

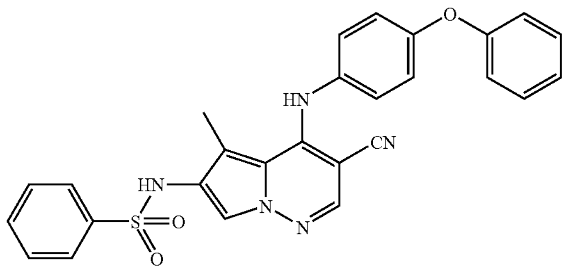

To 6-Amino-5-methyl-4-(4-phenoxy-phenylamino)-pyrrolo[1,2-b]pyridazine-3-carbonitrile hydrochloride (8.2 mg, 0.021 mmol) and DIEA (5.4 mg, 0.042 mmol) in dichloromethane (1.0 ml) was added benzenesulfonyl chloride (3.7 mg, 0.021 mmol) at RT for 2 hrs. The reaction mixture was quenched with pH 7 phosphate buffer (2 ml), dried over $Na_2SO_4$, concentrated and purified by silica gel flash chromatography to isolate 377 as a yellow film (3 mg, 29%). $[M+H]^+=496.1$.

EXAMPLE 378

Preparation of 6-[bis(phenylsulfonyl)amino]-5-methyl-4-[(4-phenoxyphenyl)amino]-7a-hydropyrrolo[1,2-e]pyridazine-3-carbonitrile (378)

378

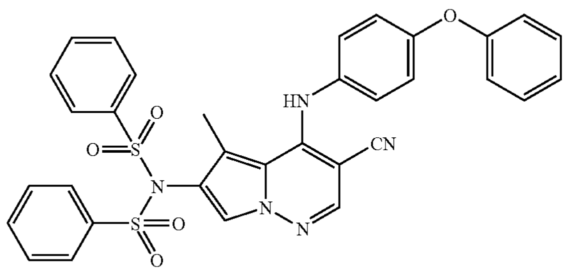

To 6-Amino-5-methyl-4-(4-phenoxy-phenylamino)-pyrrolo[1,2-b]pyridazine-3-carbonitrile hydrochloride (7 mg, 0.018 mmol) and DIEA (5.8 mg, 0.045 mmol) in 1,2-dichloromethane (1.0 ml) was added benzenesulfonyl chloride (3.9 mg, 0.022 mmol) at RT for 12 hrs. The reaction mixture was quenched with pH 7 phosphate buffer (2 ml), dried over $Na_2SO_4$, concentrated and purified by silica gel flash chromatography to isolate 378 as a yellow film (3.1 mg, 27%). $[M+H]^+=636.05$.

EXAMPLES 379

Preparation of 6-(Benzothiazol-2-ylamino)-5-methyl-4-(4-phenoxy-phenylamino)-pyrrolo[1,2-b]pyridazine-3-carbonitrile (379)

379

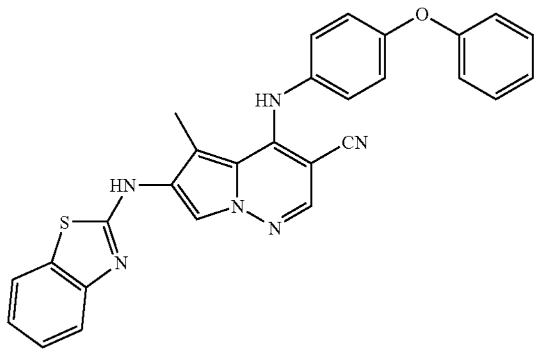

6-Amino-5-methyl-4-(4-phenoxy-phenylamino)-pyrrolo[1,2-b]pyridazine-3-carbonitrile hydrochloride (9.5 mg, 0.024 mmol) and 2-chlorobenzothiazole (4.4 mg, 0.026 mmol) in DMF (0.1 ml) were stirred at 100° C. for 12 hrs. The reaction mixture was concentrated and purified by silica gel flash chromatography to isolate 379 as a yellow film (3.3 mg, 28%). $[M+H]^+$489.14

EXAMPLE 380

Preparation of {4-[4-(6-Chloro-pyridazin-3-yloxy)-phenylamino]-3-cyano-5-methyl-pyrrolo[1,2-b]pyridazin-6-yl}-carbamic acid 2 morpholin-4-yl-ethyl ester

380

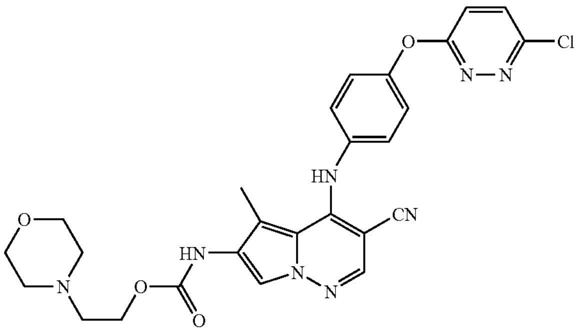

380B-Synthesis of 4-(4-Benzyloxy-phenylamino)-3-cyano-5-methyl-pyrrolo[1,2-b]pyridazine-6-carboxylic acid

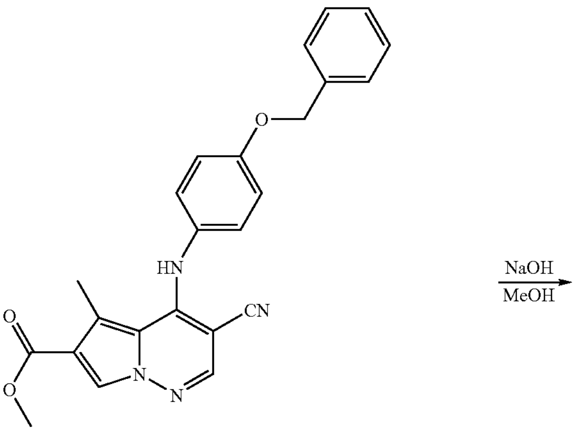

380A

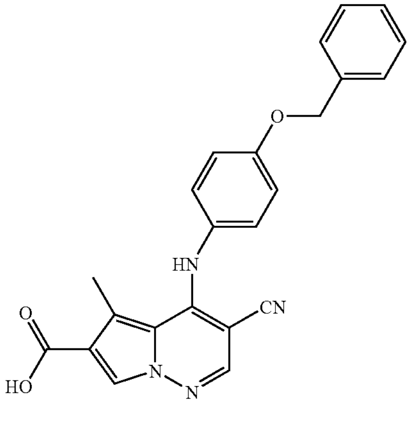

380B

To 4-(4-Benzyloxy-phenylamino)-3-cyano-5-methyl-pyrrolo[1,2-b]pyridazine-6-carboxylic acid methyl ester 380A (3.4 mmol, 1.4 g) in methanol (15 ml) was added 1N sodium hydroxide (15 ml), and the reaction mixture was heated a 65° C. for 30 hrs. The methanol was removed under vacuum, and the remaining mixture was dissolved in 1N HCl (200 ml), extracted with ethyl acetate (2×300 mL), dried over sodium sulfate. The organic layer was concentrated to afford 380B as a yellow solid (750 mg, 56%), which was taken to next step without further purification, $[M+H]^+$=399.14.

380C—Synthesis of [4-(4-Benzyloxy-phenylamino)-3-cyano-5-methyl-pyrrolo[1,2-b]pyridazin-6-yl]-carbamic acid 2-morpholin-4-yl-ethyl ester

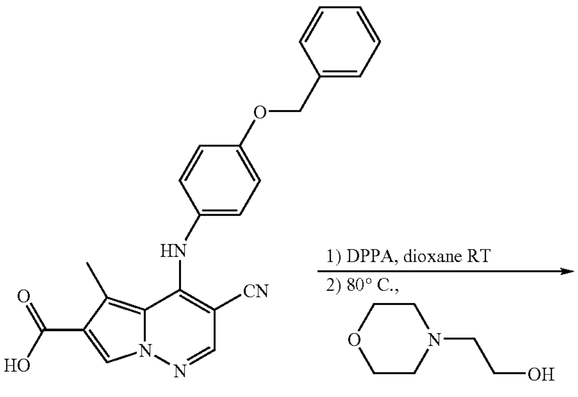

380B

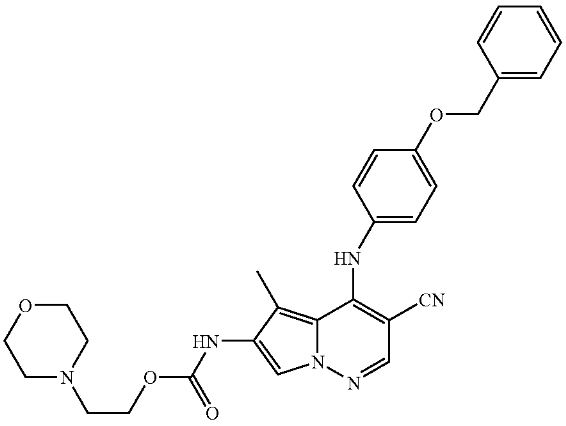

380C

[4-(4-Benzyloxy-phenylamino)-3-cyano-5-methyl-pyrrolo[1,2-b]pyridazin-6yl]-carbamic acid 2-morpholin-4-yl-ethyl ester 380B (646 mg, 1.62 mmol), DPPA (535 mg, 1.95 mmol), and triethylamine (246 mg, 2.43 mmol) in dioxane (10 ml) were stirred at RT. After 20 hrs, 4-(2-hydroxyethyl)morpholine (425 mg, 3.24 mmol) was added, and the reaction mixture was heated at 80° C. for 5 hrs. The reaction mixture was diluted with aqueous $NH_4OH$ (75 ml) and extracted with ethyl acetate (4×200 ml). The combined organic layers were dried over sodium sulfate, concentrated and purified by silica gel flash chromatography to afford 380C as a yellow solid (675 mg, 79%). $[M+H]^+$=527.13.

380D—Synthesis of [3-Cyano-4-(4-hydroxy-phenylamino)-5-methyl-pyrrolo[1,2-b]pyridazin-6-yl]-carbamic acid 2-morpholin-4-yl-ethyl ester

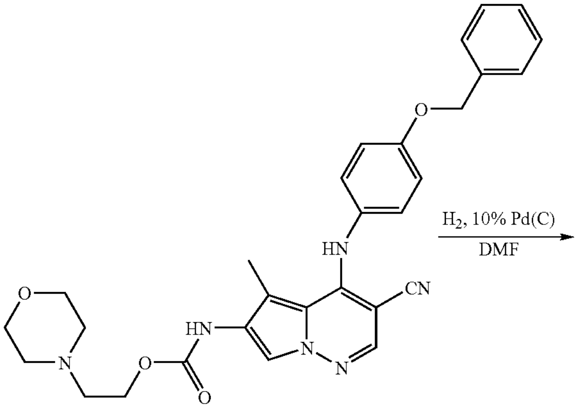

380C

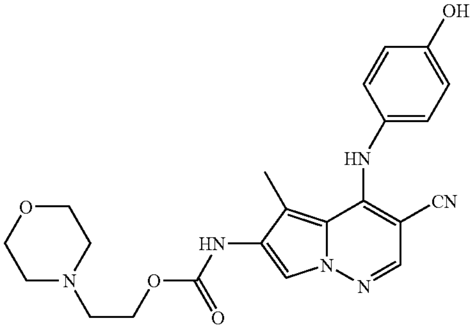

380D

[4-(4-Benzyloxy-phenylamino)-3-cyano-5-methyl-pyrrolo[1,2-b]pyridazin-6-yl]-carbamic acid 2-morpholin-4-yl-ethyl ester 380C (0.79 mmol, 420 mg) and 10% Pd(C) (180 mg) in DMF (10 ml) were stirred under $H_2$ gas (1 atm) for 24 hours. The reaction mixture was filtered to afford 380D as a yellow solid (320 mg, 92%). $[M+H]^+$=437.21.

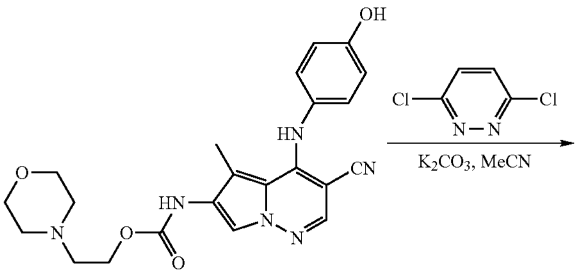

380D

-continued

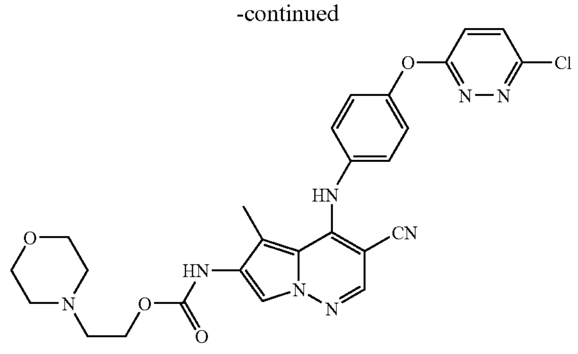

380

[3-Cyano-4-(4-hydroxy-phenylamino)-5-methyl-pyrrolo[1,2-b]pyridazin-6-yl]-carbamic acid 2-morpholin-4-yl-ethyl ester 380D (0.037 mmol, 16 mg), 6.5 mg 3,6-dichloropyridazine (0.044 mmol, 6.5 mg), and potassium carbonate (0.044 mmol, 6.1 mg) were stirred at 80° C. for 48 hrs. The reaction mixture was concentrated and purified using prep HPLC to obtain 380 as a yellow film (0.52 mg, 3%). $[M+H]^+=549.2$

EXAMPLE 381

Preparation of {3-Cyano-5-methyl-4-[4-(1-phenyl-1H-tetrazol-5-yloxy)-phenylamino]-pyrrolo[1,2-b]pyridazin-6-yl}-carbamic acid 2-morpholin-4-yl-ethyl ester

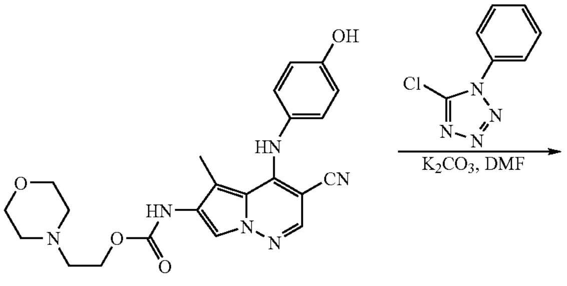

381D

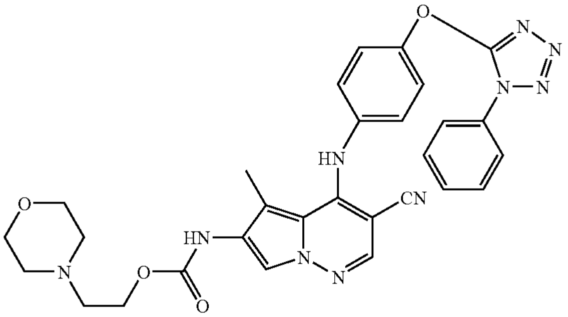

381

Compound 381 (12.7 mg, 60%) was prepared using the same procedure used to prepared compound 380 from compound 380D in example 380. $[M+H]^+=581.1$.

EXAMPLE 382

Preparation of {3-Cyano-5-methyl-4-[4-(2-nitro-phenoxy)-phenylamino]-pyrrolo[1,2-b]pyridazin-6-yl}-carbamic acid 2-morpholin-4-yl-ethyl ester

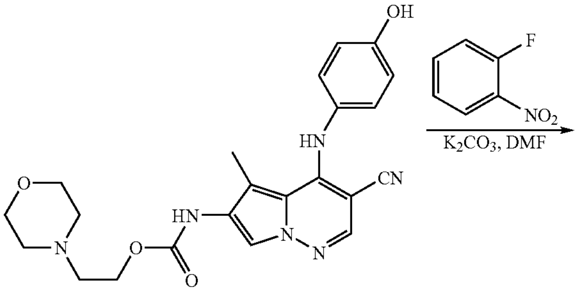

380D

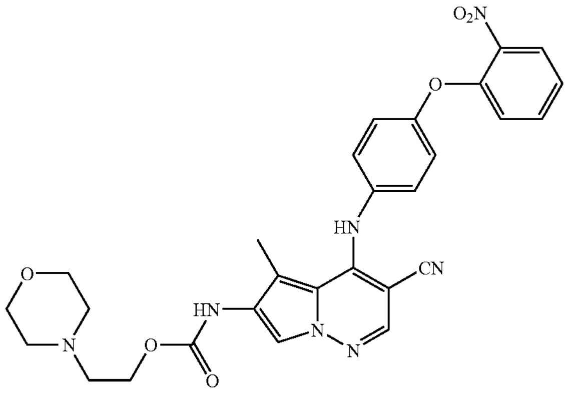

382

Compound 382 (15 mg, 36%) was prepared using the same procedure used to prepare compound 380 from compound 380D in example 380. $[M+H]^+=558.07$

EXAMPLE 383

Preparation of {4-[4-(2-Amino-phenoxy)-phenylamino]-3-cyano-5-methyl-pyrrolo[1,2-b]pyridazin-6-yl}-carbamic acid 2-morpholin-4-yl-ethyl ester

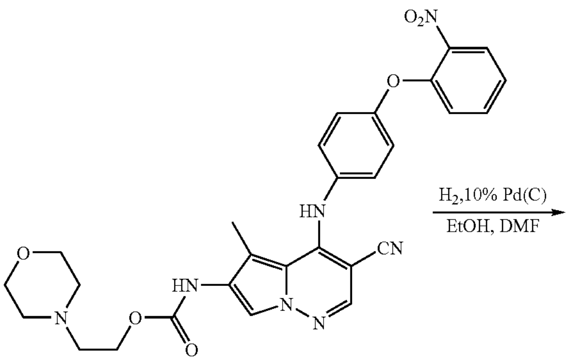

382

-continued

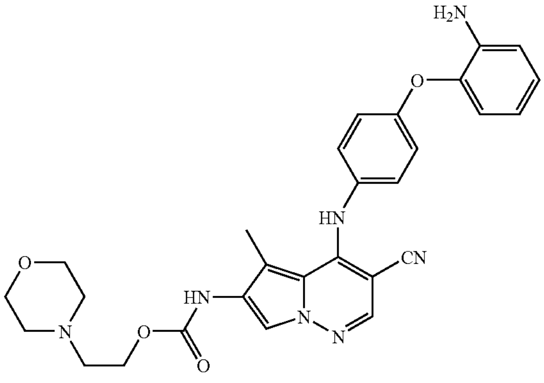

383

{3-Cyano-5-methyl-4-[4-(2-nitro-phenoxy)-phenylamino]-pyrrolo[1,2-b]pyridazin-6-yl}-carbamic acid 2-morpholin-4-yl-ethyl ester 382 (0.025 mmol, 14 mg) and 10% Pd on carbon (15 mg) in ethanol/DMF (2:1, 3 ml) were stirred at RT for 2.5 hrs under atmosphere of $H_2$ gas (1 atm). The reaction mixture was filtered and concentrated to obtain compound 383 as a brown/orange oil (13 mg, 100%). $[M+H]^+$=528.14.

EXAMPLE 384

Preparation of {4-[4-(2-Acetylamino-phenoxy)-phenylamino]-3-cyano-5-methyl-pyrrolo[1,2-b]pyridazin-6-yl}-carbamic acid 2-morpholin-4-yl-ethyl ester

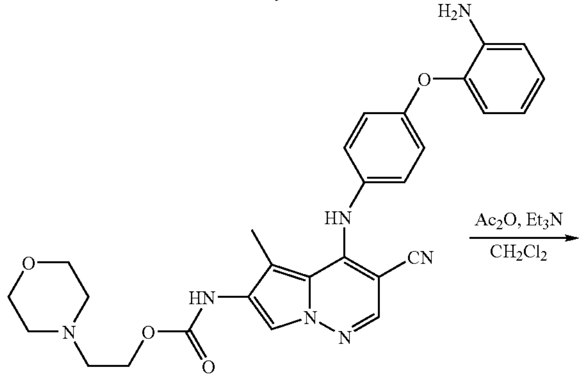

383

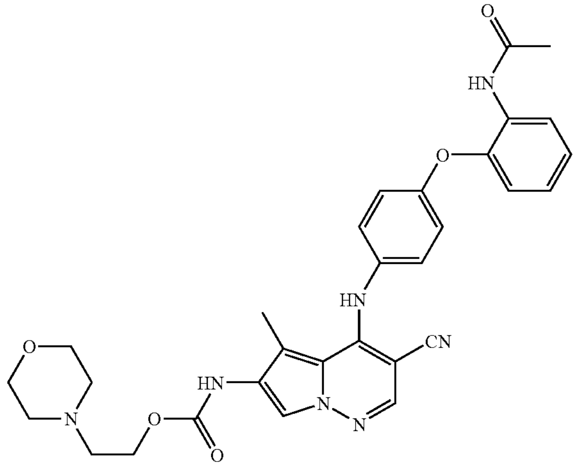

384

{4-[4-(2-Amino-phenoxy)-phenylamino]-3-cyano-5-methyl-pyrrolo[1,2-b]pyridazin-6-yl}-carbamic acid 2-morpholin-4-yl-ethyl ester 383 (0.013 mmol, 7 mg, acetic anhydride (0.44 mmol, 45 mg), and triethylamine (0.28 mmol, 28 mg) in dichloromethane (1 ml) were stirred at RT for 30 hours. The reaction mixture was diluted in saturated sodium bicarbonate (20 ml), extracted with dichloromethane (70 ml), dried over sodium sulfate, and purified by silica gel flash chromatography (5% MeOH/$CHCl_3$) to isolate compound 384 as a yellow film (1.9 mg, 27%). $[M+H]^+$=570.14.

EXAMPLE 385

Preparation of 5-Methyl-4-(4-phenoxy-phenylamino)-pyrrolo[1,2-b]pyridazine-3-carbonitrile

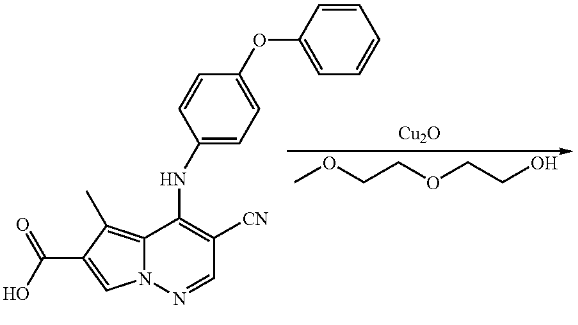

385A

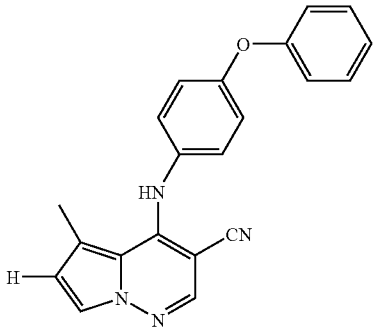

385

3-Cyano-5-methyl-4-[4-(1-vinyl-propenyloxy)-phenylamino]-pyrrolo[1,2-b]pyridazine-6-carboxylic acid 385A (32 mg, 0.083 mmol), and copper oxide (7 mg, 0.049 mmol) in di(ethylene glycol) methyl ether (2 ml) were heated at 185° C. for 21 hrs. The reaction mixture was diluted in $NH_4OH$ (aq) (25 ml), extracted with methylene chloride (75 ml), dried over sodium sulfate, and purified by silica gel flash chromatography (20% ethyl acetate in hexanes) to afford compound 385 as a yellow oil (1.6 mg, 6%). $[M+H]^+$=476.3.

EXAMPLE 386

Preparation of [4-(4-Bromo-phenylamino)-3-cyano-5-methyl-pyrrolo[1,2-b]pyridazin-6-yl]-carbamic acid 2-morpholin-4-yl-ethyl ester

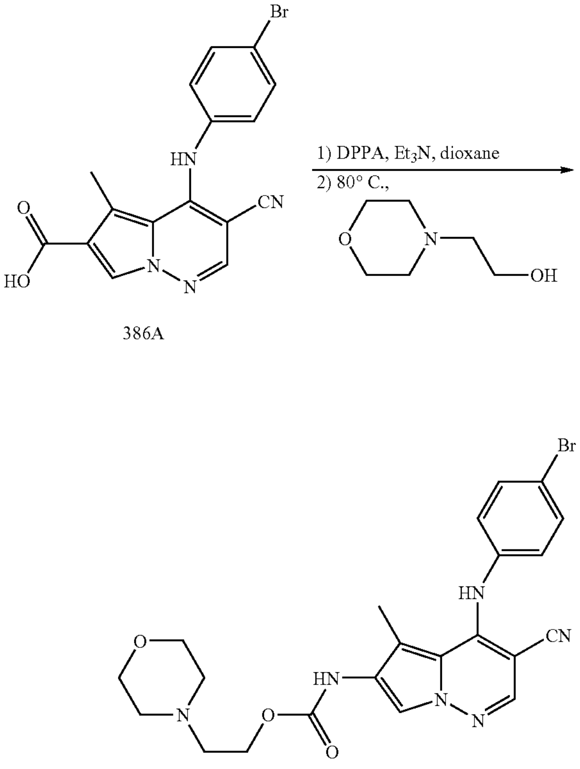

386A

386

Compound 386 was prepared from compound 386A using the same procedure used to prepare compound 380C from compound 380B (example 442). Compound 386 was isolated as a yellow solid (1.345 g, 51%). $[M+H]^+=500.9$.

EXAMPLE 387

Preparation of {3-Cyano-4-[4-(2,2-dimethyl-3-oxo-2,3-dihydro-benzofuran-7-yloxy)-phenylamino]-5-methyl-pyrrolo[1,2-b]pyridazin-6-yl}-carbamic acid 2-morpholin-4-yl-ethyl ester

387

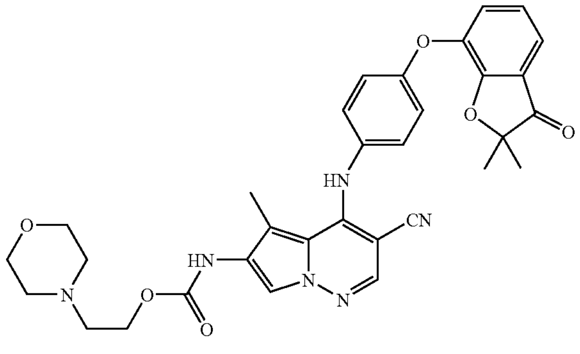

387A—Synthesis of [4-(4-Dihydroxyboron-phenylamino)-3-cyano-5-methyl-pyrrolo[1,2-b]pyridazin-6-yl]-carbamic acid 2-morpholin-4-yl-ethyl ester

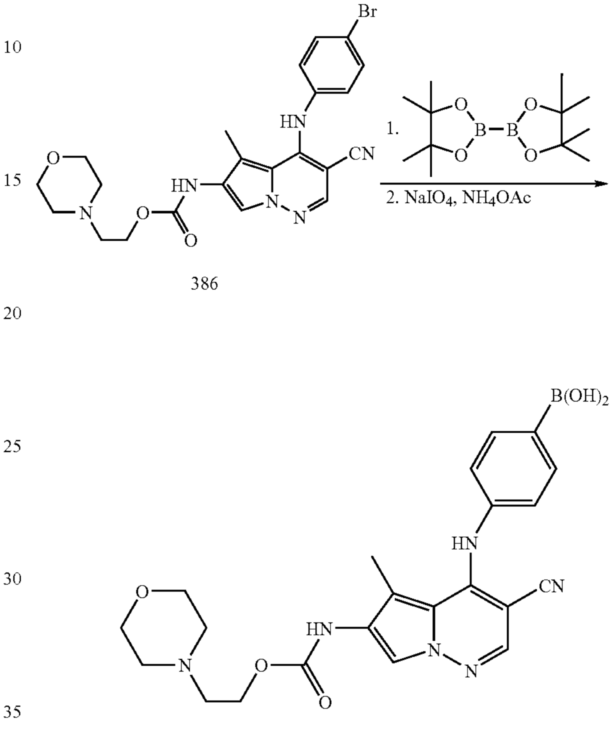

386

387A

Compound 386 (48.5 mg, 0.097 mmol), bis(pinacolato)diboron (28 mg, 0.11 mmol), [1,1'-bis(diphenylphosphino)-ferrocene]dichloropalladium (II)•$CH_2Cl_2$ (8 mg, 0.0097 mg) and potassium acetate (29 mg, 0.29 mmol) in degassed DMSO (1.0 ml) was heated at 80° C. for 12 hrs. Additional bis(pinacolato)diboron (28 mg, 0.11 mmol), [1,1'-bis(diphenylphosphino)-ferrocene]dichloropalladium (II)•$CH_2Cl_2$ (8 mg, 0.0097 mg) and potassium acetate (29 mg, 0.29 mmol) were added, and the reaction was heated at 80° C. for 4 hours. The reaction mixture was diluted with water (10 ml) and extracted with dichloromethane (2×10 ml). The pooled organic phase was washed with saturated NaCl (10 ml), dried over $Na_2SO_4$, and concentrated. The reaction mixture was dissolved in acetone/water (1:1, 1.5 ml) and treated with $NaIO_4$ (0.29 mmol, 63 mg) and $NH_4OAc$ (0.29 mmol, 23 mg). After 7 hrs, additional $NaIO_4$ (0.29 mmol, 63 mg) and $NH_4OAc$ (0.29 mmol, 23 mg) were added. After 2 hrs, the reaction mixture was diluted with water (15 ml) and extracted with 10% isopropanol/dichloromethane (3×10 ml), dried over $Na_2SO_4$, concentrated, and purified using reverse phase HPLC to isolate 387A as a yellow film (4.8 mg, 11% for two steps). $[M+H]^+=465.17$ 387—Synthesis of {3-Cyano-4-[4-(2,2-dimethyl-3-oxo-2,3-dihydro-benzofuran-7-yloxy)-phenylamino]-5-methyl-pyrrolo[1,2-b]pyridazin-6-yl}-carbamic acid 2-morpholin-4-yl-ethyl ester

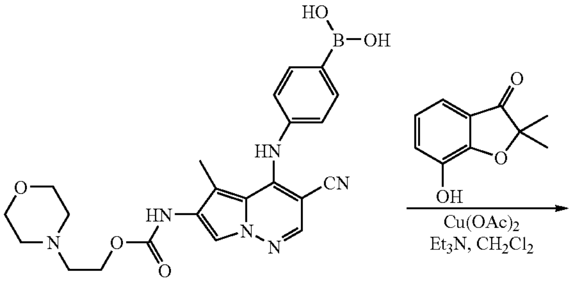

387A

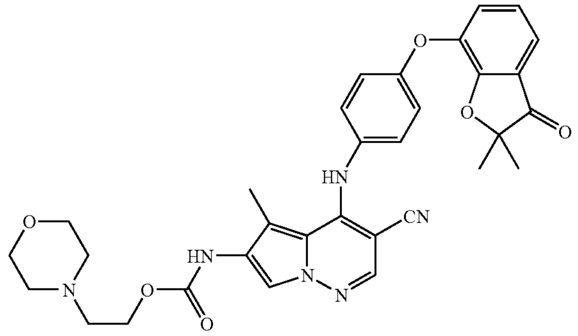

387

Compound 387A (0.010 mmol, 6.0 mg), 7-Hydroxy-2,2-dimethyl-benzofuran-3-one (0.015 mmol, 3.0 mg), copper (II) acetate (0.015 mmol, 3.0 mg), and triethylamine (10 mg) in dichloromethane (1.0 ml) were stirred at RT. After 24 hrs, the reaction mixture was concentrated, and purified using reverse phase HPLC to isolate 387 as a yellow film (0.42 mg, 7%). $[M+H]^+$=597.1

EXAMPLE 388

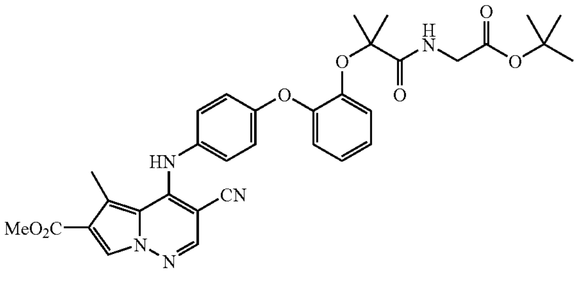

4-(4-{2-[1-(tert-Butoxycarbonylmethyl-carbamoyl)-1-methyl-ethoxy]-phenoxy}-phenylamino)-3-cyano-5-methyl-pyrrolo[1,2-b]pyridazine-6-carboxylic acid methyl ester 388A—Preparation of 2-(4-nitro-phenoxy)-phenol

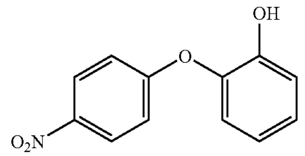

Anhydrous DMA (50 ml) was added to t-BuOK (5.46 g, 48.7 mmol) and catechol (5.00 g, 45.4 mmol) at 0° C. under argon, the mixture was heated to 120° C. over 10 min. A solution of 1-fluoro-4-nitro-benzene (6.40 g, 45.4 mmol) in anhydrous DMA (10 ml) was added dropwise over 20 min. The reaction mixture was then stirred at 130° C. for 1.5 h, cooled, and poured into 1N HCl (200 ml), extracted with EtOAc (2×50 ml). The combined extract was washed $H_2O$ (3×150 ml), brine (150 ml), dried with $Na_2SO_4$, concentrated and purified by silica gel flash column chromatography to give desired product 388A (5.56 g, 53%) as a faintly yellow solid (0%–1% ethyl acetate-$CH_2Cl_2$).

388B—Preparation of 2-methyl-2-[2-(4-nitro-phenoxy)-phenoxy]-propionic acid tert-butyl ester

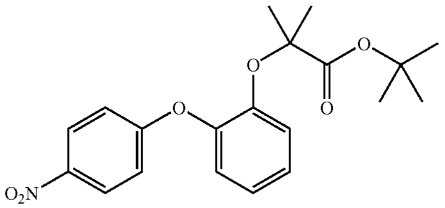

To a solution of 388A (1.70 g, 7.35 mmol) and $PPh_3$ (5.80 g, 22.1 mmol) in anhydrous THF (35 ml) was added t-butyl 2-hydroxyisobutyrate (3.83 ml, 22.1 mmol) followed by DEAD (3.47 ml, 22.1 mmol), the reaction mixture was stirred at rt for 19 h. More reagents $PPh_3$ (1.16 g, 4.41 mmol), isobutyrate (0.77 ml, 4.41 mmol) and DEAD (0.69 ml, 4.41 mmol) were added, and the mixture was stirred for another 50 h, concentrated and purified by silica gel flash column chromatography to afford 388B (2.62 g, 96%) as a light pink crystalline solid (50%–80% $CH_2Cl_2$-hexanes).

388C—Preparation of 2-[2-(4-amino-phenoxy)-phenoxy]-2-methyl-propionic acid tert-butyl ester

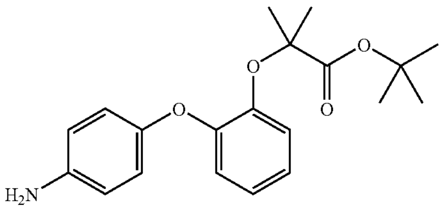

A mixture of 388B (1.20 g, 3.21 mmol), 10% Pd/C (360 mg) in MeOH (30 ml) was stirred vigorously under a balloon of $H_2$ for 1.5 h, then filtered through celite and through 0.45μ syringe filter. The filtrate was concentrated to afford 388C (1.08 g, 98%) as a faintly reddish oil. LCMS Found: $(M-tBu+2H)^+=287.9$.

388D—Preparation of 4-{4-[2-(1-tert-butoxycarbonyl-1-methyl-ethoxy)phenoxy]-phenylamino}-3-cyano-5-methyl-pyrrolo[1,2-b]pyridazine-6-carboxylicacid methyl ester

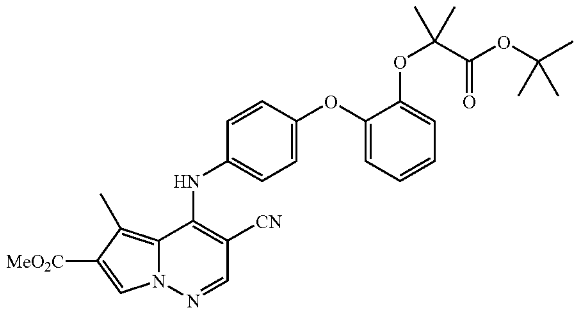

A mixture of 4-chloro-3-cyano-5-methyl-pyrrolo[1,2-b]pyridazine-6-carboxylic acid methyl ester (prepared using the procedure of Example 1D) (320 mg, 1.28 mmol), aniline 388C (440 mg, 1.28 mmol) and $K_2CO_3$ (1.77 g, 12.8 mmol) in anhydrous DMF (8 ml) was stirred at rt for 16 h. After regular workup, the residue was purified by silica gel flash column chromatography to afford 388D (651 mg, 91%) as a faintly yellow solid (0%–4% EtOAc—$CH_2Cl_2$). LCMS Found: $(M+H)^+=556.8$; $(M-tBu+2H)^+=500.9$ 388—Preparation of 4-(4-{2-[1-(tert-butoxycarbonylmethyl-carbamoyl)-1-methyl-ethoxy]-phenoxy}-phenylamino)-3-cyano-5-methyl-pyrrolo[1,2-b]pyridazine-6-carboxylic acid methyl ester

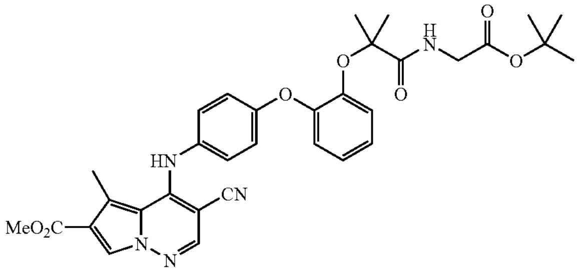

A solution of ester 388D (482 mg, 0.866 mmol) in TFA/$CH_2Cl_2$/$H_2O$ (5 ml, 48/48/4) was stirred for 1 h at rt, concentrated, the resulting residue was rotavaped with chloroform twice and $CH_2Cl_2$ once to give acid intermediate as a yellow solid. The solid was dissolved in 1,2-dichloroethane (5 ml), glycine t-butyl ester hydrochloride (203 mg, 1.21 mmol), DMAP (52.9 mg, 0.433 mmol) and DIEA (528 µl, 3.03 mmol) were added. The mixture was stirred 3 min until homogeneous, then EDC.HCl (249 mg, 1.30 mmol) was added. The reaction mixture was stirred for 2 h, concentrated, partitioned between EtOAc (50 ml) and 1N HCl (50 ml). The organic layer were washed with 1N HCl (30 ml), the combined aqueous wash layer was extracted with EtOAc (3×50 ml), the combined organic layer was washed with brine (100 ml), dried with $Na_2SO_4$ and concentrated. The residue was purified by silica gel flash column chromatography to afford a yellow crystalline solid 388 (372 mg, 70%)(10%–25% EtOAc—$CH_2Cl_2$). LCMS Found: $(M+H)^+=613.6$; $(M-tBu+2H)^+=558.2$

EXAMPLE 389

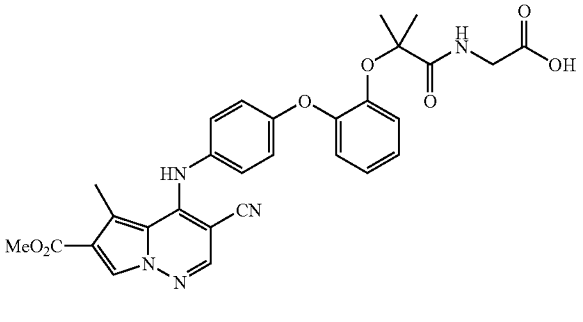

4-(4-{2-[1-(Carboxymethyl-carbamoyl)-1-methyl-ethoxy]-phenoxy}-phenylamino)-3-cyano-5-methyl-pyrrolo[1,2-b]pyridazine-6-carboxylic acid methyl ester A solution of ester 388 (292 mg, 0.476 mmol) in TFA/$CH_2Cl_2$/$H_2O$ (5 ml, 48/48/4) was stirred for 2 h at rt, concentrated and purified by silica gel flash column chromatography to afford the title compound (233 mg, 89%) as a crystalline yellow powder (4%–12% MeOH—$CH_2Cl_2$). LCMS Found: $(M+H)^+=558.0$

EXAMPLE 390

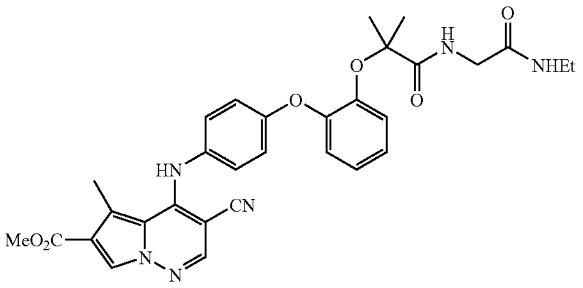

3-Cyano-4-(4-{2-[1-(ethylcarbamoylmethyl-carbamoyl)-1-methyl-ethoxy]-phenoxy}-phenylamino)-5-methyl-pyrrolo[1,2-b]pyridazine-6-carboxylic acid methyl ester To a solution of acid from Example 388 (29.2 mg, 0.0524 mmol), $EtNH_2$ (2N in THF, 31.4 µl, 0.0629 mmol) and DIEA (23.7 µl, 0.136 mmol) in dichloroethane (1.2 ml) at −10° C. was added EDC.HCl (12.1 mg, 0.0629 mmol). The reaction mixture was stirred at rt for 2 h, concentrated and purified by silica gel flash column chromatography to afford the title compound (16.2 mg, 53%) as a yellow solid (4%–10% MeOH—$CH_2Cl_2$). LCMS Found: $(M+H)^+=585.0$

EXAMPLE 391

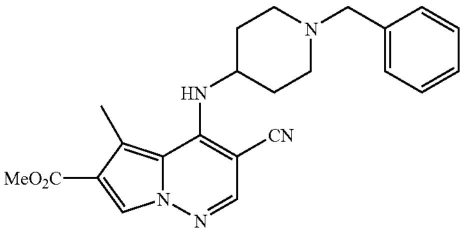

4-(1-Benzyl-piperidin-4-ylamino)-3-cyano-5-methyl-pyrrolo[1,2-b]pyridazine-6-carboxylic acid methyl ester The title compound was prepared from 4-chloro-3-cyano-5-methyl-pyrrolo[1,2-b]pyridazine-6-carboxylic acid methyl ester (prepared using the procedure of Example 1D) (65.0 mg, 0.246 mmol) and 4-amino-1-benzylpiperidine (52.6 μl, 0.258 mmol) by a route analogous to that used for the preparation of compound 388D. It (100 mg, 97%) was a white crystalline solid. LCMS Found: $(M+H)^+$=418.2

EXAMPLE 392

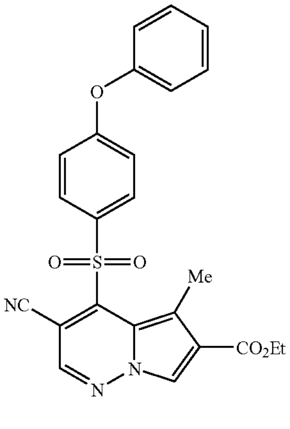

3-Cyano-5-methyl-4-(4-phenoxy-benzenesulfonyl)-pyrrolo[1,2-b]pyridazine-6-carboxylic acid ethylester 392A—Preparation of 4-phenoxybenzensulfonic acid, sodium salt

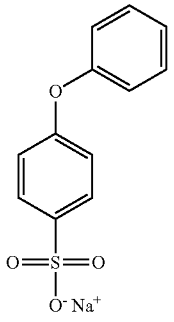

A mixture of 4-phenoxybenzensulfonyl chloride (0.46 g, 1.72 mmol), $Na_2SO_3$ (0.22 g, 1.75 mmol), $Na_2CO_3$ (0.20 g, 1.89 mmol) in water (3 ml) was heated at 100° C. for 0.5 h, small amount of precipitate was filtered off, white needles crystallized from filtrate, filtered, the solid was washed with small amount of water to give 392A (250 mg, 57%).

392B—Preparation of 3-Cyano-5-methyl-4-(4-phenoxy-benzenesulfonyl)-pyrrolo[1,2-b]pyridazine-6-carboxylic acid ethyl ester

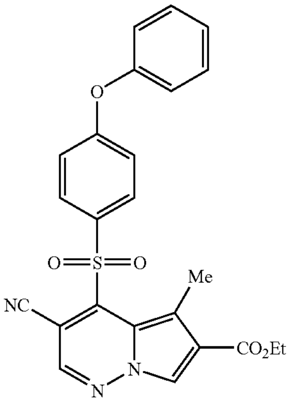

4-Chloro-3-cyano-5-methyl-pyrrolo[1,2-b]pyridazine-6-carboxylic acid ethyl ester (Example 1D) (27.0 mg, 0.10 mmol) and 392A (26.0 mg, 0.056 mmol) were dissolved in DMF (0.5 ml). The reaction mixture was stirred at rt for 2 h, evaporated, the residue was purified by silica gel flash column chromatography to afford 392B (20 mg, 43%) (0%–10% EtOAc—hexanes). LCMS Found: $(M+H)^+$=461.9

EXAMPLE 393

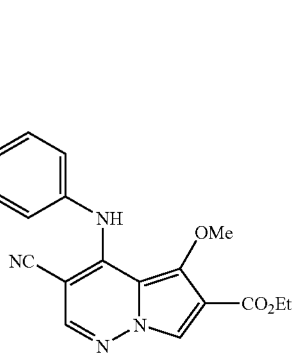

3-Cyano-5-methoxy-4-(4-phenoxy-phenylamino)-pyrrolo[1,2-b]pyridazine-6-carboxylic acid ethyl ester 393A—Preparation of (1,3-dioxo-1,3-dihydro-isoindol-2-ylamino)-acetic acid ethyl ester

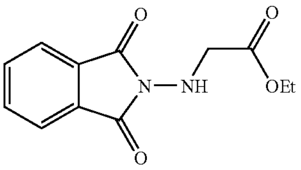

A mixture of 2-amino-isoindole-1,3-dione (5.0 g, 30.9 mmol), ethyl bromoacetate (10.32 g, 61.8 mmol), $K_2CO_3$ (8.5 g, 61.8 mmol) in DMA (38 ml) was heated at 80° C. for 7 h. After cooling to rt, the mixture was filtered, and the filtrate was diluted with EtOAc, washed with water and brine, dried and concentrated. The residue was treated with EtOAc and hexanes to give 393A (4.4 g, 57%) as yellow crystals.

393B—Preparation of 2-{[(1,3-dioxo-1,3-dihydro-isoindol-2-yl)ethoxycarbonylmethyl-amino]-methylene}-malonic acid diethyl ester

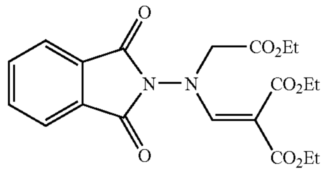

A mixture of 393A (2.4 g, 9.7 mmol) and 2-ethoxycarbonyl-but-2-enedioic acid diethyl ester (2.49 g, 10.2 mmol) was heated at 120° C. overnight. The resulting 393B was directly used in the next step without purification.

393C—Preparation of 1-(2-Ethoxycarbonyl-benzoylamino)-3-hydroxy-1H-pyrrole-2,4-dicarboxylic acid diethyl ester

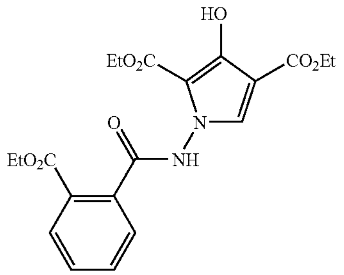

To a solution of 393B (850 mg, 2 mmol) in EtOH (5 ml) at rt was added Na metal (92 mg, 4 mmol), after stirring for 2 h, more Na metal (60 mg, 2.6 mmol) was added. The mixture was stirred at rt overnight. Saturated $NH_4Cl$ was added, the PH was adjusted to 4 with 1N $H_2SO_4$. The mixture was extracted with EtOAc, dried with $Na_2SO_4$ and concentrated to give desired product 393C.

393D—Preparation of 1-(1,3-dioxo-1,3-dihydro-isoindol-2-yl)-3-methoxy-1H-pyrrole-2,4-dicarboxylic acid diethyl ester

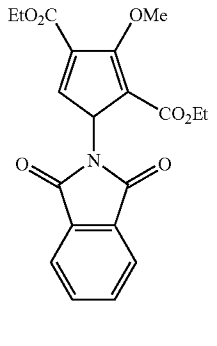

A mixture of 393C (0.84 g, 2 mmol) and $K_2CO_3$ (1.0 g, 7.25 mmol) in acetone (5 ml) was heated at 50° C. for 30 min, then cooled to rt. Dimethyl sulfate (0.29 ml, 3.0 mmol) was added, the resulting mixture was heated at 40° C. until starting material consumed, quenched with brine and extracted with EtOAc. The organic layer was dried and concentrated, the residue was purified by silica gel flash column chromatography to afford 393D (0.58 g, 74% for 3 steps from 393B) (0%–5% EtOAc—$CH_2Cl_2$).

393E—Preparation of 1-amino-3-methoxy-1H-pyrrole-2,4-dicarboxylic acid diethyl ester

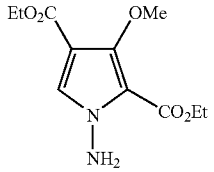

A mixture of 393D (0.58 g, 1.58 mmol) and $NH_2NH_2$ (60 μl, 2.21 mmol) in EtOH (5 ml) was stirred at rt overnight, filtered through Celite, the filtrate was concentrated and the residue was purified by silica gel flash column chromatography to give 393E (0.30 g, 75%) (0%–5% EtOAc—$CH_2Cl_2$).

393F—Preparation of 3-cyano-4-hydroxy-5-methoxy-pyrrolo[1,2-b]pyridazine-6-carboxylic acid ethyl ester

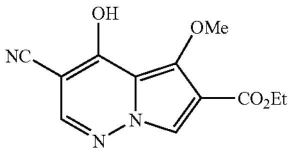

To a mixture of amine 393E (0.34 g, 1.33 mmol) in toluene (2.6 ml) was added 3,3-dimethoxy-propionitrile (0.4 ml, 2.66 mmol) and $TsOH.H_2O$ (50 mg, 0.266 mmol), the mixture was heated at 80° C. for 4 h, then DBU (0.404 mg, 2.66 mmol) was added, and heated for another 0.5 h. The residue was purified by silica gel flash column chromatography to give 0.46 g of crude 393F (10% MeOH—$CH_2Cl_2$).

393G—Preparation of 4-chloro-3-cyano-5-methoxy-pyrrolo[1,2-b]pyridazine-6-carboxylic acid ethyl ester

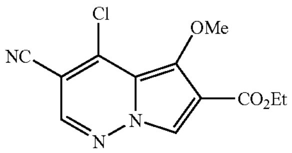

A mixture of 0.46 g of crude 393F in $POCl_3$ (5 ml) was heated at 110° C. for 1 h. Excess of $POCl_3$ was removed on a rotary evaporator, the residue was dissolved in $CH_2Cl_2$, washed with aqueous $NaHCO_3$, dried and concentrated to give 0.37 g of crude 393G which was used in next step without purification.

393—Preparation of 3-cyano-5-methoxy-4-(4-phenoxy-phenylamino)-pyrrolo[1,2-b]pyridazine-6-carboxylic acid ethyl ester

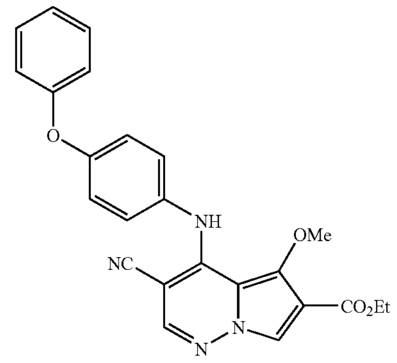

The compound 393 was prepared from 0.37 g of crude 4-chloro-3-cyano-5-methoxy-pyrrolo[1,2-b]pyridazine-6-carboxylic acid ethyl ester and 4-phenoxy-phenylamine (0.24 g, 1.30 mmol) by a route analogous to that used for the preparation of compound 388D. 0.28 g of 393 was obtained in 49% yield for 3 steps from 393F. LCMS Found: $(M+H)^+$= 429.

EXAMPLE 394

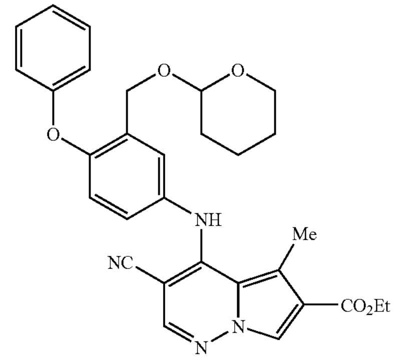

3-Cyano-5-methyl-4-[4-phenoxy-3-(tetrahydro-pyran-2-yloxymethyl)-phenylamino]-pyrrolo[1,2-b]pyridazine-6-carboxylic acid ethyl ester 394A—Preparation of (2-fluoro-5-nitro-phenyl)-methanol

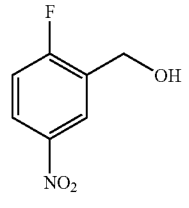

To a solution of 2-fluoro-5-nitro-benzoic acid (2.9 g, 15.7 mmol) in THF (20 ml) was slowly added 1M $BH_3$.THF (30 ml, 30 mmol) at 0° C. The reaction mixture was stirred at rt overnight, quenched carefully with MeOH until no $H_2$ evolution, evaporated and redissolved in MeOH, evaporated again to give 394A (2.7 g, 100%) as a yellow solid.

394B—Preparation of 2-(2-fluoro-5-nitro-benzyloxy)-tetrahydro-pyran

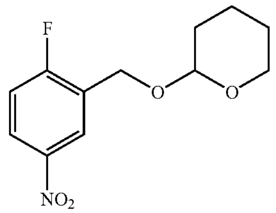

To a solution of 394A (1.8 g, 10.5 mmol) in $CH_2Cl_2$ (10 ml) was added dihydropyran (1.94 ml, 21.2 mmol) and PPTS (150 mg, 0.60 mmol). The reaction was stirred at rt overnight, washed with brine, concentrated, purified by silica gel flash column chromatography to give 394B (1.88 g, 70%) (100% $CH_2Cl_2$).

394C—Preparation of 2-(5-nitro-2-phenoxy-benzyloxy)-tetrahydro-pyran

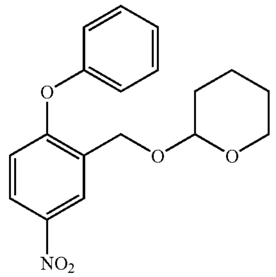

A mixture of 394B (125 mg, 0.49 mmol), phenol (55 mg, 0.59 mmol) and t-BuOK (65 mg, 0.58 mmol) in toluene (1 ml) was heated at 120° C. for 2 h. and then diluted with water, extracted with EtOAc, dried and concentrated to give 394C (145 mg, 90%).

394D—Preparation of 4-phenoxy-3-(tetrahydro-pyran-2-yloxymethyl)-phenylamine

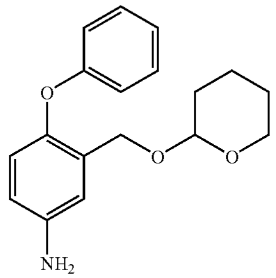

Compound 394D was prepared from 394C in quantitative yield by a route analogous to that used for the preparation of compound 388C.

394—Preparation of 3-cyano-5-methyl-4-[4-phenoxy-3-(tetrahydro-pyran-2-yloxymethyl)-phenylamino]-pyrrolo[1,2-b]pyridazine-6-carboxylic acid ethyl ester

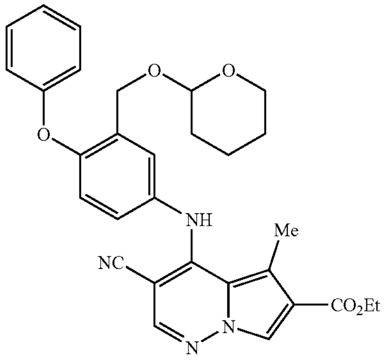

Compound 394 was prepared from 4-chloro-3-cyano-5-methyl-pyrrolo[1,2-b]pyridazine-6-carboxylic acid ethyl ester (Example 1D) (160 mg, 0.61 mmol) and 394D (180 mg, 0.60 mmol) by a route analogous to that used for the preparation of compound 388D. It has a retention time 7.69 min. (Column: HTS, 5 u, 4.6×50 mm; Gradient: 5–100% B in 8.0 min; A=0.1% TFA/$H_2O$; B=0.1% TFA/$CH_3CN$; Run time 10 min; Det: 215 nM; FR: 1.2 ml/min); MS Found: $(M-H)^+$=525.4

EXAMPLE 395

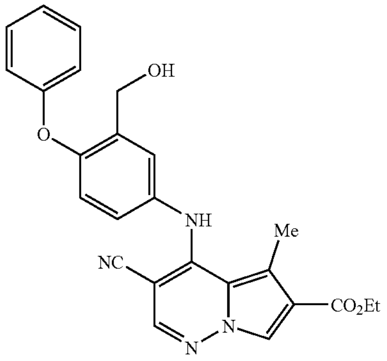

3-Cyano-4-(3-hydroxymethyl-4-phenoxy-phenylamino)-5-methyl-pyrrolo[1,2-b]pyridazine-6-carboxylic acid ethyl ester To a solution of 394 (30 mg, 0.057 mmol) in $CH_2Cl_2$ (1 ml) was added TFA (300 μl). The mixture was stirred at rt for 30 min, concentrated and purified by silica gel flash column chromatography to give the title compound (11 mg, 44%) (30% EtOAc—Hexanes). LCMS Found: $(M+H)^+$=443.2

EXAMPLE 396

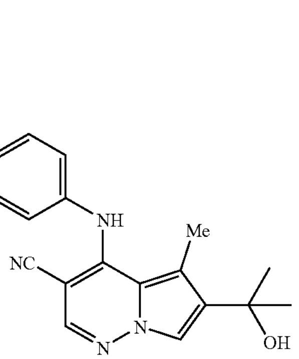

6-(1-Hydroxy-1-methyl-ethyl)-5-methyl-4-(4-phenoxy-phenylamino)-pyrrolo[1,2-b]pyridazine-3-carbonitrile 396A—Preparation of 3-cyano-5-methyl-4-(4-phenoxy-phenylamino)pyrrolo[1,2-b]pyridazine-6-carboxylic acid ethyl ester

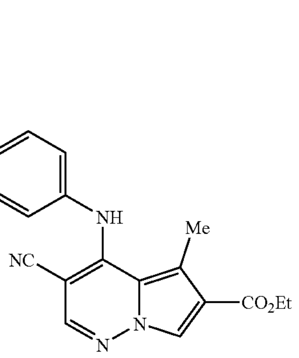

Compound 396A (1.85 g, 85%) was prepared from 4-chloro-3-cyano-5-methyl-pyrrolo[1,2-b]pyridazine-6-carboxylic acid ethyl ester (Example 1D) (1.4 g, 5.32 mmol) and 4-phenoxy-phenylamine (1.1 g, 5.94 mmol) by a route analogous to that used for the preparation of compound 388D.

396—Preparation of 6-(1-hydroxy-1-methyl-ethyl)-5-methyl-4-(4-phenoxy-phenylamino)-pyrrolo[1,2-b]pyridazine-3-carbonitrile

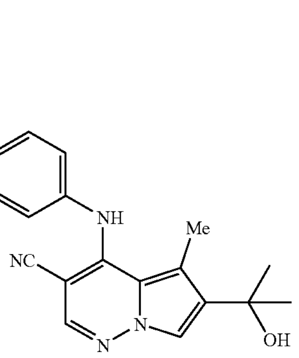

To a solution of 396A (1.85 g, 4.50 mmol) in THF (25 ml) was added a solution of 3M MeMgBr in $Et_2O$ (15 ml, 45 mmol) slowly at 0° C. The reaction mixture was warmed to rt, then heated at 50° C. for 30 min. After cooled to 0° C., the reaction was quenched with aqueous $NH_4Cl$, extracted with EtOAc, dried and concentrated to give 1.8 g of crude 396 as a yellow solid. It has a retention time 6.49 min. (Column: HTS, 5 u, 4.6×50 mm; Gradient: 5–100% B in 8.0 min; A=0.1% TFA/$H_2O$; B=0.1% TFA/$CH_3CN$; Run time 10 min; Det: 215 nM; FR: 1.2 ml/min); MS Found: $(M-H)^+$= 397.4

EXAMPLE 397

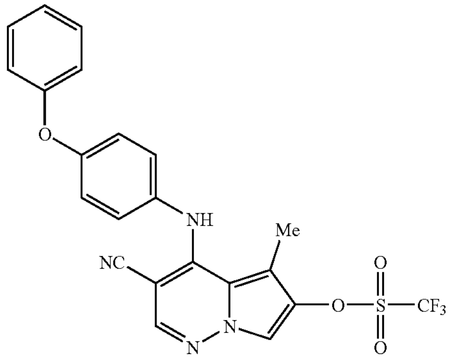

Trifluoro-methanesulfonic acid 3-cyano-5-methyl-4-(4-phenoxy-phenylamino)-pyrrolo[1,2-b]pyridazin-6-yl ester 397A—Preparation of 6-hydroxy-5-methyl-4-(4-phenoxy-phenylamino)-pyrrolo[1,2-b]pyridazine-3-carbonitrile

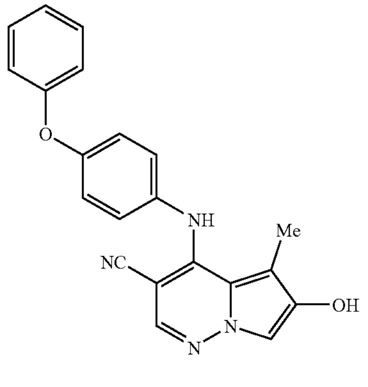

34% $H_2O_2$ (53 μl, 0.058 mmol) was added to $CH_2Cl_2$ (3 ml) at −10° C., then $BF_3.Et_2O$ (0.64 ml, 5.0 mmol) was added. After the mixture was stirred at −10° C. for 20 min, a suspension of 396 (165 mg, 0.42 mmol) in $CH_2Cl_2$ (2 ml) was added. The reaction was stirred at −10° C. for 5 min, then quenched with aq $Na_2SO_3$, extracted with EtOAc. The organic layer was dried, concentrated and purified by silica gel flash column chromatography to give 397A (125 mg, 85%) (10% EtOAc—$CH_2Cl_2$).

397—Preparation of trifluoro-methanesulfonic acid 3-cyano-5-methyl-4-(4-phenoxy-phenylamino)-pyrrolo[1,2-b]pyridazin-6-yl ester

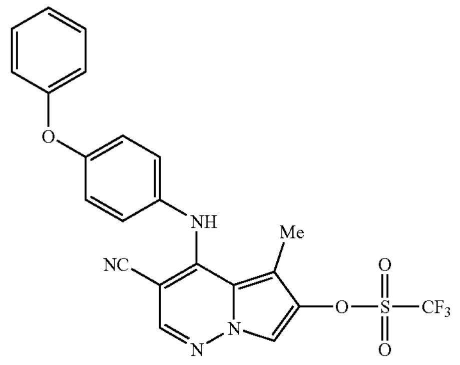

To a solution of 397A (32 mg, 0.090 mmol) in $CH_2Cl_2$ (1 ml) was added $Tf_2O$ (18 μl, 0.099 mmol) at −10° C. The reaction mixture was stirred for 5 min, diluted with EtOAc, washed with brine, dried and concentrated to give 397 (42 mg, 95%) LCMS Found: $(M+H)^+$=489.0

EXAMPLE 398

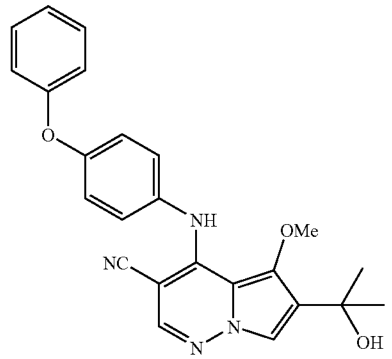

6-(1-Hydroxy-1-methyl-ethyl)-5-methoxy-4-(4-phenoxy-phenylamino)-pyrrolo[1,2-b]pyridazine-3-carbonitrile The title compound (170 mg, 98%) was prepared from 393 (180 mg, 0.42 mmol) by a route analogous to that used for the preparation of compound 396. It has a retention time of 6.49 min. (Column: HTS, 5 u, 4.6×50 mm; Gradient: 5–100% B in 8.0 min; A=0.1% TFA/$H_2O$; B=0.1% TFA/$CH_3CN$; Run time 10 min; Det: 215 nM; FR: 1.2 ml/min); MS Found: $(M-H)^+$=413.3

EXAMPLE 399

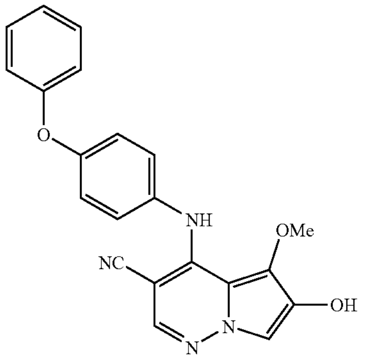

6-Hydroxy-5-methoxy-4-(4-phenoxy-phenylamino)-pyrrolo[1,2-b]pyridazine-3-carbonitrile The title compound (26 mg, 76%) was prepared from Example 398 (38 mg, 0.092 mmol) by a route analogous to that used for the preparation of compound 397A. It has a retention time of 6.08 min. (Column: HTS, 5 u, 4.6×50 mm; Gradient: 5–100% B in 8.0 min; A=0.1% TFA/$H_2O$; B=0.1% TFA/$CH_3CN$; Run time 10 min; Det: 215 nM; FR: 1.2 ml/min); MS Found: $(M+H)^+$=373.2

EXAMPLE 400

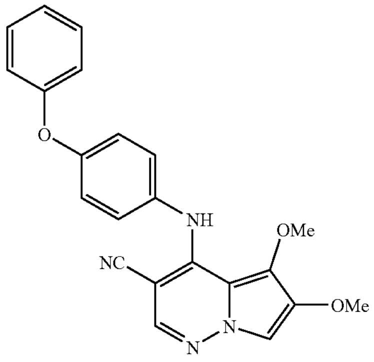

5,6-Dimethoxy-4-(4-phenoxy-phenylamino)-pyrrolo [1,2-b]pyridazine-3-carbonitrile A mixture of compound from Example 399 (14 mg, 0.038 mmol), dimethyl sulfate (4 μl, 0.042 mmol), $K_2CO_3$ (14 mg, 0.101 mmol) in acetone (0.5 ml) was stirred at rt overnight. After regular workup, the title compound (13 mg, 88%) was obtained after silica gel flash column chromatography (100% $CH_2Cl_2$). LCMS Found: $(M+H)^+$=387.1

EXAMPLE 401

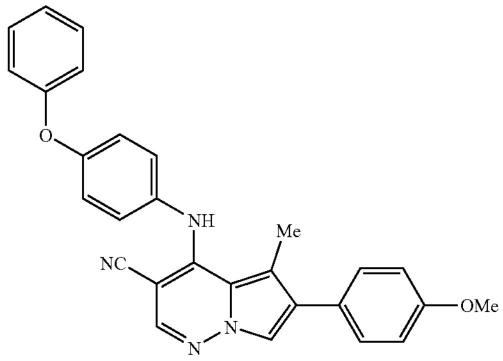

6-(4-Methoxy-phenyl)-5-methyl-4-(4-phenoxy-phenylamino)-pyrrolo[1,2-b]pyridazine-3-carbonitrile A mixture of Example 397 (24 mg, 0.049 mmol), 4-methoxybenzeneboronic acid (11 mg, 0.072 mmol), $Pd(OAc)_2$ (1.0 mg, 0.0045 mmol), 2-(dicyclohexylphosphino) biphenyl (5.0 mg, 0.014 mmol) and $K_3PO_4$ (20 mg, 0.10 mmol) in toluene (0.5 ml) was degassed with argon. The mixture was heated at 90° C. for 20 min, then directly purified by silica gel flash column chromatography to give title compound (20 mg, 92%) (10% EtOAc—hexanes). LCMS Found: $(M+H)^+$=447.2

EXAMPLE 402

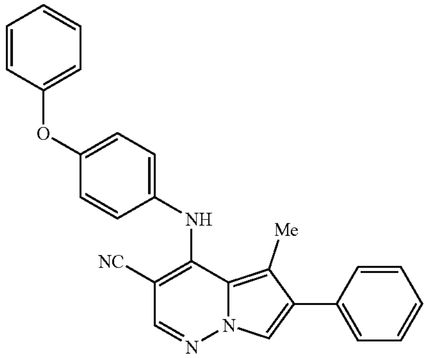

5-Methyl-4-(4-phenoxy-phenylamino)-6-phenyl-pyrrolo[1,2-b]pyridazine-3-carbonitrile The title compound was prepared from Example 397 (30 mg, 0.062) and benzeneboronic acid (12 mg, 0.098 mmol) by a route analogous to that used for the preparation of Example 401. LCMS Found: $(M+H)^+$=417.2

EXAMPLE 403

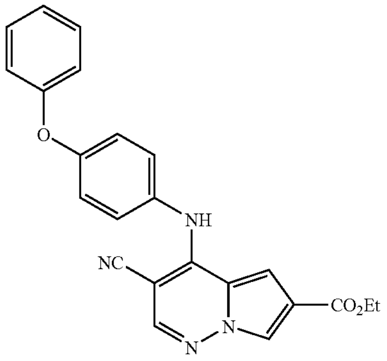

3-Cyano-4-(4-phenoxy-phenylamino)-pyrrolo[1,2-b]pyridazine-6-carboxylic acid ethyl ester

403A—Preparation of 2,4-dicarboethoxypyrrole

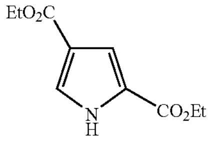

To a stirred solution of ethyl isocyanoacetate (0.02 mol, 2.3 mL) and DBU (3.0 g, 0.02 mol) in THF (30 mL) was added a solution of formaldehyde (0.6M THF solution, 16.6 mL, 0.01 mole) at 45–50° C. for a period of 15 min. After stirring for 5 hr at the same temperature, the reaction mixture was neutralized with HOAc and the solvents were removed under reduced pressure. The resulting oil was partitioned between satd. aq. $NaHCO_3$ and EtOAc. The EtOAc layer was separated, dried with $Na_2SO_4$ and concentrated in vacuo to obtain a viscous oil which was chromatographed on silica (20% EtOAc—hexanes) to give 403A (0.80 g, 38%). MS Found: $(M+H)^+$=212.0;

$^1H$ NMR ($CDCl_3$) δ 9.8 (br, 1H), 7.56 (dd, $J_1$=3.2 Hz, $J_2$=1.5 Hz, 1H), 7. (dd, $J_1$=3.2 Hz, $J_2$=1.5 Hz, 1H), 4.3 (m, 4H), 1.3 (m, 6H).

403B—Preparation of 3-cyano-4-hydroxy-pyrrolo-[1,2-b]pyridazine-6-carboxylic acid ethyl ester

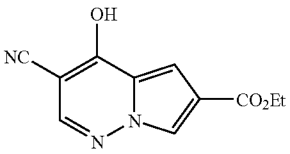

Pyrrole 403A (211 mg, 1.0 mmol) in DMF (1 mL) was slowly added to a suspension of NaH (60% suspension in mineral oil, 40 mg, 1.0 mmol,) in DMF (1 mL) at 0° C. under $N_2$. The resulting mixture was stirred at 0° C. for 15 min. and allowed to warm to RT. After stirring at RT for another 15 min, the reaction mixture was cooled to 0° C. and O-mesitylenesulfonylhydroxylamine (C. Johnson, et al, *J. Org. Chem.*, 1974, 39, 2458) (225 mg, 1.0 mmol) was added. The resulting mixture was allowed warm to RT and stirred for 14 hr and poured into satd. aq. $NH_4Cl$ solution (20 mL). The organic materials were then extracted with EtOAc (2×10 mL), dried with $Na_2SO_4$ and concentrated in vacuo to obtain an approximately 1:1 mixture of starting material and aminopyrrole which was dried in vacuo for 12 h and directly used in the next step.

The crude material obtained from the above reaction (200 mg), diethoxypropionitrile (0.2 mL) and TsOH (38 mg) in toluene (10 mL) were heated at 100° C. until the ninhydrin positive starting material almost disappeared on TLC. The reaction mixture was then allowed to cool to RT and DBU (0.04 ml, 3.0 mmol,) was added and heated at 80° C. for 6 h. Reaction mixture was then allowed to cool to RT and concentrated in vacuo to obtain a viscous oil which was redissolved in 5% $MeOH/CH_2Cl_2$ (10 mL) and washed with water (2×10 mL). The organic layer was separated, dried with $Na_2SO_4$ and concentrated in vacuo to obtain a dark brown residue which was chromatographed on silica. After removing the low polar impurities (10–20% EtOAc—hexanes), partially pure product 403B (99 mg, 43%) was obtained by eluting with 10% MeOH/EtOAc. MS Found: $(M+H)^+$=232.1

403C. Preparation of 4-chloro-3-cyano-pyrrolo[1,2-b]pyridazine-6-carboxylic acid ethyl ester

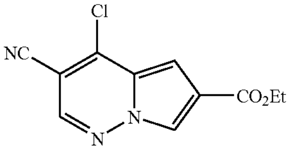

Compound 403C was prepared from 403B by a route analogous to that used for the preparation of 393G.

403—Preparation of 3-cyano-4-(4-phenoxy-phenylamino)-pyrrolo[1,2-b]pyridazine-6-carboxylic acid ethyl ester

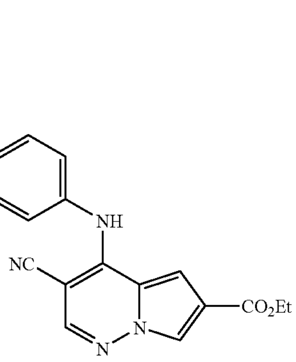

Compound 403 was prepared from 403C and 4-phenoxy-phenylamine by a route analogous to that used for the preparation of 388D. Yield: 53%. MS Found: $(M+H)^+$=399.2; $^1H$ NMR ($CDCl_3$) δ 8.1 and 7.9 (s, 1H each), 7.3 (m, 2H), 7.26 (m, 2H), 7.2 (m, 2H), 7.15 (m, 4H), 6.2 (s, 1H), 4.25 (q, J=7.2 Hz, 2H), 1.32 (t, J=7.2 Hz, 3H).

EXAMPLES 404–405

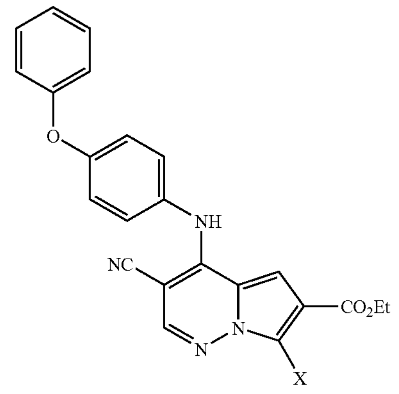

404 X = Br
405 X = Cl 404) 7-Bromo-3-cyano-4-(4-phenoxy-phenylamino)-pyrrolo[1,2-b]pyridazine-6-carboxylic acid ethyl ester or 405) 7-Chloro-3-cyano-4-(4-phenoxy-phenylamino)-pyrrolo[1,2-b]pyridazine-6-carboxylic acid ethyl ester General procedure for the preparation of 5-halo-2,4-dicarboethoxypyrrole

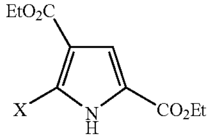

404 A: X = Br
405 A: X = Cl

To a solution of 2,4-dicarboethoxypyrrole 403A (211 mg, 1 mmol) in HOAc (2 mL) N-halosuccinamide (1.5 mmol) was added followed by $CF_3SO_3H$ (0.1 mL). The resulting mixture was stirred at RT for 4 h, then poured into water. The product was extracted with $CH_2Cl_2$ (2×10 mL). $CH_2Cl_2$ extracts were combined and washed with saturated aq. $NaHCO_3$ (3×10 mL), saturated $Na_2S_2O_3$ and water. The $CH_2Cl_2$ layer was dried with $Na_2SO_4$ and concentrated in vacuo. The resulting residue was purified on silica (10–15% EtOAc—hexanes)

404A—5-bromo-2,4-dicarboethoxypyrrole

Yield: 66%; $^1$H NMR ($CDCl_3$) δ 10.1 (br, 1H), 7.3 (s, 1H), 4.32 and 4.39 (q, J=7.1 Hz, 2H each), 1.38 (m, 6H)

405A—5-chloro-2,4-dicarboethoxypyrrole

Yield: 71%; $^1$H NMR ($CDCl_3$) δ 9.7 (br s, 1H), 7.28 (s, 1H), 4.3 (m, 4H), 1.15 and 1.27 (t, J=7.1 and 7.05, 3H each)

Preparation of 3-cyano-7-halo-4-hydroxy-pyrrolo-[1,2-b]pyridazine-6-carboxylic acid ethyl ester

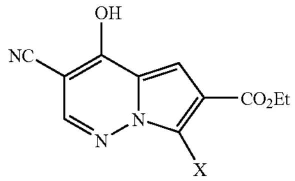

404B: X = Br
405B: X = Cl

Compounds 404B and 405B were prepared respectively from 404A and 405A by a route analogous to that used for the preparation of 403B.

404B—7-Bromo-3-cyano-4-hydroxy-pyrrolo-[1,2-b]pyridazine-6-carboxylic acid ethyl ester Yield: 36%. MS Found: $(M+H)^+$=309.2

405B—7-Chloro-3-cyano-4-hydroxy-pyrrolo-[1,2-b]pyridazine-6-carboxylic acid ethyl ester Yield: 31%. MS Found: $(M+H)^+$=266.1

Preparation of 4-chloro-3-cyano-7-halo-pyrrolo-[1,2-b]pyridazine-6-carboxylic acid ethyl ester

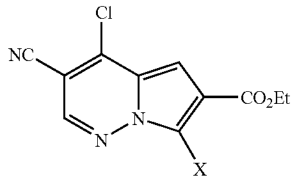

404C: X = Br
405C: X = Cl

Compounds 404C and 405C were prepared respectively from 404B and 405B by a route analogous to that used for the preparation of 393G.

Preparation of 7-halo-3-cyano-4-(4-phenoxy-phenylamino)-pyrrolo[1,2-b]pyridazine-6-carboxylic acid ethyl ester

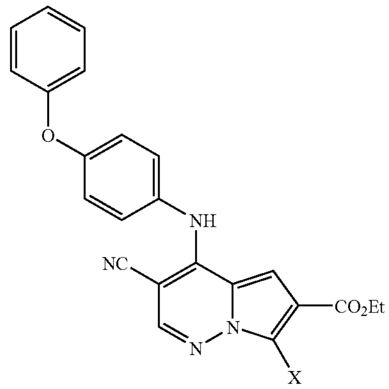

404: X = Br
405: X = Cl

Compounds 404 and 405 were prepared respectively from 404C and 405C with 4-phenoxy-phenylamine by a route analogous to that used for the preparation of 388D.

404—7-Bromo-3-cyano-4-(4-phenoxy-phenylamino0-pyrrolo[1,2-b]pyridazine-6-carboxylic acid ethyl ester Yield: 47%. MS Found: $(M+H)^+=477.1$; $^1H$ NMR ($CDCl_3$) δ 8.07 (s, 1H), 7.4 (m, 2H), 7.3 (m, 2H), 7.18 (m, 2H), 7.1 (m, 4H), 6.2 (s, 1H), 4.3 (q, J=7.1 Hz, 2H), 1.36 (t, J=7.1 Hz, 3H)

405—7-Chloro-3-cyano-4-(4-phenoxy-phenylamino0-pyrrolo[1,2-b]pyridazine-6-carboxylic acid ethyl ester Yield: 51%. MS Found: $(M+H)^+=432.1$; $^1H$ NMR ($CDCl_3$) δ 8.07 (s, 1H), 7.4 (m, 2H), 7.32 (m, 2H), 7.18 (m, 2H), 7.1 (m, 4H), 6.2 (s, 1H), 4.3 (q, J=7.0 Hz, 2H), 1.35 (t, J=7.2 Hz, 3H)

EXAMPLE 406

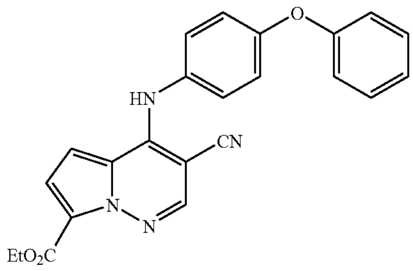

3-Cyano-4-(4-phenoxy-phenylamino)-pyrrolo[1,2-b]pyridazine-7-carboxylic acid ethyl ester 406A—Preparation of 5-formyl-1H-pyrrole-2-carboxylic acid ethyl ester

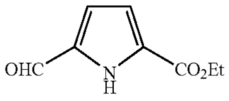

$POCl_3$ (7.8 ml, 83.7 mmol) was slowly added to DMF (7.0 ml, 90.4 mmol) at 0° C. under argon. After addition, the mixture was stirred at rt for 5 min, then anhydrous $CH_2Cl_2$ (25 ml) was added. To the resulting mixture at 0° C. was added a solution of 1H-pyrrole-2-carboxylic acid ethyl ester (10.53 g, 75.64 mmol) in $CH_2Cl_2$ (25 ml). The reaction mixture was stirred for 10 min, then refluxed for 15 min, after cooling down to rt, it was poured into ice-water, saturated $Na_2CO_3$ was added until no more bubbles forming. The mixture was extracted with EtOAc (3×150 ml), the combined EtOAc layer was washed with saturated $NaHCO_3$ (2×100 ml), saturated $Na_2CO_3$ (1×100 ml) and brine (1×150 ml), dried over $MgSO_4$, concentrated to give pure 19A (8.0 g, 63.3%) as a brownish solid.

406B—Preparation of 1H-pyrrole-2,5-dicarboxylic acid diethyl ester

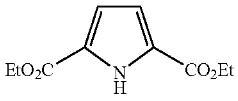

To a mixture of 406A (167 mg, 1.0 mmol), KCN (325.6 mg, 5.0 mmol) in anhydrous EtOH (20 ml) was added AcOH (85.9 μl, 1.5 mmol) followed by activated $MnO_2$ (1.643 g, 20 mmol). The reaction was stirred overnight. After workup, the residue was purified by silica gel flash column chromatography to give 406B (162 mg, 77%) as a pinkish solid (25% EtOAc—hexanes).

406C—Preparation of 1-amino-1H-pyrrole-2,5-dicarboxylic acid diethyl ester

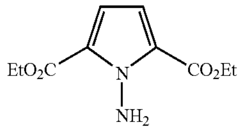

NaH (60% in mineral oil, 154.3 mg, 3.86 mmol) was rinsed with hexanes (5 ml), then anhydrous DMF (10 ml) was added, to this suspension 406B (0.68 g, 3.22 mmol) was added portionwise at 0° C., and the mixture was stirred for 1 h from 0° C. to rt. O-(2,4-dinitro-phenyl)-hydroxylamine (705.6 mg, 3.54 mmol) was added in two portions at 0° C., the reaction mixture was stirred at rt overnight. Water (50 ml) was added, the mixture was extracted with EtOAc (3×25 ml), the combined organic layer was washed with water (4×20 ml) and brine (1×20 ml), dried and concentrated. The residue was purified by silica gel flash column chromatography to give 406C (480 mg, 66%) as a yellow solid (25% EtOAc—hexanes).

406D—Preparation of 1-(dimethylamino-methyleneamino)-1H-pyrrole-2,5-dicarboxylic acid diethyl ester

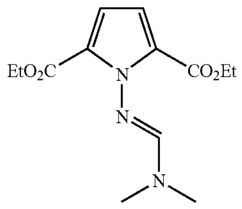

A mixture of 406C (482 mg, 2.13 mmol) and dimethoxymethyl-dimethyl-amine (1.5 ml) in anhydrous DMF (5 ml) was heated at 105° C. overnight. After the solvent was removed, the residue was purified by silica gel flash column chromatography to give 406D (546 mg, 91%) as pink crystals (25% EtOAc—hexanes). MS Found: $(M+H)^+=282.1$ 406E—Preparation of 3-cyano-4-hydroxy-pyrrolo[1,2-b]pyridazine-7-carboxylic acid ethyl ester

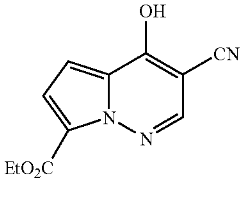

To a solution of n-BuLi (1.6 M in hexanes) (290 μl, 0.465 mmol) in THF (1 ml) was added a solution of $CH_3CN$ (19.1 mg, 0.465 mmol) in THF (2 ml) dropwise at 0° C. The mixture was stirred for 20 min, then a solution of 406D (62 mg, 0.221 mmol) in THF (5 ml) was added. After the mixture was stirred for 40 min, the reaction temperature was lowered to −78° C., AcOH (38 μl, 0.663 mmol) was added. The reaction mixture was then stirred at rt overnight. Solvent was removed, 406E (26 mg, 50%) was obtained as a yellowish solid after preparative HPLC purification. LCMS Found: $(M+H)^+=232$.

406—Preparation of 3-cyano-4-(4-phenoxy-phenylamino)-pyrrolo[1,2-b]pyridazine-7-carboxylic acid ethyl ester

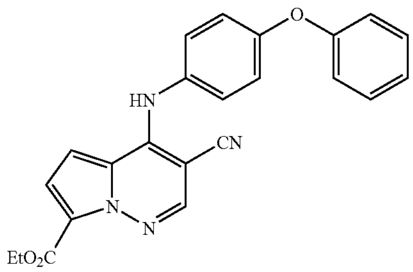

Compound 406E (110 mg, 0.476 mmol) was heated in $POCl_3$ (1 ml) at 83–100° C. for 2 h. Excess $POCl_3$ was removed on a rotary evaporator, and the residue was stripped with $CH_2Cl_2$ (2 ml). To the solid residue was added DMF (5 ml), $K_2CO_3$ (690 mg, 5 mmol) and 4-phenoxy-phenylamine (353 mg, 1.91 mmol) at 0° C. The reaction mixture was degassed and stirred at rt overnight. Solid was filtered off and the filtrate was concentrated, the residue was purified by silica gel flash column chromatography to give the 406 (147 mg, 78%) as a yellow solid (25% EtOAc—Hexanes). LCMS Found: $(M+H)^+=398.6$

EXAMPLE 407

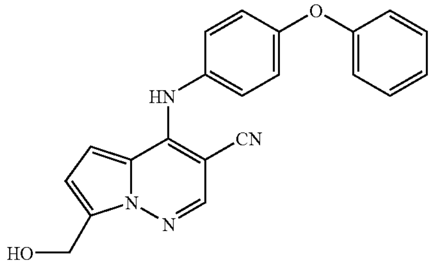

7-Hydroxymethyl-4-(4-phenoxy-phenylamino)-pyrrolo[1,2-b]pyridazine-3-carbonitrile To a solution of 406 (39.8 mg, 0.1 mmol) in THF (2 ml) was added DIBAL-H (1.0 M in $CH_2Cl_2$, 0.2 ml, 0.2 mmol) at −78° C. The reaction mixture was stirred at this temperature for 6 h, then at 0° C. for 2 h, quenched with water (0.1 ml). The solid was filtered off, and the filtrate was concentrated. The residue was purified by preparative TLC to give the title compound (22.8 mg, 64%) as a brown solid (2.5% MeOH—$CH_2Cl_2$). LCMS Found: $(M+H)^+=357$.

EXAMPLE 408

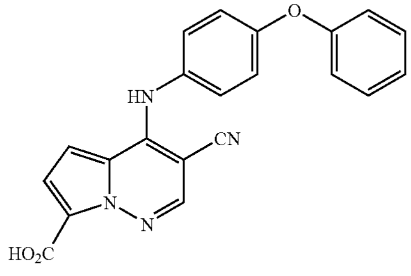

3-Cyano-4-(4-phenoxy-phenylamino)-pyrrolo[1,2-b]pyridazine-7-carboxylic acid

A mixture of 406 (15.6 mg, 0.039 mmol) and 1N NaOH (150 μl, 0.15 mmol) in EtOH (5 ml) was stirred at 50–70° C. for 15 h. 1N HCl (150 μl, 0.15 mmol) was added, solvent was removed, and the residue was purified by preparative TLC to give the title compound (14.1 mg, 98%) as a tan solid. LCMS Found: $(M+H)^+=371.1$

EXAMPLE 409

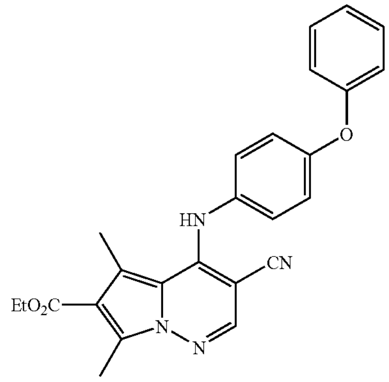

3-Cyano-5,7-dimethyl-4-(4-phenoxy-phenylamino)-pyrrolo[1,2-b]pyridazine-6-carboxylic acid ethyl ester 409A—Preparation of 1-amino-3,5-dimethyl-1H-pyrrole-2,4-dicarboxylic acid diethyl ester

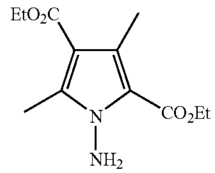

Compound 409A was prepared from 3,5-dimethyl-1H-pyrrole-2,4-dicarboxylic acid diethyl ester by a route analogous to that used for the preparation of compound 406C.

409B—Preparation of 1-(dimethylamino-methyleneamino)-3,5-dimethyl-1H-pyrrole-2,4-dicarboxylic acid diethyl ester

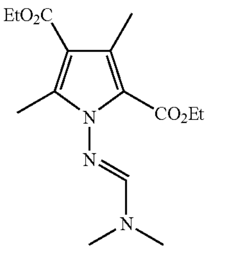

Compound 409B was prepared from 409A by a route analogous to that used for the preparation of compound 406D.

409C—Preparation of 3-cyano-4-hydroxy-5,7-dimethyl-pyrrolo[1,2-b]pyridazine-6-carboxylic acid ethyl ester

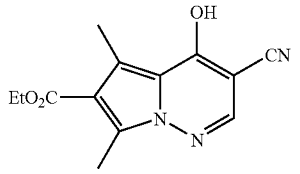

Compound 409C was prepared from 409B by a route analogous to that used for the preparation of compound 406E.

409—Preparation of 3-cyano-5,7-dimethyl-4-(4-phenoxy-phenylamino)-pyrrolo[1,2-b]pyridazine-6-carboxylic acid ethyl ester

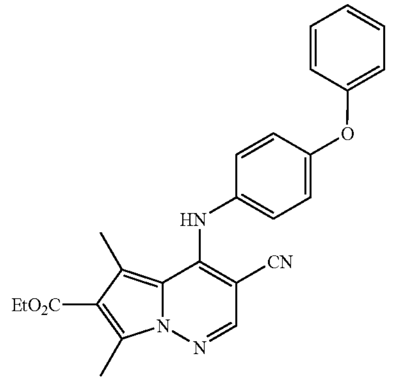

Compound 409D was prepared from 409B by a route analogous to that used for the preparation of compound 406. MS Found: $(M+H)^+=427.1$

EXAMPLE 410

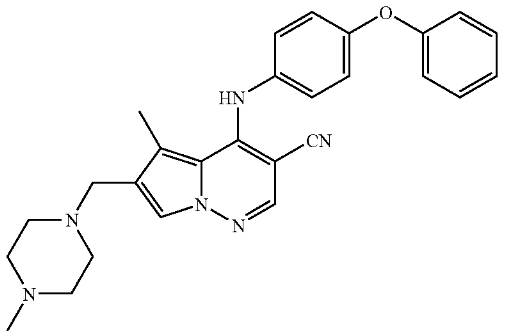

5-Methyl-6-(4-methyl-piperazin-1-ylmethyl)-4-(4-phenoxy-phenylamino)-pyrrolo[1,2-b]pyridazine-3-carbonitrile A mixture of 6-formyl-5-methyl-4-(4-phenoxy-phenylamino)-pyrrolo[1,2-b]pyridazine-3-carbonitrile (Example 8) (27 mg, 0.073 mmol) and 1-methyl-piperazine (8.1 μl, 0.073 mmol) in $CH_2Cl_2$ (2.5 ml) was stirred for 48 h, then treated with $NaBH(OAc)_3$ (46.4 mg, 0.2 mmol) and stirred for 24 h. The mixture was diluted with $CHCl_3$, washed with saturated $NaHCO_3$ and $H_2O$, dried with $Na_2SO_4$. Concentrated in vacuo and purified by prep. TLC to give the title compound (22 mg, 66%) (20% MeOH—$CHCl_3$). It has a retention time of 4.90 min (standard LCl method, 8 min run). LCMS Found: $(M+H)^+=453.1$

EXAMPLE 411

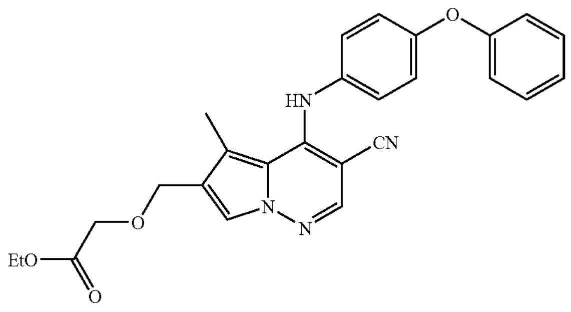

[3-Cyano-5-methyl-4-(4-phenoxy-phenylamino)-pyrrolo[1,2-b]pyridazin-6-ylmethoxy]-acetic acid ethylester A mixture of 6-hydroxymethyl-5-methyl-4-(4-phenoxy-phenylamino)-pyrrolo[1,2-b]pyridazine-3-carbonitrile (Example 3B) (36 mg, 0.097 mmol), bromo-acetic acid ethyl ester (24 mg, 0.146 mmol) and $K_2CO_3$ (67 mg, 0.48 mmol) in DMF (0.6 ml) was heated at 80° C. for 45 min, then diluted with $CHCl_3$ (50 ml), washed with $H_2O$ (2×20 ml), dried with $Na_2SO_4$. Concentrated in vacuo and purified by prep. TLC to give the title compound (12.2 mg, 28%) (50% EtOAc—hexanes). It has a retention time of 6.62 min (standard LCl method, 8 min run). MS Found: $(M+H)^+=457.1$

EXAMPLE 412

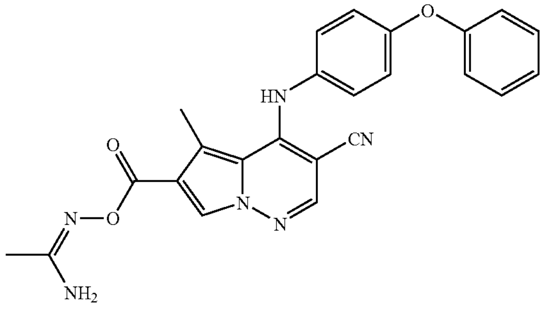

412A—Preparation of N-hydroxyacetamidine

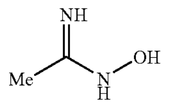

To a solution of acetonitrile (1 ml, 19 mmol) in ethanol (6 ml) was added hydroxylamine (50 wt % in $H_2O$, 5.0 ml, 76 mmol). The solution was heated to reflux for 1.5 h. Concentration of the reaction mixture in vacuo yielded 412A (1.4 g, 100%) as a white solid. $^1$HNMR (DMSO, 400 MHz): δ 3.32 (s, 3H), 5.33 (bs, 2H), 8.64 (s, 1H);

412B—Preparation of 3-cyano-5-methyl-4-(4-phenoxy-phenylamino)-pyrrolo[1,2-b]pyridazine-6-carbonyl chloride

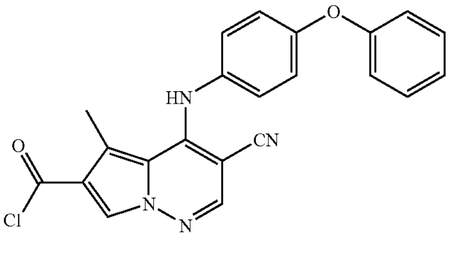

To a slurry of Example 9 (83 mg, 0.21 mmol) in 3 mL of dichloromethane at 0° C. was added oxalyl chloride (28.2 μL, 0.32 mmol) followed by 5 μL of DMF. The reaction was warmed to room temperature and then cooled to 0° C. once the reaction became homogenous. After 20 min, another 9 μL (0.5 eq) of oxalyl chloride was added. Thin-layer chromatography analysis indicated that most of the starting carboxylic acid was consumed. The reaction was concentrated in vacuo with toluene (2×5 mL), dried under vacuum and then used without further purification.

412—Preparation of 3-cyano-5-methyl-4-(4-phenoxy-phenylamino)-pyrrolo[1,2-b]pyridazine-6-carbonyl-N-hydroxylacetamidine

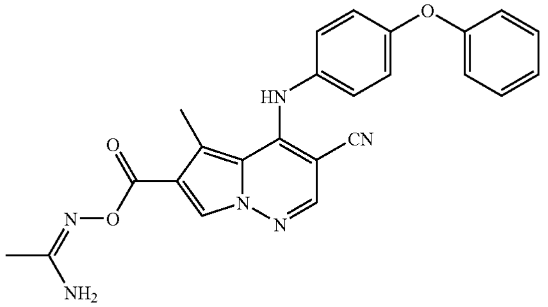

A solution of Example 412B (84.5 mg, 0.21 mmol) in $CH_2Cl_2$ (2.5 ml) was added to a solution 412A (15.5 mg, 0.21 mmol) and Hunig's base (57 mg, 0.44 mmol) in $CH_2Cl_2$ (2 ml) at 0° C. TLC shows that reaction completed immediately. The reaction mixture was diluted with $CHCl_3$ (50 ml), washed with saturated $NaHCO_3$, dried with $Na_2SO_4$. Concentrated in vacuo and purified by prep. TLC to give the title compound (40 mg, 43%) as pale yellow flakes (10% MeOH—$CHCl_3$). It has a retention time of 5.92 min (standard LCl method, 8 min run). MS Found: $(M+H)^+$= 441.0

EXAMPLE 413

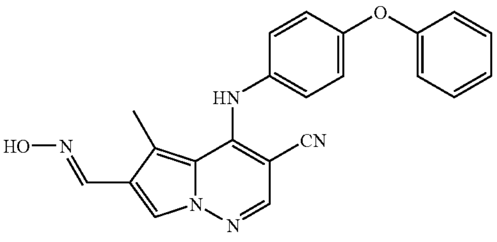

6-(Hydroxyimino-methyl)-5-methyl-4-(4-phenoxy-phenylamino)-pyrrolo[1,2-b]pyridazine-3-carbonitrile To a slurry of 6-formyl-5-methyl-4-(4-phenoxy-phenylamino)-pyrrolo[1,2-b]pyridazine-3-carbonitrile (Example 8) (37 mg, 0.1 mmol) in MeOH (1 ml) was added $H_2NOH$ (50% wt. in $H_2O$, 14 μl 0.2 mmol) at rt. The heterogeneous mixture was stirred overnight, then diluted with $H_2O$ (5 ml) and filtered, the solid was dissolved in MeOH, which was concentrated to give title compound (30 mg, 78%) as a yellow powder. It has a retention time of 6.18 min (standard LCl method, 8 min run). MS Found: $(M+H)^+$= 384.2

EXAMPLE 414

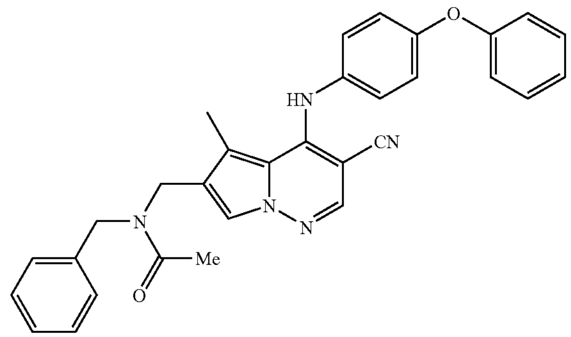

N-Benzyl-N-[3-cyano-5-methyl-4-(4-phenoxy-phenylamino)-pyrrolo[1,2-b]pyridazin-6-ylmethyl]-acetamide 414A—Preparation of 6-(benzylamino-methyl)-5-methyl-4-(4-phenoxy-phenylamino)-pyrrolo[1,2-b]pyridazine-3-carbonitrile

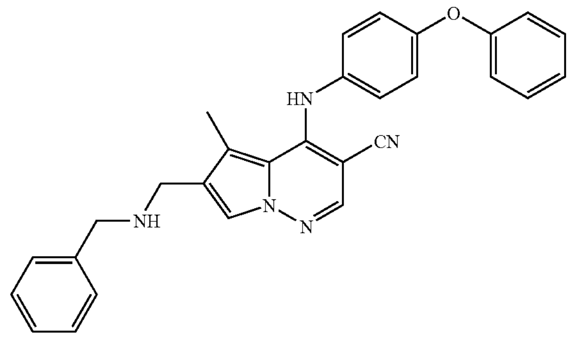

Benzylamine (10 μl, 0.09 mmol) was added to a solution of 6-formyl-5-methyl-4-(4-phenoxy-phenylamino)-pyrrolo[1,2-b]pyridazine-3-carbonitrile (Example 8) (32 mg, 0.087 mmol) in $CH_2Cl_2$/DMF (10/1) (2.2 ml). The mixture was stirred overnight, then treated with $NaBH(OAc)_3$ (55 mg, 0.26 mmol) and stirred overnight again. Diluted with $CHCl_3$, washed with saturated $NaHCO_3$ and $H_2O$, dried with $Na_2SO_4$. Concentrated in vacuo and purified by prep. TLC to give the title compound (28 mg, 70%) as yellow-green oil (10% MeOH—$CHCl_3$). It has a retention time of 6.46 min (standard LCl method, 8 min run). LCMS Found: $(M+H)^+$=460.20

414—Preparation of N-benzyl-N-[3-cyano-5-methyl-4-(4-phenoxyphenylamino)-pyrrolo[1,2-b]pyridazin-6-ylmethyl]-acetamide

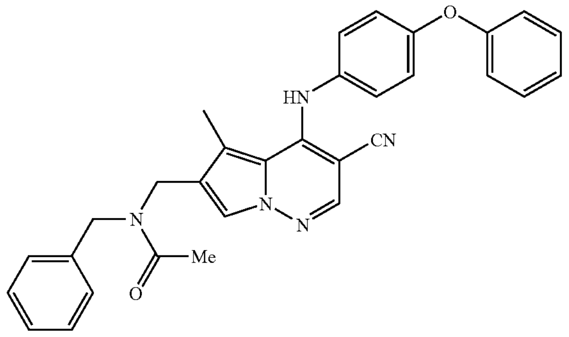

To a solution of 414A (28 mg, 0.06 mmol) and $Et_3N$ (17 μl, 0.12 mmol) in $CH_2Cl_2$ (2 ml) was added $Ac_2O$ (11 μl, 0.12 mmol), reaction completed immediately. After regular workup, the residue was purified by prep. TLC to give the 414 (25 mg, 83%) as light yellow powder (2% MeOH—$CHCl_3$). It has a retention time of 7.23 min (standard LCl method, 8 min run). MS Found: $(M+H)^+$=502.0

EXAMPLE 415

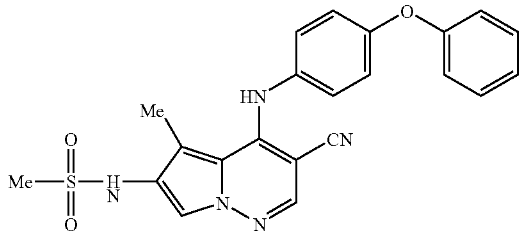

N-[3-Cyano-5-methyl-4-(4-phenoxy-phenylamino)-pyrrolo[1,2-b]pyridazin-6-yl]-methanesulfonamide To a slurry of 6-amino-5-methyl-4-(4-phenoxy-phenylamino)-pyrrolo[1,2-b]pyridazine-3-carbonitrile hydrochloride (Example 11B) (14 mg, 0.035 mmol) in $CH_2Cl_2$ (2 ml) was added N-methyl morpholine (12.3 μl, 0.113 mmol) followed by MsCl (4.5 μl, 0.057 mmol). The reaction mixture was stirred overnight, 10% citric acid (3 ml) was added. The resulting mixture was extracted with $CHCl_3$ (10 ml), the organic layer was separated and dried with $Na_2SO_4$, concentrated to give the title compound (6.9 mg, 45%). It has a retention time of 6.01 min (standard LCl method, 8 min run). MS Found: $(M+H)^+$=434.0

EXAMPLE 416

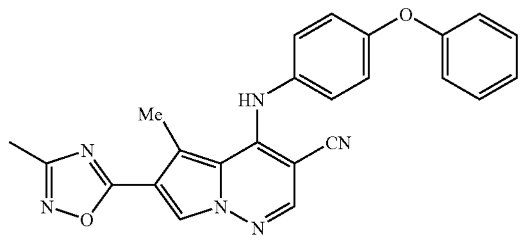

5-Methyl-6-(3-methyl-[1,2,4]oxadiazol-5-yl)-4-(4-phenoxy-phenylamino)-pyrrolo[1,2-b]pyridazine-3-carbonitrile The amidoxime from Example 412 (58 mg, 0.13 mmol) was dissolved in THF (3 ml) at 50° C., a solution of 1N TBAF in THF (0.64 ml, 0.64 mmol) was added. The reaction mixture was stirred at rt overnight, then at 60° C. for 1 h. After regular workup, the residue was purified by prep. TLC to give the title compound (17.6 mg, 32%) (20% EtOAc—hexanes). It has a retention time of 7.10 min (standard LCl method, 8 min run). MS Found: $(M+H)^+$=423.2

EXAMPLE 417

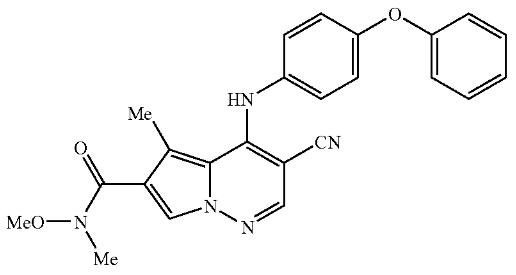

3-Cyano-5-methyl-4-(4-phenoxy-phenylamino)-pyrrolo[1,2-b]pyridazine-6-carboxylic acid methoxy-methyl-amide To a solution of 3-cyano-5-methyl-4-(4-phenoxy-phenylamino)-pyrrolo[1,2-b]pyridazine-6-carbonyl chloride (Example 412B) (181 mg, 0.45 mmol) in $CH_2Cl_2$ (3 ml) was added $Et_3N$ (160 μl, 1.13 mmol) followed by O,N-dimethylhydroxyamine hydrochloride (44 mg, 0.45 mmol) in one portion. The mixture was stirred overnight, diluted with $CHCl_3$ (20 ml), washed with water (2×20 ml), dried with $Na_2SO_4$. Concentrated in vacuo and purified by prep. TLC to give the title compound (138 mg, 72%) (50% EtOAc—hexanes). It has a retention time of 6.45 min (standard LCl method, 8 min run). LCMS Found: $(M+H)^+$=428.1

EXAMPLE 418

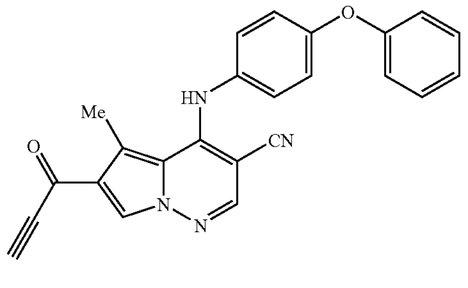

5-Methyl-4-(4-phenoxy-phenylamino)-6-propynoyl-pyrrolo[1,2-b]pyridazine-3-carbonitrile To a solution of amide from Example 417 (60 mg, 0.14 mmol) in THF (2 ml) at 0° C. was added ethynylmagnesium bromide (0.5 M in THF, 1.4 ml, 0.7 mmol). The reaction mixture was warmed to rt for 2 h, then heated at 50° C. for 2 h, and at rt overnight. Diluted with ether, washed with saturated $NaHCO_3$, dried with $Na_2SO_4$. Concentrated in vacuo and purified by prep. TLC to give the title compound (30 mg, 32%) (5% MeOH—$CHCl_3$). It has a retention time of 6.82 min (standard LCl method, 8 min run). LCMS Found: $(M+H)^+$=393.2

EXAMPLE 419

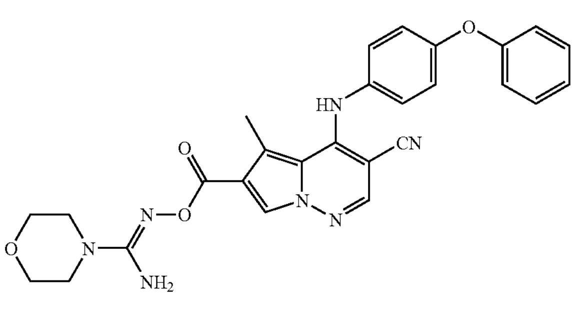

419A—Preparation of N-hydroxy-morpholine-4-carboxamidine

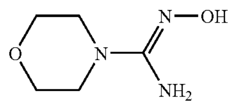

The title compound was prepared from the reaction of morpholine nitrile and hydroxylamine (equimolar amounts) by a route analogous to that used for the preparation of Example 412A to yield 419A in quantitative yield. $^1H$ NMR (400 MHz, DMSO-$d_6$) δ 8.33 (s, 1H), 5.18 (S, 2H), 3.57 (m, 4H), 2.93 (m, 4H)

419—Preparation of 3-cyano-5-methyl-4-(4-phenoxy-phenylamino)-pyrrolo[1,2-b]pyridazin-6-carbonyl-N-hydroxylmorpholinyl-acetamidine To a solution of N-hydroxy-morpholine-4-carboxamidine (Example 419A) (20.2 mg, 0.13 mmol) and Hunig's base (45 μl, 0.26 mmol) in DMF (1 ml) at −5° C. was added a solution of 3-cyano-5-methyl-4-(4-phenoxy-phenylamino)-pyrrolo[1,2-b]pyridazine-6-carbonyl chloride (Example 412B) (51 mg, 0.12 mmol) in DMF (1 ml) via syringe. The reaction mixture was warmed to rt, after 20 min, diluted with EtOAc, poured into water (50 ml), extracted with EtOAc (2×50 ml). The combined extracts were dried with $Na_2SO_4$, concentrated in vacuo and purified by prep. TLC to give the title compound (23 mg, 37%) (5% MeOH—$CHCl_3$). It has a retention time of 5.79 min (standard LC1 method, 8 min run). LCMS Found: $(M+H)^+$=512.2.

EXAMPLE 420

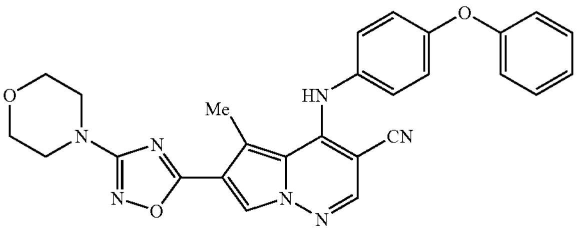

5-Methyl-6-(3-morpholin-4-yl-[1,2,4]oxadiazol-5-yl)-4-(4-phenoxy-phenylamino)-pyrrolo[1,2-b]pyridazine-3-carbonitrile To a solution of compound from Example 419 (24 mg, 0.047 mmol) in a mixed solvents of EtOH (0.5 ml) and toluene (1 ml) was added 2M $Na_2CO_3$ (2 ml, 2 mmol). The reaction mixture was stirred vigorously at 100° C. for 30 min, the organic layer was separated, the aqueous layer was extracted with EtOAc (2×5 ml), the combined organic layer was dried with $Na_2SO_4$, concentrated in vacuo and purified by silica gel column to give the title compound (10.2 mg, 44%) (5% MeOH—$CHCl_3$). It has a retention time of 7.26 min (standard LC1 method, 8 min run). LCMS Found: M+H)$^+$=494.2

EXAMPLE 421

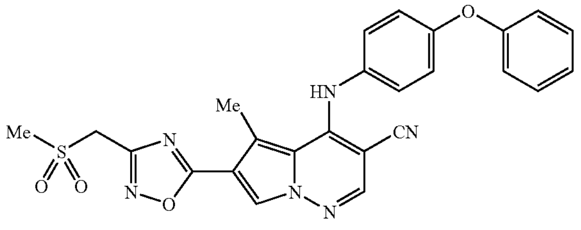

6-(3-Methanesulfonylmethyl-[1,2,4]oxadiazol-5-yl)-5-methyl-4-(4-phenoxy-phenylamino)-pyrrolo[1,2-b]pyridazine-3-carbonitrile 421A—Preparation of N-hydroxy-2-methanesulfonyl-acetamidine

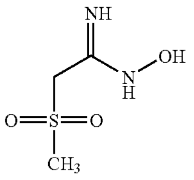

Compound 421A was prepared from methanesulfonyl-acetonitrile and hydroxylamine by a route analogous to that used for the preparation of 421A in quantative yield. $^1$HNMR (DMSO, 400 MHz): δ 2.99 (s, 3H), 3.82 (s, 2H), 5.62 (s, 2H), 9.46 (s, 1H);

421B—Preparation of 3-Cyano-5-methyl-4-(4-phenoxy-phenylamino)-pyrrolo[1,2-b]pyridazine-6-carbonyl-N-hydroxylmethanesulfonyl-acetamidine

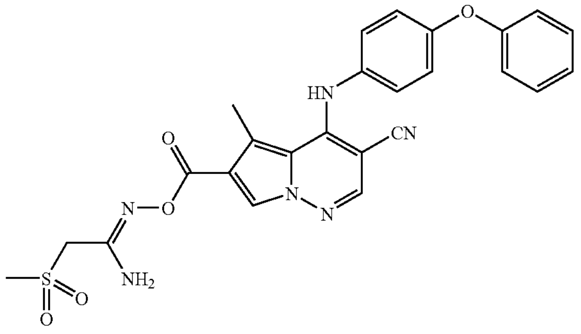

Compound 421B was preparated from 3-cyano-5-methyl-4-(4-phenoxy-phenylamino)-pyrrolo[1,2-b]pyridazine-6-carbonyl chloride (Example 412B) and 421A by a route analogous to that used for the preparation of the compound in Example 419.

421—Preparation of 6-(3-Methanesulfonylmethyl-[1,2,4]oxadiazol-5-yl)-5-methyl-4-(4-phenoxy-phenylamino)-pyrrolo[1,2-b]pyridazine-3-carbonitrile

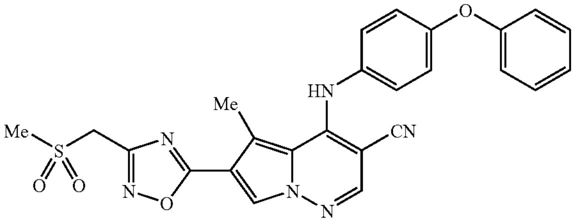

Compound 421 (7.5 mg, 47%) was prepared from 421B (17 mg, 0.032 mmol) by a route analogous to that used for the preparation of the compound in Example 420. It has a retention time of 6.41 min (standard LC1 method, 8 min run). LCMS Found: (M+H)$^+$=501.1

EXAMPLE 422

3-(Imino-hydrazino-methyl)-5-methyl-4-(4-phenoxy-phenylamino)-pyrrolo[1,2-b]pyridazine-6-carboxylic Acid Ethyl Ester

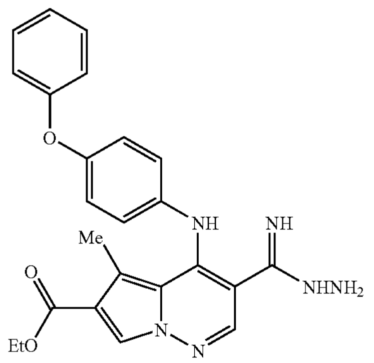

A mixture of 396A (59 mg, 0.143 mmol), $H_2NNH_2$ (22 mg, 0.7 mmol) in absolute EtOH (3 ml) was heated at 100° C. in a sealed tube for 4 h. After it was cooled to rt, filtered, purified by prep. TLC to give the title compound (24 mg, 38%) as a light yellow crystalline solid (10% MeOH—$CHCl_3$). It has a retention time of 7.12 min (standard LC1 method, 8 min run). LCMS Found: (M+H—$H_2NNH_2$)$^+$=413.2

EXAMPLE 423

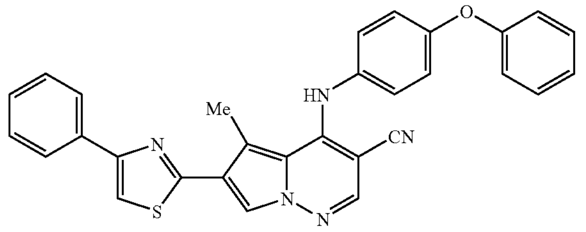

5-Methyl-4-(4-phenoxy-phenylamino)-6-(4-phenyl-thiazol-2-yl)-pyrrolo[1,2-b]pyridazine-3-carbonitrile 423A—Preparation of 3-Cyano-5-methyl-4-(4-phenoxy-phenylamino)pyrrolo [1,2-b]pyridazine-6-carbothioic Acid Amide

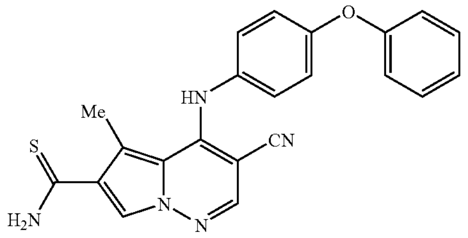

A mixture of 3-cyano-5-methyl-4-(4-phenoxy-phenylamino)-pyrrolo[1,2-b]pyridazine-6-carboxylic acid amide (Example 9) (23 mg, 0.06 mmol) and Lawessons Reagent (48.5 mg, 0.12 mmol) in toluene (2 ml) was heated at 100° C. for 5 min. After regular workup, the residue was purified by prep. TLC to give impure 423A (6 mg, 25%) (5% MeOH—$CHCl_3$). It has a retention time of 6.19 min (standard LC1 method, 8 min run). LCMS Found: $(M+H)^+$=400.2

423—Preparation of 5-Methyl-4-(4-phenoxy-phenylamino)-6-(4-phenyl-thiazol-2-yl)-pyrrolo[1,2-b]pyridazine-3-carbonitrile

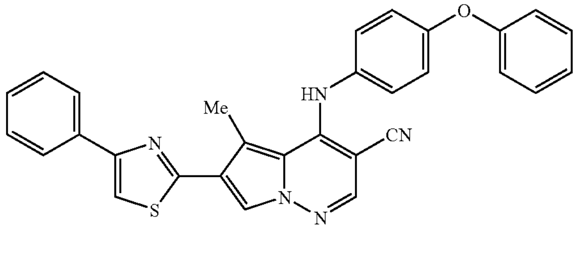

A mixture of 423A (15 mg, 0.037 mmol) and 2-bromoacetophenone (7.3 mg, 0.037 mmol) in acetone (3 ml) was heated at 70° C. for 1 h. Cooled to rt, hexanes (1 ml) was added, then the resulting mixture was cooled to −50° C., filtered, the solid was washed with hexanes to give the hydrobromide salt of 423 (14.9 mg, 69%) as a yellow powder. It has a retention time of 8.16 min (standard LC1 method, 8 min run). LCMS Found: $(M+H)^+$=500.3

EXAMPLE 424

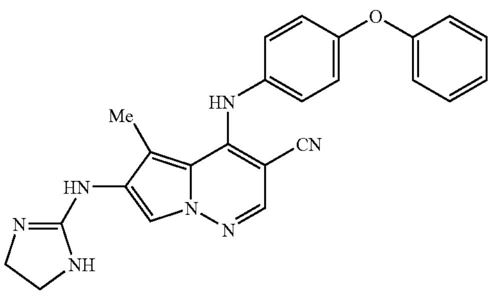

6-(4,5-Dihydro-1H-imidazol-2-ylamino)-5-methyl-4-(4-phenoxy-phenylamino)-pyrrolo[1,2-b]pyridazine-3-carbonitrile 424A—Preparation of 2-[3-Cyano-5-methyl-4-(4-phenoxy-phenylamino)-pyrrolo[1,2-b]pyridazin-6-ylamino]-4,5-dihydro-imidazole-1-carboxylic Acid Tert-butyl Ester

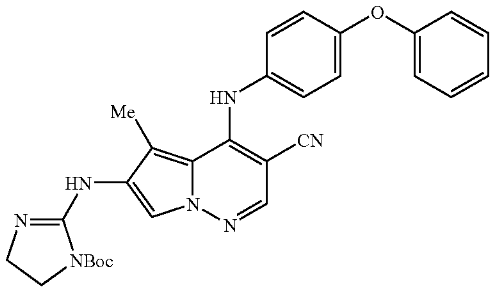

A mixture of 6-amino-5-methyl-4-(4-phenoxy-phenylamino)-pyrrolo[1,2-b]pyridazine-3-carbonitrile hydrochloride (Example 11) (49 mg, 0.125 mmol) and 2-methylsulfanyl-4,5-dihydro-imidazole-1-carboxylic acid tert-butyl ester (25.5 mg, 0.125 mmol) in MeOH (2 ml) was heated at 70° C. for 3 h, then cooled to rt and stirred overnight. The reaction mixture was diluted with $CHCl_3$ (25 ml), washed with saturated $NaHCO_3$ (10 ml) dried with $Na_2SO_4$. Concentrated in vacuo and purified by prep. TLC to give 424A (22 mg, 97%) as pale yellow flakes (5% MeOH—$CHCl_3$). It has a retention time of 6.82 min (standard LC1 method, 8 min run). MS Found: $(M+M)^+$=523.9

424—Preparation of 6-(4,5-Dihydro-1H-imidazol-2-ylamino)-5-methyl-4-(4-phenoxy-phenylamino)-pyrrolo[1,2-b]pyridazine-3-carbonitrile

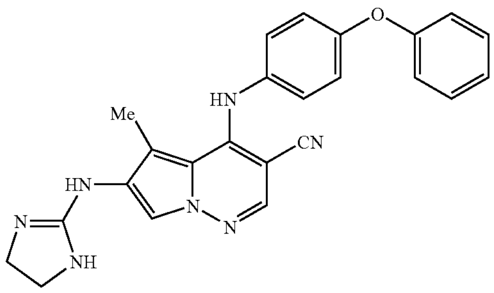

A solution of 424A (20.2 mg, 0.038 mmol) in $CH_2Cl_2$ (0.3 ml) at 0° C. was treated with TFA (300 μl) containing $H_2O$ (20 μl). Warmed to rt, stirring continued for 3 h. The reaction was then concentrated in vacuo with azotropic removal of TFA and $H_2O$ with MeOH and toluene to give the TFA salt of 424 (19.4 mg, 95%). It has a retention time of 5.68 min (standard LC1 method, 8 min run). MS Found: $(M+H)^+$=424.3

EXAMPLE 425

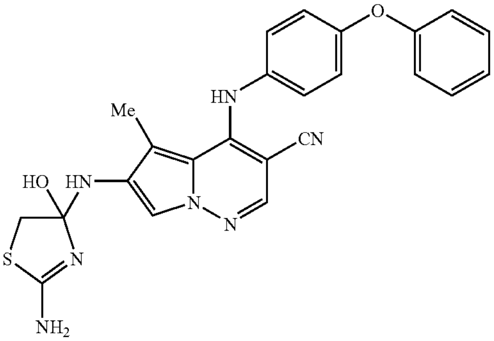

6-(2-Amino-4-hydroxy-4,5-dihydro-thiazol-4-ylamino)-5-methyl-4-(4-phenoxy-phenylamino)-pyrrolo[1,2-b]pyridazine-3-carbonitrile 425A—Preparation of 2-Bromo-N-[3-cyano-5-methyl-4-(4-phenoxy-phenylamino)-pyrrolo[1,2-b]pyridazin-6-yl]-acetamide

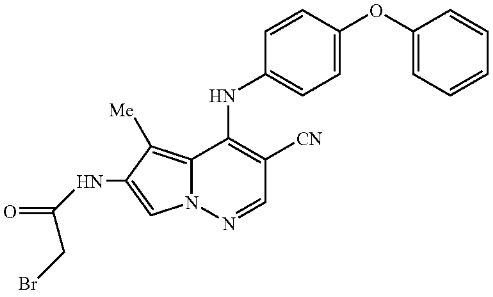

To a solution of 6-amino-5-methyl-4-(4-phenoxy-phenylamino)-pyrrolo[1,2-b]pyridazine-3-carbonitrile hydrochloride (Example 11) (130 mg, 0.33 mmol) in $CH_2Cl_2$ (4 ml) at 0° C. was added hunig's base (126 μl, 0.72 mmol) followed by bromo-acetobromide (29 μl, 0.33 mmol) dropwise. The reaction mixture was warmed to rt and stirred overnight. After regular workup, the residue was purified by prep. TLC to give crude 425A (40 mg) (10% MeOH—$CHCl_3$).

425—Preparation of 6-(2-Amino-4-hydroxy-4,5-dihydro-thiazol-4-ylamino)-5-methyl-4-(4-phenoxy-phenylamino)-pyrrolo[1,2-b]pyridazine-3-carbonitrile

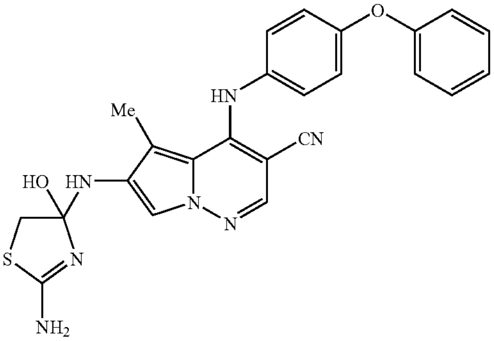

A mixture of 425A (20 mg, 0.04 mmol) and thiourea (5.4 mg, 0.068 mmol) in acetone (2 ml) was heated at 70° C. for 2.5 h, then stirred at rt overnight. Filtered, the solid was washed with cold acetone and hexanes, dried to give the hydrobromide salt of 425 (14 mg, 63%) as a white solid. It has a retention time of 5.47 min (standard LC1 method, 8 min run). MS Found: $(M+H)^+$=472.0

EXAMPLE 426

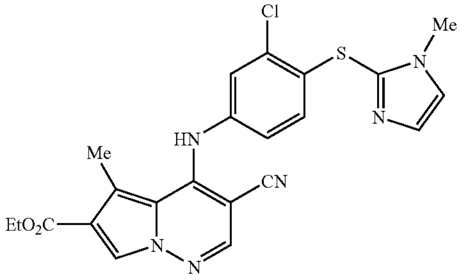

4-[3-Chloro-4-(1-methyl-1H-imidazol-2-ylsulfanyl)-phenylamino]-3-cyano-5-methyl-pyrrolo[1,2-b]pyridazine-6-carboxylic Acid Ethyl Ester 426A—Preparation of 2-(2-Chloro-4-nitro-phenylsulfanyl)-1-methyl-1H-imidazole

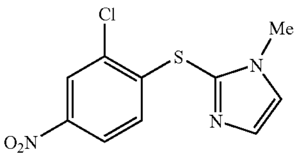

A solution of 1-methyl-1H-imidazole-2-thiol (1.14 g, 10 mmol) in THF (50 ml) under argon at 0° C. was treated with NaH (303 mg, 11.98 mmol). The mixture was warmed to rt. A solution of 2-chloro-1-fluoro-4-nitro-benzene (1.76 g, 10 mmol) in THF (50 ml) was added, and the mixture was stirred at 70° C. for 4 h, cooled to rt. Treated with EtOAc (100 ml), the mixture was washed with $H_2O$ (2×25 ml), 1N KOH (30 ml) and brine (20 ml), dried with $Na_2SO_4$. Removal of the solvent under reduced pressure gave a yellow solid. Recrystalization of the solid in $CH_2Cl_2$/hexanes gave 426A (2.31 g, 86%) as a slight yellowish solid. It has a retention time of 3.99 min (standard LC1 method, 8 min run). MS Found: $(M+H)^+$=270.1

426B—Preparation of 3-Chloro-4-(1-methyl-1H-imidazol-2-ylsulfanyl)-phenylamine

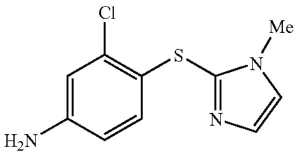

To a solution of $SnCl_2.2H_2O$ in EtOH (10 ml) at 60° C. was added 426A (1.80 g, 6.67 mmol). Concentrated HCl (8 ml) was added and the mixture was heated at 60° C. for 15 min. Cooled to rt, the mixture was concentrated under reduced pressure. The residue was basified to pH>12 and extracted with EtOAc (4×50 ml). The combined organic layers were washed with 1N KOH (20 ml), $H_2O$ (20 ml) and brine (20 ml), dried with $Na_2SO_4$. Removal of the solvent under reduced pressure gave 426B (1.31 g, 82%) as a white solid. The solid was used in next step without further purification. It has a retention time of 3.53 min (standard LC1 method, 8 min run). MS Found: $(M+H)^+$=240.1

426—Preparation of 4-[3-Chloro-4-(1-methyl-1H-imidazol-2-ylsulfanyl)-phenylamino]-3-cyano-5-methyl-pyrrolo[1,2-b]pyridazine-6-carboxylic Acid Ethyl Ester

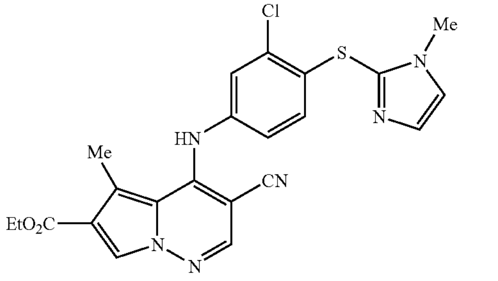

To a solution of 4-chloro-3-cyano-5-methyl-pyrrolo[1,2-b]pyridazine-6-carboxylic acid ether ester (Example 1D) (50 mg, 0.19 mmol) and 426B (45 mg, 0.19 mmol) in THF (1 ml) under argon was added NaH (6 mg, 0.25 mmol). The mixture was stirred at rt for 15 min, then at reflux for 2 h, cooled to rt. Treated with EtOAc (20 ml), the mixture was washed with $H_2O$ (3×5 ml) and brine (5 ml), dried with $Na_2SO_4$. Removal of the solvent under reduced pressure followed by flash chromatography of the residue on silica gel gave a yellow solid. Recrystalization of the solid in MeOH gave 426 (39 mg, 81%) as a dim yellow solid. It has a retention time of 5.92 min (standard LC1 method, 8 min run). MS Found: $(M+H)^+$=467.2

EXAMPLE 427

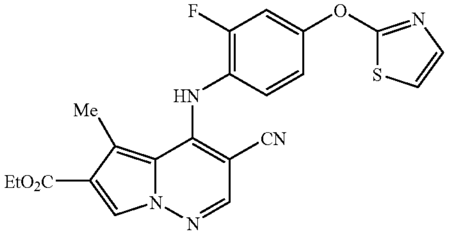

3-Cyano-4-[2-fluoro-4-(thiazol-2-yloxy)-phenylamino]-5-methyl-pyrrolo[1,2-b]pyridazine-6-carboxylic Acid Ethyl Ester 427A—Preparation of 4-Amino-3-fluoro-phenol

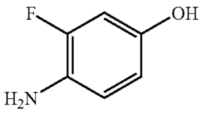

Compound 427A (1.49 g, 92%) was prepared from 3-fluoro-4-nitro-phenol (2.0 g, 12.7 mmol) by a route analogous to that used for the preparation of compound 426B. It is a yellow solid and has a retention time of 4.79 min (standard LC1 method, 8 min run). MS Found: $(M+H)^+$=128.1

427B—Preparation of 2-Fluoro-4-(thiazol-2-yloxy)-phenylamine

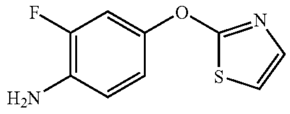

A mixture of 427A (0.814 g, 6.41 mmol), 2-bromothiazole (1.0 g, 6.10 mmol) and t-BuOK (0.821 g, 7.32 mmol) in DMA (25 ml) was stirred at 150° C. under argon for 1 h, then cooled to rt. Treated with EtOAc (150 ml), the mixture was washed with $H_2O$ (50 ml), 3N NaOH (2×50 ml), $H_2O$ (50 ml), dried with $Na_2SO_4$. Removal of the solvent under reduced pressure followed by flash chromatography of the residue on silica gel (10%–25% EtOAc-hexanes) gave 427B (1.02 g, 80%) as a colorless oil. It has a retention time of 4.02 min (standard LC1 method, 8 min run). MS Found: $(M+H)^+$=211.1

427—Preparation of 3-Cyano-4-[2-fluoro-4-(thiazol-2-yloxy)-phenylamino]-5-methyl-pyrrolo[1,2-b]pyridazine-6-carboxylic Acid Ethyl Ester

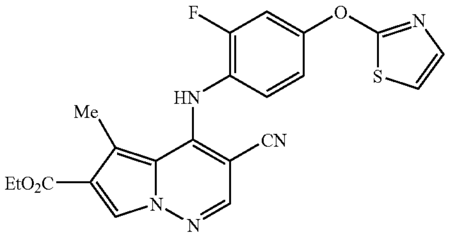

Compound 427 (361 mg, 83%) was prepared from 4-chloro-3-cyano-5-methyl-pyrrolo]1,2-b]pyridazine-6-carboxylic acid ethyl ester (Example 1D) (264 mg, 1.0 mmol) and 427B (210 mg, 1.0 mmol) by a route analogous to that used for the preparation of compound 426. It is a dim yellow solid and has a retention time of 6.76 min (standard LC1 method, 8 min run). MS Found: $(M+H)^+$=438.1

EXAMPLE 428

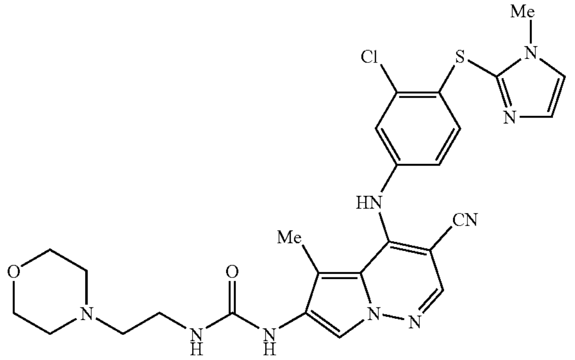

1-{4-[3-Chloro-4-(1-methyl-1H-imidazol-2-ylsulfanyl)-phenylamino]-3-cyano-5-methyl-pyrrolo[1,2-d]pyridazin-6-yl}-3-(2-morpholin-4-yl-ethyl)-urea 428A—Preparation of 4-[3-Chloro-4-(1-methyl-1H-imidazol-2-ylsulfanyl)-phenylamino]-3-cyano-5-methyl-pyrrolo[1,2-b]pyridazine-6-carboxylic Acid

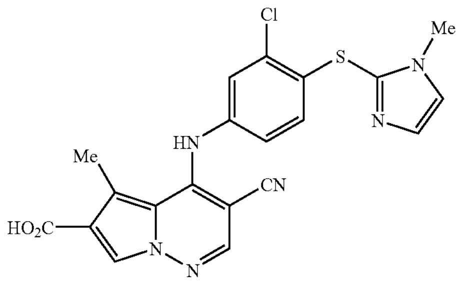

A mixture of 426 (70 mg, 0.15 mmol) and 6N NaOH (2 ml, 1.0 mmol) in a mixed solvents of EtOH/THF (2/1) (3 ml) was stirred at rt for 2 days. Neutralized with concentrated HCl to PH=6, treated with EtOAc (50 ml), the mixture was washed with $H_2O$ (2×20 ml) and brine (20 ml), dried with $Na_2SO_4$. Removal of the solvent gave 428A (55 mg, 93%) as a yellow solid. The product was used in next step without further purification. It has a retention time of 4.73 min (standard LC1 method, 8 min run). MS Found: $(M+H)^+$= 439.1

428—Preparation of 1-{4-[3-Chloro-4-(1-methyl-1H-imidazol-2-ylsulfanyl)-phenylamino]-3-cyano-5-methyl-pyrrolo[1,2-b]pyridazin-6-yl}-3-(2-morpholin-4-yl-ethyl)-urea

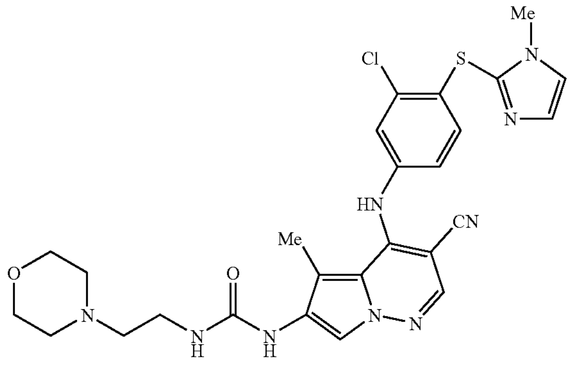

A mixture of 428A (44 mg, 0.10 mmol), $Et_3N$ (28 μl, 0.20 mmol) and DPPA (43 μl, 0.20 mmol) in dioxane (1.5 ml) was stirred under argon overnight. $TMSN_3$ (27 μl, 0.20 mmol) was added and the mixture was heated to 80° C. for 2 h, then cooled to rt. 2-Morpholin-4-yl-ethylamine (26 μl, 0.20 mmol) was added and the mixture was heated to 80° C. for 2 h, then cooled to rt. Removal of the solvent followed by flash chromatography of the residue on silica gel (3%–5% MeOH—$CH_2Cl_2$) gave a gray solid. Recrystalization of the solid in $CH_2Cl_2$/pentane gave 428 (43 mg, 75%) as a light yellow solid. It has a retention time of 3.93 min (standard LC1 method, 8 min run). MS Found: $(M+H)^+$=566.1

EXAMPLE 429

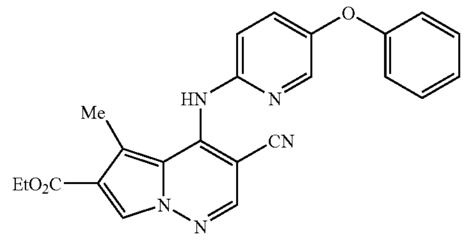

3-Cyano-5-methyl-4-(5-phenoxy-pyridin-2-ylamino)-pyrrolo[1,2-b]pyridazine-6-carboxylic Acid Ethyl Ester 429A—Preparation of 5-Fluoro-2-nitro-pyridine

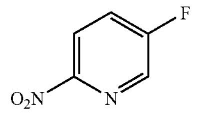

To concentrated $H_2SO_4$ at 0° C. was added 4 ml of 3% $H_2O_2$. To this solution at 0° C. was added 5-fluoro-2-amino-pyridine (250 mg, 2.23 mmol). The mixture was warmed to room temperature and stirred for 20 hr, then poured onto ice. The aqueous solution was extracted with EtOAc (3×30 ml). The combined organic layers were washed with water, brine and dried with $Na_2SO_4$. Removal of the solvent gave a light brown oil (245 mg, 77%). The product was used for next step without further purification.

429B—Preparation of 2-Nitro-5-phenoxy-pyridine

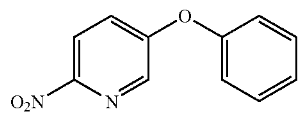

To a mixture of phenol (175 mg, 1.86 mmol) and t-BuOK (208 mg, 1.86 mmol) in DMA (4 ml) was added a solution of 5-fluoro-2-nitro-pyridine (240 mg, 1.69 mmol) in DMA (2 ml) under argon. The deep brown mixture was stirred at rt for 1 h. Treated with EtOAc (50 ml), the mixture was washed with $H_2O$ (4×10 ml) and brine (20 ml), dried with $Na_2SO_4$. Removal of the solvent under reduced pressure gave 429A (345 mg, 94%) as a brown oil. It has a retention time of 7.25 min (standard LC1 method, 8 min run). MS Found: $(M+H)^+$=217.0

429C—Preparation of 5-Phenoxy-pyridin-2-ylamine

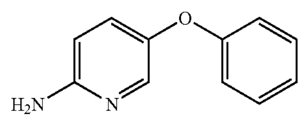

Compound 429C 119 mg, 46%) was prepared from 429B (300 mg, 1.39 mmol) by a route analogous to that used for the preparation of compound 426B. It is a dark orange oil and has a retention time of 4.28 min (standard LC1 method, 8 min run). MS Found: $(M+H)^+$=186.1

429—Preparation of 3-Cyano-5-methyl-4-(5-phenoxy-pyridin-2-ylamino)-pyrrolo[1,2-b]pyridazine-6-carboxylic Acid Ethyl Ester

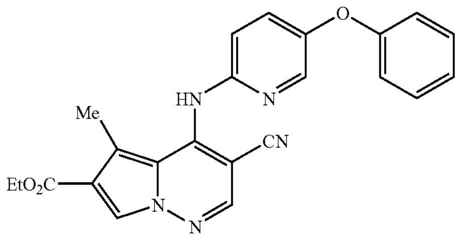

Compound 429 (21 mg, 51%) was prepared from 4-chloro-3-cyano-5-methyl-pyrrolo[1,2-b]pyridazine-6-carboxylic acid ethyl ester (Example 1D) (26 mg, 0.1 mmol) and 429C (210 mg, 1.0 mmol) by a route analogous to that used for the preparation of compound 426, DMF (1 ml) was used as solvent instead of THF. 429 is a yellow solid and has a retention time of 6.24 min (standard LC1 method, 8 min run). MS Found: $(M+H)^+$=414.2

EXAMPLE 430

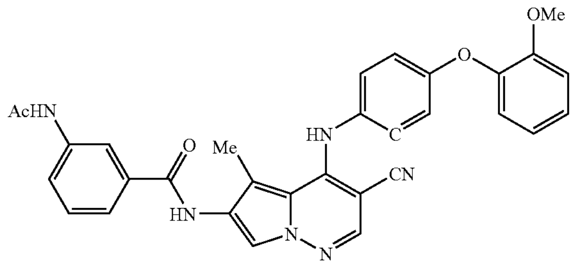

3-Acetylamino-N-{3-cyano-4-[5-(2-methoxy-phenoxy)-pyridin-2-ylamino]-5-methyl-pyrrolo[1,2-b]pyridazin-6-yl}-benzamide 430A—Preparation of 1-(2-Methoxy-phenoxy)-4-nitro-benzene

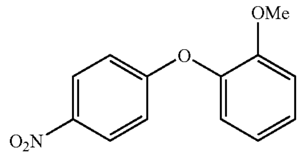

Compound 430A (7.34 g, 100%) was prepared from 1-fluoro-4-nitro-benzene (4.23 g, 30.0 mmol) and 2-methoxy-phenol (3.72 g, 30.0 mmol) by a route analogous to that used for the preparation of compound 429B. It is a bright yellow solid.

430B—Preparation of 4-(2-methoxy-phenoxy)-phenylamine

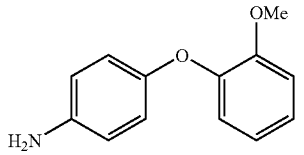

A mixture of 430A (7.34 g, 29.9 mmol) and 10% Pd/C (1.47 g, 20 wt %, 50 wt % $H_2O$) was stirred under $H_2$ balloon in MeOH (60 ml) for 12 h. The catalyst was removed by filtration on celite. The filtrate was concentrated in vacuo to give 430B (6.40 g, 99%) as a white solid. It has a retention time of 3.77 min (standard ∠Cl method, 8 min run). MS found: $(M+H)^+$=216.1

430C—Preparation of 3-Cyano-4-[4-(2-methoxy-phenoxy)-phenylamino]-5-methyl-pyrrolo[1,2-b]pyridazine-6-carboxylic Acid Methyl Ester

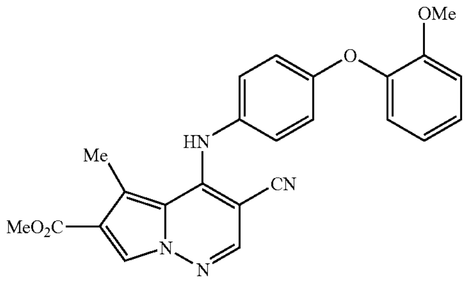

Compound 430C (1.81 g, 85%) was prepared from 4-chloro-3-cyano-5-methyl-pyrrolo[1,2-b]pyridazine-6-carboxylic acid methyl ester (prepared using the procedure of Example 1D) (1.25 g, 5.0 mmol) and 430B (1.08 g, 5.0 mmol) by a route analogous to that used for the preparation of compound 388D. It is a white solid, and has a retention time of 6.74 min (∠Cl, 8 min run). MS found, $(M+H)^+$=429.2

430D—Preparation of 3-Cyano-4-[4-(2-methoxy-phenoxy)-phenylamino]-5-methyl-pyrrolo[1,2-b]pyridazine-6-carboxylic Acid

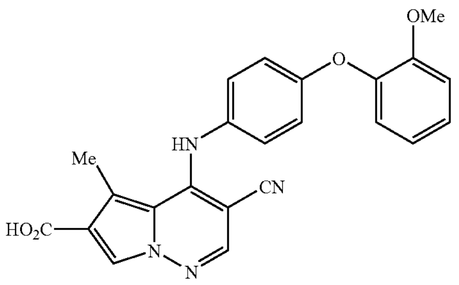

A mixture of 430C (1.60 g, 3.73 mmol) and 6N NaOH (5 ml, 30 mmol) in a mixed solvent of MeOH/THF (20 ml, 1/1) was heated at reflux for 2 h, cooled to rt. Removed half of the solvent in vacuo. The residue was treated with $H_2O$ (30 ml), washed with $CH_2Cl_2$ (3×50 ml). The aqueous layer was acidified to PH=5 and extracted with EtOAc (3×50 ml). The combined organic layers were washed with $H_2O$ (2×30 ml)

and brine (30 ml), dried with $Na_2SO_4$. Removal of the solvent under reduced pressure gave 430D (1.47 g, 95%) as a yellow powder. It has retention time of 5.88 min (∠Cl, 8 min. run). MS Found: $(M+H)^+$=415.2.

430E—Preparation of {3-Cyano-4-[4-(2-methoxy-phenoxy)-phenylamino]-5-methyl-pyrrolo[1,2-b]pyridazin-6-yl}-carbamic Acid Benzyl Ester

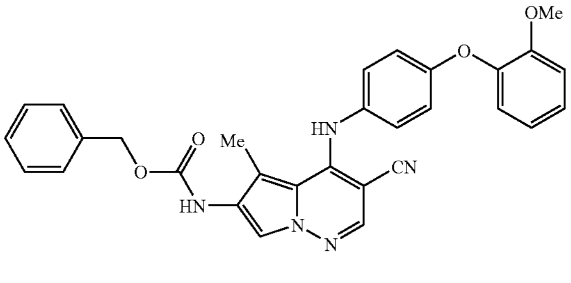

A mixture of 430D (1.24 g, 3.0 mmol), $Et_3N$ (1.67 ml, 12.0 mmol) and DPPA (1.29 ml, 6.0 mmol) in 1,4-dioxane (20 ml) was stirred at rt for 16 h under argon. Benzyl alcohol (1.86 ml, 18.0 mmol) was added. The resulting mixture was heated to 80° C. for 2.5 h, cooled to rt. Removal of the solvent in vacuo gave a brown oil. Treated with EtOAc (100 ml), the mixture was washed with $H_2O$ (3×30 ml) and brine (20 ml), dried with $Na_2SO_4$. Removal of the solvent followed by flash chromatography of the residue on silica gel ($CH_2Cl_2$ first, then 20% EtOAc-hexanes) gave 430E (1.17 g, 75%) as a light yellow solid. It has a retention time of 6.96 min (standard LC1 method, 8 min run). MS Found: $(M+H)^+$=520.2

430F—Preparation of 6-Amino-4-[4-(2-methoxy-phenoxy)-phenylamino]-5-methyl-pyrrolo[1,2-b]pyridazine-3-carbonitrile Hydrochloride

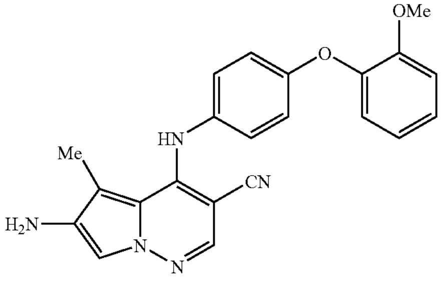

•HCl

A suspension of 43E (600 mg, 1.15 mmol) and 10% Pd/C (120 mg, 20% wt) in MeOH (20 ml) was stirred at rt under $H_2$ balloon for 4 h. HCl was added (4 M in dioxane, 5 ml). The catalyst was filtered off through celite and the filtrate was concentrated in vacuo to give the hydrochloride salt of 430F (486 mg, 100%) as a yellow solid. It has a retention time of 4.91 min (standard LC1 method, 8 min run). MS Found: $(M+H)^+$=387.3

430—Preparation of 3-Acetylamino-N-{3-cyano-4-[4-(2-methoxy-phenoxy)-phenylamino]-5-methyl-pyrrolo[1,2-b]pyridazin-6yl}-benzamide

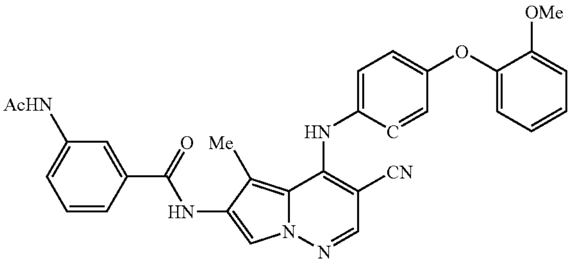

A solution of 430F (42 mg, 0.10 mmol), 3-acetylamino-benzoic acid (27 mg, 0.15 mmol), PyBrop (73 mg, 0.15 mmol) and DIEA 70 μl, 0.40 mmol) in DMF (1 ml) was stirred at room temperature for 16 h under argon. Treated with EtOAc (30 ml), the mixture was washed with $H_2O$ (3×10 ml) and brine (10 ml), dried with $Na_2SO_4$. Removal of the solvent followed by flash chromatography of the residue on silica gel (50% EtOAc-$CH_2Cl_2$) gave 430 (38 mg, 70%) as a light yellow solid. It has a retention time of 6.16 min (standard LC1 method, 8 min run). MS Found: $(M+H)^+$=547.2

EXAMPLE 431

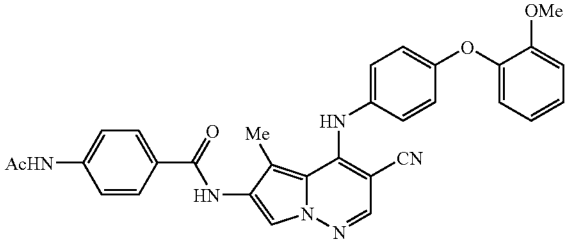

3-Acetylamino-N-{3-cyano-4-[5-(2-methoxy-phenoxy)-pyridin-2-ylamino]-5-methyl-pyrrolo[1,2-b]pyridazin-6-yl}-benzamide The title compound (27.3 mg, 50%) was prepared from the hydrochloride salt of 430F (42 mg, 0.10 mmol) and 4-acetylamino-benzoic acid (27 mg, 0.15 mmol) by a route analogous to that used for the preparation of compound 430. It is a slight yellow solid and has a retention time of 6.14 min (standard LC1 method, 8 min run). MS Found: $(M+H)^+$=547.1

EXAMPLE 432

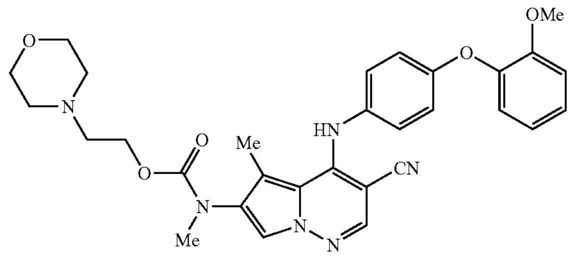

{3-Cyano-4-[4-(2-methoxy-phenoxy)-phenylamino]-5-methyl-pyrrolo[1,2-b]pyridazin-6-yl}-methyl-carbamic Acid 2-Morpholin-4-yl-ethyl Ester 432A—Preparation of {3-Cyano-4-[4-(2-methoxy-phenoxy)-phenylamino]-5-methyl-pyrrolo[1,2-b]pyridazin-6-yl}-carbamic Acid 2-Morpholin-4-yl-ethyl Ester

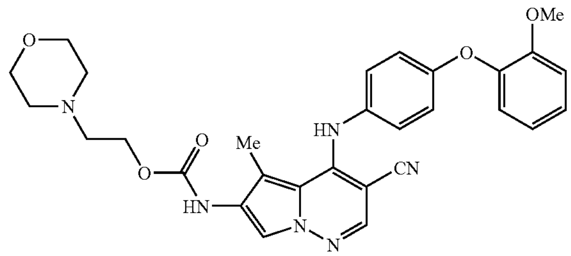

A mixture of 430D (41 mg, 0.10 mmol), $Et_3N$ (56 μl, 0.40 mmol) and DPPA (43 μl, 0.20 mmol) in dioxane (1 ml) was stirred at rt for 2 h under argon, 2-morpholin-4-yl-ethanol (49 μl, 0.40 mmol) was added. The resulting mixture was heated to 80° C. for 2 h, cooled to rt. Treated with EtOAc (20 ml), the mixture was washed with $H_2O$ (2×5 ml) and brine (10 ml), dried with $Na_2SO_4$. Removal of the solvent followed by flash chromatography of the residue on silica gel (3%–5% MeOH—$CH_2Cl_2$) gave 432A (47 mg, 88%) as a light yellow solid. It has a retention time of 5.35 min (∠Cl, 8 min. run). MS Found: $(M+H)^+$=543.2

432—Preparation of {3-Cyano-4-[4-(2-methoxy-phenoxy)-phenylamino]-5-methyl-pyrrolo[1,2-b]pyridazin-6-yl}-methyl-carbamic Acid 2-Morpholin-4-yl-ethyl Ester

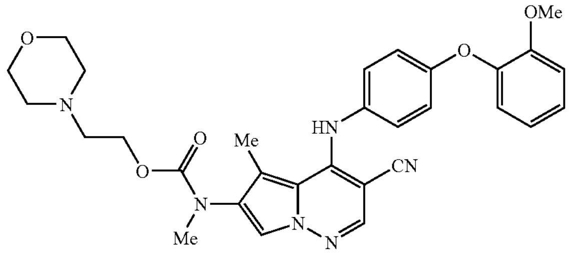

To a mixture of 432A (27 mg, 0.050 mmol) and $CH_3I$ (3.1 μl, 0.05 mmol) in THF (1 ml) was added NaH (1.5 mg, 0.06 mmol). The resulting mixture was stirred at rt for 2 h under argon. A drop of EtOH was added to quench the reaction. Removal of the solvent under reduced pressure followed by flash chromatography of the residue on silica gel (5/30/65 MeOH/EtOAc/$CH_2Cl_2$) gave 432 (17.1 mg, 62%) as a yellow oil. It has a retention time of 5.70 min (standard LC1 method, 8 min run). MS Found: $(M+H)^+$=557.1

EXAMPLE 433

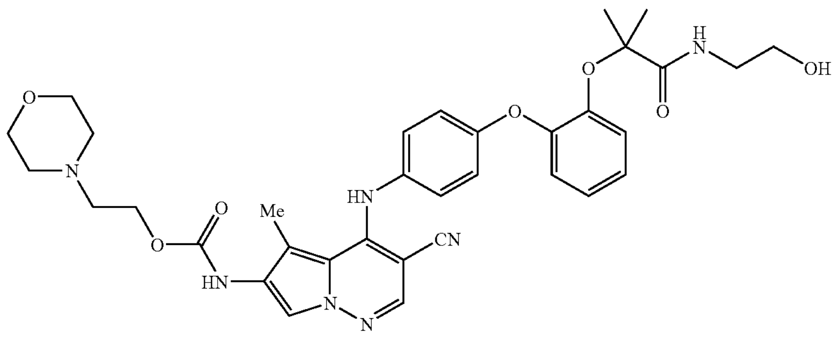

[3-Cyano-4-(4-{2-[1-(2-hydroxy-ethylcarbamoyl)-1-methyl-ethoxy]-phenoxy}-phenylamino)-5-methyl-pyrrolo[1,2-b]pyridazin-6-yl]-carbamic Acid 2-Morpholin-4-yl-ethyl Ester 433A—Preparation of 2-Methyl-2-[2-(4-nitro-phenoxy)-phenoxy]-propionic Acid Methyl Ester

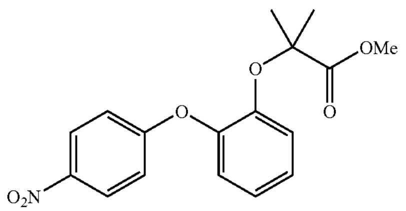

Compound 433A (5.63 g, 98%) was prepared from 1A (4.00 g, 17.3 mmol) and methyl 2-hydroxyisobutyrate (5.00 ml, 43.3 mmol) by a route analogous to that used for the preparation of compound 388B. It is a faintly yellow solid.

433B—Preparation of 2-Methyl-2-[2-(4-nitro-phenoxy)-phenoxy]-propionic Acid

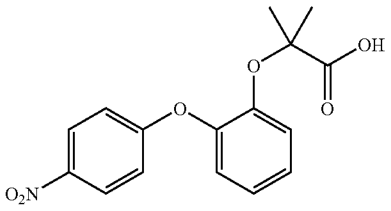

To a solution of 433A (5.05 g, 15.2 mmol) in a mixed solvent of THF/MeOH (45 ml, 2/1) was added 2N NaOH (15.2 ml, 30.4 mmol). The mixture was stirred at rt for 2.5 h, concentrated. The residue was purified by flash chromatography on silica gel (2%–5% MeOH—$CH_2Cl_2$) gave 433B (4.38 g, 91%) as a light yellow solid.

433C—Preparation of N-(2-Hydroxy-ethyl)-2-methyl-2-[2-(4-nitro-phenoxy)-phenoxy]-propionamide

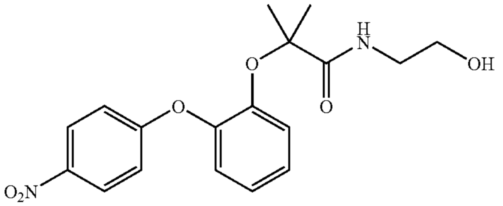

To a solution of 433B (714 mg, 2.25 mmol) in dry $CH_2Cl_2$ (10 ml) was added $(COCl)_2$ (295 μl, 3.38 mmol) followed by anhydrous DMF (17.4 μl, 0.225). The mixture was stirred at rt for 3 h, concentrated in vacuo to give the acid chloride intermediate.

To a solution of the acid chloride in dry $CH_2Cl_2$ (4 ml) at 0° C. under argon was added a solution of ethanolamine (163 μl, 2.70 mmol) and DIEA (589 μl, 3.38 mmol) in dry $CH_2Cl_2$ (4 ml). The mixture was stirred at rt for 1.25 h. Treated with EtOAc (80 ml), the mixture was washed with 1N HCl (120 ml), saturated $NaHCO_3$ (120 ml), brine and dried with $Na_2SO_4$. Removal of solvent under reduce pressure followed by flash chromatography on silica gel (10%–40% EtOAc—$CH_2Cl_2$) gave 433C (794 mg, 98%) as a faintly amber viscous oil. MS Found: $(M+H)^+$=361.0

433D—Preparation of 2-[2-(4-Amino-phenoxy)-phenoxy]-N-(2-hydroxy-ethyl)-2-methyl-propionamide

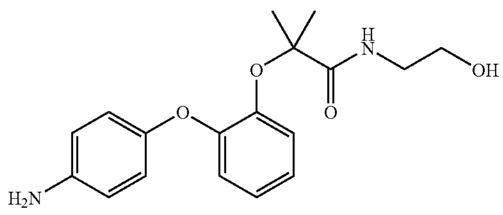

A mixture of 433C (310 mg, 0.860 mmol) and 10% Pd/C (62.0 mg, 20 wt %) in MeOH (5 ml) was stirred vigorously under balloon of $H_2$ for 1 h. Filtered through Celite followed by 0.45μ syringe filter, the filtrate was concentrated to give 46D (252 mg, 89%) as a faintly amber resin. MS Found: $(M+H)^+$=331.1

433E—Preparation of 3-Cyano-4-(4-{2-[1-(2-hydroxy-ethylcarbamoyl)-1-methyl-ethoxy]-phenoxy}-phenylamino)-5-methyl-pyrrolo[1,2-b]pyridazine-6-carboxylic Acid Ethyl Ester

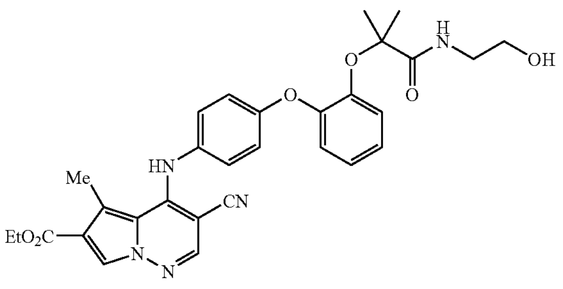

Compound 433E (146 mg, 83%) was prepared from 4-chloro-3-cyano-5-methyl-pyrrolo[1,2-b]pyridazine-6-carboxylic acid ethyl ester (Example 1D) (126 mg, 0.476 mmol) and 433D (165 mg, 0.500 mmol) by a route analogous to that used for the preparation of compound 388D. It is a cream-colored crystalline solid. LCMS Found: $(M+H)^+$=558.1

433F—Preparation of 3-Cyano-4-(4-{2-[1-(2-hydroxy-ethylcarbamoyl)-1-methyl-ethoxy]-phenoxy}-phenylamino)-5-methyl-pyrrolo[1,2-b]pyridazine-6-carboxylic Acid

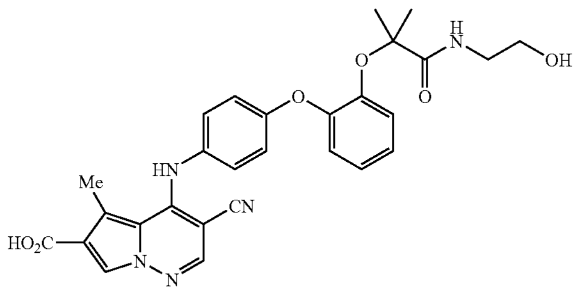

A mixture of 433E (180 mg, 0.323 mmol) and 1N NaOH (0.68 ml, 0.68 mmol) in EtOH (4 ml) was heated to reflux for 2 days, cooled to rt. Removal of the solvent in vacuo gave a gray oil. Treated with $H_2O$ (4 ml), the aqueous solution was washed with EtOAc (3×2 ml) and added to a mixture of 6N HCl (1.5 ml) and brine (5 ml). The resulting suspension was cooled to 0° C. and filtered, dried in vacuo to gave 433F (171 mg, 96%) as a dim dark solid. It has a retention time of 5.31 min (standard LC1 method, 8 min run). MS Found: $(M+H)^+$=530.0

433G—Preparation of 4-[4-(2-{1-[2-(Tert-butyl-dimethyl-silanyloxy)-ethylcarbamoyl]-1-methyl-ethoxy}-phenoxy)-phenylamino]-3-cyano-5-methyl-pyrrolo[1,2-b]pyridazine-6-carboxylic Acid

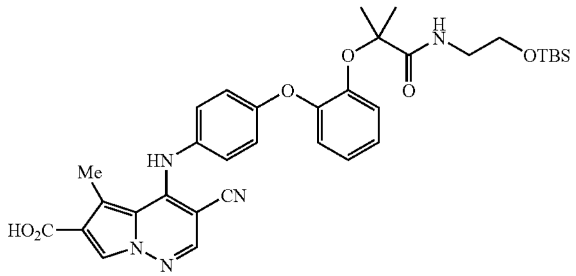

A solution of 433F (164 mg, 0.31 mmol), DIEA (0.27 ml, 1.55 mmol), DMAP (7.6 mg, 0.062 mmol) and TBSCl (140 mg, 0.93 mmol) in THF (4 ml) was stirred under argon at rt for 2 h. 1N NaOH (0.70 ml, 0.70 mmol) was added. The resulting mixture was stirred at rt for 1 h. Removal of the solvent followed by flash chromatography of the residue of silica gel (2%–5% MeOH—$CH_2Cl_2$) gave 433G (75 mg, 38%) as a yellow oil. It has a retention time of 7.43 min (standard LC1 method, 8 min run). MS Found: $(M+H)^+$=644.0

433H—Preparation of {4-[4-(2-{1-[2-(Tert-butyl-dimethyl-silanyloxy)-ethylcarbamoyl]-1-methyl-ethoxy}-phenoxy)-phenylamino]-3-cyano-5-methyl-pyrrolo[1,2-d]pyridazin-6-yl}-carbamic Acid 2-Morpholin-4-yl-ethyl Ester

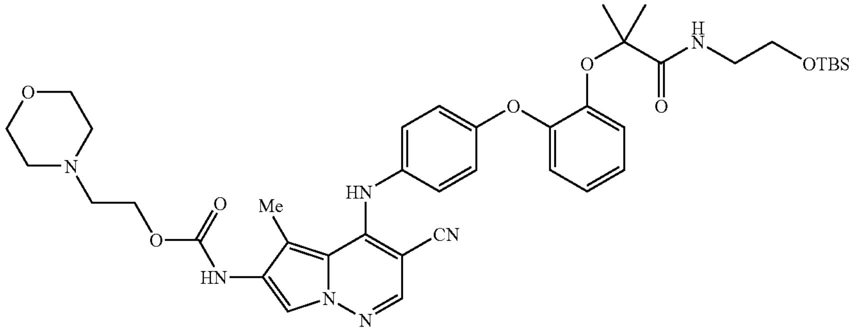

Compound 433H (28 mg, 67%) was prepared from 433G (35 mg, 0.054 mmol) and 2-morpholin-4-yl-ethanol (26 μl, 0.22 mmol) by a route analogous to that used for the preparation of compound 433A. It is a light yellow oil and has a retention time of 7.06 min (standard LC1 method, 8 min run). MS Found: $(M+H)^+$=772.3

433—Preparation of [3-Cyano-4-(4-{2-[1-(2-hydroxy-ethylcarbamoyl)-1-methyl-ethoxy]-phenoxy}-phenylamino)-5-methyl-pyrrolo[1,2-b]pyridazin-6-yl]-carbamic Acid 2-Morpholin-4-yl-ethyl Ester

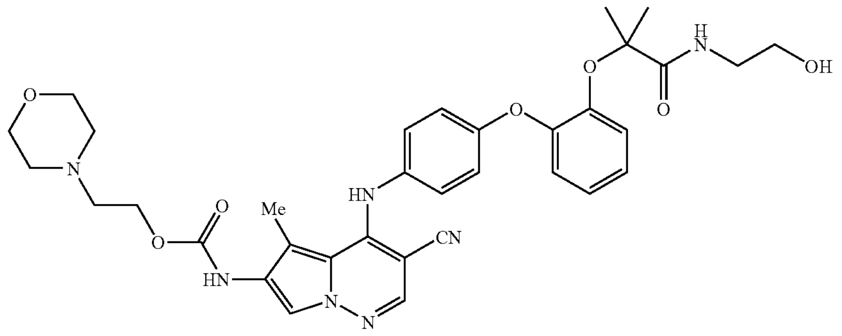

To a solution of 433H (18 mg, 0.023 mmol) in $CH_3CN$ (0.5 ml) was added HF.Pyr (70% wt/wt) (50 μl). The mixture was stirred at rt for 0.5 h. Saturated $NaHCO_3$ (2 ml) was added, saturated with solid $Na_2SO_4$. The mixture was extracted with EtOAc (3×5 ml). Removal of the solvent of the combined organic layers followed by flash chromatography of the residue on silica gel (1%–3% MeOH—$CH_2Cl_2$) gave 433 (15 mg, 98%) as a light yellow oil. It has a retention time of 4.89 min (standard LC1 method, 8 min run). MS Found: $(M+H)^+$=658.2.

EXAMPLE 434

VEGFR-2 and FGFR-1 Kinase assays

| Reagents | Final Concentration | |
|---|---|---|
| Stock Solution | VEGFR-2 | FGFR-1 |
| Tris pH 7.0 | 20 mM | 20 mM |
| BSA 10 mg/ml | 25 μg/ml | 25 □g/ml |
| $MnCl_2$ (1 M) | 1.5 mM | 0.5 mM |
| $MgCl_2$ (1 M) | — | 0.5 mM |
| DTT(1 M) | 0.5 mM | 0.5 mM |
| Enzyme Stock in 10% glycerol (1 mg/ml) | 5 ng/rxn | 20 ng/rxn |
| Polyglu/tyr (10 mg/ml) | 80 μg/ml | 30 □g/ml |
| ATP (1 mM) | 2.5 μM | 1.0 μM |
| γ-ATP (10 μCi/μl) | 0.5 μCi/ml | 0.5 μCi |

Incubation mixtures employed for VEGFR-2 or FGFR-1 assay contained the synthetic substrate polyGlu:Tyr, (4:1), ATP, ATP-γ-$^{33}$P and buffer containing $Mn^{++}$ and/or $Mg^{++}$, dithiothreitol (DTT), bovine serum albumin (BSA), and Tris buffer. The reaction was initiated by addition of enzyme and after 60 minutes was terminated by the addition of trichloroacetic acid (TCA) to a concentration of 30% on a volume percent basis. Inhibitors in accordance with the invention were brought to a concentration of 10 mM in DMSO. Assays were prepared in a 96 well format. Compounds were diluted 1:500 in DMSO and then 1:10 in water for a final DMSO concentration of 10%. Aliquots of 10 μL were added to rows B–H in a 96 well format of 10% DMSO. Aliquots of 20 μl of inhibitor solution were added to row A at a concentration 5 fold higher than running conditions. A 10 μL aliquot was transferred to each row with 10 pipetting phases for mixing, and at row F a 10 μL aliquot was discarded. Row G was a control with no compound and row H was a no-compound and no-enzyme control. Enzyme and substrate were delivered using a Tomtec Quadra station.

Plates were covered with sticky plate tops, incubated at 27° C. for 60 minutes, and then acid precipitated with TCA for 20 minutes on ice. The precipitate was transferred to UniFilter-96, GF/C microplates using either a Tomtec or Packard FilterMate harvester. Activity was determined by quantifying the incorporated radioactivity using a Packard TopCount Microplate Scintillation Counter following the addition of Microscint-20 cocktail into each dried well of the UniFilter microplates.

Tested compounds of formula I inhibited VEGFR-2 and FGFR-1 kinases with $IC_{50}$ values ≦80 μM.

EXAMPLE 435

HER1, HER2 or HER4 Kinase Assays

Compounds of interest were assayed in a kinase buffer that contained 20 mM Tris.HCl, pH 7.5, 10 mM $MnCl_2$, 0.5 mM dithiothreitol, bovine serum albumin at 0.1 mg/ml, poly(glu/tyr, 4:1) at 0.1 mg/ml, 1□M ATP, and 4□Ci/ml [□-$^{33}$P]ATP. Poly(glu/tyr, 4:1) is a synthetic polymer that serves as a phosphoryl acceptor and is purchased from Sigma Chemicals. The kinase reaction is initiated by the addition of enzyme and the reaction mixtures were incubated at 26° C. for 1 h. The reaction is terminated by the addition of EDTA to 50 mM and proteins are precipitated by the addition of trichloroacetic acid to 5%. The precipitated proteins are recovered by filtration onto Packard Unifilter plates and the amount of radioactivity incorporated is measured in a Topcount scintillation counter.

For the preparation of recombinant HER1 and HER4, the cytoplasmic sequences of the receptors were expressed in insect cells as GST fusion proteins, which were purified by affinity chromatography. The cytoplasmic sequence of HER2 was subcloned into the baculovirus expression vector pBlueBac4 (Invitrogen) and was expressed as an untagged protein in insect cells. The recombinant protein was partially purified by ion-exchange chromatography.

The instant compounds inhibit HER1, HER2, and HER4 kinases with IC50 values between 0.001 25 μM. Preferred compounds have $IC_{50}$ values between 0.001–5.0 μM. More preferred compounds have $IC_{50}$ values between 0.001–1.0 μM. Most preferred compounds have $IC_{50}$ values between 0.001–0.1 μM.

A HERG potassium channel assay may be used to screen compounds for HERG activity (see Caballero R, et al., "Direct Effects of Candesartan and Eprosartan on Human Cloned Potassium Channels Involved in Cardiac Repolarization," *Molecular Pharmacology,* 59(4), 825–36, (2001)). Accordingly, preferred compounds have lower HERG assay activity.

For the preparation of recombinant HER1, the cytoplasmic sequences of the receptor were expressed in insect cells as a GST fusion protein, which was purified by affinity chromatography. The cytoplasmic sequence of HER2 was subcloned into the baculovirus expression vector pBlueBac4 (Invitrogen) and was expressed as an untagged protein in insect cells. The recombinant protein was partially purified by ion-exchange chromatography.

Tested compounds of formula I inhibited HER-1 and HER-2 kinases with IC50 values ≦100 μM.

EXAMPLE 436

MEK-ERK Kinase Cascade Assay

An in vitro 96-well plate assay described in Example 388, above, was adopted with several modifications. Each well contained 30 □l assay buffer (Tris-HCl, pH 7.5, $MgCl_2$, DTT, BSA, Myelin basic protein (MBP), ATP and [□-$^{33}$P] ATP), 10 □l inhibitor dilutions or empty DMSO solvent and 10 □l enzyme mixture (5–10 ng MEK-EE and 100–200 ng ERK). The final concentrations in the assay were 20 mM Tris-HCl, pH 7.5, 10 mM $MgCl_2$, 0.3 mM DTT, 50 □g Myelin basic protein (MBP), 10 □M ATP and 200 nCi[□-$^{33}$P]ATP. The plates were incubated at room temperature for 60 min and reactions were terminated by the addition of 10 □l stop mixture containing 300 mM EDTA and 25 □g BSA. The samples were subjected to precipitation with TCA containing ATP (final concentrations: TCA, 3.2% and ATP, 2.3 mM). The samples were transferred to a Packard GF/C 96-well Unifilter plates using a Packard Filter Mate 196 Harvester. Following drying under light, the radioactivity of the residue in the wells was counted with a Packard Top Count microplate counter.

Since this assay is a cascade assay, inhibitors of both MEK and ERK are expected to be identified. Further in vitro analysis is required to determine whether the "hits" were attributable to the inhibition of MEK (using MEK and kinase deficient ERK) or ERK (using activated ERK and MBP) inhibitors. Nevertheless, tested compounds of formula I inhibited MEK and/or ERK with $IC_{50}$ values ≦10 μM.

EXAMPLE 437

Generation of p38 Kinases cDNAs of human p38α, β and γ isozymes were cloned by PCR. These cDNAs were subcloned in the pGEX expression vector (Pharmacia). GST-p38 fusion protein was expressed in *E. coli* and purified from bacterial pellets by affinity chromatography using glutathione agarose. p38 fusion protein was activated by incubating with constitutively active MKK6. Active p38 was separated from MKK6 by affinity chromatography. Constitutively active MKK6 was generated according to Raingeaud et al. [*Mol. Cell. Biol.,* 1247–1255 (1996)].

EXAMPLE 438

TNF-α Production by LPS-Stimulated PBMCs

Heparinized human whole blood was obtained from healthy volunteers. Peripheral blood mononuclear cells (PBMCs) were purified from human whole blood by Ficoll-Hypaque density gradient centrifugation and resuspended at a concentration of $5\times10^6$/ml in assay medium (RPMI medium containing 10% fetal bovine serum). 50 ul of cell suspension was incubated with 50 ul of test compound (4× concentration in assay medium containing 0.2% DMSO) in 96-well tissue culture plates for 5 minutes at RT. 100 ul of LPS (200 ng/ml stock) was then added to the cell suspension and the plate was incubated for 6 hours at 37° C. Following incubation, the culture medium was collected and stored at −20° C. TNF-α concentration in the medium was quantified using a standard ELISA kit (Pharmingen—San Diego, Calif.). Concentrations of TNF-α and $IC_{50}$ values for test compounds (concentration of compound that inhibited LPS-stimulated TNF-α production by 50%) were calculated by linear regression analysis.

EXAMPLE 439 p38 Assay

The assays were performed in V-bottomed 96-well plates. The final assay volume was 60 μl prepared from three 20 μl additions of enzyme, substrates (MBP and ATP) and test compounds in assay buffer (50 mM Tris pH 7.5, 10 mM $MgCl_2$, 50 mM NaCl and 1 mM DTT). Bacterially expressed, activated p38 was pre-incubated with test compounds for 10 min. prior to initiation of reaction with substrates. The reaction was incubated at 25° C. for 45 min. and terminated by adding 5 μl of 0.5 M EDTA to each sample. The reaction mixture was aspirated onto a pre-wet filtermat using a Skatron Micro96 Cell Harvester (Skatron, Inc.), then washed with PBS. The filtermat was then dried in a microwave oven for 1 min., treated with MeltilLex A scintillation wax (Wallac), and counted on a Microbeta scintillation counter Model 1450 (Wallac). Inhibition data were analyzed by nonlinear least-squares regression using Prizm (GraphPadSoftware). The final concentration of reagents in the assays are ATP, 1 μM; [γ-$^{33}$P]ATP, 3 nM,; MBP (Sigma, #M1891), 2 μg/well; p38, 10 nM; and DMSO, 0.3%.

EXAMPLE 440

TNF-α Production by LPS-Stimulated Mice

Mice (Balb/c female, 6–8 weeks of age, Harlan Labs; n=8/treatment group) were injected intraperitoneally with 50 ug/kg lipopolysaccharide (LPS; *E coli* strain 0111:B4, Sigma) suspended in sterile saline. Ninety minutes later, mice were sedated by $CO_2$:$O_2$ inhalation and a blood sample was obtained. Serum was separated and analyzed for TNF-alpha concentrations by commercial ELISA assay per the manufacturer's instructions (R&D Systems, Minneapolis, Mn.).

EXAMPLE 441

N-{3-Cyano-4-[4-(2-methoxy-phenoxy)-phenylamino]-5-methyl-pyrrolo[1,2-b]pyridazin-6-yl}-3-methanesulfonylamino-benzamide

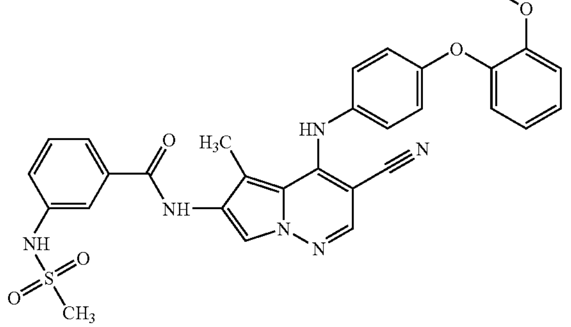

A mixture of 6-amino-4-[4-(2-methoxy-phenoxy)-phenylamino]-5-methyl-pyrrolo[1,2-b]pyridazine-3-carbonitrile (21 mg, 0.05 mmol), 3-methanesulfonylamino-benzoic acid (16 mg, 0.075 mmol), bromo-tris-pyrrolidino-phosphonium hexafluorophosphate (36 mg, 0.075 mmol) and diisopropylethyl amine (35 □L, 0.20 mmol) were stirred in 1 ml of DMF at room temperature for 10 h, followed by an additional 16 h of stirring at 60° C. The mixture was allowed to cool by to room temperature where upon it was treated with 50 ml of EtOAc. The mixture was washed with water, (3×10 ml), followed by brine (5 ml) and then dried over $Na_2SO_4$. The solvent was removed in vacuo, and the resulting residue was purified by silica gel chromatography using 20–30% gradient of EtOAc in dichoromethane to give 22.0 mg of compound XX as a light yellow solid. Retention Time: 6.56 min. (Princeton chromatography HTS column, 5 micron, 4.6×50 mm, eluting with 5–100% of acetonitrile in water over 8 minutes containing 0.1% TFA, 1.2 mL/min, monitoring at 215 nm.).

EXAMPLES 442 TO 542

Further compounds of the present invention were prepared by procedures analogous to those described above and are listed in Table 2. The chromatography techniques used to determine the retention times of the compounds listed in Table 2 are as follows:

LC1=Princeton chromatography HTS column, 5 micron, 4.6×50 mm, eluting with 5–100% of acetonitrile in water over 8 minutes containing 0.1% TFA, 1.2 mL/min, monitoring at 215 nm.

LCMS1=Princeton chromatography HTS column, 5 micron, 3.0×5.0 mm, eluting with 25–100% of acetonitrile in water over 2 minutes containing 0.1% TFA then 100% acetonitrile for 0.25 minutes, 1.2 mL/min, monitoring by electrospray mass spectroscopy.

LCMS2=Princeton chromatography HTS column, 5 micron, 3.0×50 mm, eluting with 10–100% of acetonitrile in water over 4 minutes containing 0.1% formic acid then 100% acetonitrile for 0.25 minutes, 1.2 mL/min, monitoring by electrospray mass spectroscopy.

MS method—ES positive
- Analysis in ESI mode with SIR monitoring
- Source
  - Capillary: 3.0 kV
  - Cone: 25 V
  - Source Block Temp: 150°
  - Desolvation Temp: 300°
- MS
  - Ion energy: 0.5 V
  - LM resolution: 15.0
  - HM resolution: 15.0
  - Multiplier: 650
  - Cone gas flow: 110 l/h The molecular mass of the compounds listed in Table 1 were determined by MS (ES) by the formula m/z

TABLE 2

| | Compound Structure | Compound Name |
|---|---|---|
| 442 | 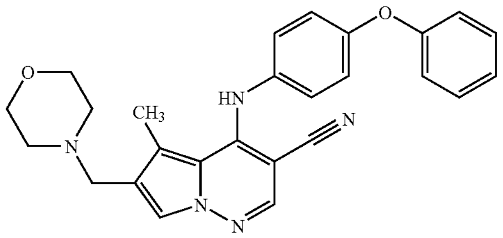 | 5-Methyl-6-morpholin-4-ylmethyl-4-(4-phenoxy-phenylamino)-pyrrolo[1,2-b]pyridazine-3-carbonitrile |
| 443 | 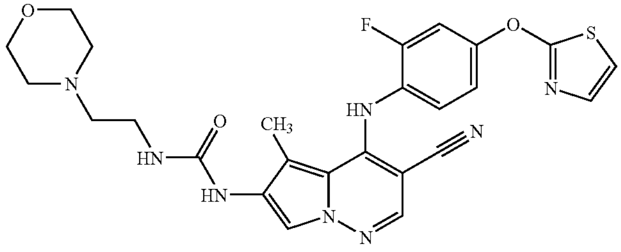 | 1-{3-Cyano-4-[2-fluoro-4-(thiazol-2-yloxy)-phenylamino]-5-methyl-pyrrolo[1,2-b]pyridazin-6-yl}-3-(2-morpholin-4-yl-ethyl)-urea |

TABLE 2-continued

| | Compound Structure | Compound Name |
|---|---|---|
| 444 | 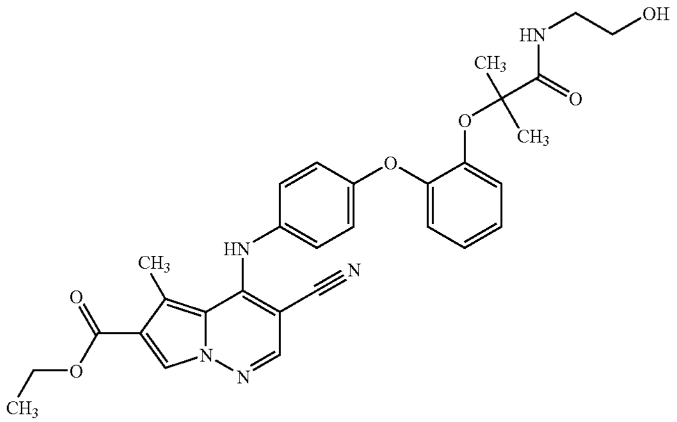 | 3-Cyano-4-(4-{2-[1-(2-hydroxy-ethylcarbamoyl)-1-methyl-ethoxy]-phenoxy}-phenylamino)-5-methyl-pyrrolo [1,2-b]pyridazine-6-carboxylic acid ethyl ester |
| 445 | 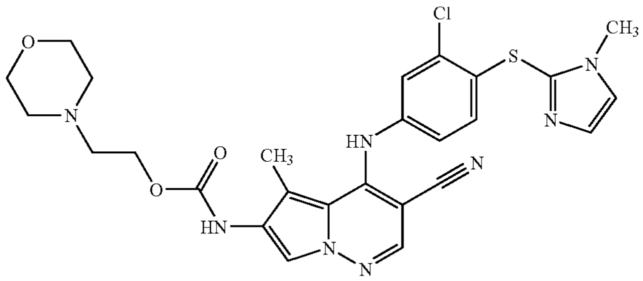 | {4-[3-Chloro-4-(1-methyl-1H-imidazol-2-ylsulfanyl)-phenylamino]-3-cyano-5-methyl-pyrrolo[1,2-b] pyridazin-6-yl}-carbamic acid 2-morpholin-4-yl-ethyl ester |
| 446 | 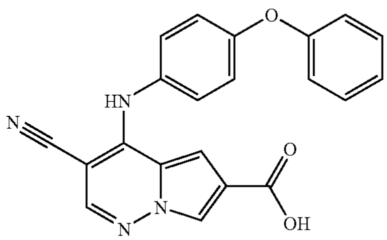 | 3-Cyano-4-(4-phenoxy-phenylamino)-pyrrolo[1,2-b]pyridazin-6-carboxylic acid |
| 447 | 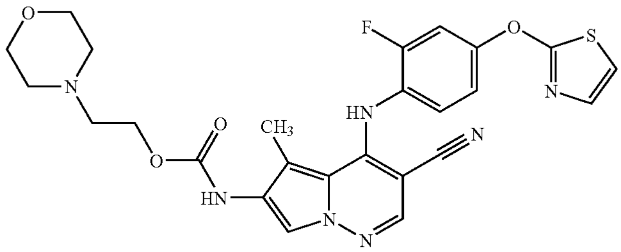 | {3-Cyano-4-[2-fluoro-4-(thiazol-2-yloxy)-phenylamino]-5-methyl-pyrrolo[1,2-b]pyridazin-6-yl}-carbamic acid 2-morpholin-4-yl-ethyl ester |
| 448 | 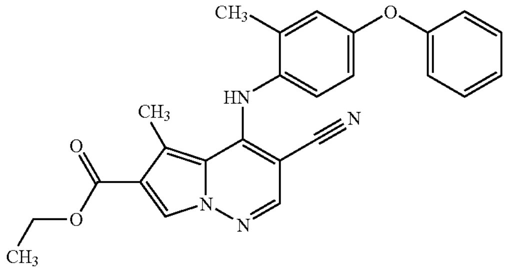 | 3-Cyano-5-methyl-4-(2-methyl-4-phenoxy-phenylamino)-pyrrolo[1,2-b]pyridazine-6-carboxylic acid ethyl ester |

TABLE 2-continued

| Compound Structure | | Compound Name |
|---|---|---|
| 449 | 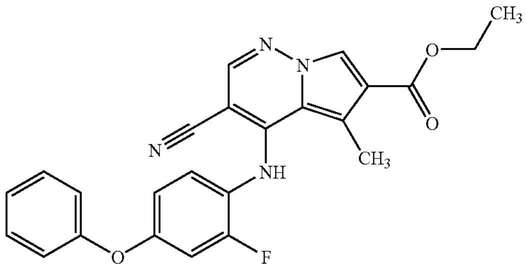 | 3-Cyano-4-(2-fluoro-4-phenoxy-phenylamino)-5-methyl-pyrrolo[1,2-b]pyridazine-6-carboxylic acid ethyl ester |
| 450 | 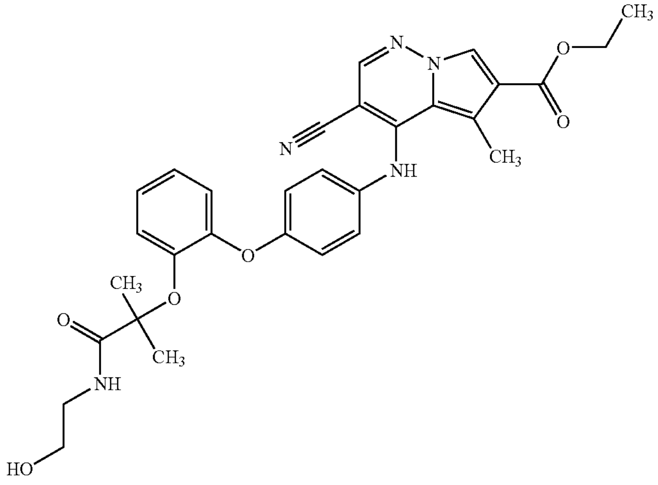 | 3-Cyano-4-(4-{2-[1-(2-hydroxy-ethylcarbamoyl)-1-methyl-ethoxy]-phenoxy}-phenylamino)-5-methyl-pyrrolo[1,2-b]pyridazin-6-carboxylic acid ethyl ester |
| 451 | 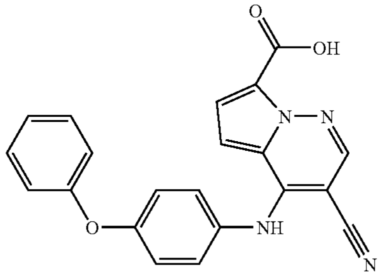 | 3-Cyano-4-(4-phenoxy-phenylamino)-pyrrolo[1,2-b]pyridazine-7-carboxylic acid |
| 452 | 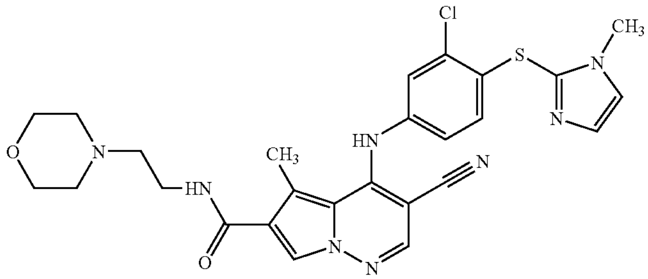 | 4-[3-Chloro-4-(1-methyl-1H-imidazol-2-ylsulfanyl)-phenylamino]-3-cyano-5-methyl-pyrrolo[1,2-b]pyridazine-6-carboxylic acid (2-morpholin-4-yl-ethyl)-amide |
| 453 | 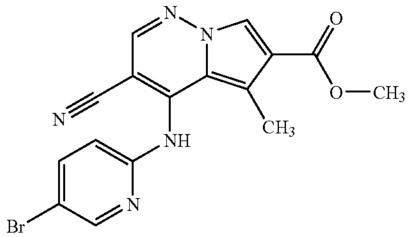 | 4-(5-Bromo-pyridin-2-ylamino)-3-cyano-5-methyl-pyrrolo[1,2-b]pyridazine-6-carboxylic acid methyl ester |

TABLE 2-continued

| Compound Structure | | Compound Name |
|---|---|---|
| 454 | 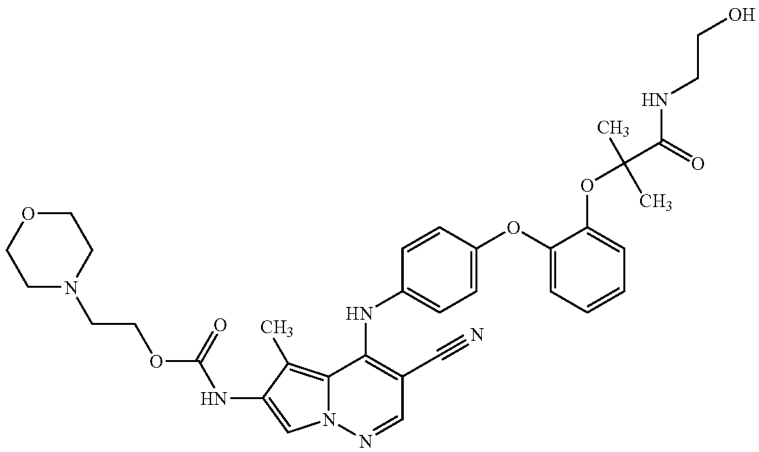 | [3-Cyano-4-(4-{2-[1-(2-hydroxy-ethylcarbamoyl)-1-methyl-ethoxy]-phenoxy}-phenylamino)-5-methyl-pyrrolo[1,2-b]pyridazin-6-yl]-carbamic acid 2-morpholin-4-yl-ethyl ester |
| 455 | 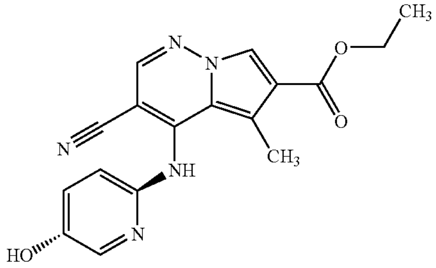 | 3-Cyano-4-(4-hydroxy-cyclohexylamino)-5-methyl-pyrrolo[1,2-b]pyridazine-6-carboxylic acid ethyl ester |
| 456 | 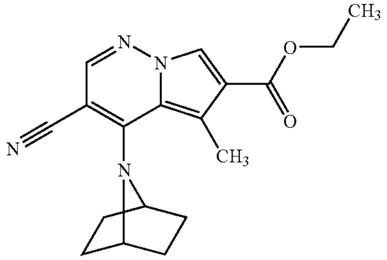 | 4-(7-Aza-bicyclo[2.2.1]hept-7-yl)-3-cyano-5-methyl-pyrrolo[1,2-b]pyridazine-6-carboxylic acid ethyl ester |
| 457 | 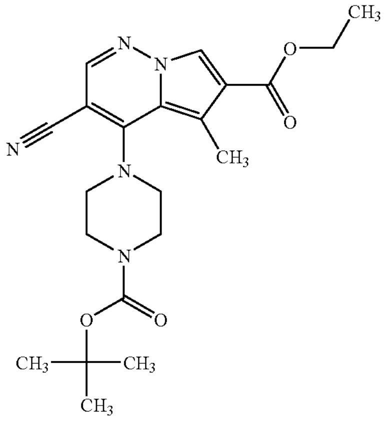 | 4-(4-tert-Butoxycarbonyl-piperazin-1-yl)-3-cyano-5-methyl-pyrrolo[1,2-b]pyridazine-6-carboxylic acid ethyl ester |

TABLE 2-continued

| Compound Structure | Compound Name |
|---|---|
| 458 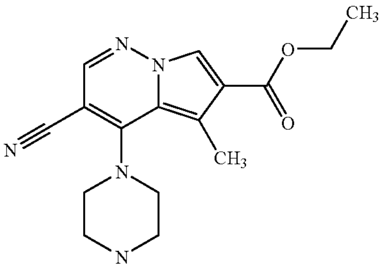 | 3-Cyano-5-methyl-4-piperazin-1-yl-pyrrolo[1,2-b]pyridazine-6-carboxylic acid ethyl ester |
| 459 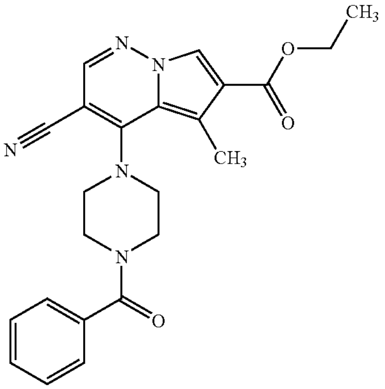 | 4-(4-Benzoyl-piperazin-1-yl)-3-cyano-5-methyl-pyrrolo[1,2-b]pyridazine-6-carboxylic acid ethyl ester |
| 460 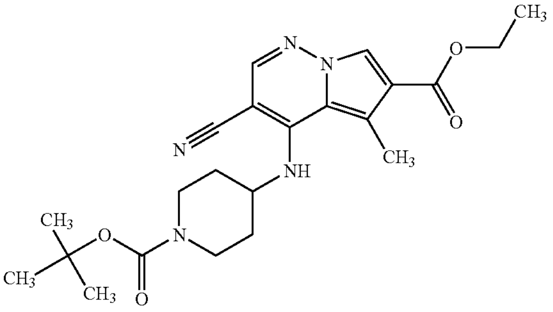 | 4-(1-tert-Butoxycarbonyl-piperidin-4-ylamino)-3-cyano-5-methyl-pyrrolo[1,2-b]pyridazine-6-carboxylic acid ethyl ester |
| 461 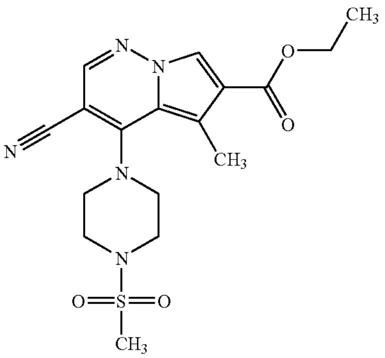 | 3-Cyano-4-(4-methanesulfonyl)-piperazin-1-yl)-5-methyl-pyrrolo[1,2-b]pyridazine-6-carboxylic acid ethyl ester |

TABLE 2-continued

| Compound Structure | | Compound Name |
|---|---|---|
| 462 | 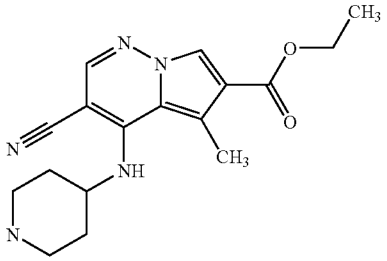 | 3-Cyano-5-methyl-4-(piperidin-4-ylamino)-pyrrolo[1,2-b]pyridazine-6-carboxylic acid ethyl ester |
| 463 | 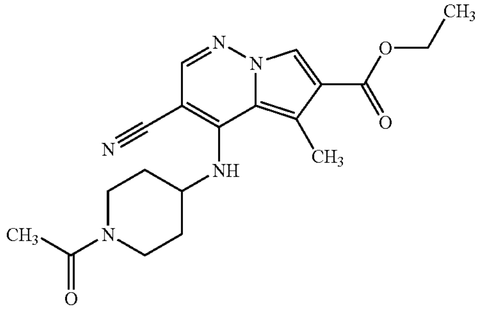 | 4-(1-Acetyl-piperidin-4-ylamino)-3-cyano-5-methyl-pyrrolo[1,2-b]pyridazine-6-carboxylic acid ethyl ester |
| 464 | 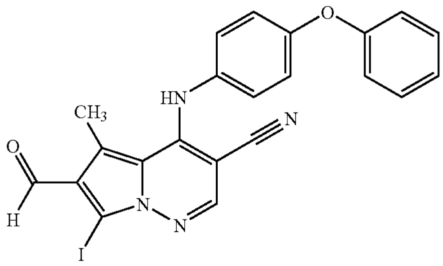 | 6-Formyl-7-iodo-5-methyl-4-(4-phenoxy-phenylamino)-pyrrolo[1,2-b]pyridazine-3-carbonitrile |
| 465 | 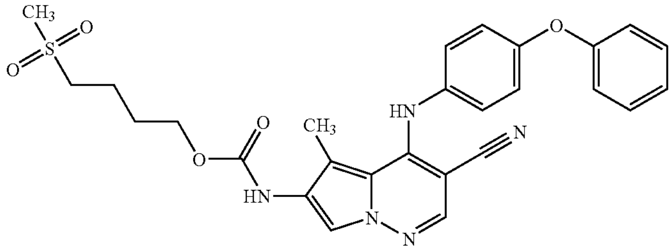 | [3-Cyano-5-methyl-4-(4-phenoxy-phenylamino)-pyrrolo[1,2-b]pyridazin-6-yl]-carbamic acid 4-methanesulfonyl-butyl ester |
| 466 | 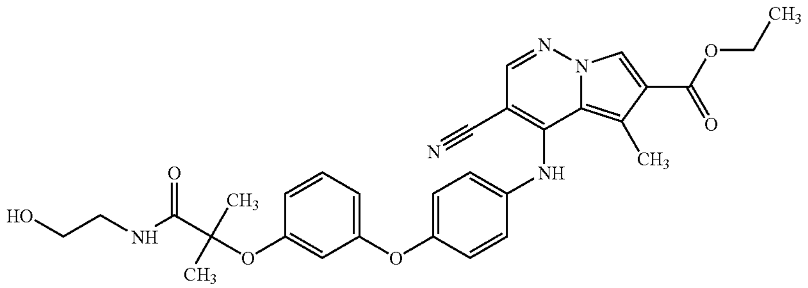 | 3-Cyano-4-(4-{3-[1-(2-hydroxy-ethylcarbamoyl)-1-methyl-ethoxy]-phenoxy}-phenylamino)-5-methyl-pyrrolo[1,2-b]pyridazine-6-carboxylic acid ethyl ester |

TABLE 2-continued

| | Compound Structure | Compound Name |
|---|---|---|
| 467 | 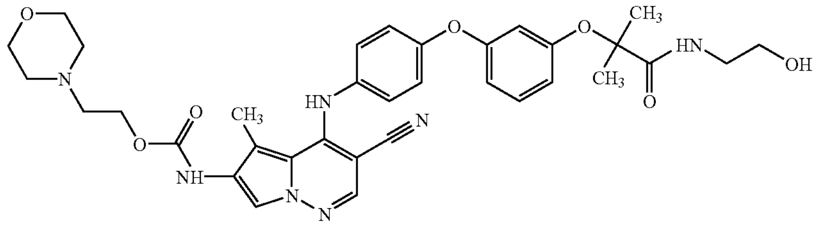 | [3-Cyano-4-(4-{3-[1-(2-hydroxy-ethylcarbamoyl)-1-methyl-ethoxy]-phenoxy}-phenylamino)-5-methyl-pyrrolo [1,2-b]pyridazin-6-yl]-carbamic acid 2-morpholin-4-yl-ethyl ester |
| 468 | 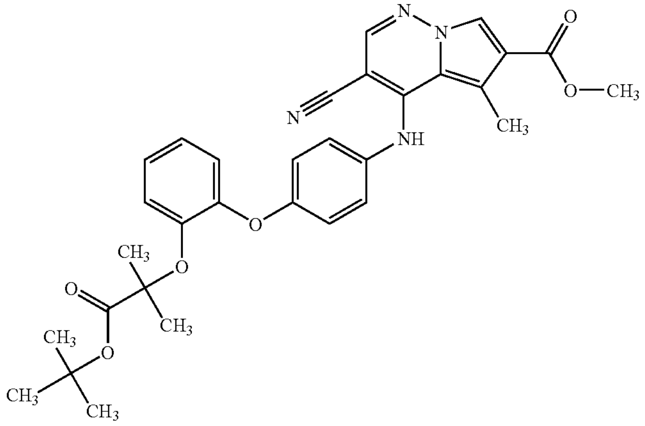 | 4-{4-[2-(1-tert-Butoxycarbonyl-1-methyl-ethoxy)-phenoxy]-phenylamino}-3-cyano-5-methyl-pyrrolo[1,2-b]pyridazine-6-carboxylic acid methyl ester |
| 469 | 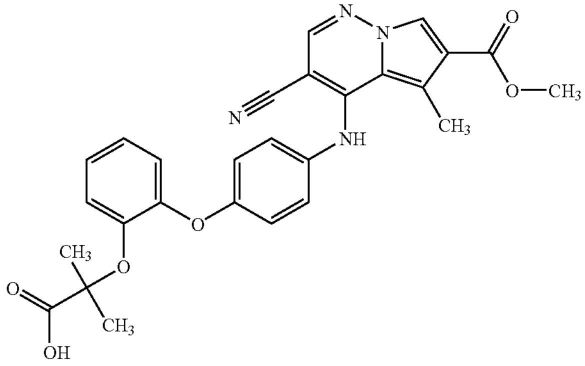 | 4-{4-[2-(1-Carboxy-1-methyl-ethoxy)-phenoxy]-phenylamino}-3-cyano-5-methyl-pyrrolo[1,2-b]pyridazine-6-carboxylic acid methyl ester |
| 470 | 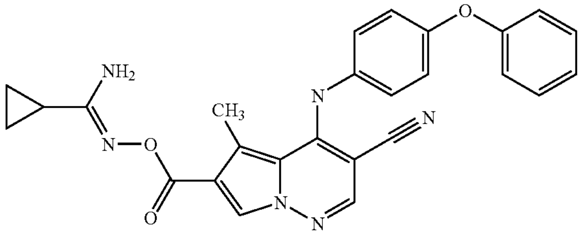 | |
| 471 | 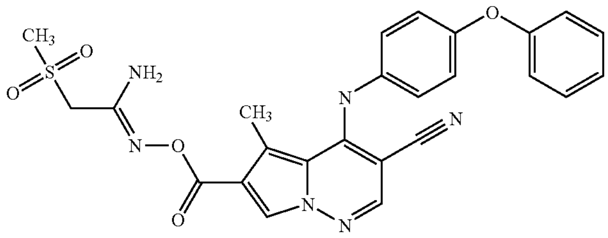 | |

TABLE 2-continued

| | Compound Structure | Compound Name |
|---|---|---|
| 472 | 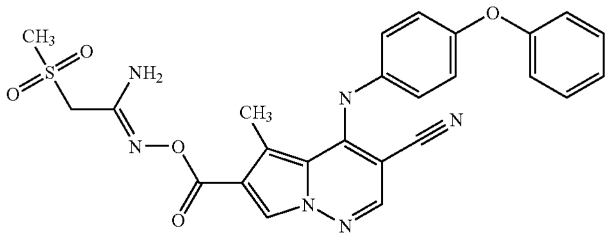 | |
| 473 | 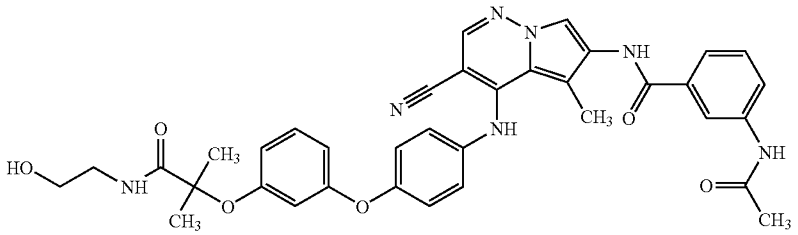 | 3-Acetylamino-N-[3-cyano-4-(4-{3-[1-(2-hydroxy-ethylcarbamoyl)-1-methyl-ethoxy]-phenoxy}-phenyl-amino)-5-methyl-pyrrolo[1,2-b]pyridazin-6-yl]-benzamide |
| 474 | 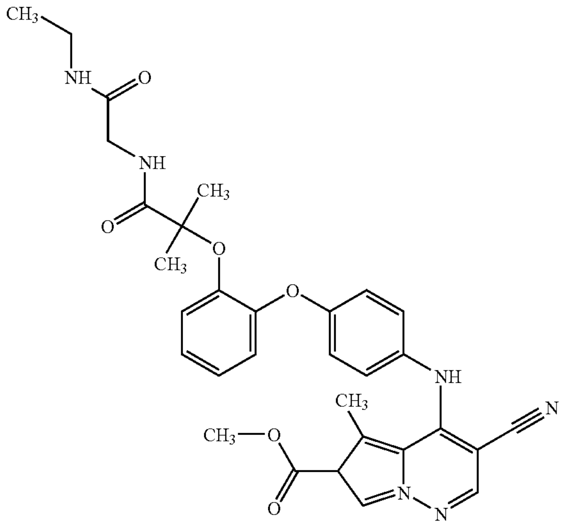 | 3-Cyano-4-(4-{2-[1-(ethylcarbamoylmethyl-carbamoyl)-1-methyl-ethoxy]-phenoxy}-phenylamino)-5-methyl-pyrrolo[1,2-b]pyridazine-6-carboxylic acid methyl ester |
| 475 | 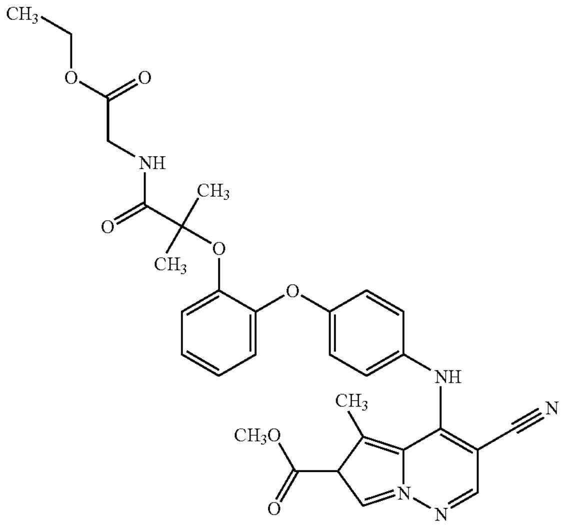 | 3-Cyano-4-(4-{2-[1-(ethoxycarbonylmethyl-carbamoyl)-1-methyl-ethoxy]-phenoxy}-phenylamino)-5-methyl-pyrrolo[1,2-b]pyridazine-6-carboxylic acid methyl ester |

TABLE 2-continued

| Compound Structure | | Compound Name |
|---|---|---|
| 476 | 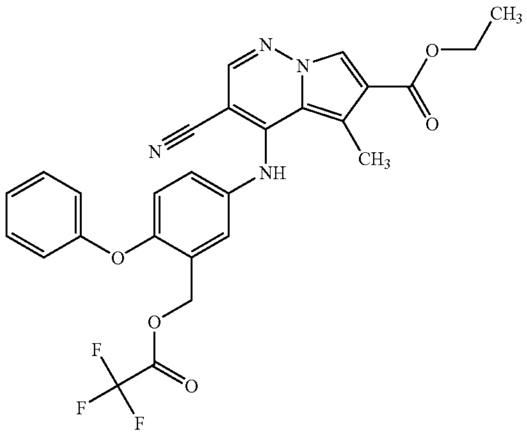 | 3-Cyano-5-methyl-4-[4-phenoxy-3-(2,2,2-trifluoro-acetoxymethyl)-phenylamino]-pyrrolo[1,2-b]pyridazine-6-carboxylic acid ethyl ester |
| 477 | 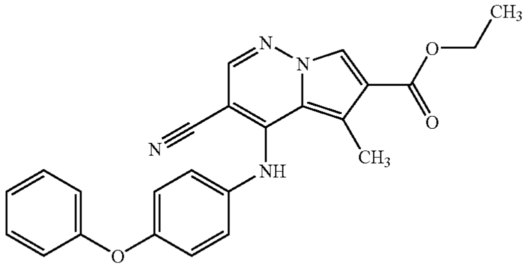 | 5-Amino-3-cyano-4-(4-phenoxy-phenylamino)-pyrrolo[1,2-b]pyridazine-6-carboxylic acid ethyl ester |
| 478 | 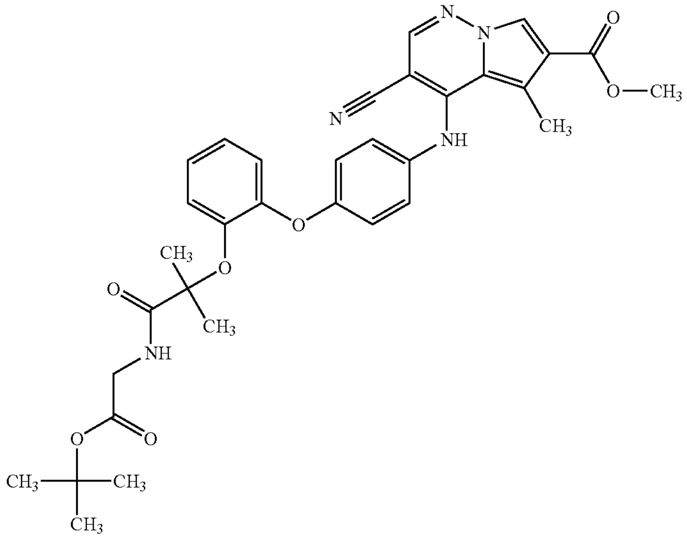 | 4-(4-{2-[1-(tert-Butoxycarbonylmethyl-carbamoyl)-1-methyl-ethoxy]-phenoxy}-phenylamino)-3-cyano-5-methyl-pyrrolo[1,2-b]pyridazine-6-carboxylic acid methyl ester |
| 479 | 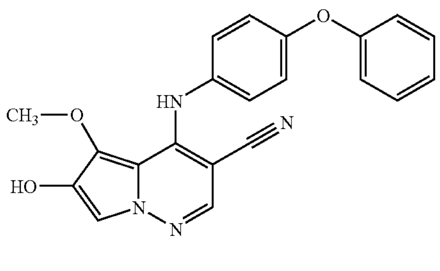 | 6-Hydroxy-5-methoxy-4-(4-phenoxy-phenylamino)-pyrrolo[1,2-b]pyridazine-3-carbonitrile |

TABLE 2-continued

| | Compound Structure | Compound Name |
|---|---|---|
| 480 | 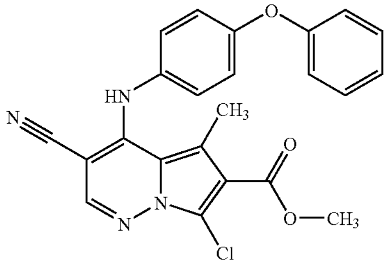 | 7-Chloro-3-cyano-5-methyl-4-(4-phenoxy-phenylamino)-pyrrolo[1,2-b]pyridazine-6-carboxylic acid methyl ester |
| 481 | 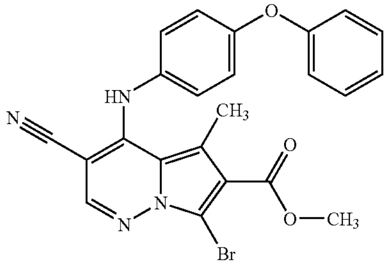 | 7-Bromo-3-cyano-5-methyl-4-(4-phenoxy-phenylamino)-pyrrolo[1,2-b]pyridazine-6-carboxylic acid methyl ester |
| 482 | 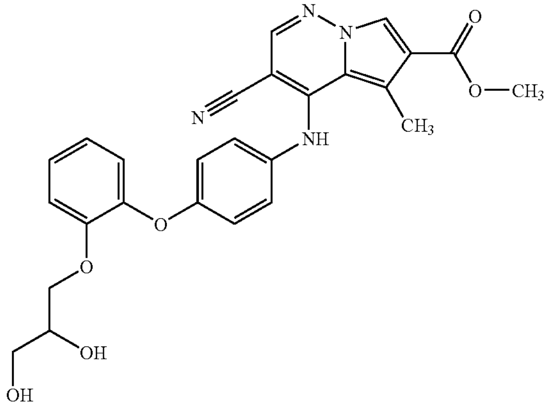 | 3-Cyano-4-{4-[2-(2,3-dihydroxy-propoxy)-phenoxy]-phenylamino}-5-methyl-pyrrolo[1,2-b]pyridazine-6-carboxylic acid methyl ester |
| 483 | 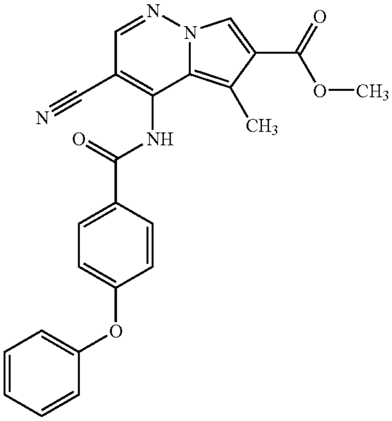 | 3-Cyano-5-methyl-4-(4-phenoxy-benzoylamino)-pyrrolo[1,2-b]pyridazine-6-carboxylic acid methyl ester |

TABLE 2-continued

| | Compound Structure | Compound Name |
|---|---|---|
| 484 | 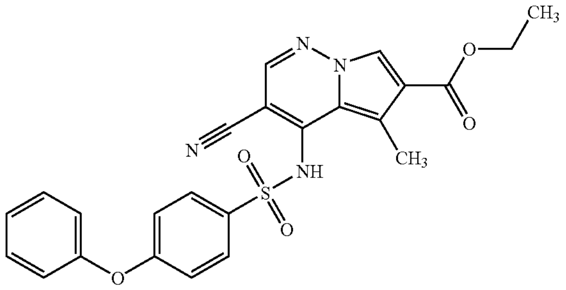 | 3-Cyano-5-methyl-4-(4-phenoxy-benzenesulfonylamino)-pyrrolo[1,2-b]pyridazine-6-carboxylic acid ethyl ester |
| 485 | 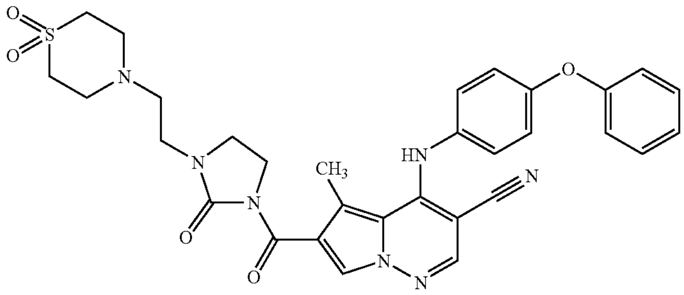 | 6-{3-[2-(1,1-Dioxo-116-thiomorpholin-4-yl)-ethyl]-2-oxo-imidazoline-1-carbonyl}-5-methyl-4-(4-phenoxy-phenylamino)-pyrrolo[1,2-b]pyridazine-3-carbonitrile |
| 486 | 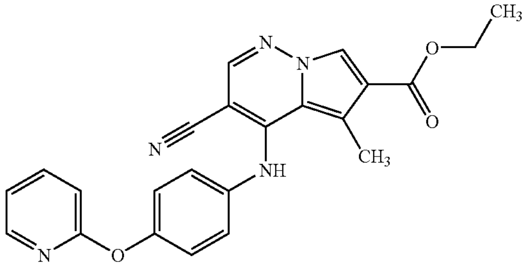 | 3-Cyano-5-methyl-4-[4-(pyridin-2-yloxy)-phenylamino]-pyrrolo[1,2-b]pyridazine-6-carboxylic acid ethyl ester |
| 487 | 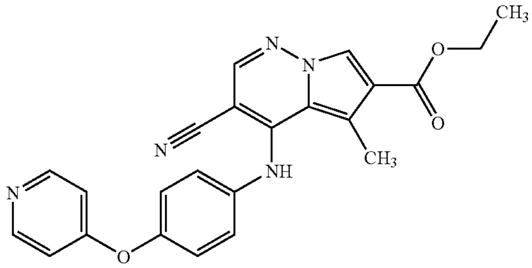 | 3-Cyano-5-methyl-4-[4-(pyridin-4-yloxy)-phenylamino]-pyrrolo[1,2-b]pyridazine-6-carboxylic acid ethyl ester |
| 488 | 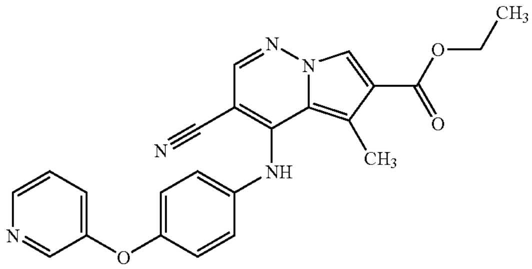 | 3-Cyano-5-methyl-4-[4-(pyridin-3-yloxy)-phenylamino]-pyrrolo[1,2-b]pyridazine-6-carboxylic acid ethyl ester |

TABLE 2-continued

| | Compound Structure | Compound Name |
|---|---|---|
| 489 | 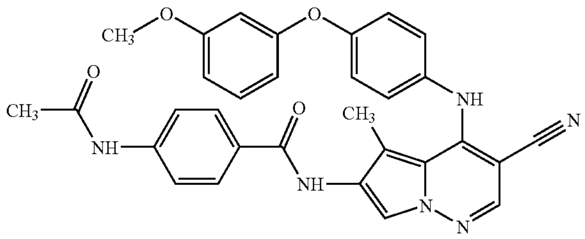 | 4-Acetylamino-N-{3-cyano-4-[4-(3-methoxy-phenoxy)-phenylamino]-5-methyl-pyrrolo[1,2-b]pyridazin-6-yl}-benzamide |
| 490 | 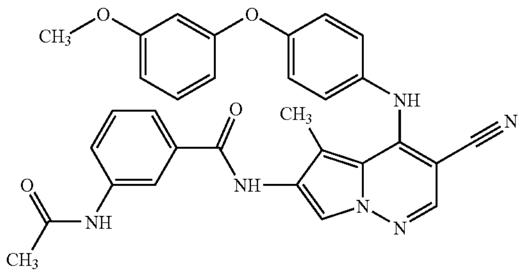 | 3-Acetylamino-N-{3-cyano-4-[4-(3-methoxy-phenoxy)-phenylamino]-5-methyl-pyrrolo[1,2-b]pyridazin-6-yl}-benzamide |
| 491 | 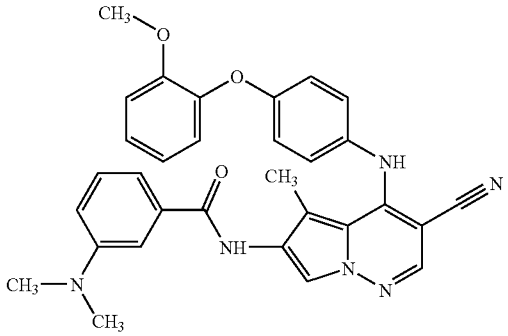 | N-{3-Cyano-4-[4-(2-methoxy-phenoxy)-phenylamino]-5-methyl-pyrrolo[1,2-b]pyridazin-6-yl}-3-dimethyl-amino-benzamide |
| 492 | 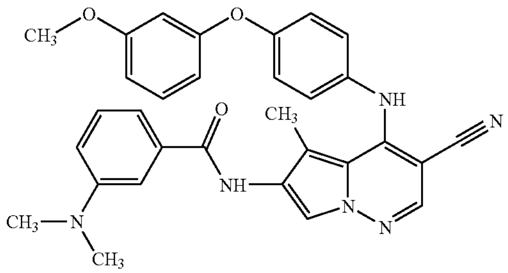 | N-{3-Cyano-4-[4-(3-methoxy-phenoxy)-phenylamino]-5-methyl-pyrrolo[1,2-b]pyridazin-6-yl}-3-dimethyl-amino-benzamide |
| 493 | 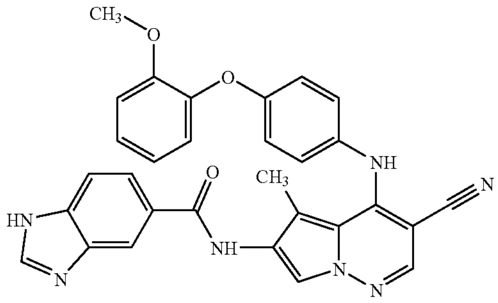 | 1H-Benzoimidazole-5-carboxylic acid {3-cyano-4-[4-(2-methoxy-phenoxy)-phenylamino]-5-methyl-pyrrolo [1,2-b]pyridazin-6-yl}-amide |

TABLE 2-continued

| | Compound Structure | Compound Name |
|---|---|---|
| 494 | 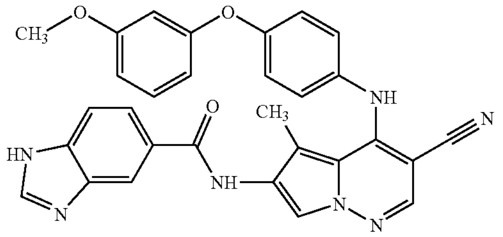 | 1H-Benzoimidazole-5-carboxylic acid {3-cyano-4-[4-(3-methoxy-phenoxy)-phenylamino]-5-methyl-pyrrolo [1,2-b]pyridazin-6-yl}-amide |
| 495 | 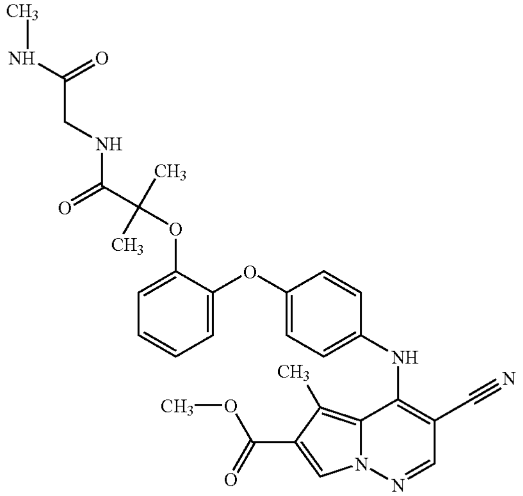 | 3-Cyano-4-(4-{2-[1-(ethylcarbamoylmethyl-carbamoyl)-1-methyl-ethoxy]-phenyoxy}-phenylamino)-5-methyl-pyrrolo[1,2-b]pyridazine-6-carboxylic acid methyl ester |
| 496 | 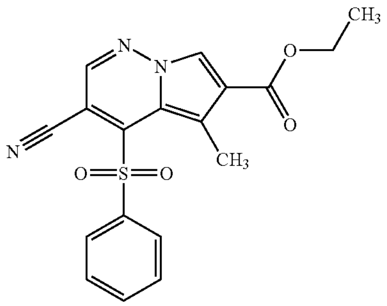 | 4-Benzenesulfonyl-3-cyano-5-methyl-pyrrolo[1,2-b]pyridazine-6-carboxylic acid ethyl ester |
| 497 | 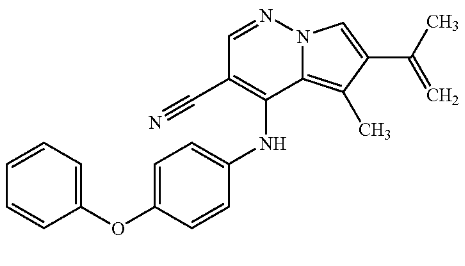 | 6-Isopropenyl-5-methyl-4-(4-phenoxy-phenylamino)-pyrrolo[1,2-b]pyridazine-3-carbonitrile |
| 498 | 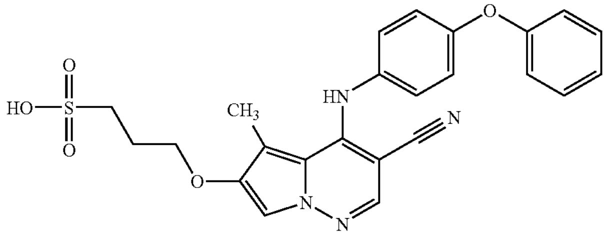 | 3-[3-Cyano-5-methyl-4-(4-phenoxy-phenylamino)-pyrrolo[1,2-b]pyridazin-6-yloxy]-propane-1-sulfonic acid |

TABLE 2-continued

| | Compound Structure | Compound Name |
|---|---|---|
| 499 | 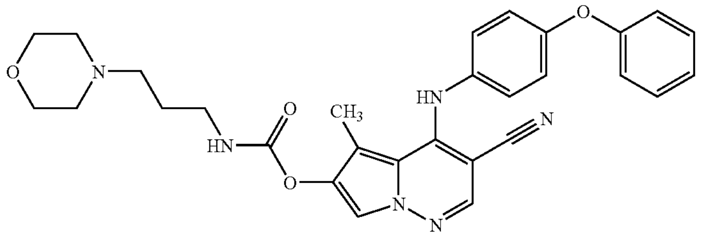 | (3-Morpholin-4-yl-propyl)-carbamic acid 3-cyano-5-methyl-4-(4-phenoxy-phenylamino)-pyrrolo[1,2-b] pyridazin-6-yl ester |
| 500 | 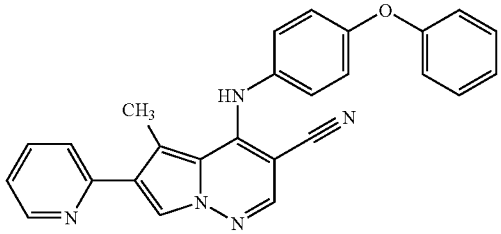 | 5-Methyl-4-(4-phenoxy-phenylamino)-6-pyridin-2-yl-pyrrolo[1,2-b]pyridazine-3-carbonitrile |
| 501 | 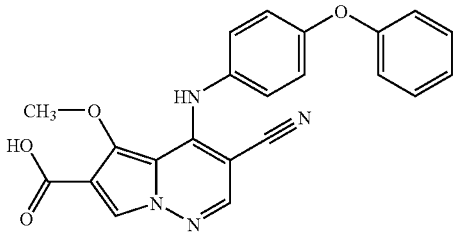 | 3-Cyano-5-methoxy-4-(4-phenoxy-phenylamino)-pyrrolo[1,2-b]pyridazine-6-carboxylic acid |
| 502 | 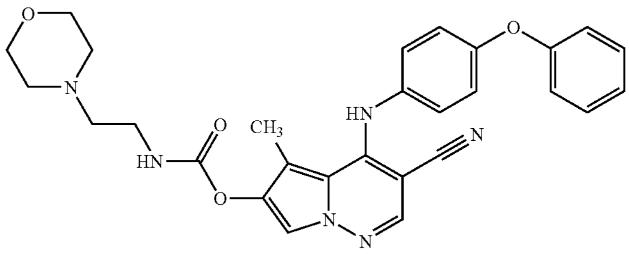 | (2-Morpholin-4-yl-ethyl)-carbamic acid 3-cyano-5-methyl-4-(4-phenoxy-phenylamino)-pyrrolo[1,2-b] pyridazin-6-yl ester |
| 503 | 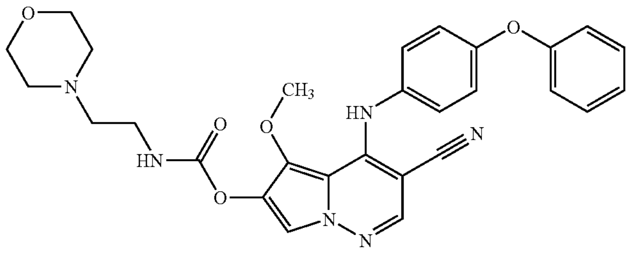 | (2-Morpholin-4-yl-ethyl)-carbamic acid 3-cyano-5-methoxy-4-(4-phenoxy-phenylamino)-pyrrolo[1,2-b]pyridazin-6-yl ester |
| 504 | 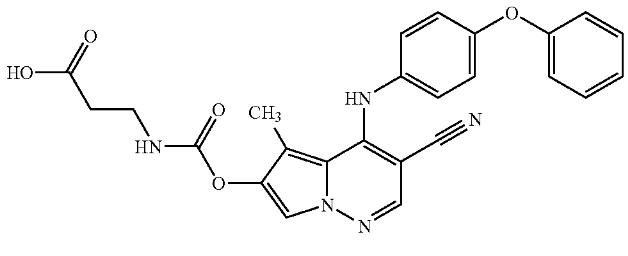 | 3-[3-Cyano-5-methyl-4-(4-phenoxy-phenylamino)-pyrrolo[1,2-b]pyridazin-6-yloxycarbonylamino]-propionic acid |

TABLE 2-continued

| | Compound Structure | Compound Name |
|---|---|---|
| 505 | 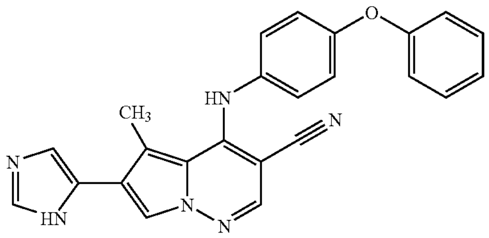 | 6-(3H-imidazol-4-yl)-5-methyl-4-(4-phenoxy-phenylamino)-pyrrolo[1,2-b]pyridazine-3-carbonitrile |
| 506 | 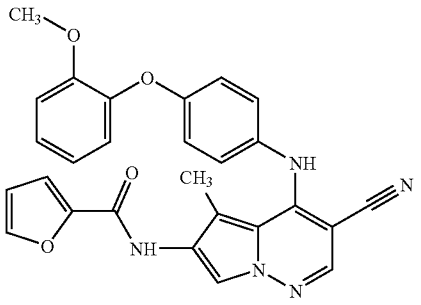 | Furan-2-carboxylic acid {3-cyano-4-[4-(2-methoxy-phenoxy)-phenylamino]-5-methyl-pyrrolo[1,2-b]pyridazin-6-yl}-amide |
| 507 | 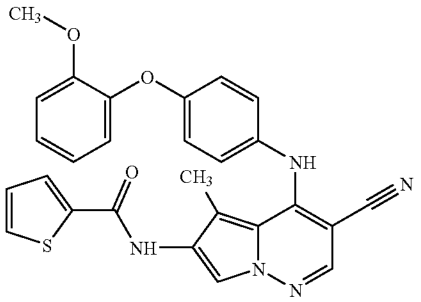 | Thiophene-2-carboxylic acid {3-cyano-4-[4-(2-methoxy-phenoxy)-phenylamino]-5-methyl-pyrrolo[1,2-b]pyridazin-6-yl}-amide |
| 508 | 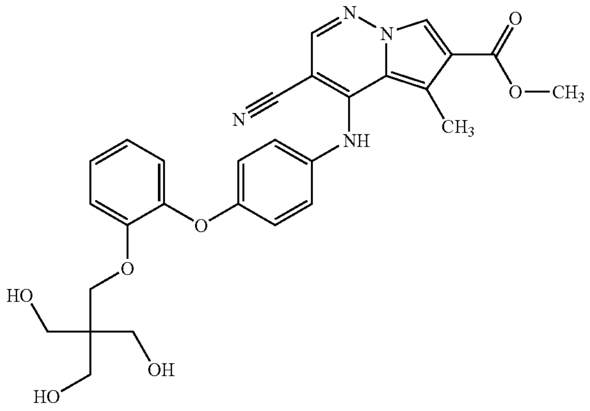 | 3-Cyano-4-{4-[2-(3-hydroxy-2,3-bis-hydroxymethyl-propoxy)-phenoxy]-phenylamino}-5-methyl-pyrrolo[1,2-b]pyridazine-6-carboxylic acid methyl ester |
| 509 | 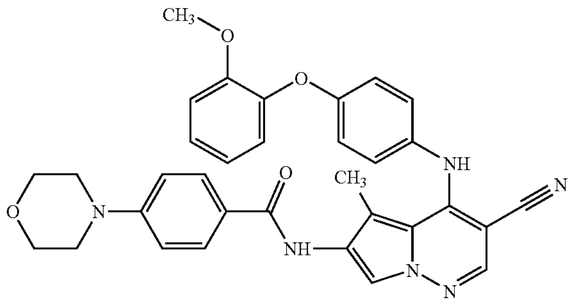 | N-{3-Cyano-4-[4-(2-methoxy-phenoxy)-phenylamino]-5-methyl-pyrrolo[1,2-b]pyridazin-6-yl}-4-morpholin-4-yl-benzamide |

TABLE 2-continued

| | Compound Structure | Compound Name |
|---|---|---|
| 510 | 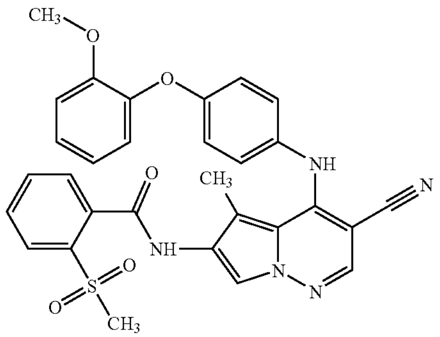 | N-{3-Cyano-4-[4-(2-methoxy-phenoxy)-phenylamino]-5-methyl-pyrrolo[1,2-b]pyridazin-6-yl}-2-methane-sulfonyl-benzamide |
| 511 | 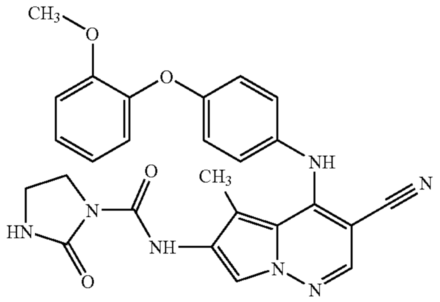 | 2-Oxo-imidazolidine-1-carboxylic acid {3-cyano-4-[4-(2-methoxy-phenoxy)-phenylamino]-5-methyl-pyrrolo [1,2-b]pyridazin-6-yl}-amide |
| 512 | 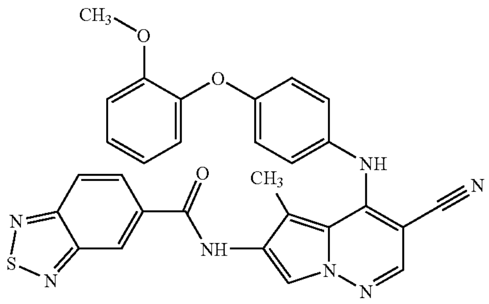 | Benzo[1,2,5]thiadiazole-5-carboxylic acid {3-cyano-4-[4-(2-methoxy-phenoxy)-phenylamino]-5-methyl-pyrrolo[1,2-b]pyridazin-6-yl}-amide |
| 513 | 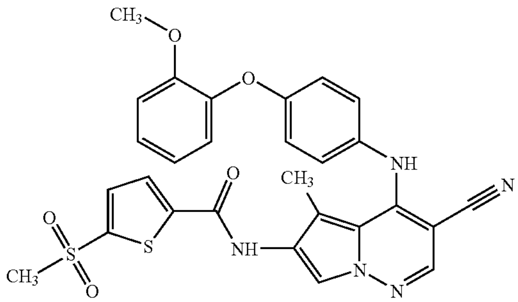 | 5-Methanesulfonyl-thiophene-2-carboxylic acid {3-cyano-4-[4-(2-methoxy-phenoxy)-phenylamino]-5-methyl-pyrrolo[1,2-b]pyridazin-6-yl}-amide |
| 514 | 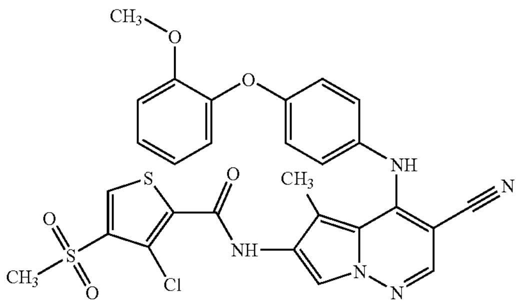 | 3-Chloro-4-methanesulfonyl-thiophene-2-carboxylic acid {3-cyano-4-[4-(2-methoxy-phenoxy)-phenylamino]-5-methyl-pyrrolo[1,2-b]pyridazin-6-yl}-amide |

TABLE 2-continued

| | Compound Structure | Compound Name |
|---|---|---|
| 515 | 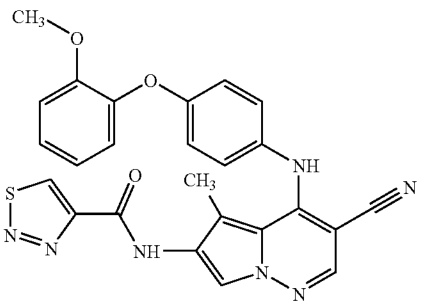 | [1,2,3]Thiadiazole-4-carboxylic acid {3-cyano-4-[4-(2-methoxy-phenoxy)-phenylamino]-5-methyl-pyrrolo [1,2-b]pyridazin-6-yl}-amide |
| 516 | 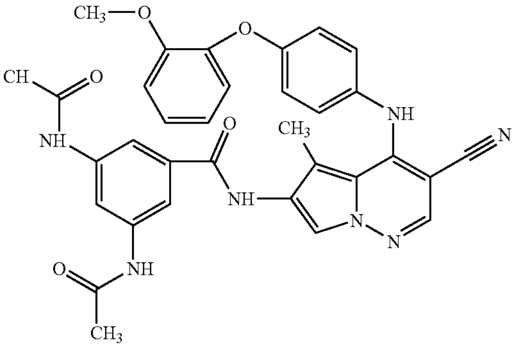 | 3,5-Bis-acetylamino-N-{3-cyano-4-[4-(2-methoxy-phenoxy)-phenylamino]-5-methyl-pyrrolo[1,2-b]pyridazin-6-yl}-benzamide |
| 517 | 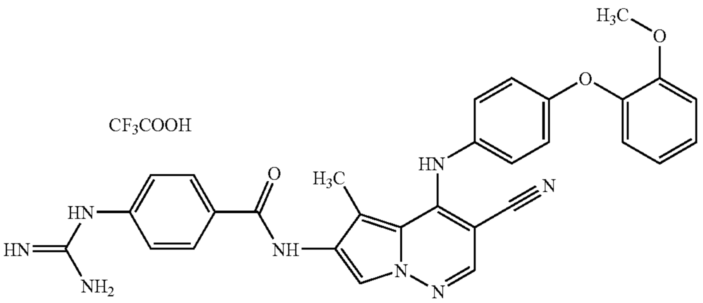 | N-{3-Cyano-4-[4-(2-methoxy-phenoxy)-phenylamino]-5-methyl-pyrrolo[1,2-b]pyridazin-6-yl}-4-guanidino-benzamide; trifluoro-acetic acid salt |
| 518 | 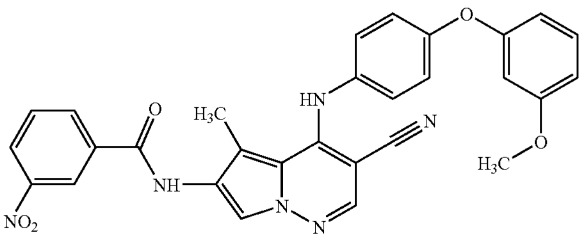 | N-{3-Cyano-4-[4-(3-methoxy-phenoxy)-phenylamino]-5-methyl-pyrrolo[1,2-b]pyridazin-6-yl}-3-nitro-benzamide |
| 519 | 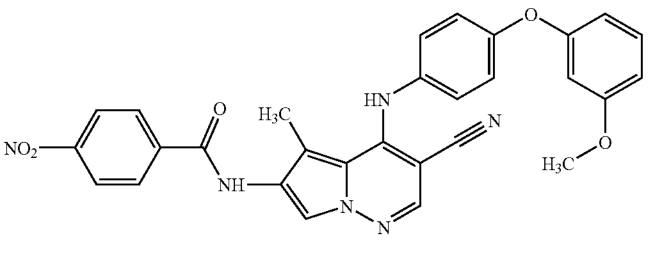 | N-{3-Cyano-4-[4-(3-methoxy-phenoxy)-phenylamino]-5-methyl-pyrrolo[1,2-b]pyridazin-6-yl}-4-nitro-benzamide |

TABLE 2-continued

| | Compound Structure | Compound Name |
|---|---|---|
| 520 | 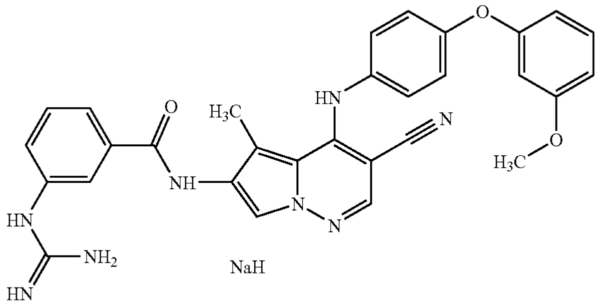 $NaH$ | N-{3-Cyano-4-[4-(2-methoxy-phenoxy)-phenylamino]-5-methyl-pyrrolo[1,2-b]pyridazin-6-yl}-3-guanidino-benzamide; trifluoro-acetic acid salt |
| 521 | 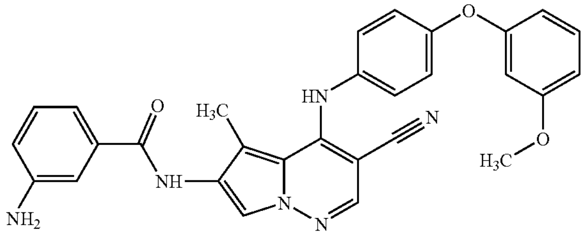 | 3-Amino-N-{3-cyano-4-[4-(3-methoxy-phenoxy)-phenylamino]-5-methyl-pyrrolo[1,2-b]pyridazin-6-yl}-benzamide |
| 522 | 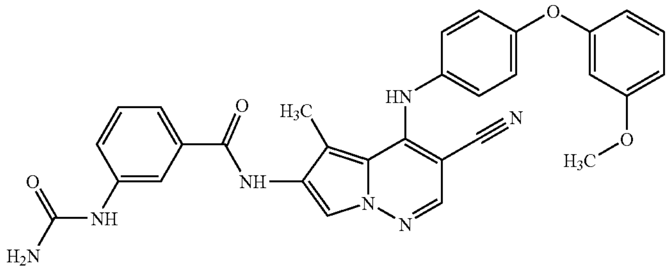 | N-{3-Cyano-4-[4-(3-methoxy-phenoxy)-phenylamino]-5-methyl-pyrrolo[1,2-b]pyridazin-6-yl}-3-ureidobenzamide |
| 523 | 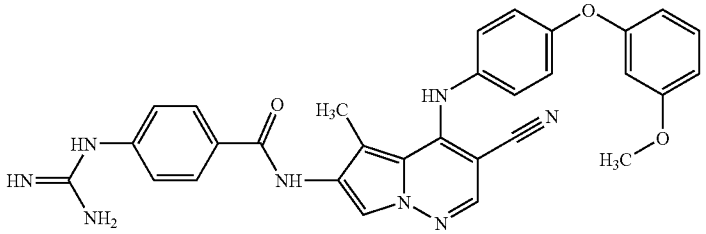 | N-{3-Cyano-4-[4-(3-methoxy-phenoxy)-phenylamino]-5-methyl-pyrrolo[1,2-b]pyridazin-6-yl}-4-guanidinobenzamide |
| 524 | 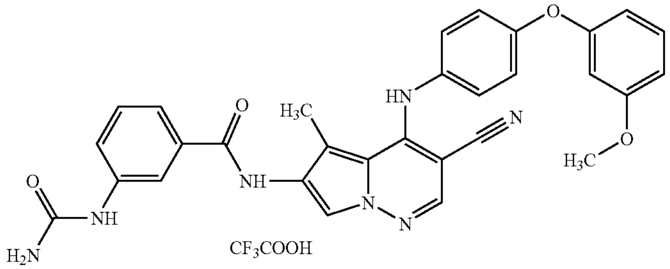 $CF_3COOH$ | N-{3-Cyano-4-[4-(3-methoxy-phenoxy)-phenylamino]-5-methyl-pyrrolo[1,2-b]pyridazin-6-yl}-3-ureidobenzamide, trifluoro-acetic acid salt |

TABLE 2-continued

| | Compound Structure | Compound Name |
|---|---|---|
| 525 | $CF_3COOH$ 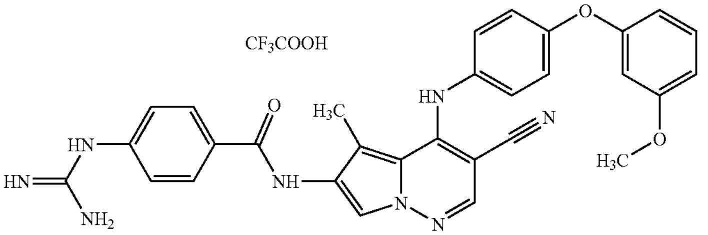 | N-{3-Cyano-4-[4-(3-methoxy-phenoxy)-phenylamino]-5-methyl-pyrrolo[1,2-b]pyridazin-6-yl}-4-guanidinobenzamide, trifluoro-acetic acid salt |
| 526 | 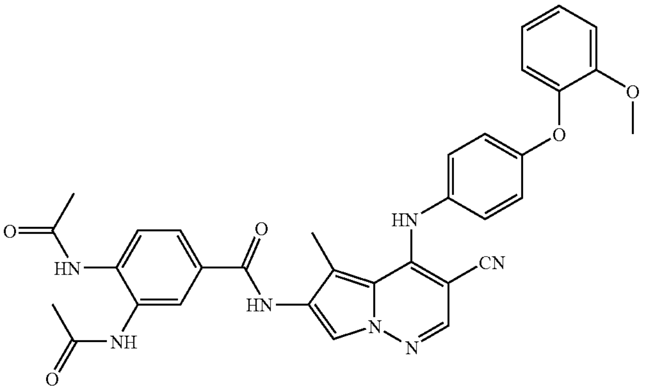 | 3,4-Bis-acetylamino-N-{3-cyano-4-[4-(2-methoxy-phenoxy)-phenylamino]-5-methyl-pyrrolo[1,2-b]pyridazin-6-yl}-benzamide |
| 527 | 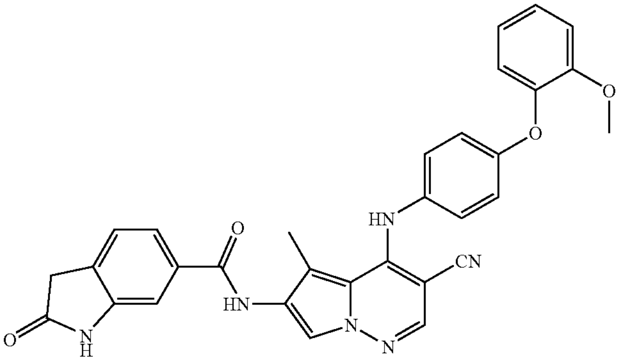 | 2-Oxo-2,3-dihydro-1H-indole-6-carboxylic acid {3-cyano-4-[4-(2-methoxy-phenoxy)-phenylamino]-5-methyl-pyrrolo[1,2-b]-pyridazin-6-yl}-amide |
| 528 | 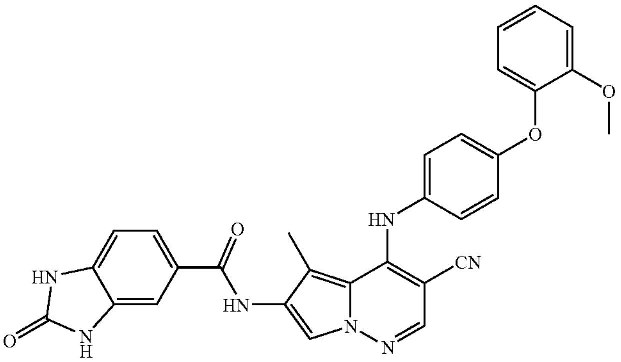 | 2-Oxo-2,3-dihydro-1H-benzoimidazole-5-carboxylic acid {3-cyano-4-[4-(2-methoxy-phenoxy)-phenylamino]-5-methyl-pyrrolo[1,2-b]pyridazin-6-yl}-amide |

TABLE 2-continued

| | Compound Structure | Compound Name |
|---|---|---|
| 529 | 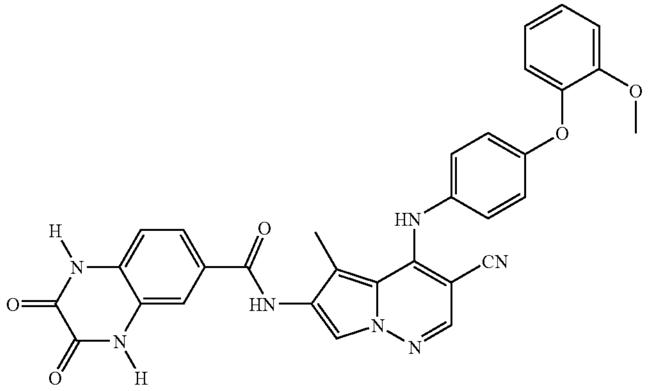 | 2,3-Dioxo-1,2,3,4-tetrahydro-quinoxaline-6-carboxylic acid {3-cyano-4-[4-(2-methoxy-phenoxy)-phenylamino]-5-methyl-pyrrolo[1,2-b]pyridazin-6-yl}-amide |
| 530 | 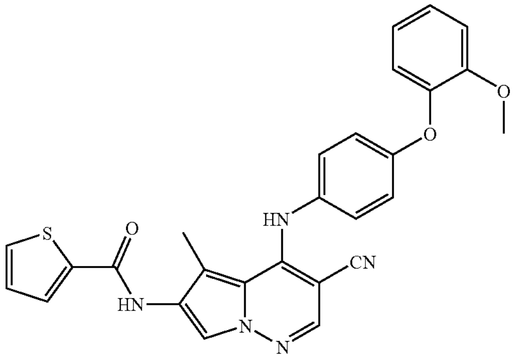 | Thiophene-2-carboxylic acid {3-cyano-4-[4-(2-methoxy-phenoxy)-phenylamino]-5-methyl-pyrrolo[1,2-b]pyridazin-6-yl}-amide |
| 531 | 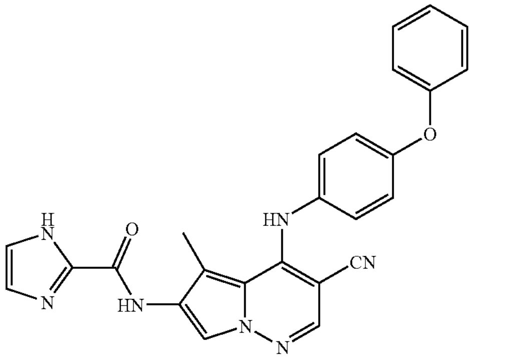 | 1H-imidazole-2-carboxylic acid [3-cyano-5-methyl-4-(4-phenoxy-phenylamino)-pyrrolo[1,2-b]pyridazin-6-yl]-amide |
| 532 | 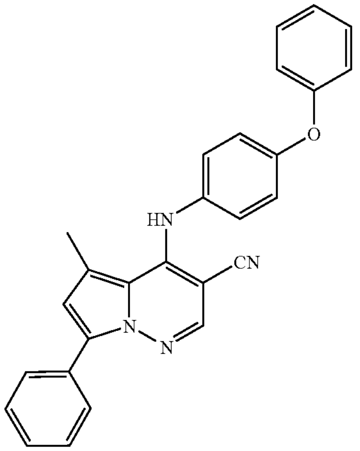 | 5-Methyl-4-(4-phenoxy-phenylamino)-7-phenyl-pyrrolo[1,2-b]pyridazine-3-carbonitrile |

TABLE 2-continued

| | Compound Structure | Compound Name |
|---|---|---|
| 533 | 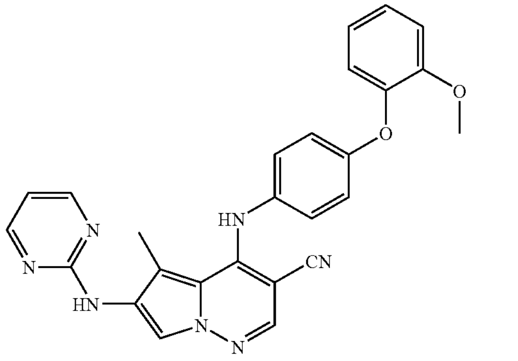 | 4-[4-(2-Methoxy-phenoxy)-phenylamino]-5-methyl-6-(pyrimidin-2-ylamino)-pyrrolo[1,2-b]pyridazine-3-carbonitrile |
| 534 | 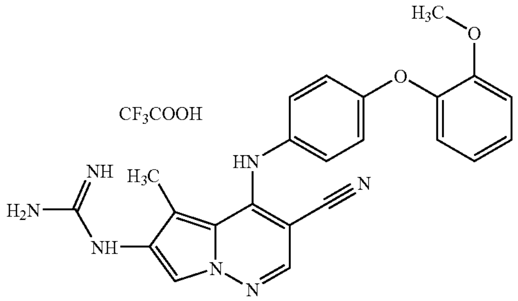 | N-{3-Cyano-4-[4-(2-methoxy-phenyoxy)-phenylamino]-5-methyl-pyrrolo[1,2-b]pyridazin-6-yl}-guanidine; trifluoro-acetic acid salt |
| 535 | 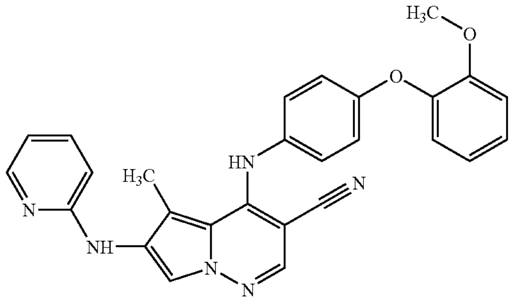 | 4-[4-(2-Methoxy-phenoxy)-phenylamino]-5-methyl-6-(pyridin-2-ylamino)-pyrrolo[1,2-b]pyridazine-3-carbonitrile |
| 536 | 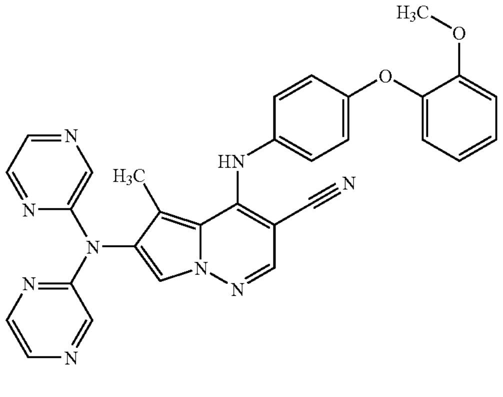 | 6-(Di-pyrazin-2-yl-amino)-4-[4-(2-methoxy-phenoxy)-phenylamino]-5-methyl-pyrrolo[1,2-b]pyridazine-3-carbonitrile |

TABLE 2-continued

| Compound Structure | | Compound Name |
|---|---|---|
| 537 | 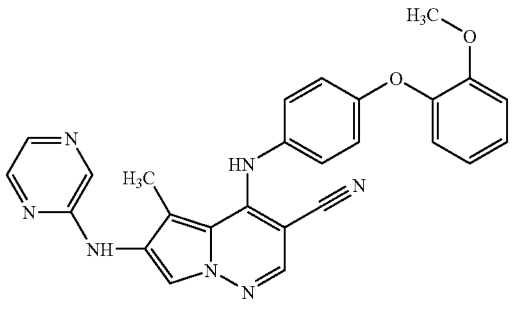 | 4-[4-(2-Methoxy-phenoxy)-phenylamino]-5-methyl-6-(pyrazin-2-ylamino)-pyrrolo[1,2-b]pyridazine-3-carbonitrile |
| 538 | 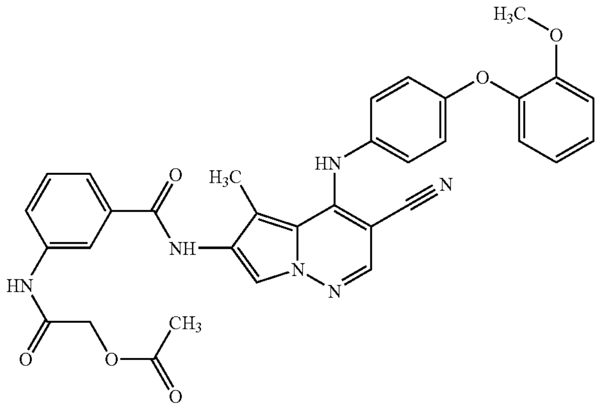 | Acetic acid (3-{3-cyano-4-[4-(2-methoxy-phenoxy)-phenylamino]-5-methyl-pyrrolo[1,2-b]pyridazin-6-yl-carbamoyl}-phenylcarbamoyl)-methyl ester |
| 539 | 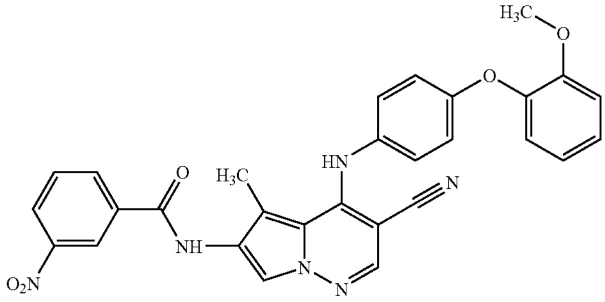 | N-{3-Cyano-4-[4-(2-methoxy-phenoxy)-phenylamino]-5-methyl-pyrrolo[1,2-b]pyridazin-6-yl}-3-nitro-benzamide |
| 540 | 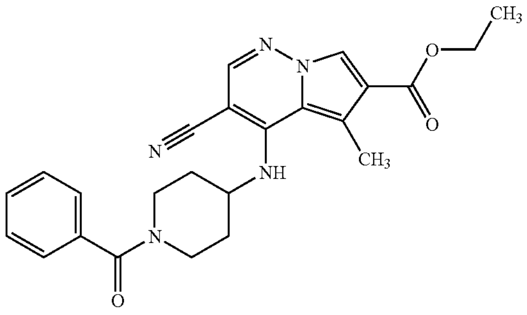 | 4-(1-Benzoyl-piperidin-4-ylamino)-3-cyano-5-methyl-pyrrolo[1,2-b]pyridazine-6-carboxylic acid ethyl ester |

TABLE 2-continued

| | Compound Structure | Compound Name |
|---|---|---|
| 541 | 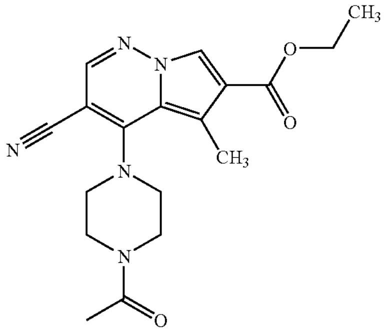 | 4-(4-Acetyl-piperazin-1-yl)-3-cyano-5-methyl-pyrrolo[1,2-b]pyridazine-6-carboxylic acid ethyl ester |
| 542 | 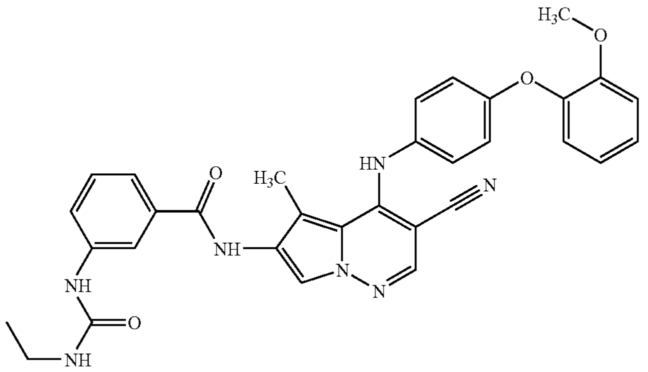 | N-{3-Cyano-4-[4-(2-methoxy-phenoxy)-phenylamino]-5-methyl-pyrrolo[1,2-b]pyridazin-6-yl}-3-(3-ethyl-ureido)-benzamide |

EXAMPLE 543

3-Cyano-5,7-dimethyl-4-(4-phenoxy-phenylamino)-pyrrolo[1,2-b]pyridazine-6-carboxylic Acid Ethyl Ester

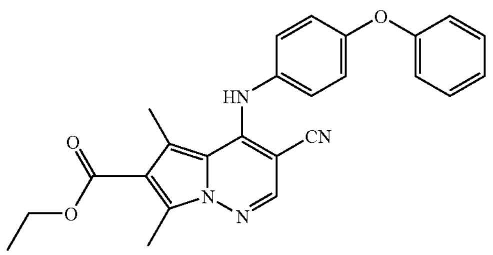

LCMS4: 97.5% at 2.05 min (retention time) (PrinctonSPHER HTS 60A5U column, 50×3.0 mm, part# 050030-1570, eluting with 25–100% aqueous acetonitrile containing 0.1% trifluoroacetic acid, 1.5 mL/min. It ramps to 100% acetonitrile at 2.2 min and holds till 3.2 min. Collection stopped at 3.4 min). MS (ELS): m/z 427.1 $[M+H]^+$.

EXAMPLE 544

7-Chloro-3-cyano-5-methyl-4-(4-phenoxy-phenylamino)-pyrrolo[1,2-b]pyridazine-6-carboxylic Acid Methyl Ester

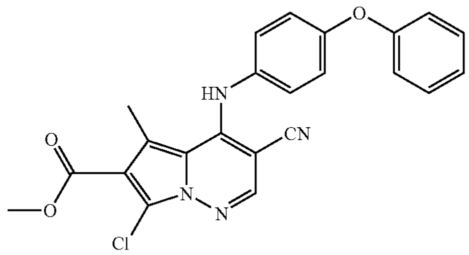

LCMS5: 100% at 1.65 min (retention time) (Phenomenex Luna C-8 columns 5 um, 3×50 mm, eluting with 25–100% aqueous acetonitrile containing 0.1% formic acid and 0.01% trifluoroacetic acid, 6.0 mL/min. It ramps to 100% acetonitrile at 1.8 min and holds till 2.25 min. Collection stopped at 2.35 min). MS (ELS): m/z 433.1 $[M+H]^+$.

Structure was also confirmed by X-ray crystallography.

EXAMPLE 545

7-Bromo-3-cyano-5-methyl-4-(4-phenoxy-phenylamino)-pyrrolo[1,2-b]pyridazine-6-carboxylic Acid Methyl Ester

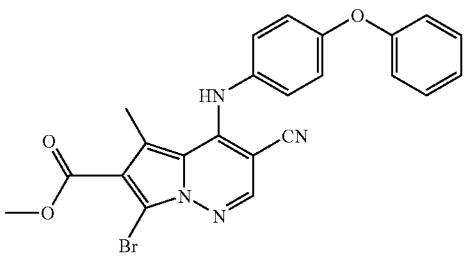

LCMS5: 100% at 1.68 min (retention time) (Phenomenex Luna C-8 columns 5 um, 3×50 mm, eluting with 25–100% aqueous acetonitrile containing 0.1% formic acid and 0.01% trifluoroacetic acid, 6.0 mL/min. It ramps to 100% acetonitrile at 1.8 min and holds till 2.25 min. Collection stopped at 2.35 min). MS (ELS): m/z 477.1 $[M+H]^+$.

EXAMPLE 546

3-Cyano-4-{4-[2-(2,3-dihydroxy-propoxy)-phenoxy]-phenylamino}-5-methyl-pyrrolo[1,2-b]pyridazine-6-carboxylic Acid Methyl Ester

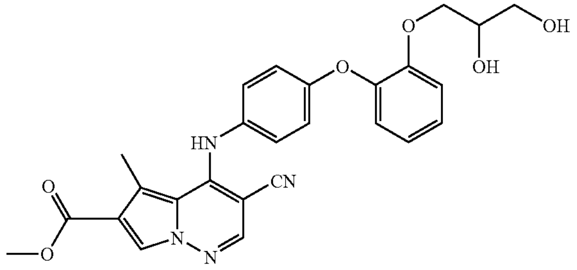

LCMS3: 99.6% at 1.37 min (retention time) (PrinctonSPHER HTS 60A5U column, 50×3.0 mm, part# 050030-1570, eluting with 25–100% aqueous acetonitrile over 2.4 min containing 0.1% trifluoroacetic acid, 1.5 mL/min. MS (ELS): m/z 489.3 $[M+H]^+$.

EXAMPLE 547

3-Cyano-4-{4-[2-(3-hydroxy-2,2-bis-hydroxymethyl-propoxy)-phenoxy]-phenylamino}-5-methyl-pyrrolo[1,2-b]pyridazine-6-carboxylic Acid Methyl Ester

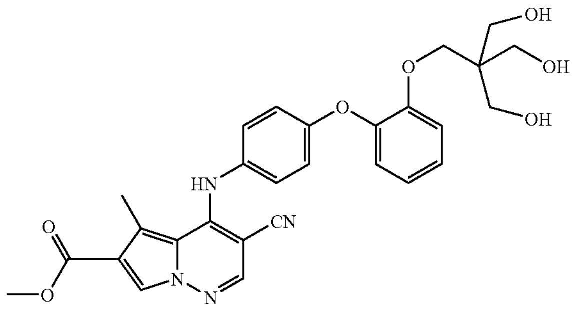

LCMS3: 99.5% at 1.21 min (retention time) (PrinctonSPHER HTS 60A5U column, 50×3.0 mm, part# 050030-1570, eluting with 25–100% aqueous acetonitrile over 2.4 min containing 0.1% trifluoroacetic acid, 1.5 mL/min. MS (ELS): m/z 533.3 $[M+H]^+$.

EXAMPLE 548

3-Cyano-4-{4-[2-(2-hydroxy-ethoxy)-phenoxy]-phenylamino}-5-methyl-pyrrolo[1,2-b]pyridazine-6-carboxylic Acid Methyl Ester

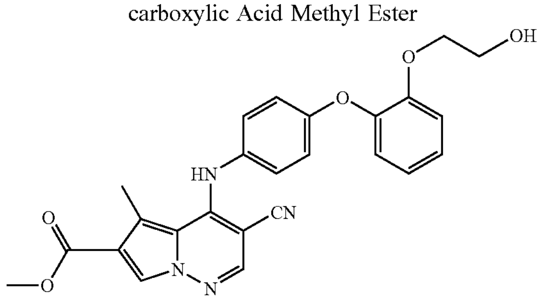

LCMS3: 99.8% at 1.60 min (retention time) (PrinctonSPHER HTS 60A5U column, 50×3.0 mm, part# 050030-1570, eluting with 25–100% aqueous acetonitrile over 2.4 min containing 0.1% trifluoroacetic acid, 1.5 mL/min. MS (ELS): m/z 459.3 $[M+H]^+$.

EXAMPLE 549

3-Cyano-4-(4-{2-[2-(2-hydroxy-ethoxy)-ethoxy]-phenoxy}-phenylamino)-5-methyl-pyrrolo]1,2-b]pyridazine-6-carboxylic Acid Methyl Ester

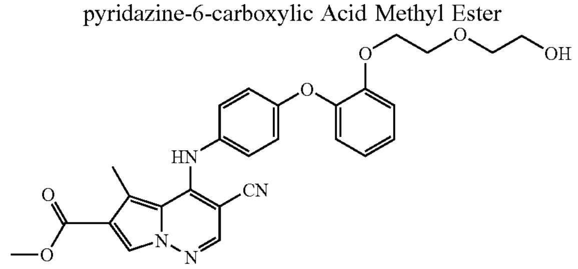

LCMS3: 99.8% at 1.70 min (retention time) (PrinctonSPHER HTS 60A5U column, 50×3.0 mm, part# 050030-1570, eluting with 25–100% aqueous acetonitrile over 2.4 min containing 0.1% trifluoroacetic acid, 1.5 mL/min. MS (ELS): m/z 503.3 $[M+H]^+$.

LCMS5:

Hardware

- Leap Technologies PAL.HTS injector with 4-Channel Eluate LC Valve System controlled by software
- Waters 1525 Binary HPLC system controlled by software
- Micromass ZQ Electrospray MS equipped with 4-channel-MUX capabilities controlled by software
- 4 Sedere Sedex 75 ELS detectors controlled by contact closure
- Ticoscen, Inc. Gas AC Mizer 2000 which turns off ELS gases controlled by contact closure
- Phenomenex Luna C-8 columns 5 um, 3×50 mm
- Alltech 2 um PEEK encased frits LC Method

| Time | % Solv. A | % Solv. B | Flow |
|---|---|---|---|
| 0.00 | 75.0 | 25.0 | 6.00 |
| 1.80 | 0.0 | 100.0 | 6.00 |
| 2.25 | 0.0 | 100.0 | 6.00 |
| 2.35 | 75.0 | 25.0 | 6.00 |

Solvent A = Water + 0.1% Formic Acid + 0.01% TFA
Solvent B = Acetonitrile + 0.1% Formic Acid + 0.01% TFA MS method—ES positive
Analysis in ESI mode with SIR monitoring
Source
Capillary: 3.0 kV
Cone: 25 V
Source Block Temp: 150°
Desolvation Temp: 300°
MS
Ion energy: 0.5 V
LM resolution: 15.0
HM resolution: 15.0
Multiplier: 650
Cone gas flow: 110 l/h The entire disclosures of the publications cited above are incorporated herein by reference. While certain preferred embodiments of the present invention have been described and specifically exemplified above, it is not intended that the invention be limited to such embodiments. Various modifications may be made to the invention without departing from the scope and spirit thereof as set forth in the following claims.

What is claimed is:

1. A compound selected from the group consisting of

3-Cyano-4-[4-(cyano-phenyl-methyl)-phenylamino]-5-methyl-pyrrolo[1,2-b]pyridazine-6-carboxylic acid ethyl ester, 2-[3-Cyano-6-ethoxycarbonyl-4-(4-phenoxy-phenylamino)-pyrrolo[1,2-b]pyridazin-5-ylmethyl]-malonic acid diethyl ester, 5-Methyl-4-(4-phenoxy-phenylamino)-6-phenylamino-pyrrolo[1,2-b]pyridazine-3-carbonitrile, 3-Cyano-5-methyl-4-(4-phenoxy-phenylamino)-pyrrolo[1,2-b]pyridazine-6-carboxylic acid (2-amino-phenyl)-amide, 6-(1H-Benzoimidazol-2-yl)-5-methyl-4-(4-phenoxy-phenylamino)-pyrrolo[1,2-b]pyridazine-3-carbonitrile, N-[3-Cyano-5-methyl-4-(4-phenoxy-phenylamino)-pyrrolo[1,2-b]pyridazin-6-yl]-2-fluoro-benzamide, 5-Methyl-6-(2-methyl-4-oxo-4H-quinazolin-3-yl)-4-(4-phenoxy-phenylamino)-pyrrolo[1,2-b]pyridazine-3-carbonitrile, 6-Benzylamino-5-methyl-4-(4-phenoxy-phenylamino)-pyrrolo[1,2-b]pyridazine-3-carbonitrile, N-[3-Cyano-5-methyl-4-(4-phenoxy-phenylamino)-pyrrolo[1,2-b]pyridazin-6-yl]-benzenesulfonamide, 6-[bis(phenylsulfonyl)amino]-5-methyl-4-[(4-phenoxyphenyl)amino]-7a-hydropyrrolo[1,2-e]pyridazine-3-carbonitrile, 6-(Benzothiazol-2-ylamino)-5-methyl-4-(4-phenoxy-phenylamino)-pyrrolo[1,2-b]pyridazine-3-carbonitrile, {4-[4-(6-Chloro-pyridazin-3-yloxy)-phenylamino]-3-cyano-5-methyl-pyrrolo[1,2-b]pyridazin-6-yl}-carbamic acid 2-morpholin-4-yl-ethyl ester, {3-Cyano-5-methyl-4-[4-(1-phenyl-1H-tetrazol-5-yloxy)-phenylamino]-pyrrolo[1,2-b]pyridazin-6-yl}-carbamic acid 2-morpholin-4-yl-ethyl ester, {3-Cyano-5-methyl-4-[4-(2-nitro-phenoxy)-phenylamino]-pyrrolo[1,2-b]pyridazin-6-yl}-carbamic acid 2-morpholin-4-yl-ethyl ester, {4-[4-(2-Amino-phenoxy)-phenylamino]-3-cyano-5-methyl-pyrrolo[1,2-b]pyridazin-6-yl}-carbamic acid 2-morpholin-4-yl-ethyl ester, {4-[4-(2-Acetylamino-phenoxy)-phenylamino]-3-cyano-5-methyl-pyrrolo[1,2-b]pyridazin-6-yl}-carbamic acid 2-morpholin-4-yl-ethyl ester, 5-Methyl-4-(4-phenoxy-phenylamino)-pyrrolo[1,2-b]pyridazine-3-carbonitrile,

[4-(4-Bromo-phenylamino)-3-cyano-5-methyl-pyrrolo[1,2-b]pyridazin-6-yl]-carbamic acid 2-morpholin-4-yl-ethyl ester, {3-Cyano-4-[4-(2,2-dimethyl-3-oxo-2,3-dihydro-benzofuran-7-yloxy)-phenylamino]-5-methyl-pyrrolo[1,2-b]pyridazin-6-yl}-carbamic acid 2-morpholin-4-yl-ethyl ester, 4-(4-{2-[1-(tert-Butoxycarbonylmethyl-carbamoyl)-1-methyl-ethoxy]-phenoxy}-phenylamino)-3-cyano-5-methyl-pyrrolo[1,2-b]pyridazine-6-carboxylic acid methyl ester, 4-(4-{2-[1-(Carboxymethyl-carbamoyl)-1-methyl-ethoxy]-phenoxy}-phenylamino)-3-cyano-5-methyl-pyrrolo[1,2-b]pyridazine-6-carboxylic acid methyl ester, 3-Cyano-4-(4-{2-[1-(ethylcarbamoylmethyl-carbamoyl)-1-methyl-ethoxy]-phenoxy}-phenylamino)-5-methyl-pyrrolo[1,2-b]pyridazine-6-carboxylic acid methyl ester, 4-(1-Benzyl-piperidin-4-ylamino)-3-cyano-5-methyl-pyrrolo[1,2-b]pyridazine-6-carboxylic acid methyl ester, 3-Cyano-5-methyl-4-(4-phenoxy-benzenesulfonyl)-pyrrolo[1,2-b]pyridazine-6-carboxylic acid ethylester, 3-Cyano-5-methoxy-4-(4-phenoxy-phenylamino)-pyrrolo[1,2-b]pyridazine-6-carboxylic acid ethyl ester, 3-Cyano-5-methyl-4-[4-phenoxy-3-(tetrahydro-pyran-2-yloxymethyl)-phenylamino]-pyrrolo[1,2-b]pyridazine-6-carboxylic acid ethyl ester, 3-Cyano-4-(3-hydroxymethyl-4-phenoxy-phenylamino)-5-methyl-pyrrolo[1,2-b]pyridazine-6-carboxylic acid ethyl ester, 6-(1-Hydroxy-1-methyl-ethyl)-5-methyl-4-(4-phenoxy-phenylamino)-pyrrolo[1,2-b]pyridazine-3-carbonitrile, Trifluoro-methanesulfonic acid 3-cyano-5-methyl-4-(4-phenoxy-phenylamino)-pyrrolo[1,2-b]pyridazin-6-yl ester, 6-(1-Hydroxy-1methyl-ethyl)-5-methoxy-4-(4-phenoxy-phenylamino)-pyrrolo[1,2-b]pyridazine-3-carbonitrile, 6-Hydroxy-5-methoxy-4-(4-phenoxy-phenylamino)-pyrrolo[1,2-b]pyridazine-3-carbonitrile, 5,6-Dimethoxy-4-(4-phenoxy-phenylamino)-pyrrolo[1,2-b]pyridazine-3-carbonitrile, 6-(4-Methoxy-phenyl)-5-methyl-4-(4-phenoxy-phenylamino)-pyrrolo[1,2-b]pyridazine-3-carbonitrile, 5-Methyl-4-(4-phenoxy-phenylamino)-6-phenyl-pyrrolo[1,2-b]pyridazine-3-carbonitrile, 3-Cyano-4-(4-phenoxy-phenylamino)-pyrrolo[1,2-b]pyridazine-6-carboxylic acid ethyl ester, 7-Bromo-3-cyano-4-(4-phenoxy-phenylamino)-pyrrolo[1,2-b]pyridazine-6-carboxylic acid ethyl ester, 7-Chloro-3-cyano-4-(4-phenoxy-phenylamino)-pyrrolo[1,2-b]pyridazine-6-carboxylic acid ethyl ester, 3-Cyano-4-(4-phenoxy-phenylamino)-pyrrolo[1,2-b]pyridazine-7-carboxylic acid ethyl ester, 7-Hydroxymethyl-4-(4-phenoxy-phenylamino)-pyrrolo[1,2-b]pyridazine-3-carbonitrile, 3-Cyano-4-(4-phenoxy-phenylamino)-pyrrolo[1,2-b]pyridazine-7-carboxylic acid, 3-Cyano-5,7-dimethyl-4-(4-phenoxy-phenylamino)-pyrrolo[1,2-b]pyridazine-6-carboxylic acid ethyl ester, 5-Methyl-6-(4-methyl-piperazin-1-ylmethyl)-4-(4-phenoxy-phenylamino)-pyrrolo[1,2-b]pyridazine-3-carbonitrile

[3-Cyano-5-methyl-4-(4-phenoxy-phenylamino)-pyrrolo[1,2-b]pyridazin-6-ylmethoxy]-acetic acid ethylester, 3-cyano-5-methyl-4-(4-phenoxy-phenylamino)-pyrrolo[1,2-b]pyridazine-6-carbonyl-N-hydroxylacetamidine, 6-(Hydroxyimino-methyl)-5-methyl-4-(4-phenoxy-phenylamino)-pyrrolo[1,2-b]pyridazine-3-carbonitrile, N-Benzyl-N-[3-cyano-5-methyl-4-(4-phenoxy-phenylamino)-pyrrolo[1,2-b]pyridazin-6-ylmethyl]-acetamide, N-[3-Cyano-5-methyl-4-(4-phenoxy-phenylamino)-pyrrolo[1,2-b]pyridazin-6-yl]-methanesulfonamide, 5-Methyl-6-(3-methyl-[1,2,4]oxadiazol-5-yl)-4-(4-phenoxy-phenylamino)-pyrrolo[1,2-b]pyridazine-3-carbonitrile, 3-Cyano-5-methyl-4-(4-phenoxy-phenylamino)-pyrrolo[1,2-b]pyridazine-6-carboxylic acid methoxy-methyl-amide, 5-Methyl-4-(4-phenoxy-phenylamino)-6-propynoyl-pyrrolo[1,2-b]pyridazine-3-carbonitrile, 3-cyano-5-methyl-4-(4-phenoxy-phenylamino)-pyrrolo[1,2-b]pyridazine-6-carbonyl-N-hydroxymorpholinyl-acetamidine, 5-Methyl-6-(3-morpholin-4-yl-[1,2,4]oxadiazol-5-yl)-4-(4-phenoxy-phenylamino)-pyrrolo[1,2-b]pyridazine-3-carbonitrile, 6-(3-Methanesulfonylmethyl-[1,2,4]oxadiazol-5-yl)-5-methyl-4-(4-phenoxy-phenylamino)-pyrrolo[1,2-b]pyridazine-3-carbonitrile, 3-(Imino-hydrazino-methyl)-5-methyl-4-(4-phenoxy-phenylamino)-pyrrolo[1,2-b]pyridazine-6-carboxylic acid ethyl ester, 5-Methyl-4-(4-phenoxy-phenylamino)-6-(4-phenyl-thiazol-2-yl)-pyrrolo[1,2-b]pyridazine-3-carbonitrile, 6-(4,5-Dihydro-1H-imidazol-2-ylamino)-5-methyl-4-(4-phenoxy-phenylamino)-pyrrolo[1,2-b]pyridazine-3-carbonitrile, 6-(2-Amino-4-hydroxy-4,5-dihydro-thiazol-4-ylamino)-5-methyl-4-(4-phenoxy-phenylamino)-pyrrolo[1,2-b]pyridazine-3-carbonitrile, 4-[3-Chloro-4-(1-methyl-1H-imidazol-2-ylsulfanyl)-phenylamino]-3-cyano-5-methyl-pyrrolo[1,2-b]pyridazine-6-carboxylic acid ether ester, 3-Cyano-4-[2-fluoro-4-(thiazol-2-yloxy)-phenylamino]-5-methyl-pyrrolo[1,2-b]pyridazine-6-carboxylic acid ethyl ester, 1-{4-[3-Chloro-4-(1-methyl-1H-imidazol-2-ylsulfanyl)-phenylamino]-3-cyano-5-methyl-pyrrolo[1,2-b]pyridazin-6-yl}-3-(2-morpholin-4-yl-ethyl)-urea, 3-Cyano-5-methyl-4-(5-phenoxy-pyridin-2-ylamino)-pyrrolo[1,2-b]pyridazine-6-carboxylic acid ethyl ester, 3-Acetylamino-N-{3-cyano-4-[5-(2-methoxy-phenoxy)-pyridin-2-ylamino]-5-methyl-pyrrolo[1,2-b]pyridazin-6-yl}-benzamide, 3-Acetylamino-N-{3-cyano-4-[5-(2-methoxy-phenoxy)-pyridin-2-ylamino]-5-methyl-pyrrolo[1,2-b]pyridazin-6-yl}-benzamide, {3-Cyano-4-[4-(2-methoxy-phenoxy)-phenylamino]-5-methyl-pyrrolo[1,2-b]pyridazin-6-yl}-methyl-carbamic acid 2-morpholin-4-yl-ethyl ester,

[3-Cyano-4-(4-{2-[1-(2-hydroxy-ethylcarbamoyl)-1-methoxy-ethoxy]-phenoxy}-phenylamino)-5-methyl-pyrrolo[1,2-b]pyridazin-6-yl]-carbamic acid 2-morpholin-4-yl-ethyl ester, N-{3-Cyano-4-[4-(2-methoxy-phenoxy)-phenylamino]-5-methyl-pyrrolo[1,2-b]pyridazin-6-yl}-3-methanesulfonylamino-benzamide, 5-Methyl-6-morpholin-4-ylmethyl-4-(4-phenoxy-phenylamino)-pyrrolo[1,2-b]pyridazine-3-carbonitrile, 1-{3-Cyano-4-[2-fluoro-4-(thiazol-2-yloxy)-phenylamino]-5-methyl-pyrrolo[1,2-b]pyridazin-6-yl}-3-(2-morpholin-4-yl-ethyl)-urea, 3-Cyano-4-(4-{2-[1-(2-hydroxy-ethylcarbamoyl)-1-methyl-ethoxy]-phenoxy}-phenylamino)-5-methyl-pyrrolo[1,2-b]pyridazine-6-carboxylic acid ethyl ester, {4-[3-Chloro-4-(1-methyl-1H-imidazol-2-ylsulfanyl)-phenylamino]-3-cyano-5-methyl-pyrrolo[1,2-b]pyridazin-6-yl}-carbamic acid 2-morpholin-4-yl-ethyl ester, 3-Cyano-4-(4-phenoxy-phenylamino)-pyrrolo[1,2-b]pyridazine-6-carboxylic acid, {3-Cyano-4-[2-fluoro-4-(thiazol-2-yloxy)-phenylamino]-5-methyl-pyrrolo[1,2-b]pyridazin-6-yl}-carbamic acid 2-morpholin-4-yl-ethyl ester, 3-Cyano-5-methyl-4-(2-methyl-4-phenoxy-phenylamino)-pyrrolo[1,2-b]pyridazine-6-carboxylic acid ethyl ester, 3-Cyano-4-(2-fluoro-4-phenoxy-phenylamino)-5-methyl-pyrrolo[1,2-b]pyridazine-6-carboxylic acid ethyl ester, 3-Cyano-4-(4-{2-[1-(2-hydroxy-ethylcarbamoyl)-1-methyl-ethoxy]-phenoxy}-phenylamino)-5-methyl-pyrrolo[1,2-b]pyridazine-6-carboxylic acid ethyl ester, 3-Cyano-4-(4-phenoxy-phenylamino)-pyrrolo[1,2-b]pyridazine-7-carboxylic acid, 4-[3-Chloro-4-(1-methyl-1H-imidazol-2-ylsulfanyl)-phenylamino]-3-cyano-5-methyl-pyrrolo[1,2-b]pyridazine-6-carboxylic acid (2-morpholin-4-yl-ethyl)-amide, 4-(5-Bromo-pyridin-2-ylamino)-3-cyano-5-methyl-pyrrolo[1,2-b]pyridazine-6-carboxylic acid methyl ester,

[3-Cyano-4-(4-{2-[1-(2-hydroxy-ethylcarbamoyl)-1-methyl-ethoxy]-phenoxy}-phenylamino)-5-methyl-pyrrolo[1,2-b]pyridazin-6-yl]-carbamic acid 2-morpholin-4-yl-ethyl ester, 3-Cyano-4-(4-hydroxy-cyclohexylamino)-5-methyl-pyrrolo[1,2-b]pyridazine-6-carboxylic acid ethyl ester, 4-(7-Aza-bicyclo[2.2.1]hept-7-yl)-3-cyano-5-methyl-pyrrolo[1,2-b]pyridazine-6-carboxylic acid ethyl ester, 4-(4-tert-Butoxycarbonyl-piperazin-1-yl)-3-cyano-5-methyl-pyrrolo[1,2-b]pyridazine-6-carboxylic acid ethyl ester, 3-Cyano-5-methyl-4-piperazin-1-yl-pyrrolo[1,2-b]pyridazine-6-carboxylic acid ethyl ester, 4-(4-Benzoyl-piperazin-1-yl)-3-cyano-5-methyl-pyrrolo[1,2-b]pyridazine-6-carboxylic acid ethyl ester, 4-(1-tert-Butoxycarbonyl-piperidin-4-ylamino)-3-cyano-5-methyl-pyrrolo[1,2-b]pyridazine-6-carboxylic acid ethyl ester, 3-Cyano-4-(4-methanesulfonyl-piperazin-1-yl)-5-methyl-pyrrolo[1,2-b]pyridazine-6-carboxylic acid ethyl ester, 3-Cyano-5-methyl-4-(piperidin-4-ylamino)-pyrrolo[1,2-b]pyridazine-6-carboxylic acid ethyl ester, 4-(1-Acetyl-piperidin-4-ylamino)-3-cyano-5-methyl-pyrrolo[1,2-b]pyridazine-6-carboxylic acid ethyl ester, 6-Formyl-7-iodo-5-methyl-4-(4-phenoxy-phenylamino)-pyrrolo[1,2-b]pyridazine-3-carbonitrile,

[3-Cyano-5-methyl-4-(4-phenoxy-phenylamino)-pyrrolo[1,2-b]pyridazin-6-yl]-carbamic acid 4-methanesulfonyl-butyl ester, 3-Cyano-4-(4-{3-[1-(2-hydroxy-ethylcarbamoyl)-1-methyl-ethoxy]-phenoxy}-phenylamino)-5-methyl-pyrrolo[1,2-b]pyridazine-6-carboxylic acid ethyl ester,

[3-Cyano-4-(4-{3-[1-(2-hydroxy-ethylcarbamoyl)-1-methyl-ethoxy]-phenoxy}-phenylamino)-5-methyl-pyrrolo[1,2-b]pyridazin-6-yl]-carbamic acid 2-morpholin-4-yl-ethyl ester, 4-{4-[2-(1-tert-Butoxycarbonyl-1-methyl-ethoxy)-phenoxy]-phenylamino}-3-cyano-5-methyl-pyrrolo[1,2-b]pyridazine-6-carboxylic acid methyl ester, 4-{4-[2-(1-Carboxy-1-methyl-ethoxy)-phenoxy]-phenylamino}-3-cyano-5-methyl-pyrrolo[1,2-b]pyridazine-6-carboxylic acid methyl ester, 3-Acetylamino-N-[3-cyano-4-(4-{3-[1-(2-hydroxy-ethylcarbamoyl)-1-methyl-ethoxy]-phenoxy}-phenylamino)-5-methyl-pyrrolo[1,2-b]pyridazin-6-yl]-benzamide, 3-Cyano-4-(4-{2-[1-(ethylcarbamoylmethyl-carbamoyl)-1-methyl-ethoxy]-phenoxy}-phenylamino)-5-methyl-pyrrolo[1,2-b]pyridazine-6-carboxylic acid methyl ester, 3-Cyano-4-(4-{2-[1-(ethoxycarbonylmethyl-carbamoyl)-1-methyl-ethoxy]-phenoxy}-phenylamino)-5-methyl-pyrrolo[1,2-b]pyridazine-6-carboxylic acid methyl ester, 3-Cyano-5-methyl-4-[4-phenoxy-3-(2,2,2-trifluoro-acetoxymethyl)-phenylamino]-pyrrolo[1,2-b]pyridazine-6-carboxylic acid ethyl ester, 5-Amino-3-cyano-4-(4-phenoxy-phenylamino)-pyrrolo[1,2-b]pyridazine-6-carboxylic acid ethyl ester, 4-(4-{2-[1-(tert-Butoxycarbonylmethyl-carbamoyl)-1-methyl-ethoxy]-phenoxy}-phenylamino)-3-cyano-5-methyl-pyrrolo[1,2-b]pyridazine-6-carboxylic acid methyl ester, 6-Hydroxy-5-methoxy-4-(4-phenoxy-phenylamino)-pyrrolo[1,2-b]pyridazine-3-carbonitrile, 7-Chloro-3-cyano-5-methyl-4-(4-phenoxy-phenylamino)-pyrrolo[1,2-b]pyridazine-6-carboxylic acid methyl ester, 7-Bromo-3-cyano-5-methyl-4-(4-phenoxy-phenylamino)-pyrrolo[1,2-b]pyridazine-6-carboxylic acid methyl ester, 3-Cyano-4-{4-[2-(2,3-dihydroxy-propoxy)-phenoxy]-phenylamino}-5-methyl-pyrrolo[1,2-b]pyridazine-6-carboxylic acid methyl ester, 3-Cyano-5-methyl-4-(4-phenoxy-benzoylamino)-pyrrolo[1,2-b]pyridazine-6-carboxylic acid methyl ester, 3-Cyano-5-methyl-4-(4-phenoxy-benzenesulfonylamino)-pyrrolo[1,2-b]pyridazine-6-carboxylic acid ethyl ester, 6-{3-[2-(1,1-Dioxo-1l6-thiomorpholin-4-yl)-ethyl]-2-oxo-imidazoline-1-carbonyl]-5-methyl-4-(4-phenoxy-phenylamino)-pyrrolo[1,2-b]pyridazine-3-carbonitrile, 3-Cyano-5-methyl-4-[4-(pyridin-2-yloxy)-phenylamino]-pyrrolo[1,2-b]pyridazine-6-carboxylic acid ethyl ester, 3-Cyano-5-methyl-4-[4-(pyridin-4-yloxy)-phenylamino]-pyrrolo[1,2-b]pyridazine-6-carboxylic acid ethyl ester, 3-Cyano-5-methyl-4-[4-(pyridin-3-yloxy)-phenylamino]-pyrrolo[1,2-b]pyridazine-6-carboxylic acid ethyl ester, 4-Acetylamino-N-{3-cyano-4-[4-(3-methoxy-phenoxy)-phenylamino]-5-methyl-pyrrolo[1,2-b]pyridazin-6-yl}-benzamide, 3-Acetylamino-N-{3-cyano-4-[4-(3-methoxy-phenoxy)-phenylamino]-5-methyl-pyrrolo[1,2-b]pyridazin-6-yl}-benzamide, N-{3-Cyano-4-[4-(2-methoxy-phenoxy)-phenylamino]-5-methyl-pyrrolo[1,2-b]pyridazin-6-yl}-3-dimethylamino-benzamide, N-{3-Cyano-4-[4-(3-methoxy-phenoxy)-phenylamino]-5-methyl-pyrrolo[1,2-b]pyridazin-6-yl}-3-dimethylamino-benzamide, 1H-Benzoimidazole-5-carboxylic acid {3-cyano-4-[4-(2-methoxy-phenoxy)-phenylamino]-5-methyl-pyrrolo[1,2-b]pyridazin-6-yl}-amide, 1H-Benzoimidazole-5-carboxylic acid {3-cyano-4-[4-(3-methoxy-phenoxy)-phenylamino]-5-methyl-pyrrolo[1,2-b]pyridazin-6-yl}-amide, 3-Cyano-4-(4-{2-[1-(ethylcarbamoylmethyl-carbamoyl)-1-methyl-ethoxy]-phenoxy}-phenylamino)-5-methyl-pyrrolo[1,2-b]pyridazine-6-carboxylic acid methyl ester, 4-Benzenesulfonyl-3-cyano-5-methyl-pyrrolo[1,2-b]pyridazine-6-carboxylic acid ethyl ester, 6-Isopropenyl-5-methyl-4-(4-phenoxy-phenylamino)-pyrrolo[1,2-b]pyridazine-3-carbonitrile, 3-[3-Cyano-5-methyl-4-(4-phenoxy-phenylamino)-pyrrolo[1,2-b]pyridazin-6-yloxy]-propane-1-sulfonic acid, (3-Morpholin-4-yl-propyl)-carbamic acid 3-cyano-5-methyl-4-(4-phenoxy-phenylamino)-pyrrolo[1,2-b]pyridazin-6-yl ester, 5-Methyl-4-(4-phenoxy-phenylamino)-6-pyridin-2-yl-pyrrolo[1,2-b]pyridazine-3-carbonitrile, 3-Cyano-5-methoxy-4-(4-phenoxy-phenylamino)-pyrrolo[1,2-b]pyridazine-6-carboxylic acid, (2-Morpholin-4-yl-ethyl)-carbamic acid 3-cyano-5-methyl-4-(4-phenoxy-phenylamino)-pyrrolo[1,2-b]pyridazin-6-yl ester, (2-Morpholin-4-yl-ethyl)-carbamic acid 3-cyano-5-methoxy-4-(4-phenoxy-phenylamino)-pyrrolo[1,2-b]pyridazin-6-yl ester, 3-[3-Cyano-5-methyl-4-(4-phenoxy-phenylamino)-pyrrolo[1,2-b]pyridazin-6-yloxycarbonylamino]-propionic acid, 6-(3H-Imidazol-4-yl)-5-methyl-4-(4-phenoxy-phenylamino)-pyrrolo]1,2-b]pyridazine-3-carbonitrile, Furan-2-carboxylic acid {3-cyano-4-[4-(2-methoxy-phenoxy)-phenylamino]-5-methyl-pyrrolo[1,2-b]pyridazin-6-yl}-amide, Thiophene-2-carboxylic acid {3-cyano-4-[4-(2-methoxy-phenoxy)-phenylamino]-5-methyl-pyrrolo[1,2-b]pyridazin-6-yl}-amide, 3-Cyano-4-{4-[2-(3-hydroxy-2,2-bis-hydroxymethyl-propoxy)-phenoxy]-phenylamino}-5-methyl-pyrrolo[1,2-b]pyridazine-6-carboxylic acid methyl ester, N-{3-Cyano-4-[4-(2-methoxy-phenoxy)-phenylamino]-5-methyl-pyrrolo[1,2-b]pyridazin-6-yl}-4-morpholin-4-yl-benzamide, N-{3-Cyano-4-[4-(2-methoxy-phenoxy)-phenylamino]-5-methyl-pyrrolo[1,2-b]pyridazin-6-yl}-2-methanesulfonyl-benzamide, 2-Oxo-imidazolidine-1-carboxylic acid {3-cyano-4-[4-(2-methoxy-phenoxy)-phenylamino]-5-methyl-pyrrolo[1,2-b]pyridazin-6-yl}-amide, Benzo[1,2,5]thiadiazole-5-carboxylic acid {3-cyano-4-[4-(2-methoxy-phenoxy)-phenylamino]-5-methyl-pyrrolo[1,2-b]pyridazin-6-yl}-amide, 5-Methanesulfonyl-thiophene-2-carboxylic acid {3-cyano-4-[4-(2-methoxy-phenoxy)-phenylamino]-5-methyl-pyrrolo[1,2-b]pyridazin-6-yl}-amide 3-Chloro-4-methanesulfonyl-thiophene-2-carboxylic acid {3-cyano-4-[4-(2-methoxy-phenoxy)-phenylamino]-5-methyl-pyrrolo[1,2-b]pyridazin-6-yl}-amide,

[1,2,3Thiadiazole-4-carboxylic acid {3-cyano-4-[4-(2-methoxy-phenoxy)-phenylamino]-5-methyl-pyrrolo[1,2-b]pyridazin-6-yl}-amide, 3,5-Bis-acetylamino-N-{3-cyano-4-[4-(2-methoxy-phenoxy)-phenylamino]-5-methyl-pyrrolo[1,2-d]pyridazin-6-yl}-benzamide, N-{3-Cyano-4-[4-(2-methoxy-phenoxy)-phenylamino]-5-methyl-pyrrolo[1,2-b]pyridazin-6-yl}-4-guanidino-benzamide; trifluoro-acetic acid salt, N-{3-Cyano-4-[4-(3-methoxy-phenoxy)-phenylamino]-5-methyl-pyrrolo[1,2-b]pyridazin-6-yl}-3-nitro-benzamide, N-{3-Cyano-4-[4-(3-methoxy-phenoxy)-phenylamino]-5-methyl-pyrrolo[1,2-b]pyridazin-6-yl}-4-nitro-benzamide, N-{3-Cyano-4-[4-(2-methoxy-phenoxy)-phenylamino]-5-methyl-pyrrolo[1,2-b]pyridazin-6-yl}-3-guanidino-benzamide; trifluoro-acetic acid salt, 3-Amino-N-{3-cyano-4-[4-(3-methoxy-phenoxy)-phenylamino]-5-methyl-pyrrolo[1,2-b]pyridazin-6-yl}-benzamide, N-{3-Cyano-4-[4-(3-methoxy-phenoxy)-phenylamino]-5-methyl-pyrrolo[1,2-b]pyridazin-6-yl}-3-ureido-benzamide, N-{3-Cyano-4-[4-(3-methoxy-phenoxy)-phenylamino]-5-methyl-pyrrolo[1,2-b]pyridazin-6-yl}-4-guanidino-benzamide, N-{3-Cyano-4-[4-(3-methoxy-phenoxy)-phenylamino]-5-methyl-pyrrolo[1,2-b]pyridazin-6-yl}-3-ureido-benzamide, trifluoro-acetic acid salt, N-{3-Cyano-4-[4-(3-methoxy-phenoxy)-phenylamino]-5-methyl-pyrrolo[1,2-b]pyridazin-6-yl}-4-guanidino-benzamide, trifluoro-acetic acid salt, 3,4-Bis-acetylamino-N-{3-cyano-4-[4-(2-methoxy-phenoxy)-phenylamino]-5-methyl-pyrrolo[1,2-b]pyridazin-6-yl}-benzamide, 2-Oxo-2,3-dihydro-1H-indole-6-carboxylic acid {3-cyano-4-[4-(2-methoxy-phenoxy)-phenylamino]-5-methyl-pyrrolo[1,2-b]pyridazin-6-yl}-amide, 2-Oxo-2,3-dihydro-1H-benzoimidazole-5-carboxylic acid {3-cyano-4-[4-(2-methoxy-phenoxy)-phenylamino]-5-methyl-pyrrolo[1,2-b]pyridazin-6-yl}-amide, 2,3-Dioxo-1,2,3,4-tetrahydro-quinoxaline-6-carboxylic acid {3-cyano-4-[4-(2-methoxy-phenoxy)-phenylamino]-5-methyl-pyrrolo[1,2-b]pyridazin-6-yl}-amide, Thiophene-2-carboxylic acid {3-cyano-4-[4-(2-methoxy-phenoxy)-phenylamino]-5-methyl-pyrrolo[1,2-b]pyridazin-6-yl}-amide, 1H-Imidazole-2-carboxylic acid [3-cyano-5-methyl-4-(4-phenoxy-phenylamino)-pyrrolo[1,2-b]pyridazin-6-yl]-amide, 5-Methyl-4-(4-phenoxy-phenylamino)-7-phenyl-pyrrolo[1,2-b]pyridazine-3-carbonitrile, 4-[4-(2-Methoxy-phenoxy)-phenylamino]-5-methyl-6-(pyrimidin-2-ylamino)-pyrrolo[1,2-b]pyridazine-3-carbonitrile, N-{3-Cyano-4-[4-(2-methoxy-phenoxy)-phenylamino]-5-methyl-pyrrolo[1,2-b]pyridazin-6-yl}-guanidine; trifluoro-acetic acid salt, 4-[4-(2-Methoxy-phenoxy)-phenylamino]-5-methyl-6-(pyridin-2-ylamino)-pyrrolo[1,2-b]pyridazine-3-carbonitrile, 6-(Di-pyrazin-2-yl-amino)-4-[4-(2-methoxy-phenoxy)-phenylamino]-5-methyl-pyrrolo[1,2-b]pyridazine-3-carbonitrile, 4-[4-(2-Methoxy-phenoxy)-phenylamino]-5-methyl-6-(pyrazin-2-ylamino)-pyrrolo[1,2-b]pyridazine-3-carbonitrile, Acetic acid (3-{3-cyano-4-[4-(2-methoxy-phenoxy)-phenylamino]-5-methyl-pyrrolo[1,2-b]pyridazin-6-ylcarbamoyl}-phenylcarbamoyl)-methyl ester, N-{3-Cyano-4-[4-(2-methoxy-phenoxy)-phenylamino]-5-methyl-pyrrolo[1,2-b]pyridazin-6-yl}-3-nitro-benzamide, 4-(1-Benzoyl-piperidin-4-ylamino)-3-cyano-5-methyl-pyrrolo[1,2-b]pyridazine-6-carboxylic acid ethyl ester, 4-(4-Acetyl-piperazin-1-yl)-3-cyano-5-methyl-pyrrolo[1,2-b]pyridazine-6-carboxylic acid ethyl ester, N-{3-Cyano-4-[4-(2-methoxy-phenoxy)-phenylamino]-5-methyl-pyrrolo[1,2-b]pyridazin-6-yl}-3-(3-ethyl-ureido)-benzamide, 3-Cyano-5,7-dimethyl-4-(4-phenoxy-phenylamino)-pyrrolo[1,2-b]pyridazine-6-carboxylic acid ethyl ester, 7-Chloro-3-cyano-5-methyl-4-(4-phenoxy-phenylamino)-pyrrolo[1,2-b]pyridazine-6-carboxylic acid methyl ester, 7-Bromo-3-cyano-5-methyl-4-(4-phenoxy-phenylamino)-pyrrolo[1,2-b]pyridazine-6-carboxylic acid methyl ester, 3-Cyano-4-{4-[2-(2,3-dihydroxy-propoxy)-phenoxy]-phenylamino}-5-methyl-pyrrolo[1,2-b]pyridazine-6-carboxylic acid methyl ester, 3-Cyano-4-{4-[2-(3-hydroxy-2,2-bis-hydroxymethyl-propoxy)-phenoxy]-phenylamino}-5-methyl-pyrrolo[1,2-b]pyridazine-6-carboxylic acid methyl ester, 3-Cyano-4-{4-[2-(2-hydroxy-ethoxy)phenoxy]-phenylamino}-5-methyl-pyrrolo[1,2-b]pyridazine-6-carboxylic acid methyl ester, and 3-Cyano-4-(4-{2-[2-(2-hydroxy-ethoxy)-ethoxy]-phenoxy}-phenylamino)-5-methyl-pyrrolo[1,2-b]pyridazine-6-carboxylic acid methyl ester, or a pharmaceutically acceptable salt thereof.

2. A pharmaceutical composition comprising one or more compounds according to claim 1 and one or more pharmaceutically acceptable carriers therefor.

* * * * *